US011155602B2

(12) United States Patent
Krystal et al.

(10) Patent No.: US 11,155,602 B2
(45) Date of Patent: Oct. 26, 2021

(54) POLYPEPTIDES TARGETING HIV FUSION

(71) Applicant: VIIV Healthcare (No.5) Limited, Middlesex (GB)

(72) Inventors: Mark R. Krystal, Wallingford, CT (US); David L. Wensel, Waltham, MA (US); Jonathan Davis, Waltham, MA (US)

(73) Assignee: VIIV HEALTHCARE UK (No. 5) LIMITED

( * ) Notice: Subject to any disclaimer, the term of this patent is extended or adjusted under 35 U.S.C. 154(b) by 74 days.

(21) Appl. No.: 16/533,941

(22) Filed: Aug. 7, 2019

(65) Prior Publication Data

US 2019/0359688 A1  Nov. 28, 2019

Related U.S. Application Data

(62) Division of application No. 15/568,830, filed as application No. PCT/US2016/027424 on Apr. 14, 2016, now Pat. No. 10,407,490.

(60) Provisional application No. 62/257,474, filed on Nov. 19, 2015, provisional application No. 62/152,271, filed on Apr. 24, 2015.

(51) Int. Cl.

| C07K 14/78 | (2006.01) |
|---|---|
| C07K 14/005 | (2006.01) |
| A61K 47/60 | (2017.01) |
| A61P 31/18 | (2006.01) |
| C07K 14/765 | (2006.01) |
| C07K 14/79 | (2006.01) |
| A61K 38/00 | (2006.01) |

(52) U.S. Cl.
CPC .............. *C07K 14/78* (2013.01); *A61K 47/60* (2017.08); *A61P 31/18* (2018.01); *C07K 14/005* (2013.01); *C07K 14/765* (2013.01); *C07K 14/79* (2013.01); *A61K 38/00* (2013.01); *C07K 2319/00* (2013.01); *C07K 2319/30* (2013.01); *C07K 2319/31* (2013.01); *C12N 2740/16122* (2013.01)

(58) Field of Classification Search
CPC ......... A61K 47/60; A61K 38/00; A61P 31/18; C12N 2740/16122; C07K 14/78; C07K 14/005; C07K 14/765; C07K 14/79; C07K 2319/00; C07K 2319/30; C07K 2319/31

See application file for complete search history.

(56) References Cited

U.S. PATENT DOCUMENTS

| 2007/0048282 A1 | 3/2007 | Rosen et al. |
| 2009/0022720 A1 | 1/2009 | Fischer et al. |

FOREIGN PATENT DOCUMENTS

| WO | WO 2011/077093 A1 | 6/2011 |
| WO | WO 2011/130354 A1 | 10/2011 |
| WO | WO-2014/165093 A2 | 10/2014 |
| WO | WO 2014/206336 A1 | 12/2014 |

OTHER PUBLICATIONS

Eckert, D.M. and Kim, P.S., "Design of P potent inhibitors of HIV-1 entry from the gp41-N-peptide region", *Proc. Natl. Acad. Sci. USA*, 98(20):11187-92 (2001).
Greenberg, et al, Resistance to enfuvirtide, the first HIV fusion inhibitor, Journal of Antimicrobial Chemotherapy, 54:333-340 (2004).
Haqqani, et al., "Entry inhibitors and their use in the treatment of HIV-1 infection" *Antiviral Research*; 98(2):158-170 (2013).
Jain, et al, "Mutual prodrugs containing bio-cleavable and drug releasable disulfide linkers", *Bioorganic Chemistry*, 49:40-48 (2013).
Krystal, M., et al. HIV-1 Combinectin BMS-986197: A Long-Acting Inhibitor With Multiple Modes of Action. Conference on Retroviruses and Opportunistic Infections (CROI): Conference Abstract, Feb. 22, 2016.

*Primary Examiner* — Li N Komatsu
(74) *Attorney, Agent, or Firm* — Craig T. Ajmo

(57) ABSTRACT

The invention is directed to polypeptides comprising a CD4 binding moiety, a gp41 binding moiety, a HIV fusion peptide inhibitor moiety and combinations thereof. More specifically, the present invention relates to polypeptides comprising a fibronectin-based scaffold domain protein that binds CD4, a fibronectin-based scaffold domain protein that binds the N17 domain of gp41, and a HIV fusion peptide inhibitor or combinations thereof. The invention also relates to the use of the innovative proteins in therapeutic applications to treat HIV.

7 Claims, 13 Drawing Sheets

Specification includes a Sequence Listing.

FIG. 2

Fc fusion-Combinectin 3137 (full protein is a homo-dimer of this sequence) [SEQ ID NO:4]
**DKTHTCPPCPAPELLGGPSVFLFPPKPKDTLMISRTPEVTCVVVDVSHEDPEVKF
NWYVDGVEVHNAKTKPREEQYASTYRVVSVLTVLHQDWLNGKEYKCKVSNK
ALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHN
HYTQKSLSLSP*ESPEPETPEDESPEPETPEDE*GVSDVPRDLEVVAATPTSLLISWDAP
AVTVHSYHIQYWPLGSYQRYQVFSVPGSKSTATISGLKPGVEYQIRVYAETGRGESD
QSLGWIQIGYRTE*ESPEPETPEDE*GVSDVPRDLEVVAATPTSLLISWQYKVHPYRYYR
ITYGETGGNSPVQEFTVPSVLSTAEISGLKPGVDYTITVYAVTRGVDSAPISINYRTPG
*GGGSGGGGSGGGGSGGGG*SEYEARIEALIRAAQEQQEKNEAALRELYKWAL Fc fusion-Combinectin 3151 (full protein is a homo-dimer of this sequence) [SEQ ID NO:6]
**DKTHTCPPCPAPELLGGPSVFLFPPKPKDTLMISRTPEVTCVVVDVSHEDPEVKF
NWYVDGVEVHNAKTKPREEQYASTYRVVSVLTVLHQDWLNGKEYKCKVSNK
ALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHN
HYTQKSLSLSP*ESPEPETPEDESPEPETPEDE*GVSDVPRDLEVVAATPTSLLISWDAP
AVTVHSYHIQYWPLGSYQRYQVFSVPGSKSTATISGLKPGVEYQIRVYAETGRGESD
QSLGWIQIGYRTE*ESPEPETPEDE*GVSDVPRDLEVVAATPTSLLISWEYNVNPYRYYR
ITYGETGGNSPVQEFTVPSVLSSAQISGLKPGVDYTITVYAVTRGVDSAPISINYRTPG
*GGGSGGGGSGGGGSGGGG*SEYEARIEALIRAAQEQQEKNEAALRELWKWAS

FIG. 2 (continued)

HSA fusion-Combinectin 3191 [SEQ ID NO:8]

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKR
YKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICE
NQDSISSKLKECCEKPLLEKSHCIAEVENDEMPADLPSLAADFVESKDVCKNYAE
AKDVFLGMFLYEYARRHPDYSVVLLLRLAKTYETTLEKCCAAADPHECYAKVF
DEFKPLVEEPQNLIKQNCELFEQLGEYKFQNALLVRYTKKVPQVSTPTLVEVSR
NLGKVGSKCCKHPEAKRMPCAEDYLSVVLNQLCVLHEKTPVSDRVTKCCTESL
VNRRPCFSALEVDETYVPKEFNAETFTFHADICTLSEKERQIKKQTALVELVKH
KPKATKEQLKAVMDDFAAFVEKCCKADDKETCFAEEGKKLVAASQAALGL*ESP
EPETPEDESPEPETPEDE*GVSDVPRDLEVVAATPTSLLISWDAPAVTVHSYHIQYWPL
GSYQRYQVFSVPGSKSTATISGLKPGVEYQIRVYAETGRGESDQSLGWIQIGYRTP*ES
PEPETPEDE*GVSDVPRDLEVVAATPTSLLISWEYKVHPYRYYRITYGETGGNSPVQEF
TVPSVLSSAEISGLKPGVDYTITVYAVTYGIDSPPISINYRTEG*GGGSGGGGSGGGGSG
GGG*SEYEARIEALIRAAQEQQEKNEAALRELYKWAL

FIG. 2 (continued)

HSA fusion-Combinectin 3202 [SEQ ID NO:10]

DAHKSEVAHRFKDLGEENFKALVLIAFAQYLQQAPFEDHVKLVNEVTEFAKTC
VADESAENCDKSLHTLFGDKLCTVATLRETYGEMADCCAKQEPERNECFLQHK
DDNPNLPRLVRPEVDVMCTAFHDNEETFLKKYLYEIARRHPYFYAPELLFFAKR
YKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICE
NQDSISSKLKECCEKPLLEKSHCIAEVENDEMPADLPSLAADFVESKDVCKNYAE
AKDVFLGMFLYEYARRHPDYSVVLLLRLAKTYETTLEKCCAAADPHECYAKVF
DEFKPLVEEPQNLIKQNCELFEQLGEYKFQNALLVRYTKKVPQVSTPTLVEVSR
NLGKVGSKCCKHPEAKRMPCAEDYLSVVLNQLCVLHEKTPVSDRVTKCCTESL
VNRRPCFSALEVDETYVPKEFNAETFTFHADICTLSEKERQIKKQTALVELVKH
KPKATKEQLKAVMDDFAAFVEKCCKADDKETCFAEEGKKLVAASQAALGL*GG*
*GGSGGGGSGGGGSGGGGSGGGGS*<u>GVSDVPRDLEVVAATPTSLLISWDAPAVTVHSY
HIQYWPLGSYQRYQVFSVPGSKSTATISGLKPGVEYQIRVYAETGGADSDQSFGWIQI
GYRTP</u>*ESPEPETPEDE*<u>GVSDVPRDLEVVAATPTSLLISWEYKVHPYRYYRITYGETGG
NSPVQEFTVPSVLSTAEISGLKPGVDYTITVYAVTRGVDSAPISINYRTP</u>*GGGGSGGG
GSGGGGSGGGG*<u>TIAEYAARIEALIRAAQEQQEKNEAALRELYKWAS</u>

FIG. 5

Anti-N17 Adnectin™ – HIV fusion peptide inhibitor Combinectin (SEQ ID NO: 410)
GSVSDVPRDLEVVAATPTSLLISWEYKVNAYRYYRITYGETGGNSPVQEFTVPSVLS
TATISGLKPGVDYTITVYAVTYGVDSDPISINYRTEID*GGGGSGGGGSGGGGSGGGG*A
RIEEYAARIEALIRAAQEQQEKNEAALRELYKWAS Anti-N17 Adnectin™ – HIV fusion peptide inhibitor Combinectin (SEQ ID NO: 411)
GSVSDVPRDLEVVAATPTSLLISWEYKVNAYRYYRITYGETGGNSPVQEFTVPSVLS
TATISGLKPGVDYTITVYAVTYGVDSDPISINYRTEID*GGGGSGGGGSGGGGSGGGG*T
IAEYAARIEALIRAAQEQQEKNEAALRELYKWAS Anti-N17 Adnectin™ – HIV fusion peptide inhibitor Combinectin (SEQ ID NO: 412)
GSVSDVPRDLEVVAATPTSLLISWEYKVNAYRYYRITYGETGGNSPVQEFTVPSVLS
TATISGLKPGVDYTITVYAVTYGVDSDPISINYRTEID*GGGGSGGGGSGGGGSGGGG*S
EYEARIEALIRAAQEQQEKNEAALRELYKWAS Anti-N17 Adnectin™ – HIV fusion peptide inhibitor Combinectin (SEQ ID NO: 413)
GVSDVPRDLEVVAATPTSLLISWKYKVHPYRYYRITYGETGGNSPVQEFTVPSVLST
ATISGLKPGVDYTITVYAVTYGVNSLPISINYRTEID*GGGGSGGGGSGGGGSGGGG*TE
YEARIEALIRAAQEQQEKNEAALRELKEWASIWN Anti-N17 Adnectin™ – HIV fusion peptide inhibitor Combinectin (SEQ ID NO: 414)
GVSDVPRDLEVVAATPTSLLISWDAPAVTVGWYHIGYNVEGEPASYQYFRVPGSKS
TATISGLKPGVEYMIFVNAVTGSGAREEFSLPISINYRTEID*GGGGSGGGGSGGGGSG
GGG*SEYEARIEALIRAAQEQQEKNEAALRELDKWTGVWGNYEKV Anti-N17 Adnectin™ – HIV fusion peptide inhibitor Combinectin (SEQ ID NO:415)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELFKWAS

FIG. 5 (continued)

Anti-N17 Adnectin™ – HIV fusion peptide inhibitor Combinectin (SEQ ID NO:416)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQQKNEAALRELDKWAS Anti-N17 Adnectin™ – HIV fusion peptide inhibitor Combinectin (SEQ ID NO:417)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWAS Anti-N17 Adnectin™ – HIV fusion peptide inhibitor Combinectin (SEQ ID NO:418)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELLKWAS Anti-N17 Adnectin™ – HIV fusion peptide inhibitor Combinectin (SEQ ID NO:419)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELQKWAS Anti-N17 Adnectin™ – HIV fusion peptide inhibitor Combinectin (SEQ ID NO:420)
GSVSDVPRDLEVVAATPTSLLISWEYKVHPYRYYRITYGETGGNSPVQEFTVPSVLST
ATISGLKPGVDYTITVYAVTYGDDSAPISINYRTEID*GGGGSGGGGSGGGGSGGGG*SR
IEALIRAAQEQQEKNEAALRELDKWAS Anti-N17 Adnectin™ – HIV fusion peptide inhibitor Combinectin (SEQ ID NO:421)
GVSDVPRDLEVVAATPTSLLISWVAGAEDYQYYRITYGETGGNSPVQEFTVPHDLVT
ATISGLKPGVDYTITVYAVTDMMHVEYTEHPISINYRTEID*GGGGSGGGGSGGGGSG
G*AIAEYAARIEALIRAAQEQQEKNEAALRELDKWAS

FIG. 5 (continued)

Anti-N17 Adnectin™ – HIV fusion peptide inhibitor Combinectin (SEQ ID NO:422)
GVSDVPRDLEVVAATPTSLLISWKYKVHPYRYYRITYGETGGNSPVQEFTVPSVLST
ATISGLKPGVDYTITVYAVTYGVNSLPISINYRTEID*GGGGSGGGGSGGGGSGGGG*TE
YEARIEALIRAAQEQQEKNEAALRELDK Anti-N17 Adnectin™ – HIV fusion peptide inhibitor Combinectin (SEQ ID NO:423)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWTS Anti-N17 Adnectin™ – HIV fusion peptide inhibitor Combinectin (SEQ ID NO:424)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWASLWI Anti-N17 Adnectin™ – HIV fusion peptide inhibitor Combinectin (SEQ ID NO:425)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWASRWN Anti-N17 Adnectin™ – HIV fusion peptide inhibitor Combinectin (SEQ ID NO:426)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWASSWN Anti-N17 Adnectin™ – HIV fusion peptide inhibitor Combinectin (SEQ ID NO:427)
GVSDVPRDLEVVAATPTSLLISWDAPAVTVRYYRITYGETGGNSPVQEFTVPGSKST
ATISGLKPGVDYTITVYAVTGRGESPASSKPISINYRTEID*GGGGSGGGGSGGGGSGG
GG*SRIEALIRAAQEQQEKNEAALRELYKWGS

FIG. 5 (continued)

Anti-N17 Adnectin™ – HIV fusion peptide inhibitor Combinectin (SEQ ID NO: 428)

GVSDVPRDLEVVAATPTSLLISWEYKVNNYRYYRITYGETGGNSPVQEFTVPSVLST
ATISGLKPGVDYTITVYAVTYGVHSSPISINYRTEID*GGGGSGGGGSGGGGSGGGG*SRI
EALIRAAQEQQEKNEAALRELDK

POLYPEPTIDES TARGETING HIV FUSION

CROSS-REFERENCE TO RELATED APPLICATIONS

This application is a divisional of U.S. application Ser. No. 15/568,830, filed on 24 Oct. 2017, now U.S. Pat. No. 10,407,490, which is a 371 of International PCT/US2016/027424 filed on 14 Apr. 2016, which claims priority to U.S. Provisional Application Ser. Nos. 62/152,271, filed Apr. 24, 2015, and 62/257,474, filed Nov. 19, 2015; the entire contents of which are incorporated herein by reference.

FIELD OF THE INVENTION

The invention is directed to polypeptides comprising a CD4 binding moiety, a gp41 binding moiety, a HIV fusion peptide inhibitor moiety and combinations thereof. More specifically, the present invention relates to polypeptides comprising a fibronectin-based scaffold domain protein that binds CD4, a fibronectin-based scaffold domain protein that binds the N17 domain of gp41, and a HIV fusion peptide inhibitor or combinations thereof. The invention also relates to the use of the innovative proteins in therapeutic applications to treat HIV.

BACKGROUND OF THE INVENTION

Acquired immunodeficiency syndrome (AIDS) is the result of infection by the retrovirus known as human immunodeficiency virus (HIV). It remains a major medical problem, with an estimated 35 million people infected worldwide at the end of 2013. During that year, there were 2.1 million new infections, with 1.5 million people dying from complications due to AIDS.

Current therapy for HIV-infected individuals consists of a combination of approved anti-retroviral agents. Over two dozen drugs are currently approved for HIV infection, either as single agents, fixed dose combinations or single tablet regimens, the latter two containing 2-4 approved agents. These agents belong to a number of different classes, targeting either a viral enzyme or the function of a viral protein during the virus life cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one entry inhibitor, maraviroc, targets the host CCR5 protein, while the other, enfuvirtide, is a peptide that targets the gp41 region of the viral gp160 protein). In addition, a pharmacokinetic enhancer with no antiviral activity (cobicistat) has been approved for use in combinations with antiretroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g., CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads>500 copies/ml (Oette, M. et al., "Primary HIV Drug Resistance and Efficacy of First-Line Antiretroviral Therapy Guided by Resistance Testing", *J. Acq. Imm. Def. Synd.,* 41(5):573-581 (2006)). Among these patients, 76% had viruses that were resistant to one or more classes of antiretroviral agents. As a result, new drugs are needed that are more convenient, have high genetic barriers to the development of resistance and have improved safety over current agents.

It is now well known that cells can be infected by HIV through a process by which fusion occurs between the cellular membrane and the viral membrane. The generally accepted model of this process is that the viral envelope glycoprotein complex (gp120/gp41) interacts with cell surface receptors on the membranes of the target cells. Following binding of gp120 to cellular receptors (e.g., CD4 in combination with a chemokine co-receptor such as CCR5 or CXCR4), a conformational change is induced in the gp120/gp41 complex that allows gp41 to insert into the membrane of the target cell and mediate membrane fusion. As these entry processes occur on the cell membrane, they are amenable for inhibition by macrocmolecules, which include biologic peptides (Haqqani et al., Antiviral Res., 98:158 (2013)). For instance, the approved antiviral peptide enfuvirtide (FUZEON®) targets a region of gp41 involved in membrane fusion. Larger polypeptides such as monoclonal antibodies can also inhibit different aspects of virus entry. A monoclonal antibody targeting the first step of virus entry, interaction with the cellular receptor CD4 (ibalizumab; Bruno et al., *J. Antimicrob. Chemother.,* 65:1839 (2010)), as well as a monoclonal antibody targeting the co-receptor CCR5 (PRO-140; Tenorio, *Curr. HIV/AIDS Rep.,* 8:1 (2011)) have both shown positive results in Phase 2a trials. These antibodies also have the property of being long acting antiretrovirals, with potential dosing regimens of weekly to monthly (Jacobson et al., *J. Infect. Dis.,* 201:1481 (2010); Jacobson et al., *Antimicrob. Agents Chemother.,* 53:450 (2009)).

Another property of peptide entry inhibitors is that enhanced or synergistic potency can be obtained if two peptide inhibitors are attached to each other, or if a single inhibitor is localized near the site of action through binding to membrane biomolecules. Thus, attaching a fusion peptide inhibitor to a monoclonal antibody targeting CCR5 (Kopetzki et al., *Virol. J.,* 5:56 (2008)) or attaching a cholesterol moiety to the C-terminus of a peptide fusion inhibitor to place it at the surface of the target cell membrane (Ingallinela et al., *Proc. Natl. Acad. Sci. USA,* 106:5801 (2009); Augusto et al., *J. Antimicrob. Chemother.,* 69:1286 (2014)) drastically increases the potency of the combined molecule compared to the separate molecules. Similarly, bispecific antibodies consisting of anti-HIV-1 neutralizing antibody fragments targeting gp120 fused to ibalizumab showed synergistic increases in potency compared to the individual inhibitors (Sun et al., *J. Acquir. Immune Defic. Syndr.,* 66:473 (2014)). The Combinectin molecules of the invention makes use of these various properties.

SUMMARY OF THE INVENTION

The invention is directed to polypeptides comprising a CD4 binding moiety, a gp41 binding moiety, a HIV fusion peptide inhibitor moiety and combinations thereof.

One embodiment of the invention is directed to polypeptides comprising a fibronectin-based scaffold domain protein that binds CD4, a fibronectin-based scaffold domain protein that binds the N17 domain of gp41, and a HIV fusion peptide inhibitor.

In one embodiment of the invention, the three domains are connected to each other by linkers. In another embodiment of the invention, the three domains may be connected to each other in any order. In another embodiment of the invention, the polypeptide comprises an amino acid sequence at least 80%, 85%, 90%, 95%, 98%, 99% or 100% identical to the non-linker regions of SEQ ID NO: 3, 5, 7 or 9.

The invention is also directed to polypeptides comprising a fibronectin-based scaffold domain protein that binds CD4 and a fibronectin-based scaffold domain protein that binds the N17 domain of gp41. In one embodiment of the invention, the two domains are connected to each other by linkers. In another embodiment of the invention, the two domains may be connected to each other in any order.

The invention is also directed to polypeptides comprising a fibronectin-based scaffold domain protein that binds CD4 and a HIV fusion peptide inhibitor. In one embodiment of the invention, the two domains are connected to each other by linkers. In another embodiment of the invention, the two domains may be connected to each other in any order.

The invention is also directed to polypeptides comprising a fibronectin-based scaffold domain protein that binds the N17 domain of gp41, and a HIV fusion peptide inhibitor. In one embodiment of the invention, the two domains are connected to each other by linkers. In another embodiment of the invention, the two domains may be connected to each other in any order. In another embodiment of the invention, the polypeptide comprises an amino acid sequence at least 80%, 85%, 90%, 95%, 98%, 99% or 100% identical to the non-linker regions of SEQ ID NO: 410-428.

Another embodiment of the invention is also directed to polypeptides comprising three active domains, a fibronectin-based scaffold domain protein that binds CD4, a gp41 binding moiety and a HIV fusion peptide inhibitor moiety. The invention is also directed to polypeptides comprising a fibronectin-based scaffold domain protein that binds gp41, a CD4 binding moiety and a HIV fusion peptide inhibitor moiety. The invention is also directed to polypeptides comprising a CD4 binding moiety, a gp41 binding moiety and a HIV fusion peptide inhibitor. In one embodiment of the invention, the two domains are connected to each other by linkers. In another embodiment of the invention, the two domains may be connected to each other in any order.

The invention is also directed to polypeptides comprising two active domains, a fibronectin-based scaffold domain protein that binds CD4 and a gp41 binding moiety. The invention is also directed to polypeptides comprising a fibronectin-based scaffold domain protein that binds gp41 and a CD4 binding moiety. The invention is also directed to polypeptides comprising a CD4 binding moiety and a HIV fusion peptide inhibitor. The invention is also directed to polypeptides comprising a gp41 binding moiety and a HIV fusion peptide inhibitor. In one embodiment of the invention, the two domains are connected to each other by linkers. In another embodiment of the invention, the two domains may be connected to each other in any order.

Another embodiment of the invention is also directed to anti-CD4 Adnectin™ anti-N17 Adnectin™, or HIV fusion peptide inhibitors. In another embodiment of the invention, the polypeptide comprises an amino acid sequence at least 80%, 85%, 90%, 95%, 98%, 99% or 100% identical to the non-linker regions of SEQ ID NO: 95-114 or SEQ ID NO: 115-371 or SEQ ID NO: 372-392, respectively.

In another embodiment of the invention, a pharmacokinetic (PK) moiety is attached to the polypeptides of the invention. Examples of a PK moiety include but are not limited to polyethylene glycol, sialic acid, Fc, Fc fragment, transferrin, serum albumin (HSA), a serum albumin binding protein, and a serum immunoglobulin binding protein. In one embodiment of the invention, the PK moiety may be attached to the linker regions, or the N- or C-terminus of the polypeptide of the invention. In another embodiment of the invention, the polypeptide comprises an amino acid sequence at least 80%, 85%, 90%, 95%, 98%, 99% or 100% identical to the non-linker regions of SEQ ID NO: 4, 6, 8 or 10.

The invention is also directed to a polypeptide comprising the amino acid sequence of any one of the sequences shown in SEQ ID NO: 3-10.

The invention is also directed to a pharmaceutical composition comprising one or more of the polypeptides of the invention and a carrier.

The invention also provides a method of treating HIV in a subject comprising administering an effective amount of the polypeptides of the invention.

BRIEF DESCRIPTION OF THE FIGURES

FIG. 2 shows the amino acid sequences of Fc fusion-Combinectin 3137_(SEQ ID NO:4), 3151_(SEQ ID NO:6) and human serum albumin (HSA) fusion-Combinectin 3191_(SEQ ID NO:8), and 3202_(SEQ ID NO:10). The Fc and HSA sequences are in bold. The anti-CD4 Adnectin sequences are underlined. The anti-N17 Adnectin sequences are double underlined. The HIV inhibitor peptide sequences are underlined in bold. The linker sequences are italicized.

FIG. 5 shows the amino acid sequences of anti-N17 Adnectin™ in combination with an HIV fusion peptide inhibitor, which correspond to the sequences described in Table 4 minus the N-terminus and C-terminus extended regions. The anti-N17 Adnectin™ sequences are double underlined. The HIV fusion peptide inhibitor sequences are underlined in bold. The linker sequences are italicized.

DETAILED DESCRIPTION OF THE INVENTION

Definitions

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

"Polypeptide" as used herein refers to any sequence of two or more amino acids, regardless of length, post-translation modification, or function. "Polypeptide", "peptide", and "protein" are used interchangeably herein. Polypeptides can be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

Figure 1:
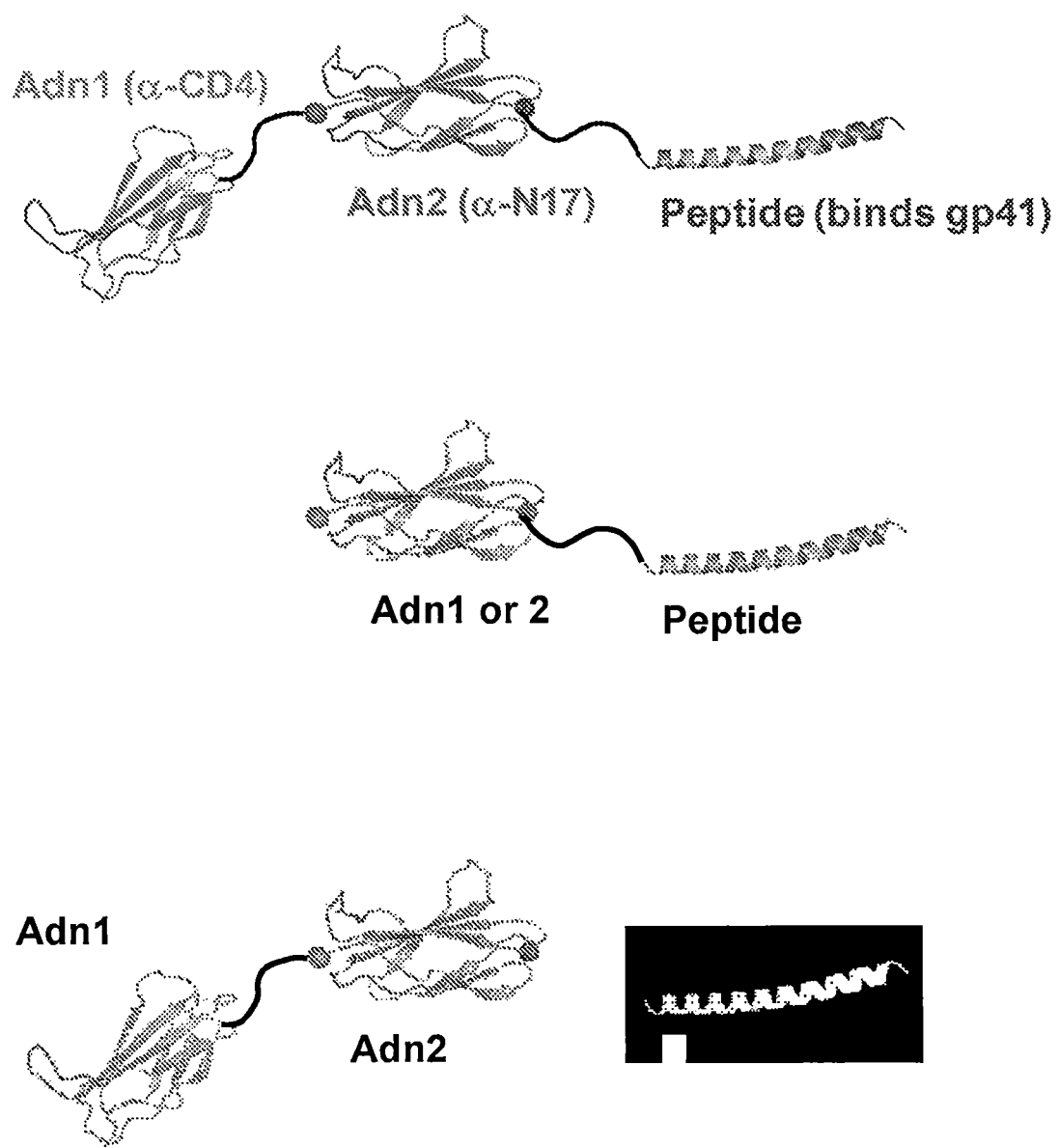
FIG. 1 is a diagram of alternative Combinectins. One of the Adnectin™ binds CD4, a second Adnectin™ binds the HR1 region of gp41. The peptide also binds in the HR1 region of gp41. The different components of the Combinectin are connected to each other in any order by linkers. Any of the Combinectins may have a PK moiety attached, such as HSA or Fc.
Figure 3:
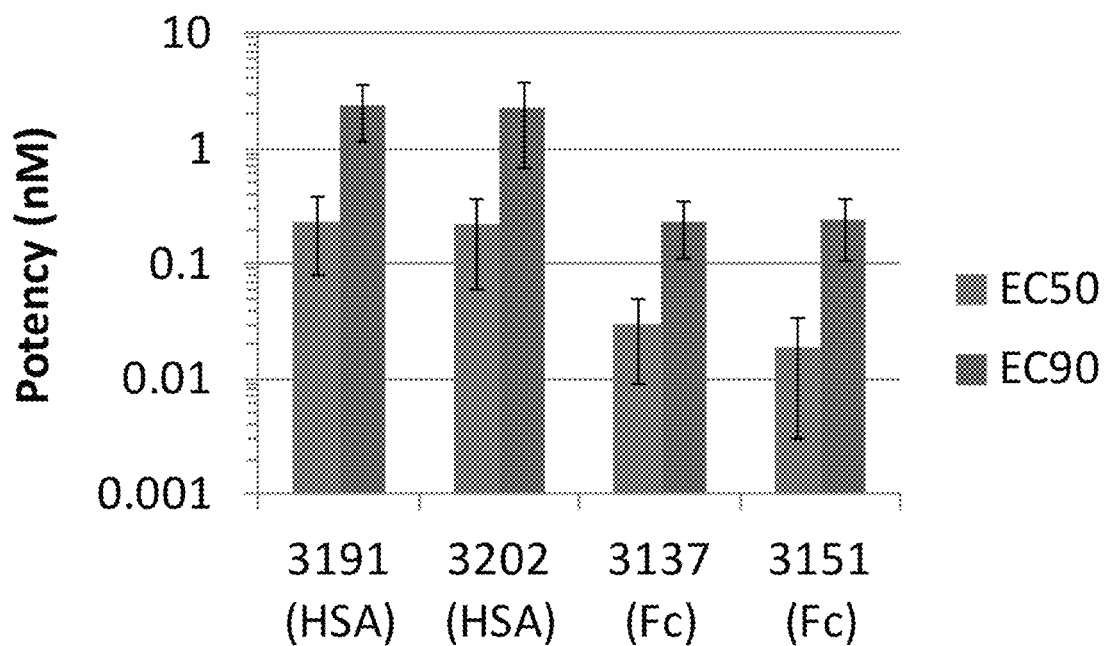
FIG. 3 shows the potency ($EC_{50}$ and $EC_{90}$) of Combinectin 3137, 3151, 3191 and 3202, as described in Example 2.
Figure 4:
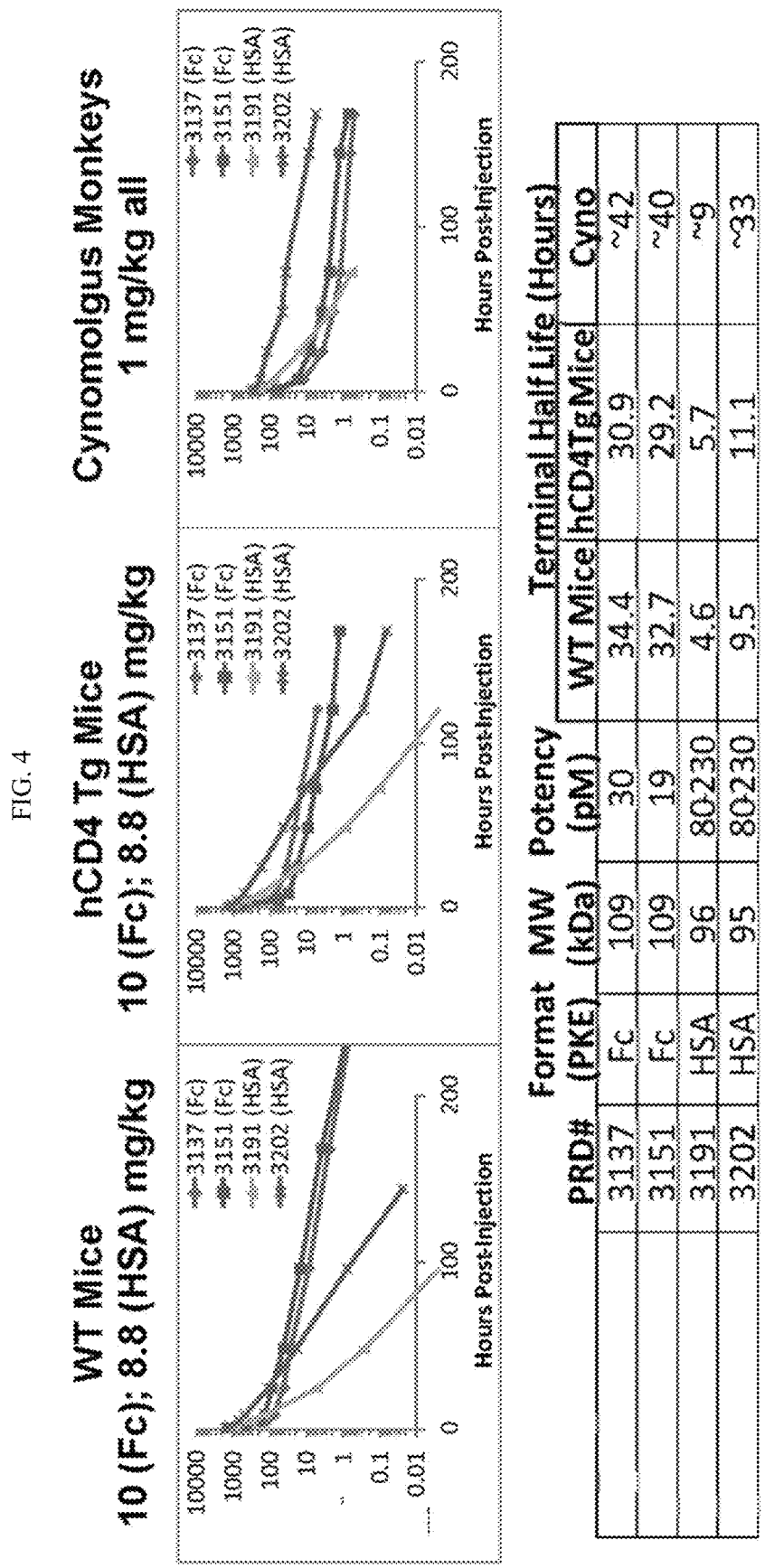
FIG. 4 shows the PK properties of Combinectin 3137, 3151, 3191 and 3202 as described in Example 3.

The peptides of the invention may include, for example, proteins derived from the tenth type III domain of fibronectin that have been modified to bind to CD4 or N17 domain of gp41 and are referred to herein as, "anti-CD4 Adnectin™", "anti-N17 Adnectin™", "CD4 Adnectin™" or "gp41 Adnectin™". The polypeptides of the invention may also include peptides modeled after the heptad repeat 2 (HR2) region of HIV envelope glycoprotein gp41, which inhibit fusion by binding the heptad repeat 1 (HR1) region of gp41 and are referred to herein as "HIV fusion peptide inhibitor" or "fusion peptide inhibitor". The polypeptides of the invention also include "Combinectins" comprising an anti-CD4 Adnectin™ linked to an anti-N17 Adnectin™ linked to a HIV fusion peptide inhibitor (FIG. 1). Alternatively, the Combinectin comprises an anti-CD4 Adnectin™ linked to an anti-N17 Adnectin™ or an anti-N17 Adnectin™ linked to a HIV fusion peptide inhibitor or an anti-CD4 Adnectin™ linked to a HIV fusion peptide inhibitor.

A "polypeptide chain", as used herein, refers to a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include recombinant host cell proteins and other proteinaceous or nonproteinaceous solutes. In one embodiment, the polypeptides will be purified (1) to greater than 95% by weight of polypeptide as determined by the Lowry method, and most preferably more than 99% by weight, or (2) to homogeneity by SDS-PAGE under reducing or nonreducing condition using Coomassie blue or, silver stain. Ordinarily, isolated polypeptide will be prepared by at least one purification step.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR®) software. Those skilled in the art can readily determine appropriate parameters for measuring alignment, including any algorithms needed to achieve maximal alignment over the full-length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, "conservative substitution" denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. By "substituted" or "modified" the present invention includes those amino acids that have been altered or modified from naturally occurring amino acids. As such it should be understood that in the context of the present invention a conservative substitution is recognized in the art as a substitution of one amino acid for another amino acid that has similar properties.

As used herein, the term "binding site" refers to the site or portion of a protein (e.g., CD4, gp41) that interacts or binds to a particular protein of the invention (e.g., as an epitope is recognized by an antibody). Binding sites can be formed from contiguous amino acids or noncontiguous amino acids juxtaposed by tertiary folding of a protein. Binding sites formed by contiguous amino acids are typically retained on exposure to denaturing solvents, whereas binding sites formed by tertiary folding are typically lost on treatment of denaturing solvents.

The binding site for an anti-CD4 moiety or anti-N17moiety of the invention may be determined by application of standard techniques typically used for epitope mapping of antibodies including, but not limited to protease mapping and mutational analysis. Alternatively, a binding site can be determined by competition assay using a reference protein (e.g., another Adnectin™ or antibody) which binds to the same polypeptide, e.g., CD4 or gp41. If the test protein and reference molecule (e.g., another Adnectin™ or antibody) compete, then they bind to the same binding site or to binding sites sufficiently proximal such that binding of one molecule interferes with the other.

The terms "specifically binds", "specific binding", "selective binding", and "selectively binds", as used interchangeably herein refers to a protein that exhibits affinity for a CD4 or gp41, but does not significantly bind (e.g., less than about 10% binding) to a different polypeptide as measured by a technique available in the art such as, but not limited to, Scatchard analysis and/or competitive binding assays (e.g., competition ELISA, BIACORE® SPR assay). The term is also applicable where e.g., a binding domain of a protein of the invention is specific for CD4 or gp41.

The term "preferentially binds" as used herein refers to the situation in which the peptides of the invention bind CD4 or gp41 at least about 20% greater than it binds a different polypeptide as measured by a technique available in the art such as, but not limited to, Scatchard analysis and/or competitive binding assays (e.g., competition ELISA, BIACORE® SPR assay).

As used herein, the term "cross-reactivity" refers to a protein which binds to more than one distinct protein having identical or very similar binding sites.

The term "$K_d$", as used herein, is intended to refer to the dissociation equilibrium constant of a particular Adnectin™-protein, fusion peptide inhibitor-protein or Combinectin-protein (e.g., CD4 and/or gp41) interaction or the affinity of an Adnectin™ fusion peptide inhibitor or Combinectin for a protein (e.g., CD4 and/or gp41), as measured using a surface plasmon resonance assay or a cell binding assay. A "desired $K_d$", as used herein, refers to a $K_d$ of a protein of the invention that is sufficient for the purposes contemplated. For example, a desired $K_d$ may refer to the $K_d$ of a Combinectin required to elicit a functional effect in an in vitro assay, e.g., a cell-based luciferase assay.

The term "$k_{on}$", as used herein, is intended to refer to the association rate constant for the association of, for example, a Combinectin into the Combinectin/protein complex.

The term "$k_{off}$", as used herein, is intended to refer to the dissociation rate constant for the dissociation of, for example, a Combinectin from the Combinectin/protein complex.

The term "$IC_{50}$", as used herein, refers to the concentration of, for example, a Combinectin that inhibits a response, either in an in vitro or an in vivo assay, to a level that is 50% of the maximal inhibitory response, i.e., halfway between the maximal inhibitory response and the untreated response.

The terms "inhibit" or "neutralize" as used herein with respect to an activity of a protein of the invention means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher.

The term "PK" is an acronym for "pharmacokinetic" and encompasses properties of a compound including, by way of example, absorption, distribution, metabolism, and elimination by a subject. A "PK modulation protein" or "PK moiety" as used herein refers to any protein, peptide, or moiety that affects the pharmacokinetic properties of a biologically active molecule when fused to or administered together with the biologically active molecule. Examples of a PK modulation protein or PK moiety include PEG, human serum albumin (HSA) binders (as disclosed in U.S. Publication No. 2005/0287153, U.S. Pat. No. 7,696,320, PCT Publication Nos. WO 2009/083804 and WO 2009/133208), human serum albumin, Fc or Fc fragments and variants thereof, and sugars (e.g., sialic acid).

The term "CD4 binding moiety" refers to any moiety that blocks HIV surface protein gp120 binding to the CD4 receptor on CD4+ T cells. The CD4 binding moiety may be anti-CD4-Adnectin™, -antibody (such as ibalizumab), -domain antibody (dAb), -antibody fragments (Fab), -bispecific antibody and fusion protein thereof.

The term "gp41 binding moiety" refers to any moiety that interferes with the interaction of the viral envelope glycoprotein complex (gp120/gp41) with T cells. The gp41 binding moiety may be anti-gp41-Adnectin™, -antibody (Ab), -domain antibody (dAb), -antibody fragments (Fab), -bispecific antibody and fusion protein thereof.

A "HIV fusion peptide inhibitor moiety" refers to any moiety that inhibits fusion by binding the heptad repeat 1 (HR1) region of gp41. Examples of fusion peptide inhibitor moiety include peptides derived from the NHR and CHR regions of gp41, designated NHR and CHR peptides, respectively. Enfuvirtide is an example of a CHR peptide.

The peptides of the invention may include, for example, the CD4 monoclonal antibody ibalizumab, an anti-N17 Adnectin™ and a HIV fusion peptide inhibitor. Alternatively, the peptides of the invention may include an anti-CD4 Adnectin™, an anti-N17 Adnectin™ and the HIV fusion peptide inhibitor enfuvirtide.

The "half-life" of an amino acid sequence or compound can generally be defined as the time taken for the serum concentration of the polypeptide to be reduced by 50%, in vivo, for example, due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may, for example, generally involve the steps of suitably administering to a subject a suitable dose of the amino acid sequence or compound of the invention; collecting blood samples or other samples from the subject at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is, for example, made to the standard handbooks, such as Kenneth, A. et al., *Chemical Stability of Pharmaceuticals: A Handbook for Pharmacists* and in Peters et al., *Pharmacokinetic Analysis: A Practical Approach* (1996). Reference is also made to Gibaldi, M. et al., *Pharmacokinetics*, Second Rev. Edition, Marcel Dekker (1982).

Half-life can be expressed using parameters such as the $t_{1/2}$-alpha, $t_{1/2}$-beta, HL_Lambda_z, and the area under the curve (AUC). In the present specification, an "increase in half-life" refers to an increase in any one of these parameters, any two of these parameters, any three of these parameters or all four of these parameters.

The notations "mpk", "mg/kg", or "mg per kg" refer to milligrams per kilogram. All notations are used interchangeably throughout the present disclosure.

The terms "individual", "subject", and "patient", used interchangeably herein, refer to an animal, preferably a mammalian (including a nonprimate and a primate), including, but not limited to, murines, simians, humans, mammalian farm animals (e.g., bovine, porcine, ovine), mammalian sport animals (e.g., equine), and mammalian pets (e.g., canine and feline); preferably the term refers to humans. In a certain embodiment, the subject, is a mammal, is preferably a human and is infected with HIV.

The term "therapeutically effective amount" refers to at least the minimal dose, but less than a toxic dose, of an agent which is necessary to impart a therapeutic benefit to a subject. For example, a therapeutically effective amount of a Combinectin of the invention is an amount which in mammals, preferably humans, results in a significant decline in circulating HIV within the infected individual.

Overview

The present invention provides novel polypeptides that bind to CD4 and/or gp41. The polypeptides comprising a CD4 binding moiety, a gp41 binding moiety, a HIV fusion peptide inhibitor moiety and combinations thereof. More specifically, the present invention relates to polypeptides comprising a fibronectin-based scaffold domain protein that binds CD4, a fibronectin-based scaffold domain protein that binds the N17 domain of gp41, and a HIV fusion peptide inhibitor or combinations thereof (herein referred to as "Combinectins").

In order to identify CD4 and gp41 Adnectins™, soluble CD4 (extracellular domain) and gp41 (various artificial constructs designed to display a triple-helical segment mimicking a portion of gp41) were presented to large synthetic libraries of Adnectins™. Adnectins™ that survived several rounds of selection were screened for CD4 or gp41 binding, for biophysical properties, and for HIV-1 inhibitory activity. The best anti-CD4 and anti-N17 Adnectin™ sequences that emerged from the screenings were mutated and subjected to further rounds of selection with increased selective pressure, achieved by lowering the target concentration and/or selecting for anti-CD4 or gp41 Adnectins™ with fast on-rates and/or slow off-rates. From this optimization process, multiple families of Adnectins™, some that targeted CD4, and others targeting gp41, were identified as HIV-1 specific inhibitors with favorable biochemical and biophysical activity.

An optimized gp41-targeting helical peptide was developed starting with sequences related to gp41 HR2 and containing changes for improving potency and breadth across HIV strains as well as increasing the resistance barrier. Peptides were produced at times synthetically and at other times as genetic fusions to inert or active Adnectins™. Optimal N- and C-terminal positions were determined in fusions to a member of the gp41 Adnectin™ family. To identify mutations that would further increase potency, an N-terminally trimmed peptide with modest potency was used, so that improvements would be more easily detected. Small libraries of the inert Adnectin™-peptide fusion were made comprising single and multiple point mutations, then the proteins were expressed and screened for biophysical properties and HIV-1 inhibitory activity. The final family of peptides consisted of optimal length peptides with various combinations of the sequences that had the most favorable profiles.

I. Fibronectin Based Scaffolds—Adnectins™

One aspect of the application provides anti-CD4 and anti-N17 Adnectins™comprising a fibronectin type III (Fn3) domain in which part or all of one or more of the solvent accessible loops has been randomized or mutated. In some embodiments, one or more residues in one or more of the non-loop beta strands has also been randomized or mutated.

In some embodiments, the Fn3 domain is an Fn3 domain derived from the tenth type 3 module of human fibronectin ($^{10}$Fn3):

VSDVPRDLEVVAATPTSLLISWDAPAVTVRYYRI-TYGETGGNSPVQEFTVPGS KSTATIS-GLKPGVDYTITVYAVTGRGDSPASSKPISINYRT (SEQ ID NO:1) (BC, CD, DE, and FG loops are underlined)

```
(BC, CD, DE, and FG loops are underlined)
                                              (SEQ ID NO: 1)
VSDVPRDLEVVAATPTSLLISWDAPAVTVRYYRITYGETGGNSPVQE

FTVPGSKSTATISGLKPGVDYTITVYAVTGRGDSPASSKPISINYRT
```

In other embodiments, the non-ligand binding sequences of $^{10}$Fn3, i.e., the "$^{10}$Fn3 scaffold", may be altered, provided that the $^{10}$Fn3 retains ligand binding function and/or structural stability. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (see, e.g., PCT Publication No. WO 02/04523). A variety of additional alterations in the $^{10}$Fn3 scaffold that are either beneficial or neutral have been disclosed. See, for example, Baton et al., *Protein Eng.,* 15(12):1015-1020 (December 2002); Koide et al., *Biochemistry,* 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87.

Accordingly, in some embodiments, the anti-CD4 or anti-N17 Adnectin™ of the invention is a $^{10}$Fn3 polypeptide that is at least 40%, 50%, 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 40%, 50%, 60%, 65%, 70%, 75%, 80%, 85%, 90%, 95% or 100% identical to the sequence of a corresponding beta or beta-like strand of SEQ ID NO:1, provided that such variation does not disrupt the stability of the polypeptide in physiological conditions.

In some embodiments, the invention provides one or more Adnectins™ comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, CD, DE, and FG with an altered amino acid sequence relative to the sequence of the corresponding loop of the human $^{10}$Fn3 domain. In some embodiments, the Adnectins™ of the present invention comprise an $^{10}$Fn3 domain comprising an amino acid sequence at least 40%, 50%, 60%, 65%, 70%, 75%, 80%, 85%, 90%, 95%, 98%, 99% or 100% identical to the non-loop regions of SEQ ID NO:1, wherein at least one loop selected from BC, CD, DE, and FG is altered. In some embodiments, the BC and FG loops are altered, and in some embodiments, the BC, DE, and FG loops are altered, i.e., the $^{10}$Fn3 domains comprise non-naturally occurring loops. In some embodiments, the AB, CD and/or the EF loops are altered. In some embodiments the CD and FG loops are altered. In some embodiments the solvent-accessible amino acids in the strands between loops are altered, with or without alteration of the adjoining loops. By "altered" is meant one or more amino acid sequence alterations relative to a template sequence (corresponding human fibronectin domain) and includes amino acid additions, deletions, substitutions or a combination thereof. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, CD, DE, and FG may be extended or shortened in length relative to the corresponding human fibronectin loop. In some embodiments, the length of the loop may be extended by 1-25 amino acids. In some embodiments, the length of the loop may be decreased by 1-11 amino acids. To optimize antigen binding, therefore, a loop of $^{10}$Fn3 may be altered in length as well as in sequence to obtain the greatest possible flexibility and affinity in antigen binding.

In some embodiments, the Adnectins™ comprise a Fn3 domain that comprises an amino acid sequence at least 40%, 50%, 60%, 65%, 70%, 75%, 80%, 85%, 90%, 95%, 98%, 99%, or 100% identical to the non-loop regions of SEQ ID NO:1, wherein at least one loop selected from BC, CD, DE, and FG is altered. In some embodiments, the altered BC loop has up to 1, 2, 3, 4, 5, 6, 7, 8 or 9 amino acid substitutions, up to 1, 2, 3, or 4 amino acid deletions, up to 1, 2, 3, 4, 5, 6, 7, 8, 9, or 10 amino acid insertions, or a combination thereof. In some embodiments, the altered CD loop has up to 1, 2, 3, 4, 5, 6, 7, 8, 9, 10, or 11 amino acid substitutions, up to 1, 2, 3, 4, 5, or 6 amino acid deletions, up to 1, 2, 3, 4, 5, 6, 7, 8, 9, or 10 amino acid insertions, or a combination thereof. In some embodiments, the altered DE loop has up to 1, 2, 3, 4, 5, or 6 amino acid substitutions, up to 1, 2, 3, or 4 amino acid deletions, up to 1, 2, 3, 4, 5, 6, 7, 8, 9, 10, 11, 12, or 13 amino acid insertions, or a combination thereof. In some embodiments, the FG loop has up to 1, 2, 3, 4, 5, 6, 7, 8, 9, 10, 11, 12 or 13 amino acid substitutions, up to 1, 2, 3, 4, 5, 6, 7, 8, 9, 10, or 11 amino acid deletions, up to 1, 2, 3, 4, 5, 6, 7, 8, 9, 10, 11, 12, 13, 14, 15, 16, 17, 18, 19, 20, 21, 22, 23, 24, or 25 amino acid insertions, or a combination thereof.

Extension Sequences

In certain embodiments, the Adnectin™ molecules of the present invention may be modified to comprise an N-terminal extension sequence and/or a C-terminal extension. For example, an MG sequence may be placed at the N-terminus of the $^{10}$Fn3 defined by SEQ ID NO: 1. The M will usually be cleaved off, leaving a G at the N-terminus. The Adnectins™ described herein may also comprise alternative C-terminal tail sequences, referred to herein as truncated C-terminal or C-terminal extension sequences. Further, truncated version may be used as therapeutic molecules in the truncated form, or alternative C-terminal extensions, such as His6 tag, may be added to the truncated version. In certain embodiments, the C-terminal extension sequences (also called "tails"), comprise E and D residues, and may be between 8 and 50, 10 and 30, 10 and 20, 5 and 10, and 2 and 4 amino acids in length. In certain embodiments, the first residue of a C-terminal extension is a proline. In certain other embodiments, the first residue of a C-terminal extension is a glutamic acid.

In some embodiments, the N-terminus may be extended by up to 1, 2, 3, 4, 5, 6, 7, 8, 9, 10, 11, 12, 13, 14, 15, or more amino acids, which may be altered in any way, before or after rounds of selection, in order to improve target binding, stability, or both. In other embodiments, the C-terminus may be extended by up to 1, 2, 3, 4, 5, 6, 7, 8, 9, 10, 11, 12, 13, 14, 15, or more amino acids, which may be altered in any way, before or after rounds of selection, in order to improve target binding, stability, or both. In still other embodiments, both the N- and C-termini may be extended in this manner.

Anti-CD4 Adnectin™

The amino acid sequence of anti-CD4 Adnectin™ loop region CD and FG of the invention include but are not limited to those listed in Table 1 below. The CD loops described in Table 1 replace R30 through T49 of $^{10}$Fn3 defined by SEQ ID NO:1. The FG loops described in Table 1 replace D67 through N91 of $^{10}$Fn3 defined by SEQ ID NO:1.

Table 1 also lists the $IC_{50}$ values for each anti-CD4 Adnectin™ comprising the listed CD/FG loop combinations.

TABLE 1

| CD4 Adnectin ™-CD and FG loop combinations | | | |
|---|---|---|---|
| CD loop | FG loop | $IC_{50}$, µM | SEQ ID NO |
| HSYHIQYWPLGSYQRYQVFS | EYQIRVYAETGGADSDQSMGWIQIG | 0.0025 | 13, 14 |
| LSYHIQYWPLGLYQAYQVFS | EYQIRVYAETGRGESPASFGWIQIG | 0.0060 | 15, 16 |
| HAYHIQYWPLGFYQGYQVFS | EYQIRVYAETGLGDAHQSLGWIQIG | 0.0072 | 17, 18 |
| LAYHIQYWPLGWYQRYQIFS | EYQIRVYAETGRGESPASFGWIQIG | 0.0075 | 19, 20 |
| LAYHIQYWPLGWYQRYQVFS | EYQIRVYAETGRGESPASFGWIQIG | 0.0082 | 21, 22 |
| HFYHIQYWPLGLYHLYQVFS | EYQIRVYAETGRGESPASFGWIQIG | 0.0087 | 23, 24 |

TABLE 1-continued

CD4 Adnectin™-CD and FG loop combinations

| CD loop | FG loop | IC$_{50}$, μM | SEQ ID NO |
|---|---|---|---|
| YSYHIQYWPLGWYHRYQVFS | EYQIRVYAETGADDPVQALGWIQIG | 0.0099 | 25, 26 |
| RCYHIQYWPLGLYPLYQVFS | EYQIRVYAETGDESSVQPFGWIQIG | 0.0115 | 27, 28 |
| YSYHIQYWPLGWYQRYQVFS | EYQIRVYAETDGGRSQQSFGWIQIG | 0.0118 | 29, 30 |
| SSYHIQYWPLGAYQRYQVFS | EYQIRVYAETGRGESPASFGWIQIG | 0.0158 | 31, 32 |
| HAYHIQYWPLGLYQRYQVFS | EYQIRVYAETGRGESPASFGWIQIG | 0.0165 | 33, 34 |
| HAYYIQYWPLGSYQFYQVFA | EYQIRVYAETGRGESPASFGWIQIG | 0.0213 | 35, 36 |
| HSYHIQYWPLGSYLRYQVFS | EYQIRVYAETGRGESPASFGWIQIG | 0.0214 | 37, 38 |
| LSYHIQYWPLGFYQRYQVFS | EYQIRVYAETGRGESPASFGWIQIG | 0.0230 | 39, 40 |
| SAYHIQYWPLGWYHRYQIFS | EYQIRVYAETGRGESPASFGWIQIG | 0.0239 | 41, 42 |
| YSYHIQYWPLGAYSRHQLFS | EYQIRVYAETGGDGSEMYFGWIQIG | 0.0260 | 43, 44 |
| LAYHIQYWPLGWYHLYQVFS | EYQIRVYAETGRGESPASFGWIQIG | 0.0272 | 45, 46 |
| LAYHIQYWPLGWYQLYKVFS | DYQIRVYAETSGESSEQYLGWIQIG | 0.0287 | 47, 48 |
| HSYHIQYWPLGWYQLYQVFS | EYQIRVYAETEVDSGQHSFGWIQIG | 0.0290 | 49, 50 |
| LAYHIQYWPLGWYQRYQIFS | EYQIRVYAETGESGAQQSFGWIQIG | 0.0297 | 51, 52 |
| QSYHIQYWPLGAYQLYQLFS | EYQIRVYAETGRGESPASFGWIQIG | 0.0323 | 53, 54 |
| HAYHIQYWPLGFYQGYQVFS | EYQIRVYADTGRGYQLSYSWIQIGY | 0.0353 | 55, 56 |
| FRYHIQYWPLGGYERYQVFT | EYQIRVYAETGRGESPASFGWIQIG | 0.0410 | 57, 58 |
| HSYHIQYWPLGSYHLYQLFS | EYQIRVYAETGRGESPASFGWIQIG | 0.0411 | 59, 60 |
| HSYHIQYWPLGWYQLYQVFT | EYQIRVYAETGGFGSPPNFGWIQIG | 0.0436 | 61, 62 |
| QFYHIQYWPLGSYQRYQVFS | EYQIRVYAETGRGESPASFGWIQIG | 0.0509 | 63, 64 |
| NSYHIQYWPLGWYHRYQVFS | EYQIRVYAETGRGESPASFGWIQIG | 0.0517 | 65, 66 |
| HSYHIQYWPLGRYQLYQVFS | EYQIRVYAETGRGESPASFGWIQIG | 0.0562 | 67, 68 |
| LAYHIQYWPLGWYHLYQIFS | EYQIRVYAETGGVGWHHSFGWIQIG | 0.0587 | 69, 70 |
| HVYHIQYWPLGWYPRYQVFS | EYQIRVYAETGRGESPASFGWIQIG | 0.0604 | 71, 72 |
| HSYHIPYWELAWYQRYQVFS | EYQIRVYAETGRGESPASFGWIQIG | 0.0637 | 73, 74 |

TABLE 1-continued

CD4 Adnectin ™-CD and FG loop combinations

| CD loop | FG loop | IC$_{50}$, μM | SEQ ID NO |
|---|---|---|---|
| ESYHIQYWPLGLYHRYQVFS | EYQIRVYAETGRGESPASFGWIQIG | 0.0688 | 75, 76 |
| LAYHIQYWPLGWYQAYQVFS | EYQIRVYAETGRGESPASFGWIQIG | 0.0703 | 77, 78 |
| YLYHIQYWPLGWYHRYQVFT | EYQIRVYAETGRGESPASFGWIQIG | 0.0715 | 79, 80 |
| RFYHIQYWPLGWYHCYQVFV | EYQIRVYAQTGDGSSQEYFGWIQIG | 0.0839 | 81, 82 |
| HSYHIQYWPLGWYYRYQVFS | EYQIRVYAETGGSGSQQYVVGWIQIG | 0.0869 | 83, 84 |
| HAYHIQYWPLGFYQGYQVFS | EYQIRVYAETGRGESPASFGWIQIG | 0.0875 | 85, 86 |
| HSYHIQYWPLGLYVLYQVFS | EYQIRVYAETGAGGSEHSFGWIQIG | 0.1059 | 87, 88 |
| LSYHIQYWPLGRYERYQVFS | EYQIRVYAETVGGESLDSFSWIQIG | 0.1277 | 89, 90 |
| LSYHIQYWPLGWYQLYQVFY | EYQIRVYAETRVGGSVASFGWIQIG | 0.1600 | 91, 92 |
| LAYHIQYWPLGRYQLYQVFS | EYQIRVYAETGRGESPASFGWIQIG | 0.4281 | 93, 94 |

In some embodiments, anti-CD4 Adnectin™ of the invention comprises an amino acid sequence at least 80%, 85%, 90%, 95%, 98%, 99% or 100% identical to the CD/FG loop region combinations of SEQ ID NOs: 13-94.

In some embodiments, anti-CD4 Adnectin™ of the invention comprises an amino acid sequence at least 80%, 85%, 90%, 95%, 98%, 99% or 100% identical to any one of the CD loop regions of SEQ ID NOs: 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93.

In some embodiments, anti-CD4 Adnectin™ of the invention comprises an amino acid sequence at least 80%, 85%, 90%, 95%, 98%, 99% or 100% identical to any one of the FG loop regions of SEQ ID NOs: 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94.

Figure 6:
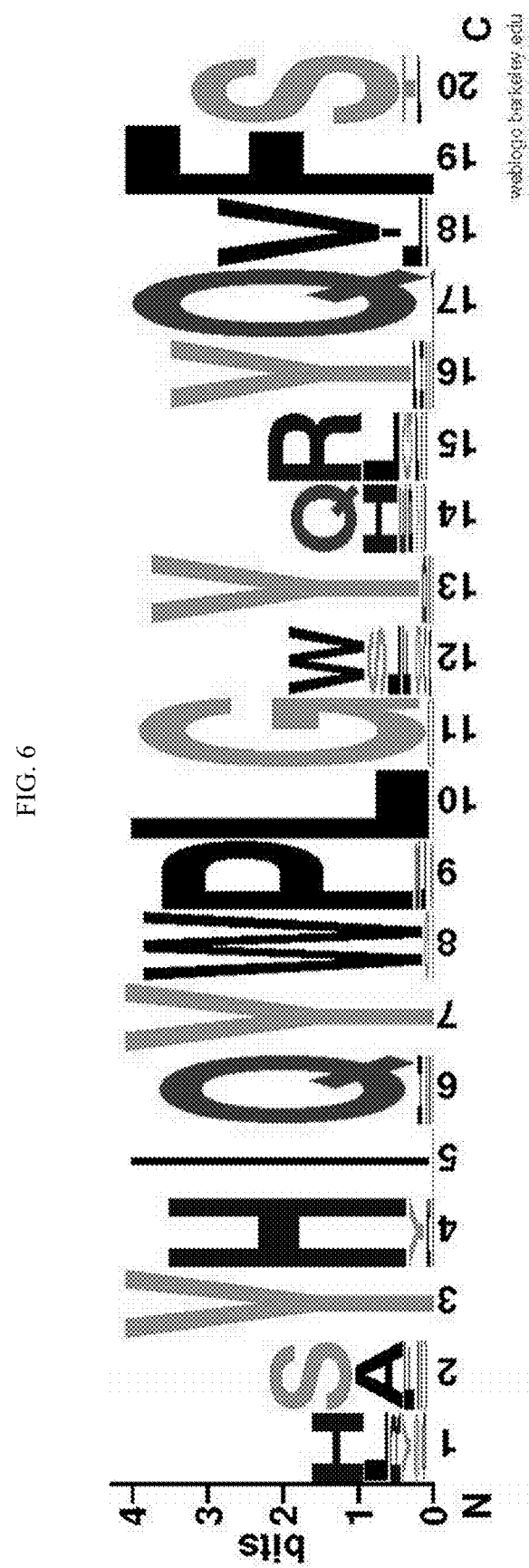
FIG. 6 shows the WebLogo for the CD loop of anti-CD4 Adnectin™. WebLogo generates sequence logos, graphical representations of the patterns within a multiple sequence alignment. Each logo consists of stacks of letters, one stack for each position in the sequence. The overall height of each stack indicates the sequence conservation at that position (measured in bits), whereas the height of symbols within the stack reflects the relative frequency of the corresponding amino or nucleic acid at that position (Crooks, G. E. et al., "WebLogo: A sequence logo generator", *Genome Research*, 14:1188-1190 (2004)).

WebLogo (≤weblogo.berkeley.edu≥) was used to identify consensus sequences for anti-CD4 Adnectin™. Y32, I34, Y36, Q46 and F48 of the anti-CD4 Adnectin™ CD loop are conserved amino acids (see FIG. 6). In some embodiments, the anti-CD4 Adnectin™ comprises one or more of the conserved amino acids Y32, I34, Y36, Q46 and F48.

Figure 7:
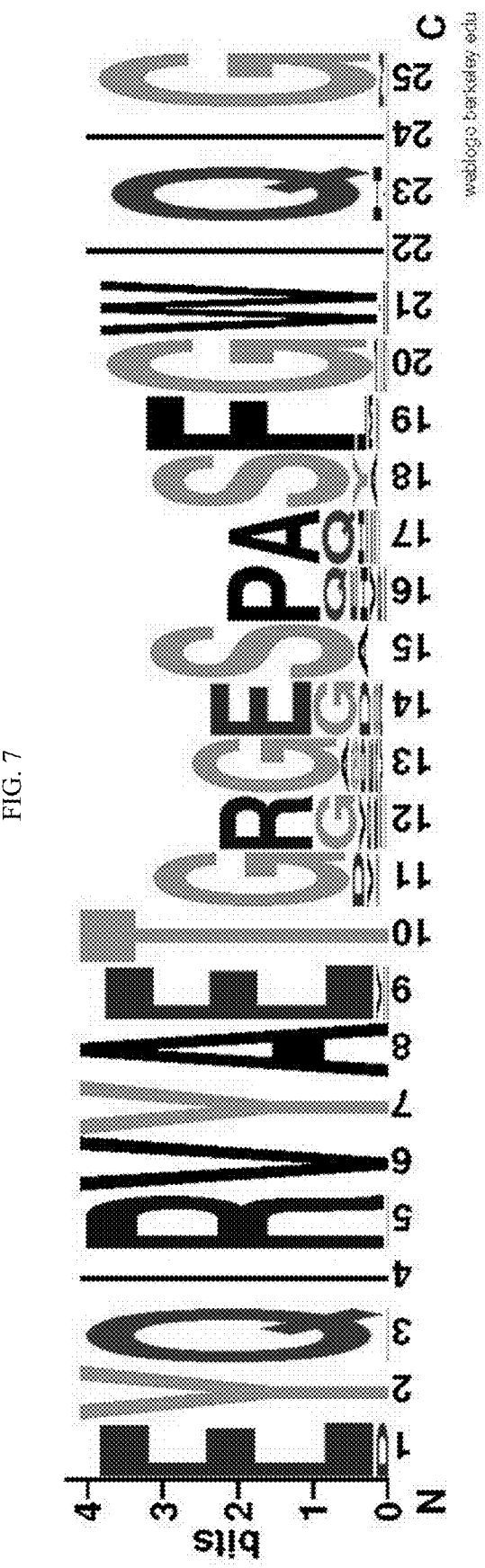
FIG. 7 shows the WebLogo for the FG loop of anti-CD4 Adnectin™ (Schneider, T. D. et al., "Sequence Logos: A New Way to Display Consensus Sequences", *Nucleic Acids Res.*, 18:6097-6100 (1990)).

WebLogo identified Y68, I70, V72, A74, T76, I88 and I90 of the anti-CD4 Adnectin™ FG loop as conserved amino acids (see FIG. 7). In some embodiments, the anti-CD4 Adnectin™ comprises one or more of the conserved amino acids Y68, I70, V72, A74, T76, I88 and I90.

In some embodiments, the anti-CD4 Adnectin™ comprises one or more of the conserved amino acids Y32, I34, Y36, Q46, F48, Y68, I70, V72, A74, T76, I88 and I90.

The full length amino acid sequence of anti-CD4 Adnectin™ of the invention include but are not limited to those listed in Table 2 below. Table 2 also lists the antiviral EC$_{50}$ values for each anti-CD4 Adnectin™

TABLE 2

Anti-CD4 Adnectin ™

| SEQ ID NO | Antiviral EC$_{50}$ (nM) | Anti-CD4 Adnectin ™ Protein Sequence |
|---|---|---|
| 95 | 48 | MASTSGVSDVPRDLEVVAATPTSLLISWDAPAVTVHSYHIQYWPLGWYQRYQVFSVPGSKSTATISGLKPEVEYQIRVYAETGGGGSQQSFGWIQIGYRTEGSGSHHHHHH |
| 96 | 7.8 | MGVSDVPRDLEVVAATPTSLLISWDAPAVTVQSYHIQYWPLGSYQRYQVFSVPGSKSTATISGLKPGVEYQIRVYAETGGADSDQSMGWIQIGYRTEGDKPSQHHHHHH |
| 97 | 11 | MGVSDVPRDLEVVAATPTSLLISWDAPAVTVHSYHIQYWPLGWYQRYQVFSVPGSKSTATISGLKPGVEYQIRVYAETRSGLADESFGWIQIGYRTEGDKPSQHHHHHH |

TABLE 2-continued

Anti-CD4 Adnectin ™

| SEQ ID NO | Antiviral EC$_{50}$ (nM) | Anti-CD4 Adnectin ™ Protein Sequence |
|---|---|---|
| 98 | 4.9 | MGVSDVPRDLEVVAATPTSLLISWDAPAVTVHSYHIQ YWPLGSYQRYQVFSVPGSKSTATISGLKPGVEYQIRV YAETGGADSDQSMGWIQIGYRTEGDKPSQHHHHHH |
| 99 | 8.5 | MGHHHHHHGGVSDVPRDLEVVAATPTSLLISWDAPA VTVHSYHIQYWPLGSYQRYQVFSVPGSKSTATISGLK PGVEYQIRVYAETGGADSDQSFGWIQIGYRTPES |
| 100 | 6 | MASTSGSSSYLMPSDLEVVAATPTSLYIHWYPIASTIIN FRITYGETGGNSPVQEFTVPGSQVHATISGLKPGVDYT ITVYAVHYEHKYSELWMGHPISINYRTEGSGSHHHHH H |
| 101 | >400 | MASTSGSASYLIPSDLEVVAATPTSLSIYWYPVASTIIN FRITYVETGGNSPVQEFTVPGSKSTATISGLKPGVDYTI TVYAVHYEQKYSEYWIGHPISINYRTEGSGSHHHHHH |
| 102 | >5500 | MASTSGSSPYLMPYDLEVVAATPTSLFIRWYGSASSIV KFRITYGETGGNSPVQEFTVGGTQLHATISGLKPGVD YTITVYAVHFEHKYSELWIGHPISINYRTEGSGSHHHH RH |
| 103 | 255 | MASTSGYTSYPIPYDLEVVAATPTSLYIHWYWIAATII SFRITYGETGGNSPVQEFTVPAGQDHATISGLKPGVDY TITVYAVHYEEEYSEFWTGHPISINYRTEGSGSHHHHH H |
| 104 | 500 | MASTSGTHWFYSIPHDLEVVAATPTSLTIAWEPPHHT AMGYRITYGETGGNSPVQEFTVPGGYTTAYISGLKPG VDYTITVYAAYYEREYSEHWISHPISINYRTEGSGSHH HHHH |
| 105 | 300 | MASTSGEFYHTKYPYDLEVVAATPTSLEISWRSPTRD WQWFRITYGETGGNSPVQEFTVAGPYRNAIISGLKPG VDYTITVYADVYMPSEGGLVVDTYHPISINYRTEGSG SHHHHHH |
| 106 | 2400 | MASTSGQAYPEYYFVDLEVVAATPTSLLISWSKPYYN AYSYRITYGETGGNSPVQEFTVLGHDTRAVISGLKPG VDYTITVYAMFIEYIDQEIWHAHPISINYRTEGSGSHH HHHH |
| 107 | 500 | MGVSDVPRDLEVVAATPTSLLISWDEHTDIYRYYRIT YGETGGNSPVQEFTVPAMEHTATISGLKPGVDYTITV YAVTHVYPIMIHQYPISINYRTEIDKPSQHHHHHH |
| 108 | 170 | MASTSGVSDVPRDLEVVAATPTSLLISWDAPAVTVLE YQIDYHPAAVWHALQRFTVPGSKSTATISGLKPGVHY KISVTATTHADNESIMWHPISIYYRTEGSGSHHHHHH |
| 109 | 320 | MGVSDVPRDLEVVAATPTSLLISWDYPTVTPRYYRIT YGETGGNSPVQEFTVPEYIGTATISGLKPGVDYTITVY AVTNDTTIYSISRPISINYRTEIDKPSQHHHHHH |
| 110 | 28.6 | MGHHHHHHGGVSDVPRDLEVVAATPTSLLISWDAPA VTVHSYHIQYWPLGSYQRYQVFSVPGSKSTATISGLK PGVEYQIRVYAETGRGESDQSLGWIQIGYRTEES |
| 111 | 20.0 | MGHHHHHHGGVSDVPRDLEVVAATPTSLLISWDAPA VTVHSYHIQYWPLGSYQRYQVFSVPGSKSTATISGLK PGVEYQIRVYAETGRGESDQSFGWIQIGYRTEES |
| 112 | 18.4 | MGHHHHHHGGVSDVPRDLEVVAATPTSLLISWDAPA VTVHSYHIQYWPLGSYQRYQVFSVPGSKSTATISGLK PGVEYQIRVYAETGRGESDQSLGWIQIGYRTPES |
| 113 | 15.4 | MGHHHHHHGGVSDVPRDLEVVAATPTSLLISWDAPA VTVHSYHIQYWPLGSYQRYQVFSVPGSKSTATISGLK PGVEYQIRVYAETGRGESDQSFGWIQIGYRTPES |
| 114 | 12.6 | MGHHHHHHGGVSDVPRDLEVVAATPTSLLISWDAPA VTVHAYHIQYWPLGFYQGYQVFSVPGSKSTATISGLK PGVEYQIRVYAETGLGDAHQSLGWIQIGYRTPES |

In some embodiments, the anti-CD4 Adnectin™ of the invention comprises an amino acid sequence at least 70%, 75%, 80%, 85%, 90%, 95%, 98%, 99% or 100% identical to any one of SEQ ID NOs: 95-114.

In some embodiments, the anti-CD4 Adnectin™ of the invention comprises an amino acid sequence at least 70%, 75%, 80%, 85%, 90%, 95%, 98%, 99% or 100% identical to any one of SEQ ID NOs: 95-114, excluding any N-terminus extended region.

In some embodiments, the anti-CD4 Adnectin™ of the invention comprises an amino acid sequence at least 70%, 75%, 80%, 85%, 90%, 95%, 98%, 99% or 100% identical to any one of SEQ ID NOs: 95-114, excluding any C-terminus extended region.

In some embodiments, the anti-CD4 Adnectin™ of the invention comprises an amino acid sequence at least 70%, 75%, 80%, 85%, 90%, 95%, 98%, 99% or 100% identical to any one of SEQ ID NOs: 95-114, excluding both the N-terminus and C-terminus extended regions.

In other embodiments, anti-CD4 Adnectin™ comprises an amino acid sequence at least 80%, 85%, 90%, 95%, 98%, 99% or 100% identical to the CD loop and FG loop regions of SEQ ID NOs: 95-114.

Anti-N17 Adnectin™

The full length amino acid sequence of anti-N17 Adnectin™ protein of the invention include but are not limited to those listed in Table 3 below. Table 3 also lists the antiviral $EC_{50}$ values for each anti-N17 Adnectin™.

TABLE 3

Anti-N17 Adnectin ™

| SEQ ID NO | Antiviral $EC_{50}$ (nM) | Anti-N17 Adnectin ™ Protein Sequence |
|---|---|---|
| 115 | 130 | MGVSDVPRDLEVVAATPTSLLISWEYKVNNYRYYRITY GETGGNSPVQEFTVPSVLSTATISGLKPGVDYTITVYAV TYGVHSSPISINYRTEIDKPSQHHHHHH |
| 116 | 50 | MASTSGVSDVPRDLEVVAATPTSLLISWDAPAVTVEQY YIAYYVEGEPSSYQYFRVPGSKSTATISGLKPGVLYHIY VNAVTGSGLRPEFSLPIRIKYRTEGSGSHHHHHH |
| 117 | 42 | MGHHHHHHGGSVSDVPRDLEVVAATPTSLLISWEYKV HPYRYYRITYGETGGNSPVQEFTVPSVLSTATISGLKPG VDYTITVYAVTYGDDSAPISINYRTEID |
| 118 | 28 | MGVSDVPRDLEVVAATPTSLLISWKYKVHPYRYYRITY GETGGNSPVQEFTVPSVLSTATISGLKPGVDYTITVYAV TYGVNSLPISINYRTEIDKPSQHHHHHH |
| 119 | >1,000 | MGVSDVPRDLEVVAATPTSLLISWDAPAVTVGWYHIGY NVEGEPASYQYFRVPGSKSTATISGLKPGVEYMIFVNAV TGSGAREEFSLPISINYRTEGSGSHHHHHH |
| 120 | 39 | MGHHHHHHGGVSDVPRDLEVVAATPTSLLISWEYNVN PYRYYRITYGETGGNSPVQEFTVPSVLSSAQISGLKPGV DYTITVYAVTRGVDSAPISINYRTPGG |
| 121 | 57 | MGHHHHHHGGVSDVPRDLEVVAATPTSLLISWEYNVN PYRYYRITYGETGGNSPVQEFTVPSVLSTAEISGLKPGV DYTITVYAVTYGVDSDPISINYRTPGG |
| 122 | 6 | MGHHHHHHGGVSDVPRDLEVVAATPTSLLISWQYKVH PYRYYRITYGETGGNSPVQEFTVPSVLSTAEISGLKPGV DYTITVYAVTRGVDSAPISINYRTPGG |
| 123 | 28 | MGVSDVPRDLEVVAATPTSLLISWEYKVHPYRYYRITY GETGGNSPVQEFTVPSVLSTATISGLKPGVDYTITVYAV TRGVDSAPISINYRTEIDKPSQHHHHHH |
| 124 | 6 | MGVSDVPRDLEVVAATPTSLLISWEYKVHPYRYYRITY GETGGNSPVQEFTVPSVLSTAEISGLKPGVDYTITVYAV TRGVDSAPISINYRTPIDKPSQHHHHHH |
| 125 | 4342 | MGHHHHHHGGVSDVPRDLEVVAATPTSLLISWEYKVH PYRYYRITYGETGGNSPVQEFTVPSVLSTATISGLKPGV DYTITVYAVTYGVQSDPISINYRTPGG |
| 126 | 8 | MGVSDVPRDLEVVAATPTSLLISWEYKVHPYRYYRITY GETGGNSPVQEFTVPSVLSTATISGLKPGVDYTITVYAV TYGIQSPPISINYRTEIDKPSQHHHHHH |
| 127 | 9 | MGHHHHHHGGVSDVPRDLEVVAATPTSLLISWQYKVH PYRYYRITYGETGGNSPVQEFTVPSVLSSAQISGLKPGV DYTITVYAVTYGIESSPISINYRTPGG |
| 128 | 18 | MGHHHHHHGGVSDVPRDLEVVAATPTSLLISWEYKVH PYRYYRITYGETGGNSPVQEFTVPSVLSSAEISGLKPGVD YTITVYAVTYGIDSSPISINYRTPGG |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 129 | 11 | MGVSDVPRDLEVVAATPTSLLISWEYKVHPYRYYRITY GETGGNSPVQEFTVPSVLSSAEISGLKPGVDYTITVYAV TYGIDSPPISINYRTEIDKPSQHHHHHH |
| 130 | 42 | MGHHHHHHGGSVSDVPRDLEVVAATPTSLLISWEYNV HYDRYYRITYGETGGNSPVQEFTVPSVLSTATISGLKPG VDYTITVYAVTDGVHSSPISINYRTEID |
| 131 | 5 | MGHHHHHHGGSVSDVPRDLEVVAATPTSLLISWEYKV HPYRYYRITYGETGGNSPVQEFTVPSVLSTATISGLKPG VDYTITVYAVTYGDLSAPISINYRTEID |
| 132 | 5 | MGHHHHHHGGSVSDVPRDLEVVAATPTSLLISWDAPA VTVEEYYIGYYVEFEPSSYQWFTVPGSKSTATISGLKPG VEYSIYVNAVTGMGMQPEMSLPISINYRTEGS |
| 133 | 42 | MGHHHHHHGGSVSDVPRDLEVVAATPTSLLISWEYKV HYDRYYRITYGETGGNSPVQEFTVPSVLSTATISGLKPG VDYTITVYAVTYGVDSDPISINYRTEID |
| 134 | 5 | MGHHHHHHGGSVSDVPRDLEVVAATPTSLLISWDAPA VTVEQYYIAYYDEKEPSSYQYFRVPGSKSTATISGLKPG VEYAIFVNAVTRSGVLPEFSLPISINYRTEGS |
| 135 | >1,000 | MGHHHHHHGGSVSDVPRDLEVVAATPTSLLISWKYNV NAYRYYRITYGETGGNSPVQEFTVPSVLSTATISGLKPG VDYTITVYAVTYGVHSSPISINYRTEID |
| 136 | 5 | MGHHHHHHGGSVSDVPRDLEVVAATPTSLLISWDAPA VVTVEQYYIGYYVEAEPSSYQYFFVPGSKSTATISGLKPG VDYAIFVNAVTASGRGPEYSLPISINYRTEGS |
| 137 | 80 | MGVSDVPRDLEVVAATPTSLLISWHDGIGEERYYRITYG ETGGNSPVQEFTVPMDDITATISGLKPGVDYTITVYAVT VGDVISVLHEPISINYRTEIDKPSQHHHHHH |
| 138 | 3300 | MGVSDVPRDLEVVAATPTSLLISWHYPFEGYVTYYRIT YGETGGNSHVQEFTVPVGYTTATISGLKPGVDYTITVYA VTSSKGYVYFPISINYRTEIDKPSQHHHHHH |
| 139 | 130 | MGVSDVPRDLEVVAATPTSLLISWEDPEAAVRYYRITY GETGGNSPVQEFTVPINDLHSYLSGLKPGVDYTITVYAV TEATVMYVLDEPISINYRTEIDKPSQHHHHHH |
| 140 | 950 | MGVSDVPRDLEVVAATPTSLLISWDLLEDMSRYYRITY GETGGNSPVQEFTVPTDAYTATISGLKPGVDYTITVYAV TQDSHVIELSYPISINYRTEIDKPSQHHHHHH |
| 141 | 3 | MGVSDVPRDLEVVAATPTSLLISWQYKVHPYRYYRITY GETGGNSPVQEFTVPSVLSTATISGLKPGVDYTITVYAV TYGIQSPPISINYRTEIDKPSQHHHHHH |
| 142 | 55 | MGVSDVPRDLEVVAATPTSLLISWRYRVHPYRYYRITY GETGGNSPVQEFTVPSVLSTATISGLKPGVDYTITVYAV TDGVQSSPISINYRTEIDKPSQHHHHHH |
| 143 | 20 | MGVSDVPRDLEVVAATPTSLLISWEYNVNPYRYYRITY GETGGNSPVQEFTVPSVLSTATISGLKPGVDYTITVYAV TYGIESSPISINYRTEIDKPSQHHHHHH |
| 144 | 20 | MGVSDVPRDLEVVAATPTSLLISWQYKVHPYRYYRITY GETGGNSPVQEFTVPSVLSTATISGLKPGVDYTITVYAV TYGVESSPISINYRTEIDKPSQHHHHHH |
| 145 | 11 | MGVSDVPRDLEVVAATPTSLLISWEYKVHPYRYYRITY GETGGNSPVQEFTVPSVLSTATISGLKPGVDYTITVYAV TYGVNSLPISINYRTEIDKPSQHHHHHH |
| 146 | 11 | MGVSDVPRDLEVVAATPTSLLISWEYKVHPYRYYRITY GETGGNSPVQEFTVPSVLSTATISGLKPGVDYTITVYAV TYGIDSPPISINYRTEIDKPSQHHHHHH |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 147 | 28 | MGVSDVPRDLEVVAATPTSLLISWEYKVHPYRYYRITYGETGGNSPVQEFTVPSVLSTATISGLKPGVDYTITVYAVTYGVDSDPISINYRTEIDKPSQHHHHHH |
| 148 | 14 | MGVSDVPRDLEVVAATPTSLLISWEYNVNPYRYYRITYGETGGNSPVQEFTVPSVLSTATISGLKPGVDYTITVYAVTYGIDSPPISINYRTEIDKPSQHHHHHH |
| 149 | 3 | MGHHHHHHGGSVSDVPRDLEVVAATPTSLLISWEYKVHPYRYYRITYGETGGNSPVQEFTVPSVLSTATISGLKPGVDYTITVYAVTYGKDSAPISINYRTEID |
| 150 | 18 | MGVSDVPRDLEVVAATPTSLLISWEYNVNPYRYYRITYGETGGNSPVQEFTVPSVLSTATISGLKPGVDYTITVYAVTYGVESSPISINYRTEIDKPSQHHHHHH |
| 151 | 11 | MGVSDVPRDLEVVAATPTSLLISWEYKVHPYRYYRITYGETGGNSPVQEFTVPSVLSTATISGLKPGVDYTITVYAVTYGIDSSPISINYRTEIDKPSQHHHHHH |
| 152 | 20 | MGVSDVPRDLEVVAATPTSLLISWEYNVNPYRYYRITYGETGGNSPVQEFTVPSVLSTATISGLKPGVDYTITVYAVTYGVQSDPISINYRTEIDKPSQHHHHHH |
| 153 | 8 | MGHHHHHHGGSVSDVPRDLEVVAATPTSLLISWEYKVHPYRYYRITYGETGGNSPVQEFTVPSVLSTAQISGLKPGVDYTITVYAVTYGDDSAPISINYRTEID |
| 154 | 8 | MGVSDVPRDLEVVAATPTSLLISWEYNVNPYRYYRITYGETGGNSPVQEFTVPSVLSTATISGLKPGVDYTITVYAVTYGVNSLPISINYRTEIDKPSQHHHHHH |
| 155 | 9 | MGVSDVPRDLEVVAATPTSLLISWQYKVHPYRYYRITYGETGGNSPVQEFTVPSVLSTATISGLKPGVDYTITVYAVTHGVHSAPISINYRTEIDKPSQHHHHHH |
| 156 | 43 | MGVSDVPRDLEVVAATPTSLLISWEYKVNPWRYYRITYGETGGNSPVQEFTVPSVLSTATISGLKPGVDYTITVYAVTYGIESSPISINYRTEIDKPSQHHHHHH |
| 157 | 43 | MGVSDVPRDLEVVAATPTSLLISWQYKVHPYRYYRITYGETGGNSPVQEFTVPSVLSTATISGLKPGVDYTITVYAVTYGVNSIPISINYRTEIDKPSQHHHHHH |
| 158 | 85 | MGVSDVPRDLEVVAATPTSLLISWEYKVHYDRYYRITYGETGGNSPVQEFTVPSVLSTATISGLKPGVDYTITVYAVTYGIQSPPISINYRTEIDKPSQHHHHHH |
| 159 | 23 | MGHHHHHHGGSVSDVPRDLEVVAATPTSLLISWEYKVHPYRYYRITYGETGGNSPVQEFTVPSVLSTATISGLKPGVDYTITVYAVTYGDDSAPISIPYRTPGG |
| 160 | 58 | MGVSDVPRDLEVVAATPTSLLISWEYKVDPYRYYRITYGETGGNSPVQEFTVPSVLSTATISGLKPGVDYTITVYAVTYGVESSPISINYRTEIDKPSQHHHHHH |
| 161 | 13 | MGHHHHHHGGSVSDVPRDLEVVAATPTSLLISWEYKVHPYRYYRITYGETGGNSPVQEFTVPSVLSSAEISGLKPGVDYTITVYAVTYGDDSAPISINYRTEID |
| 162 | 35 | MGHHHHHHGGSVSDVPRDLEVVAATPTSLLISWEYKVHPYRYYRITYGETGGNSPVQEFTVPSVLSSAQISGLKPGVDYTITVYAVTYGDDSAPISINYRTEID |
| 163 | 35 | MGHHHHHHGGSVSDVPRYLEVVAATPTSLLISWQYKVHPYRWYRITYGETGGNSPVQEFTVPSVLSTATISGLKPGVDYTITVYAVTYGVNSIPISINYRTEID |
| 164 | 35 | MGHHHHHHGGSVSDVPRDLEVVAATPTSLLISWKYQVHAYRYYRITYGETGGNSPVQEFTVPSVLSTATISGLKPGVDYTITVYAVTYGVYSAPISINYRTEID |

TABLE 3-continued

Anti-N17 Adnectin ™

| SEQ ID NO | Antiviral EC₅₀ (nM) | Anti-N17 Adnectin ™ Protein Sequence |
|---|---|---|
| 165 | 42 | MGHHHHHHGGSVSDVPRDLEVVAATPTSLLISWEYKV NPYRYYRITYGETGGNSPVQEFTVPSVLSTATISGLKPG VDYTITVYAVTYGVHSSPISINYRTEID |
| 166 | 50 | MGHHHHHHGGSVSDVPRDLEVVAATPTSLLISWKYNL HPYRYYRITYGETGGNSPVQEFTVPSVLSTATISGLKPG VDYTITVYAVTYGIISEPISINYRTEID |
| 167 | 42 | MGHHHHHHGGSVSDVPRDLEVVAATPTSLLISWEYRV NPYRYYRITYGETGGNSPVQEFTVPSVLSTATISGLKPG VDYTITVYAVTYGVQSPPISINYRTEID |
| 168 | 42 | MGHHHHHHGGSVSDVPRDLEVVAATPTSLLISWEYKV NAYRYYRITYGETGGNSPVQEFTVPSVLSTATISGLKPG VDYTITVYAVTYGVLSPPISINYRTEID |
| 169 | 5 | MGHHHHHHGGSVSDVPRDLEVVAATPTSLLISWEYNV NPYRYYRITYGETGGNSPVQEFTVPSVLSTATISGLKPG VDYTITVYAVTRGVDSAPISINYRTEID |
| 170 | 5 | MGHHHHHHGGSVSDVPRDLEVVAATPTSLLISWEYKVS PYRYYRITYGETGGNSPVQEFTVPSVLSTATISGLKPGV DYTITVYAVTFGIRSSPISINYRTEID |
| 171 | 35 | MGHHHHHHGGSVSDVPRDLEVVAATPTSLLISWKYQV HAYRYYRITYGETGGNSPVQEFTVPSVLSTATISGLKPG VDYTITVYAVTYGIISEPISINYRTEID |
| 172 | 5 | MGHHHHHHGGSVSDVPRDLEVVAATPTSLLISWEYKV DPYRYYRITYGETGGNSPVQEFTVPSVLSTATISGLKPG VDYTITVYAVTYGIDSSPISINYRTEID |
| 173 | 5 | MGHHHHHHGGAVSDVPRDLEVVAATPTSLLISWEYKV NPWRYYRITYGETGGNSPVQEFTVPSVLSTATISGLKPG VDYTITVYAVTYGVHSSPISINYRTEID |
| 174 | 5 | MGHHHHHHGGSVSDVPRDLEVVAATPTSLLISWEYNV NAYRYYRITYGETGGNSPVQEFTVPSVLSTATISGLKPG VDYTITVYAVTYGIISEPISINYRTEID |
| 175 | 5 | MGHHHHHHGGSVSDVPRDLEVVAATPTSLLISWEYKV HYDRYYRITYGETGGNSPVQEFTVPSVLSTATISGLKPG VDYTITVYAVTYGVQSTPISINYRTEID |
| 176 | >1,000 | MGHHHHHHGGSVSDVPRDLEVVAATPTSLLISWEYKV HHDRYYRITYGETGGNSPVQEFTVPSVLSTATISGLKPG VDYTITVYAVTYGIESSPISINYRTEID |
| 177 | 252 | MGHHHHHHGGSVSDVPRDLEVVAATPTSLLISWEYKV HPYRYYRITYGETGGNSPVQEFTVPSVLSTATISGLKPG VDYTITVYAVTYGDDSAPISIPYRTPGG |
| 178 | 631 | MGHHHHHHGGSVSDVPRDLEVVAATPTSLLISWEYKV HPYRYYRITYGETGGNSPVQEFTVPSVLSTATISGLKPG VDYTITVYAVTYGXDSXPISINYRTEID |
| 179 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDDSRPISINYRTEID |
| 180 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGKDSAPISINYRTEID |
| 181 | 631 | MGHHHHHHGGSVSDVPRDLEVVAATPTSLLISWEYKV HPYRYYRITYGETGGNSPVQEFTVPSVLSTATISGLKPG VDYTITVYAVTYGDHSAPISINYRTEID |
| 182 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDQSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 183 | 20 | MGHHHHHHGGSVSDVPRDLEVVAATPTSLLISWEYKV HPYRYYRITYGETGGNSPVQEFTVPSVLSTATISGLKPG VDYTITVYAVTYGIDSAPISINYRTEID |
| 184 | 20 | MGHHHHHHGGSVSDVPRDLEVVAATPTSLLISWEYKV HPYRYYRITYGETGGNSPVQEFTVPSVLSTATISGLKPG VDYTITVYAVTYGDVSAPISINYRTEID |
| 185 | 252 | MGHHHHHHGGSVSDVPRDLEVVAATPTSLLISWEYKV HPYRYYRITYGETGGNSPVQEFTVPSVLSTATISGLKPG VDYTITVYAVTYGXDSAPISINYRTEID |
| 186 | 2830 | MGHHHHHHGGSVSDVPRDLEVVAATPTSLLISWEYKV HPYRYYRITYGETGGNSPVQEFTVPSVLSTATISGLKPG VDYTITVYAVTYGEDSAPISINYRTEID |
| 187 | 86 | MGHHHHHHGGSVSDVPRDLEVVAATPTSLLISWEYKV HPYRYYRITYGETGGNSPVQEFKVPSVLSTATISGLKPG VDYTITVYAVTYGDDSAPISINYRTEID |
| 188 | 86 | MGHHHHHHGGSVSDVPRDLEVVAATPTSLLISWEYKV HPYRYYRITYGETGGNSPVQEFTVPSVLSTATISGLKPG VDYTITVYAVTYGDLSAPISINYRTEID |
| 189 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGKDSAPISINYRTEID |
| 190 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGADSAPISINYRTEID |
| 191 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGTDSAPISINYRTEID |
| 192 | 2830 | MGHHHHHHGGSVSDVPRDLEVVAATPTSLLISWEYKV HPYRYYRITYGETGGNSPVQEFTVPSVLSTATISGLKPG VDYTITVYAVTYGTDSAPISINYRTEID |
| 193 | 252 | MGHHHHHHGGSVSDVPRDLEVVAATPTSLLISWEYKV HPYRYYRITYGETGGNSPVQEFTVPSVLSTATISGLKPG VDYTITVYAVTYGKDSAPISINYRTEID |
| 194 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDPSAPISINYRTEID |
| 195 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDDSQPISINYRTEID |
| 196 | 86 | MGHHHHHHGGSVSDVPRDLEVVAATPTSLLISWEYKV HPYRYYRITYGETGGNSPVQEFTVPSVLSTATISGLKPG VDYTITVYAVTYGDVSAPISINYRTEID |
| 197 | 81 | MGHHHHHHGGSVSDVPRDLEVVAATPTSLLISWEYKV HPYRYYRITYGETGGNSPVQEFTVPSVLSTATISGLKPG VDYTITVYAVTYGDDSGPISINYRTEID |
| 198 | 2830 | MGHHHHHHGGSVSDVPRDLEVVAATPTSLLISWEYKV HPYRYYRITYGETGGNSPVQEFTVPSVLSTATISGLKPG VDYTITVYAVTYGDDSAPISIQYRTEID |
| 199 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDDSQPISINYRTEID |
| 200 | >1,000 | MGHHHHHHGGSVSDVPRDLEVVAATPTSLLISWEYKV HPYRYYRITYTETGGNSPVQEFTVPSVLSTATISGLKPGV DYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
| --- | --- | --- |
| 201 | 20 | MGHHHHHHGGSVSDVPRDLEVVAATPTSLLISWEYKVHPYRYYRITYGETGGNSPVQEFTVPSVLSTATISGLKPGVDYTITVYAVTYGDQSAPISINYRTEID |
| 202 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSKPISINYRTEID |
| 203 | 86 | MGHHHHHHGGSVSDVPRDLEVVAATPTSLLISWEYKVHPYRYYRITYGETGGNSPVQEFTVPSVLSTATISGLKPGVDYTITVYAVTYGDDSGPISINYRTEID |
| 204 | 0 | MGHHHHHHGGSVSDVPRDLEVVAATPTSLLISWEYKVHPYRYYRITYRETGGNSPVQEFTVPSVLSTATISGLKPGVDYTITVYAVTYGDDSAPISINYRTEID |
| 205 | 86 | MGHHHHHHGGSVSDVPRDLEVVAATPTSLLISWEYDVHPYRYYRITYGETGGNSPVQEFTVPSVLSTATISGLKPGVDYTITVYAVTYGDDSAPISINYRTEID |
| 206 | 237 | MGHHHHHHGGSVSDVPRDLEVVAATPTSLLISWEYKVHPYRYYRITYGETGGNSPVQEFTVPSVLSTATISGLKPGVDYTITVYAVTYGDDSKPISINYRTEID |
| 207 | >1,000 | MGHHHHHHGGSVSDVPRDLEVVAATPTSLLISWEYKVHPYRYYRITYWETGGNSPVQEFTVPSVLSTATISGLKPGVDYTITVYAVTYGDDSAPISINYRTEID |
| 208 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSTPISINYRTEID |
| 209 | 20 | MGHHHHHHGGSVSDVPRDLEVVAATPTSLLISWEYKVHPYRYYRITYGETGGNSPVQEFTVPSVLSTATISGLKPGVDYTITVYAVTYGDDSTPISINYRTEID |
| 210 | 143 | MGHHHHHHGGSVSDVPRDLEVVAATPTSLLISWEYKVHPYRYYRITYGETGGNSPVQEFTVPSVLSTATISGLKPGVDYTITVYAVTYGDDSSPISINYRTEID |
| 211 | 631 | MGHHHHHHGGSVSDVPRDLEVVAATPTSLLISWEYKVHPYRYYRITYGETGGNSPVQEFTVPSVLSTATISGLKPGVDYTITVYAVTRGDDSAPISINYRTEID |
| 212 | 86 | MGHHHHHHGGSVSDVPRDLEVVAATPTSLLISWEYKVHPYRYYRITYGETGGNSPVQEFTVPSVLSTATISGLKPGVDYTITVYAVTHGDDSAPISINYRTEID |
| 213 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSWPISINYRTEID |
| 214 | >1,000 | MGHHHHHHGGSVSDVPRDLEVVAATPTSLLISWEYKVHPYRYYRITYGETGGNSPVQEFTVPSVLSTATISGLKPGVDYTITVYAVTHGDDSAPISINYRTEID |
| 215 | >1,000 | MGHHHHHHGGSVSDVPRDLEVVAATPTSLLISWKYDVHPYRYYRITYGETGGNSPVQEFTVPSVLSTATISGLKPGVDYTITVYAVTYGDDSAPISINYRTEID |
| 216 | >1,000 | MGHHHHHHGGSVSDVPRDLEVVAATPTSLLISWEYKVHPYRYYRITYGETGGNSPVQEFTVPSVLSTATISDLKPGVDYTITVYAVTYGDDSHPISINYRTEID |
| 217 | >1,000 | MGHHHHHHGGSVSDVPRDLEVVAATPTSLLISWEYKVHPYRYYRITYGETGGNSPVQEFTVPSVLSTATISGLKPGVDYTITVYAVTRGDDSAPISINYRTEID |
| 218 | 62 | MGHHHHHHGGSVSDVPRDLEVVAATPTSLLISWEYKVHPYRYYRITYGETGGNSPVQEFTVPSVLSTATIRGLKPGVDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 219 | >1,000 | MGHHHHHHGGSVSDVPRDLEVVAATPTSLLISWKYKV HPYRYYRITYGETGGNSPVQEFTVPSVLSTATISGLKPG VDYTITVYAVTYGDDSAPISINYRTEID |
| 220 | 86 | MGHHHHHHCGSVSDVPRDLEVVAATPTSLLISWEYKV AHNRYYRITYGETGGNSPVQEFTVPSVLSTATISGLKPG VDYTITVYAVTYGDDSAPISINYRTEID |
| 221 | >1,000 | MGHHHHHHGGSVSDVPRDLEVVAATPTSLLISWEYKV YGYRYYRITYGETGGNSPVQEFTVPSVLSTATISGLKPG VDYTITVYAVTYGDDSAPISINYRTEID |
| 222 | >1,000 | MGHHHHHHGGSVSDVPRDLEVVAATPTSLLISWEYKV DHQRYYRITYGETGGNSPVQEFTVPSVLSTATISGLKPG VDYTITVYAVTYGDDSAPISINYRTEID |
| 223 | >1,000 | MGHHHHHHGGSVSDVPRDLEVVAATPTSLLISWEYKV DYRRYYRITYGETGGNSPVQEFTVPSVLSTATISGLKPG VDYTITVYAVTYGDDSAPISINYRTEID |
| 224 | >1,000 | MGHHHHHHGGSVSDVPRDLEVVAATPTSLLISWEYKV AYDRYYRITYGETGGNSPVQEFTVPSVLSTATISGLKPG VDYTITVYAVTYGDDSAPISINYRTEID |
| 225 | >1,000 | MGHHHHHHGGSVSDVPRDLEVVAATPTSLLISWEYKV TSYRYYRITYGETGGNSPVQEFTVPSVLSTATISGLKPGV DYTITVYAVTYGDDSAPISINYRTEID |
| 226 | 631 | MGHHHHHHGGSVSDVPRDLEVVAATPTSLLISWEYKV HPYRYYRIIHETGNSPVQEFTVPSVLSTATISGLKPGVD YTITVYAVTYGDDSAPISINYRTEID |
| 227 | >1,000 | MGHHHHHHGGSVSDVPRDLEVVAATPTSLLISWEYKV HPYRYYRITYGETGGNSPVQEFTVPSVLSTATISGLKPG VDYTITVYAVTYGDDSAPISINYRKEAEL |
| 228 | >1,000 | MGHHHHHHGGSVSDVPRDLEVVAATPTSLLISWEYKV NHQRYYRITYGETGGNSPVQEFTVPSVLSTATISGLKPG VDYTITVYAVTYGDDSAPISINYRTEID |
| 229 | >1,000 | MGHHHHHHGGSVSDVPRDLEVVAATPTSLLISWEYKV DHRRYYRITYGETGGNSPVQEFTVPSVLSTATISGLKPG VDYTITVYAVTYGDDSAPISINYRTEID |
| 230 | 17 | MGVSDVPRDLEVVAATPTSLLISWEYKVHPYRYYRITY GETGGNSPVQEFTVPSVLSTATISGLKPGVDYTITVYAV TYGVDSDPISINYRTDDKPSQHHHHHH |
| 231 | 10 | MGVSDVPRDLEVVAATPTSLLISWEYKVHPYRYYRITY GETGGNSPVQEFTVPSVLSTATISGLKPGVDYTITVYAV TYGVNSIPISINYRTEIDKPSQHHHHHH |
| 232 | 47 | MGVSDVPRDLEVVAATPTSLLISWEYKVNAYRYYRITY GETGGNSPVQEFTVPSVLSTATISGLKPGVDYTITVYAV TYGIESSPISINYRTEIDKPSQHHHHHH |
| 233 | 55 | MGVSDVPRDLEVVAATPTSLLISWEYKVHPYRYYRITY GETGGNSPVQEFTVPSVLSTATISGLKPGVDYTITVYAV TDGVQSSPISINYRTEIDKPSQHHHHHH |
| 234 | 20 | MGVSDVPRDLEVVAATPTSLLISWEYKVNAYRYYRITY GETGGNSPVQEFTVPSVLSTATISGLKPGVDYTITVYAV TYGIDSSPISINYRTEIDKPSQHHHHHH |
| 235 | 29 | MGVSDVPRDLEVVAATPTSLLISWEYKVHYDRYYRITY GETGGNSPVQEFTVPSVLSTATISGLKPGVDYTITVYAV TNGVLSSPISINYRTEIDKPSQHHHHHH |
| 236 | 85 | MGVSDVPRDLEVVAATPTSLLISWEYKVNPWRYYRITY GETGGNSPVQEFTVPSVLSTATISGLKPGVDYTITVYAV TRGVDSAPISINYRTEIDKPSQHHHHHH |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 237 | 31 | MGVSDVPRDLEVVAATPTSLLISWEYKVHPXRYYRITYGETGGNSPVQEFTVPSVLSTATISGLKPGVDYTITVYAVTYGVBSXPISINYRTEIDKPSQHHHHHH |
| 238 | 11 | MGVSDVPRDLEVVAATPTSLLISWEYKVNPWRYYRITYGETGGNSPVQEFTVPSVLSTATISGLKPGVDYTITVYAVTYGIQSPPISINYRTEIDKPSQHHHHHH |
| 239 | 4 | MGVSDVPRDLEVVAATPTSLLISWQYKVHPYRWYRITYGETGGNSPVQEFTVPSVLSTATISGLKPGVDYTITVYAVTYGVNSIPISINYRTEIDKPSQHHHHHH |
| 240 | 5 | MGVSDVPRDLEVVAATPTSLLISWEYKVSPYRYYRITYGETGGNSPVQEFTVPSVLSTATISGLKPGVDYTITVYAVTYGVNSIPISINYRTEIDKPSQHHHHHH |
| 241 | 8 | MGVSDVPRDLEVVAATPTSLLISWEYKVNPWRYYRITYGETGGNSPVQEFTVPSVLSTATISGLKPGVDYTITVYAVTYGVNSLPISINYRTEIDKPSQHHHHHH |
| 242 | 0 | MGVSDVPRDLEVVAATPTSLLISWEYNVHYDRYYRITYGETGGNSPVQEFTVPSVLSTATISGLKPGVDYTITVYAVTYGVDSDPISINYRTEIDKPSQHHHHHH |
| 243 | 48 | MGVSDVPRDLEVVAATPTSLLISWEYKVNPWRYYRITYGETGGNSPVQEFTVPSVLSTATISGLKPGVDYTITVYAVTYGVDSDPISINYRTEIDKPSQHHHHHH |
| 244 | 58 | MGVSDVPRDLEVVAATPTSLLISWEYKVDPYRYYRITYGETGGNSPVQEFTVPSVLSTATISGLKPGVDYTITVYAVTYGVDSDPISINYRTEIDKPSQHHHHHH |
| 245 | 50 | MGHHHHHHGGSVSDVPRDLEVVAATPTSLLISWKYQVHAYRYYRITYGETGGNSPVQEFTVPSVLSTATINGLKPGVDYTITVYAVTYGIISEPISINYRTEID |
| 246 | >1,000 | MGHHHHHHGGSVSDVPRDLEVVAATPTSLLISWEYKVNYNRYYRITYGETGGNSPVQEFTVPSVLSTATISGLKPGVDYTITVYAVTEGVQSAPISINYRTEID |
| 247 | 2 | MGHHHHHHGGSVSDVPRDLEVVAATPTSLLISWEYKVHPYRYYRITYGETGGNSPVQEFTVPSVLSTATISGLKPGVDYTITVYAVTYGDDSAPISINYRTPGG |
| 248 | >1,000 | MGHHHHHHGGSVSDVPRDLEVVAATPTSLLISWEYKVHPYRYYRITYGETGGNTPVQEFRVPSVLSTATISGLKPGVDYTITVYAVTYADASAPISINYRTEID |
| 249 | 83 | MGHHHHHHGGSVSDVPRDLEVVAATPTSLLISWEYKVHPYRYYRITYGETGGNSPVQEFTVPSVLSSATLNGLKPGVDYTITVYAVTYGDDSAPISINYRTEID |
| 250 | 218 | MGHHHHHHGGSVSDVPRDLEVVAATPTSLLISWEYKVHPYRYYRITYGETGGNSPVQEFTVPSVLSSAKISGLKPGVDYTITVYAVTYGDDSAPISINYRTEID |
| 251 | 186 | MGHHHHHHGGSVSDVPRDLEVVAATPTSLLISWEYKVHPYRYYRITYGETGGNSPVQEFNVPSVLSTATISGLKPGVDYTITVYAVTYGDDSAPISINYRTEID |
| 252 | >1,000 | MGHHHHHHGGSVSDVPRDLEVVAATPTSLLISWEYKVAHRRYYRITYGETGGNSPVQEFTVPSVLSTATISGLKPGVDYTITVYAVTYGDDSAPISINYRTEID |
| 253 | >1,000 | MGHHHHHHGGSVSDVPRDLEVVAATPTSLLISWEYKVDAYRYYRITYGETGGNSPVQEFTVPSVLSTATISGLKPGVDYTITVYAVTYGDDSAPISINYRTEID |
| 254 | >1,000 | MGHHHHHHGGSVSDVPRDLEVVAATPTSLLISWEYKVDSYRYYRITYGETGGNSPVQEFTVPSVLSTATISGLKPGVDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 255 | 136 | MGHHHHHHGGSVSDVPRDLEVVAATPTSLLISWEYKV HPYRYYRITYGETGGNSPVQEFTVPSVLSTATISGLKPG VDYTITVYAVTYGDDSAPISINYRTEID |
| 256 | 170 | MGHHHHHHGGSVSDVPRDLEVVAATPTSLLISWEYKV HPYRYYRITYGETGGNSPVQEFTVPSVLSTATISGLKPG VDYTITVYAVTYGDASAPISINYRTEID |
| 257 | >1,000 | MGHHHHHHGGSVSDVPRDLEVVAATPTSLLISWEYKV HPYRYYRITYGETGGNSPVQEFTVPSVLSTATISGLKPG VDYTITVYAVTNGDDSAPISINYRTEID |
| 258 | 195 | MGHHHHHHGGSVSDVPRDLEVVAATPTSLLISWEYKV HPYRYYRITYGETGGNSPVQEFTVPSVLSSATIRGLKPG VDYTITVYAVTYGDDSAPISINYRTEID |
| 259 | 135 | MGHHHHHHGGSVSDVPRDLEVVAATPTSLLISWEYKV HPYRYYRITYGETGGNSPVQEFTVPSVLSTAKISGLKPG VDYTITVYAVTYGDDSAPISINYRTEID |
| 260 | 188 | MGHHHHHHGGSVSDVPRDLEVVAATPTSLLISWEYKV HPYRYYRITYGETGGNSPVQEFRVPSVLSTATISGLKPG VDYTITVYAVTYGDDSAPISINYRTEID |
| 261 | >1,000 | MGHHHHHHGGSVSDVPRDLEVVAATPTSLLISWEYKV APWRYYRITYGETGGNSPVQEFTVPSVLSTATISGLKPG VDYTITVYAVTYGDDSAPISINYRTEID |
| 262 | >1,000 | MGHHHHHHGGSVSDVPRDLEVVAATPTSLLISWEYKV DGWRYYRITYGETGGNSPVQEFTVPSVLSTATISGLKPG VDYTITVYAVTYGDDSAPISINYRTEID |
| 263 | >1,000 | MGHHHHHHGGSVSDVPRDLEVVAATPTSLLISWEYKV DTWRYYRITYGETGGNSPVQEFTVPSVLSTATISGLKPG VDYTITVYAVTYGDDSAPISINYRTEID |
| 264 | 209 | MGHHHHHHGGSVSDVPRDLEVVAATPTXLLISWEYKV HPYRYYRITYGETGGNSPVQEFTVPSVLSTATISGLKPG VDYTITVYAVTYGDDSAPISINYRTEID |
| 265 | 63 | MGHHHHHHGGSVSDVPRDLEVVAATPTSLLISWEYKV HPYRYYRITYGETGGNSPVQEFTVPSVLSTATISGLKPG VDYTITVYAVTYGADSAPISINYRTEID |
| 266 | >1,000 | MGHHHHHHGGSVSDVPRDLEVVAATPTSLLISWEYKV HPYRYYRITYGETGGNSPVQEFTVPSVLSTATISGLKPG VDYTITVYAVTRGDDSAPISINYRTEID |
| 267 | >1,000 | MGHHHHHHGGSVSDVPRDLEVVAATPTSLLISWEYKV HPYRYYRITYGETGGNSPVQDFTVPSVLSTATIRGLKPG VDYTITVYAVTYGDDSAPISINYRTEID |
| 268 | 2 | MGHHHHHHGGSVSDVPRDLEVVAATPTSLLISWEYKV HPYRYYRITYGETGGNSPVQEFTVPSVLSTANISGLKPG VDYTITVYAVTYGDDSAPISINYRTEID |
| 269 | 184 | MGHHHHHHGGSVSDVPRDLEVVAATPTSLLISWEYKV HPYRYYRITYGETGGNSPVQAFTVPSVLSTATISGLKPG VDYTITVYAVTYGDDSAPISINYRTEID |
| 270 | >1,000 | MGHHHHHHGGSVSDVPRDLEVVAATPTSLLISWEYKV APYRYYRITYGETGGNSPVQEFTVPSVLSTATISGLKPG VDYTITVYAVTYGDDSAPISINYRTEID |
| 271 | >1,000 | MGHHHHHHGGSVSDVPRDLEVVAATPTSLLISWEYKV DGYRYYRITYGETGGNSPVQEFTVPSVLSTATISGLKPG VDYTITVYAVTYGDDSAPISINYRTEID |
| 272 | >1,000 | MGHHHHHHGGSVSDVPRDLEVVAATPTSLLISWEYKV DTYRYYRITYGETGGNSPVQEFTVPSVLSTATISGLKPG VDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 273 | >1,000 | MGHHHHHHGGSVSDVPRDLEVVAATPTSLLISWEYEV HPYRYYRITYGETGGNSPVQEFTVPSVLSTATISGLKPG VDYTITVYAVTYGDDSAPISINYRTEID |
| 274 | 115 | MGHHHHHHGGSVSDVPRDLEVVAATPTSLLISWEYRV HPYRYYRITYGETGGNSPVQEFTVPSVLSTATISGLKPG VDYTITVYAVTYGDDSAPISINYRTEID |
| 275 | 180 | MGHHHHHHGGSVSDVPRDLEVVAATPTSLLISWEYKV HPYRYYRITYGETGGNSPVQSFTVPSVLSTATISGLKPGV DYTITVYAVTYGADSAPISINYRTEID |
| 276 | 16 | MGHHHHHHGGSVSDVPRDLEVVAATPTSLLISWEYKV HPYRYYRITYGETGGNSPVQEFTVPSVLSTATIRGLKPG VDYTITVYAVTYGDDSAPISINYRTEID |
| 277 | >1,000 | MGHHHHHHGGSVSDVPRDLEVVAATPTSLLISWEYKV HPYRYYRITYGETGGNSPVQDFTVPSVLSTATISGLKPG VDYTITVYAVTYGDDSAPISINYRTEID |
| 278 | >1,000 | MGHHHHHHGGSVSDVPRDLEVVAATPTSLLISWEYKV ARWRYYRITYGETGGNSPVQEFTVPSVLSTATISGLKPG VDYTITVYAVTYGDDSAPISINYRTEID |
| 279 | >1,000 | MGHHHHHHGGSVSDVPRDLEVVAATPTSLLISWEYKV DHQRYYRITYGETGGNSPVQEFTVPSVLSTATISGLKPG VDYTITVYAVTYGDDSAPISINYRTEID |
| 280 | >1,000 | MGHHHHHHGGSVSDVPRDLEVVAATPTSLLISWEYKV DYGRYYRITYGETGGNSPVQEFTVPSVLSTATISGLKPG VDYTITVYAVTYGDDSAPISINYRTEID |
| 281 | >1,000 | MGHHHHHHGGSVSDVPRDLEVVAATPTSLLISWKYGV HPYRYYRITYGETGGNSPVQEFTVPSVLSTATISGLKPG VDYTITVYAVTYGDDSAPISINYRTEID |
| 282 | 56 | MGHHHHHHGGSVSDVPRDLEVVAATPTSLLISWEYSVH PYRYYRITYGETGGNSPVQEFTVPSVLSTATISGLKPGV DYTITVYAVTYGDDSAPISINYRTEID |
| 283 | >1,000 | MGHHHHHHGGSVSDVPRDLEVVAATPTSLLISWEYKV HPYRYYRITYGETGGNSPVQEFTVPSVLSTATISGLKPG VDYTITVYAVTDGDDSAPISINYRTEID |
| 284 | >1,000 | MGHHHHHHGGSVSDVPRDLEVVAATPTSLLISWEYKV HPYRYYRITYGETGGNSPVQEFTVPSVLSTATISGLKPG VDYTITVYAVTSGDDSAPISINYRTEID |
| 285 | 397 | MGHHHHHHGGSVSDVPRDLEVVAATPTSLLISWEYKV HPYRYYRITYGETGGNSPVQEFTVPSVLSSATLRGLKPG VDYTITVYAVTYGDDSAPISINYRTEID |
| 286 | >1,000 | MGHHHHHHGGSVSDVPRDLEVVAATPTSLLISWEYKV AAWRYYRITYGETGGNSPVQEFTVPSVLSTATISGLKPG VDYTITVYAVTYGDDSAPISINYRTEID |
| 287 | >1,000 | MGHHHHHHGGSVSDVPRDLEVVAATPTSLLISWEYKV ATWRYYRITYGETGGNSPVQEFTVPSVLSTATISGLKPG VDYTITVYAVTYGDDSAPISINYRTEID |
| 288 | >1,000 | MGHHHHHHGGSVSDVPRDLEVVAATTTSLLISWEYKV DYHRYYRITYGETGGNSPVQEFTVPSVLSTATISGLKPG VDYTITVYAVTYGDDSAPISINYRTEID |
| 289 | >1,000 | MGHHHHHHGGSVSDVPRDLEVVAATPTSLLISWEYGV HPYRYYRITYGETGGNSPVQEFTVPSVLSTATISGLKPG VDYTITVYAVTYGDDSAPISINYRTEID |
| 290 | 138 | MGHHHHHHGGSVSDVPRDLEVVAATPTSLLISWKYXV HPYRYYRITYGETGGNSPVQEFTVPSVLSTATISGLKPG VDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 291 | >1,000 | MGHHHHHHGGSVSDVPRDLEVVAATPTSLLISWEYKVHPYRYYRITYGETGGNSPVQEFTVPSVLSTATISGLKPGVDYTITVYAVTGGDDSAPISINYRTEID |
| 292 | 52 | MGHHHHHHGGSVSDVPRDLEVVAATPTSLLISWEYKVHPYRYYRITYGETGGNSPVQEFTVPSVLSTATIHGLKPGVDYTITVYAVTYGDDSAPISINYRTEID |
| 293 | >1,000 | MGHHHHHHGGSVSDVPRDLEVVAATPTSLLISWEYKVHPYRYYRITYGETGGNSPVQEFTVPSVLSTATLRGLKPGVDYTITVYAVTYGDDSAPISINYRTEID |
| 294 | 101 | MGHHHHHHGGSVSDVPRDLEVVAATPTSLLISWEYKVHPYRYYRITYGETGGNSPVQEFTVPSVLSSATISGLKPGVDYTITVYAVTYGDDSAPISINYRTEID |
| 295 | >1,000 | MGHHHHHHGGSVSDVPRDLEVVAATPTSLLISWEYKVAAYRYYRITYGETGGNSPVQEFTVPSVLSTATISGLKPGVDYTITVYAVTYGDDSAPISINYRTEID |
| 296 | >1,000 | MGHHHHHHGGSVSDVPRDLEVVAATPTSLLISWEYKVATYRYYRITYGETGGNSPVQEFTVPSVLSTATISGLKPGVDYTITVYAVTYGDDSAPISINYRTEID |
| 297 | 30 | MGHHHHHHGGSVSDVPRDLEVVAATPTSLLISWEYKVDPWRYYRITYGETGGNSPVQEFTVPSVLSTATISGLKPGVDYTITVYAVTYGDDSAPISINYRTEID |
| 298 | >1,000 | MGHHHHHHGGSVSDVPRDLEVVAATPTSLLISWEYKVDYQRYYRITYGETGGNSPVQEFTVPSVLSTATISGLKPGVDYTITVYAVTYGDDSAPISINYRTEID |
| 299 | >1,000 | MGHHHHHHGGSVSDVPRDLEVVAATPTSLLISWKYKVHPYRYYRITYGETGGNSPVQEFTVPSVLSTATISGLKPGVDYTITVYAVTYGDDSAPISINYRTEID |
| 300 | 132 | MGHHHHHHGGSVSDVPRDLEVVAATPTSLLISWEYXVHPYRYYRITYGETGGNSPVQEFTVPSVLSTATISGLKPGVDYTITVYAVTYGDDSAPISINYRTEID |
| 301 | >1,000 | MGHHHHHHGGSVSDVPRDLEVVAATPTSLLISWEYKVHPYRYYRITYGETGGNSPVQEFTVPSVLSTATISGLKPGVDYTITVYAVTHGDDFAPISINYRTEMLI |
| 302 | 4 | MGHHHHHHGGSVSDVPRDLEVVAATPTSLLISWEYKVHPYRYYRITYGETGGNSPVQEFTVPSVLSSATINGLKPGVDYTITVYAVTYGDDSAPISINYRTEID |
| 303 | 109 | MGHHHHHHGGSVSDVPRDLEVVAATPTSLLISWEYKVHPYRYYRITYGETGGNSPVQEFKVPSVLSTATISGLKPGVDYTITVYAVTYGDDSAPISINYRTEID |
| 304 | >1,000 | MGHHHHHHGGSVSDVPRDLEVVAATPTSLLISWEYKVAHDRYYRITYGETGGNSPVQEFTVPSVLSTATISGLKPGVDYTITVYAVTYGDDSAPISINYRTEID |
| 305 | 83 | MGHHHHHHGGSVSDVPRDLEVVAATPTSLLISWEYKVDPYRYYRITYGETGGNSPVQEFTVPSVLSTATISGLKPGVDYTITVYAVTYGDDSAPISINYRTEID |
| 306 | >1,000 | MGHHHHHHGGSVSDVPRDLEVVAATPTSLLISWEYKVDYRRYYRITYGETGGNSPVQEFTVPSVLSTATISGLKPGVDYTITVYAVTYGDDSAPISINYRTEID |
| 307 | 205 | MGHHHHHHGGSVSDVPRDLEVVAATPTGLLISWEYKVHPYRYYRITYGETGGNSPVQEFTVPSVLSTATISGLKPGVDYTITVYAVTYGDDSAPISINYRTEID |
| 308 | >1,000 | MGHHHHHHGGSVSDVPRDLEVVAATPTSLLISWEYKVNAWRYYRITYGETGGNSPVQEFTVPSVLSTATISGLKPGVDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 309 | >1,000 | MGHHHHHHGGSVSDVPRDLEVVAATPTSLLISWEYKV HPYRYYRITYGETGGNSPVQEFTVPSVLSTATISGLKPG VDYTITVYAVTHGDDSAPISINYRTEID |
| 310 | 62 | MGHHHHHHGGSVSDVPRDLEVVAATPTSLLISWEYKV HPYRYYRITYGETGGNSPVQEFTVPSVLSTATINGLKPG VDYTITVYAVTYGDDSAPISINYRTEID |
| 311 | 42 | MGHHHHHHGGSVSDVPRDLEVVAATPTSLLISWEYKV HPYRYYRITYGETGGNSPVQEFTVPSVLSTAEISGLKPG VDYTITVYAVTYGDDSAPISINYRTEID |
| 312 | 37 | MGHHHHHHGGSVSDVPRDLEVVAATPTSLLISWEYKV HPYRYYRITYGETGGNSPVQEFLVPSVLSTATISGLKPG VDYTITVYAVTYGDDSAPISINYRTEID |
| 313 | >1,000 | MGHHHHHHGGSVSDVPRDLEVVAATPTSLLISWEYKV AHGRYYRITYGETGGNSPVQEFTVPSVLSTATISGLKPG VDYTITVYAVTYGDDSAPISINYRTEID |
| 314 | >1,000 | MGHHHHHHGGSVSDVPRDLEVVAATPTSLLISWEYKV AYKRYYRITYGETGGNSPVQEFTVPSVLSTATISGLKPG VDYTITVYAVTYGDDSAPISINYRTEID |
| 315 | >1,000 | MGHHHHHHGGSVSDVPRDLEVVAATPTSLLISWEYKV DRWRYYRITYGETGGNSPVQEFTVPSVLSTATISGLKPG VDYTITVYAVTYGDDSAPISINYRTEID |
| 316 | 331 | MGHHHHHHGGSVSDVPRDLEVVAATPTSLLISWEYAV HPYRYYRITYGETGGNSPVQEFTVPSVLSTATISGLKPG VDYTITVYAVTYGDDSAPISINYRTEID |
| 317 | >1,000 | MGHHHHHHGGSVSDVPRDLEVVAATPTSLLISWEYKV NAYRYYRITYGETGGNSPVQEFTVPSVLSTATISGLKPG VDYTITVYAVTYGDDSAPISINYRTEID |
| 318 | >1,000 | MGHHHHHHGGSVSDVPRDLEVVAATPTSLLISWEYKV NGYRYYRITYGETGGNSPVQEFTVPSVLSTATISGLKPG VDYTITVYAVTYGDDSAPISINYRTEID |
| 319 | >1,000 | MGHHHHHHGGSVSDVPRDLEVVAATPTSLLISWEYKVS HGRYYRITYGETGGNSPVQEFTVPSVLSTATISGLKPGV DYTITVYAVTYGDDSAPISINYRTEID |
| 320 | >1,000 | MGHHHHHHGGSVSDVPRDLEVVAATPTSLLISWEYKV TTWRYYRITYGETGGNSPVQEFTVPSVLSTATISGLKPG VDYTITVYAVTYGDDSAPISINYRTEID |
| 321 | 55 | MGHHHHHHGGSVSDVPRDLEVVAATPTSLLISWEYKV HPYRYYRITYGETGGNSPVQEFTVPSVLSSAZLSGLKPG VDYTITVYAVTYGDDSAPISINYRTEID |
| 322 | 96 | MGHHHHHHGGSVSDVPRDLEVVAATPTSLLISWEYKV HPYRYYRITYGETGGNSPVQEFTVPSVLSTATISGLKPG VDYTITVYAVTYGTDSAPISINYRTEID |
| 323 | 126 | MGHHHHHHGGSVSDVPRDLEVVAATPTSLLISWEYKV HPYRYYRITYGETGGNSPVQEFTVPSVLSTATISGLKPG VDYTITVYAVTYGDQSAPISINYRTEID |
| 324 | 487 | MGHHHHHHGGSVSDVPRDLEVVAATPTSLLISWEYKV HPYRYYRITYGETGGNSPVQEFTVPSVLSTATISGLKPG VDYTITVYAVTYGDDSNPISINYRTEID |
| 325 | >1,000 | MGHHHHHHGGSVSDVPRDLEVVAATPTSLLISWEYKV NHDRYYRITYGETGGNSPVQEFTVPSVLSTATISGLKPG VDYTITVYAVTYGDDSAPISINYRTEID |
| 326 | >1,000 | MGHHHHHHGGSVSDVPRDLEVVAATPTSLLISWEYKVS HRRYYRITYGETGGNSPVQEFTVPSVLSTATISGLKPGV DYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 327 | >1,000 | MGHHHHHHGGSVSDVPRDLEVVAATPTSLLISWEYKVTYERYYRITYGETGGNSPVQEFTVPSVLSTATISGLKPGVDYTITVYAVTYGDDSAPISINYRTEID |
| 328 | 63 | MGHHHHHHGGSVSDVPRDLEVVAATPTSLLISWEYKVHPYRYYRITYGETGGNSPVQEFTVPSVLSSATXXGLKPGVDYTITVYAVTYGDDSAPISINYRTEID |
| 329 | 102 | MGHHHHHHGGSVSDVPRDLEVVAATPTSLLISWEYKVHPYRYYRITYGETGGNSPVQEFTVPSVLSTATISGLKPGVDYTITVYAVTYGDVSAPISINYRTEID |
| 330 | 99 | MGHHHHHHGGSVSDVPRDLEVVAATPTSLLISWEYKVHPYRYYRITYGETGGNSPVQEFTVPSVLSTATISGLKPGVDYTITVYAVTYGDDSPPISINYRTEID |
| 331 | 100 | MGHHHHHHGGSVSDVPRDLEVVAATPTSLLISWEYKVHPYRYYRITYGETGGNSPVQEFTVPSVLSTATISGLKPGVDYTITVYAVTYGDDSXPISINYRTEID |
| 332 | >1,000 | MGHHHHHHGGSVSDVPRDLEVVAATPTSLLISWEYKVNRWRYYRITYGETGGNSPVQEFTVPSVLSTATISGLKPGVDYTITVYAVTYGDDSAPISINYRTEID |
| 333 | >1,000 | MGHHHHHHGGSVSDVPRDLEVVAATPTSLLISWEYKVSPWRYYRITYGETGGNSPVQEFTVPSVLSTATISGLKPGVDYTITVYAVTYGDDSAPISINYRTEID |
| 334 | >1,000 | MGHHHHHHGGSVSDVPRDLEVVAATPTSLLISWEYKVTYRRYYRITYGETGGNSPVQEFTVPSVLSTATISGLKPGVDYTITVYAVTYGDDSAPISINYRTEID |
| 335 | 112 | MGHHHHHHGGSVSDVPRDLEVVAATPTSLLISWEYKVHPYRYYRITYGETGGNSPVQEFTVPSVLSTATISGLKPGVDYTITVYAVTYGDESAPISINYRTEID |
| 336 | 171 | MGHHHHHHGGSVSDVPRDLEVVAATPTSLLISWEYKVHPYRYYRITYGETGGNSPVQEFTVPSVLSTATISGLKPGVDYTITVYAVTYGDDSDPISINYRTEID |
| 337 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSYPISINYRTEID |
| 338 | >1,000 | MGHHHHHHGGSVSDVPRDLEVVAATPTSLLISWEYKVNRYRYYRITYGETGGNSPVQEFTVPSVLSTATISGLKPGVDYTITVYAVTYGDDSAPISINYRTEID |
| 339 | >1,000 | MGHHHHHHGGSVSDVPRDLEVVAATPTSLLISWEYKVSRWRYYRITYGETGGNSPVQEFTVPSVLSTATISGLKPGVDYTITVYAVTYGDDSAPISINYRTEID |
| 340 | >1,000 | MGHHHHHHGGSVSDVPRDLEVVAATPTSLLISWEYKVXXYRYYRITYGETGGNSPVQEFTVPSVLSTATISGLKPGVDYTITVYAVTYGDDSAPISINYRTEID |
| 341 | >1,000 | MGHHHHHHGGSVSDVPRDLEVVAATPTSLLISWEYKVHPYRYYRITYGETGGNSPVQSFTVPSVLSTATISGLKPGVDYTITVYAVTYGDDSAPISINYRTEID |
| 342 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGIDSAPISINYRTEID |
| 343 | 122 | MGHHHHHHGGSVSDVPRDLEVVAATPTSLLISWEYKVHPYRYYRITYGETGGNSPVQEFTVPSVLSTATISGLKPGVDYTITVYAVTYGDHSAPISINYRTEID |
| 344 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSEPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 345 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSRPISINYRTEID |
| 346 | 83 | MGHHHHHHGGSVSDVPRDLEVVAATPTSLLISWEYKVHPYRYYRITYGETGGNSPVQEFTVPSVLSTATISGLKPGVDYTITVYAVTYGDDSAPISIQYRTEID |
| 347 | >1,000 | MGHHHHHHGGSVSDVPRDLEVVAATPTSLLISWEYKVNYRRYYRITYGETGGNSPVQEFTVPSVLSTATISGLKPGVDYTITVYAVTYGDDSAPISINYRTEID |
| 348 | >1,000 | MGHHHHHHGGSVSDVPRDLEVVAATPTSLLISWEYKVSTWRYYRITYGETGGNSPVQEFTVPSVLSTATISGLKPGVDYTITVYAVTYGDDSAPISINYRTEID |
| 349 | >1,000 | MGHHHHHHGGSVSDVPRDLEVVAATPTSLLISWEYKVYAYRYYRITYGETGGNSPVQEFTVPSVLSTATISGLKPGVDYTITVYAVTYGDDSAPISINYRTEID |
| 350 | 191 | MGHHHHHHGGSVSDVPRDLEVVAATPTSLLISWEYKVHPYRYYRITYGETGGNSPVQTFTVPSVLSTATISGLKPGVDYTITVYAVTYGDDSAPISINYRTEID |
| 351 | 215 | MGHHHHHHGGSVSDVPRDLEVVAATPTSLLISWEYKVHPYRYYRITYGETGGNSPVQAFTVPSVLSTATISGLKPGVDYTITVYAVTYGKDSAPISINYRTEID |
| 352 | 77 | MGHHHHHHGGSVSDVPRDLEVVAATPTSLLISWEYKVHPYRYYRITYGETGGNSPVQEFTVPSVLSTATISGLKPGVDYTITVYAVTYGDLSAPISINYRTEID |
| 353 | 19 | MGHHHHHHGGSVSDVPRDLEVVAATPTSLLISWEYKVHPYRYYRITYGETGGNSPVQEFTVPSVLSTATISGLKPGVDYTITVYAVTYGDDSGPISINYRTEID |
| 354 | >1,000 | MGHHHHHHGGSVSDVPRDLEVVAATPTSLLISWEYKVSAWRYYRITYGETGGNSPVQEFTVPSVLSTATISGLKPGVDYTITVYAVTYGDDSAPISINYRTEID |
| 355 | >1,000 | MGHHHHHHGGSVSDVPRDLEVVAATPTSLLISWEYKVSTYRYYRITYGETGGNSPVQEFTVPSVLSTATISGLKPGVDYTITVYAVTYGDDSAPISINYRTEID |
| 356 | 31 | MGHHHHHHGGSVSDVPRDLEVVAATPTSLLISWEYKVHPYRYYRITYGETGGNSPVQEFTVPSVLSTAELSGLKPGVDYTITVYAVTYGDDSAPISINYRTEID |
| 357 | 178 | MGHHHHHHGGSVSDVPRDLEVVAATPTSLLISWEYKVHPYRYYRITYGETGGNSPVQEFTVPSVLSTATISGLKPGVDYTITVYAVTYGDLSAPISINYRTEID |
| 358 | >1,000 | MGHHHHHHGGSVSDVPRDLEVVAATPTSLLISWEYKVHPYRYYRITYGETGGNSPVQEFTVPSVLSTATISGLKPGVDYTITVYAVTYGDDSTPISINYRTEID |
| 359 | >1,000 | MGHHHHHHGGSVSDVPRDLEVVAATPTSLLISWEYKVSAYRYYRITYGETGGNSPVQEFTVPSVLSTATISGLKPGVDYTITVYAVTYGDDSAPISINYRTEID |
| 360 | >1,000 | MGHHHHHHGGSVSDVPRDLEVVAATPTSLLISWEYKVTGYRYYRITYGETGGNSPVQEFTVPSVLSTATISGLKPGVDYTITVYAVTYGDDSAPISINYRTEID |
| 361 | >1,000 | MGHHHHHHGGSVSDVPRDLEVVAATPTSLLISWEYKVYHGRYYRITYGETGGNSPVQEFTVPSVLSTATISGLKPGVDYTITVYAVTYGDDSAPISINYRTEID |
| 362 | 121 | MGHHHHHHGGSVSDVPRDLEVVAATPTSLLISWEYKVHPYRYYRITYGETGGNSPVQEFTVPSVLSTAKLSGLKPGVDYTITVYAVTYGDDSAPISINYRTEID |

TABLE 3-continued

Anti-N17 Adnectin ™

| SEQ ID NO | Antiviral EC$_{50}$ (nM) | Anti-N17 Adnectin ™ Protein Sequence |
|---|---|---|
| 363 | 130 | MGHHHHHHGGSVSDVPRDLEVVAATPTSLLISWEYKV HPYRYYRITYGETGGNSPVQEFTVPSVLSTATISGLKPG VDYTITVYAVTYGNDSAPISINYRTEID |
| 364 | 89 | MGHHHHHHGGSVSDVPRDLEVVAATPTSLLISWEYKV HPYRYYRITYGETGGNSPVQEFTVPSVLSTATISGLKPG VDYTITVYAVTYGDPSAPISINYRTEID |
| 365 | >1,000 | MGHHHHHHGGSVSDVPRDLEVVAATPTSLLISWEYKVS GYRYYRITYGETGGNSPVQEFTVPSVLSTATISGLKPGV DYTITVYAVTYGDDSAPISINYRTEID |
| 366 | >1,000 | MGHHHHHHGGSVSDVPRDLEVVAATPTSLLISWEYKV YHNRYYRITYGETGGNSPVQEFTVPSVLSTATISGLKPG VDYTITVYAVTYGDDSAPISINYRTEID |
| 367 | 300 | MGHHHHHHGGSVSDVPRDLEVVAATPTSLLISWEYKV HPYRYYRITYGETGGNSPVQEFTVPSVLSSAQLSGLKPG VDYTITVYAVTYGDDSAPISINYRTEID |
| 368 | 62 | MGHHHHHHGGSVSDVPRDLEVVAATPTSLLISWEYKV HPYRYYRITYGETGGNSPVQEFTVPSVLSTATISGLKPG VDYTITVYAVTYGTDSAPISINYRTEID |
| 369 | 155 | MGHHHHHHGGSVSDVPRDLEVVAATPTSLLISWEYKV HPYRYYRITYGETGGNSPVQEFTVPSVLSTATISGLKPG VDYTITVYAVTYGDPSAPISINYRTEID |
| 370 | 335 | MGHHHHHHGGSVSDVPRDLEVVAATPTSLLISWEYKV HPYRYYRITYGETGGNSPVQEFTVPSVLSTATISGLKPG VDYTITVYAVTYGDDSKPISINYRTEID |
| 371 | 114 | MGHHHHHHGGSVSDVPRDLEVVAATPTSLLISWEYKV HPYRYYRITYGETGGNSPVQEFTVPSVLSTATISGLKPG VDYTITVYAVTYGIDSTPISINYRTEID |

In some embodiments, the anti-N17 Adnectin™ of the invention comprises an amino acid sequence at least 70%, 75%, 80%, 85%, 90%, 95%, 98%, 99% or 100% identical to any one of SEQ ID NOs: 115-371.

In some embodiments, the anti-N17 Adnectin™ of the invention comprises an amino acid sequence at least 70%, 75%, 80%, 85%, 90%, 95%, 98%, 99% or 100% identical to any one of SEQ ID NOs: 115-371, excluding any N-terminus extended region.

In some embodiments, the anti-N17 Adnectin™ of the invention comprises an amino acid sequence at least 70%, 75%, 80%, 85%, 90%, 95%, 98%, 99% or 100% identical to any one of SEQ ID NOs: 115-371, excluding any C-terminus extended region.

In some embodiments, the anti-N17 Adnectin™ of the invention comprises an amino acid sequence at least 70%, 75%, 80%, 85%, 90%, 95%, 98%, 99% or 100% identical to any one of SEQ ID NOs: 115-371, excluding both the N-terminus and C-terminus extended regions.

In other embodiments, anti-N17 Adnectin™ comprises an amino acid sequence at least 80%, 85%, 90%, 95%, 98%, 99% or 100% identical to the BC loop, DE loop and FG loop regions of SEQ ID NOs: 115-371.

Analysis of the sequences above indicate that S52, V53, L54 and S55 of the anti-N17 Adnectin™ DE loop are conserved amino acids. In some embodiments, the anti-N17 Adnectin™ comprises one or more of the conserved amino acids S52, V53, L54 and S55.

Additionally, analysis of the sequences above indicate that Y24 of the anti N17 Adnectin™ BC loop is a conserved amino acid. In some embodiments, position 26 of the anti-N17 Adnectin™ BC loop is valine or leucine.

Analysis of the sequences above indicate that G78 and S85 of the anti-N17 Adnectin™ FG loop are conserved amino acids. In some embodiments, the anti-N17 Adnectin™ comprises one or more of the conserved amino acids G78 and S85. In some embodiments, position 79 of the anti-N17 Adnectin™ FG loop is valine or isoleucine.

In some embodiments, the anti-N17 Adnectin™ comprises one or more of the conserved amino acids Y24, V26, L26, S52, V53, L54, S55 G78, V79, I79 and S85.

Point mutation analysis of the anti-N17 Adnectin™ showed advantages of mutating several $^{10}$Fn3 non-loop scaffold positions. Specifically, mutating positions T56 and T58 boosted potency. In some embodiments, the anti-N17 Adnectin™ comprises mutating T58 to Asn, Glu, or Gln.

II. HIV Fusion Peptide Inhibitors

The amino acid sequence of gp41, and its variation among different strains of HIV-1, is well known. The fusogenic domain (often called the fusion peptide, or FP) is believed to be involved in insertion into and disruption of the target cell membrane. The transmembrane domain, containing the transmembrane anchor sequence, is located toward the C-terminal end of the protein. Between the fusogenic domain and transmembrane anchor are two distinct regions, known as heptad repeat (HR) regions, each region having a plurality of heptads. The amino acid sequence comprising the HR1 region and the amino acid sequence comprising the HR2 region are each relatively conserved regions in the HIV-1 envelope protein. A representative sequence of the external domain of gp41 (clade B consensus) is as follows:

```
                                                            (SEQ ID NO: 2)
512 AVGIGAMFL GFLGAAGSTM GAASVTLTVQ ARQLLSGIVQ QQNNLLRAIE

561 AQQHLLQLTV WGIKQLQARV LAVERYLKDQ QLLGIWGCSG KLICTTAVPW

611 NASWSNKSLD EIWNNMTWME WEREIDNYTG LIYTLIEESQ NQQEKNEQEL

661 LELDKWASLW NWFDITNWLW YIK
```

The fusion peptide consists of approximately the first 23 amino acids, Ala512-Ser534. The HR1 region has a plurality of contiguous 7 amino acid residue stretches or "heptads" (the 7 amino acids in each heptad designated "a" through "g"), with a predominance of hydrophobic residues at the first ("a") and fourth ("d") positions which interact homotypically to form the core of the 3-helix bundle structure. Neutral polar amino acids such as Glutamine may also occupy these positions. One representative heptad begins with Leu545. A highly conserved portion of HR1 consists of the 17 residues from Leu565 to Leu581, and is called "N17".

The C-terminal portion of gp41 comprises the HR2 region, which is believed to form an alpha helical structure during the fusion process, and bind into the grooves of the HR1 triple helical structure. HR2 also comprises heptads, though they do not interact homotypically but rather interact with amino acids from HR1. One representative heptad begins at Trp628.

HIV Fusion Peptide Inhibitor

The HIV fusion peptide inhibitor of the invention include but are not limited to the following sequences:

| HIV Fusion Peptide Inhibitor Sequence | SEQ ID NO |
|---|---|
| SEYEARIEALIRAAQEQQEKNEAALRELYKWAL | 372 |
| SEYEARIEALIRAAQEQQEKNEAALRELWKWAS | 373 |
| TIAEYAARIEALIRAAQEQQEKNEAALRELYKWAS | 374 |
| ARIEEYAARIEALIRAAQEQQEKNEAALRELYKWAS | 375 |
| SEYEARIEALIRAAQEQQEKNEAALRELYKWAS | 376 |
| TEYEARIEALIRAAQEQQEKNEAALRELKEWASIWN | 377 |
| SEYEARIEALIRAAQEQQEKNEAALRELDKWTGVWGNYEKV | 378 |
| SRIEALIRAAQEQQEKNEAALRELFKWAS | 379 |
| SRIEALIRAAQEQQQKNEAALRELDKWAS | 380 |
| SRIEALIRAAQEQQEKNEAALRELYKWAS | 381 |
| SRIEALIRAAQEQQEKNEAALRELLKWAS | 382 |
| SRIEALIRAAQEQQEKNEAALRELQKWAS | 383 |
| SRIEALIRAAQEQQEKNEAALRELDKWAS | 384 |
| AIAEYAARIEALIRAAQEQQEKNEAALRELDKWAS | 385 |
| TEYEARIEALIRAAQEQQEKNEAALRELDK | 386 |
| SRIEALIRAAQEQQEKNEAALRELYKWTS | 387 |
| SRIEALIRAAQEQQEKNEAALRELYKWASLWI | 388 |
| SRIEALIRAAQEQQEKNEAALRELYKWASRWN | 389 |
| SRIEALIRAAQEQQEKNEAALRELYKWASSWN | 390 |
| SRIEALIRAAQEQQEKNEAALRELYKWGS | 391 |
| SRIEALIRAAQEQQEKNEAALRELDK | 392 |

In some embodiments, the HIV fusion peptide inhibitor comprises an amino acid sequence at least 70%, 75%, 80%, 85%, 90%, 95%, 98%, 99% or 100% identical to any one of SEQ ID NOs: 372-392.

Figure 8:
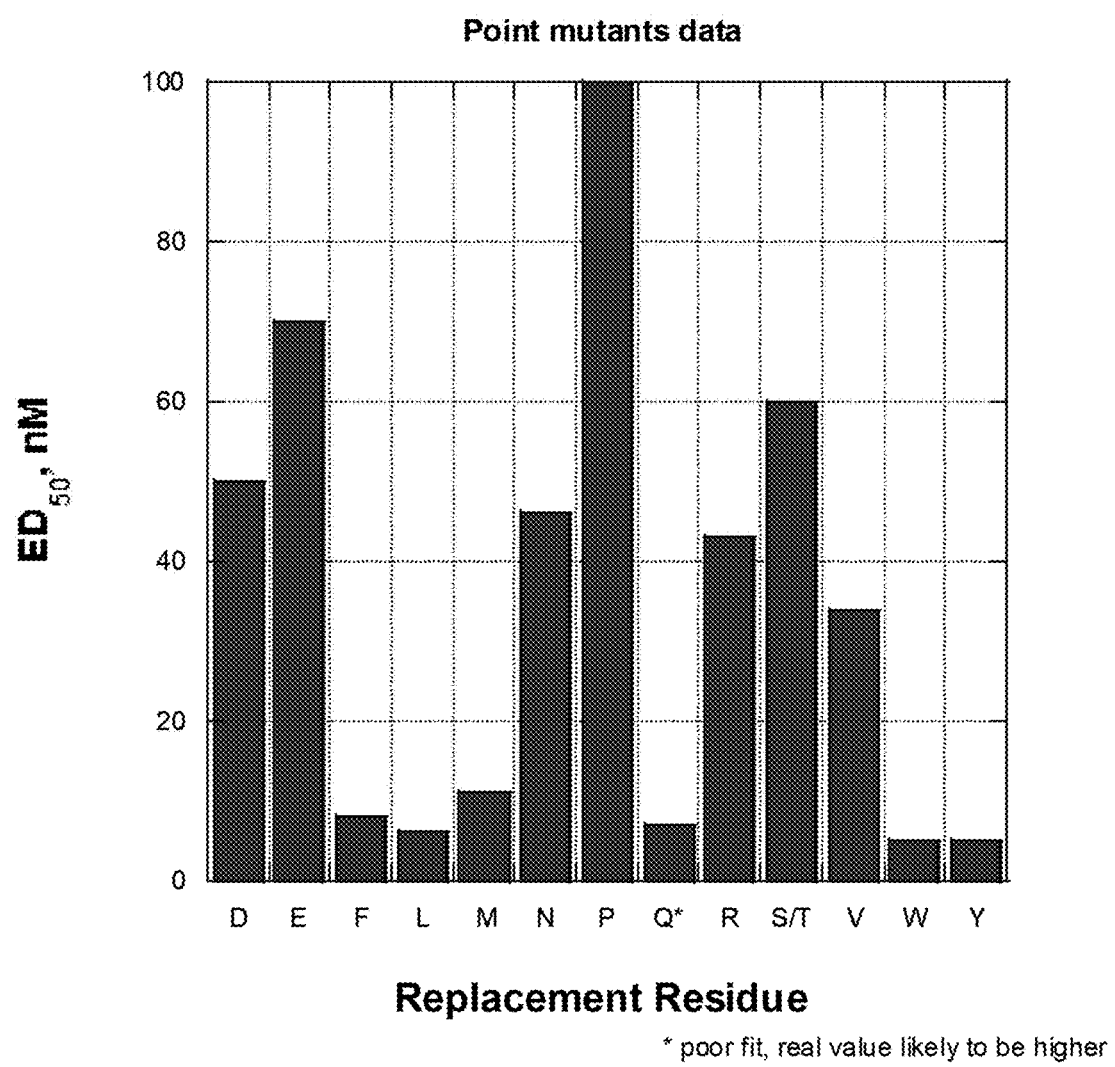
FIG. 8 shows point mutation data for the HIV fusion peptide inhibitor. The aspartic acid (D) near the C-terminus of the HIV fusion peptide inhibitor was replaced with the amino acids listed along the x axis.

Point mutations in the C-terminal region of the HIV fusion peptide inhibitor were seen to boost potency. In some embodiments, a hydrophobic replacement of the aspartic acid (D) near the C-terminus of the HIV fusion peptide inhibitor provided at least a 10× increase in potency (FIG. 8). In some embodiments, the HIV fusion peptide inhibitor comprises replacing "DK" with "YK", "LK", "FK" or "WK".

Other point mutation studies in the C-terminal region showed how the C-terminal amino acids "WAS" can be mutated with good effects on potency. In some embodiments, the HIV fusion peptide inhibitor comprises replacing C-terminal amino acids "WAS" to "WFS" or "WAL".

III. Linkers

The various components of the Combinectin of the invention may be covalently or non-covalently linked. In some embodiments, the PK moiety may be directly or indirectly linked to a Combinectin via a polypeptide linker.

Suitable linkers are those which allow the separate domains to fold independently of each other forming a three dimensional structure that permits high affinity binding to a target molecule.

The disclosure provides a number of suitable linkers that meet these requirements, including glycine-serine based linkers, glycine-proline based linkers. The Examples described herein demonstrate that the Combinectin domains joined via polypeptide linkers retain their target binding function. In some embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 393), $G(GS)_6$ (SEQ ID NO: 394), and $G(GS)_7G$ (SEQ ID NO: 395). Other linkers contain glutamic acid, and include, for example, $(GSE)_5$ (SEQ ID NO: 396) and GGSEGGSE (SEQ ID NO: 397). Other exemplary glycine-serine linkers include $(GS)_4$ (SEQ ID NO: 398), $(GGGGS)_7$ (SEQ ID NO: 399), $(GGGGS)_5$ (SEQ ID NO: 400), $(GGGGS)_4$ (SEQ ID NO: 401 $(GGGGS)_3G$ (SEQ ID NO: 402). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 403) and $(GP)_5G$ (SEQ ID NO: 404). In other embodiments, the linker may be a proline-alanine based linker having between 3 and 30, 10 and 30, and 3 and 20 amino acids in length. Examples of proline alanine based linkers include, for example, $(PA)_3$ (SEQ ID NO: 405), $(PA)_6$ (SEQ ID NO: 406) and $(PA)_9$ (SEQ ID NO: 407). In some embodiments, the linker is a glutamic acid-proline based linker. These linkers comprise glutamic acid and proline residues and may be between 3 and 30, 10 and 30, and 3 and 20 amino acids in length. Examples include linkers having an amino acid sequence ESPEPETPEDE (SEQ ID NO: 408) and $(ESPEPETPED)_2E$ (SEQ ID NO: 409). It is contemplated, that the optimal linker length and amino acid composition may be determined by routine experimentation by methods well known in the art.

Linkers or spacers, may be introduced at the N-terminus of the anti-CD4 moiety, the C-terminus of the anti-CD4 moiety, the N-terminus of the anti-gp41 moiety, the C-terminus of the anti-gp41 moiety, the N-terminus of the HIV fusion peptide inhibitor, or combinations thereof. In some embodiments the preferred linkers between the anti-CD4 Adnectin™ and anti-N17 Adnectin™ are short glutamine-proline rich linkers. In some embodiments the preferred linker between the anti-N17 Adnectin™ and HIV fusion peptide inhibitor are flexible glycine-serine rich linkers.

IV. Anti-N17 Adnectin™ Linked to a HIV Fusion Peptide Inhibitor Combinectin

The amino acid sequences of anti-N17 Adnectin™-HIV fusion peptide inhibitor Combinectin of the invention include but are not limited to those listed in Table 4 below. Table 4 also lists the antiviral $EC_{50}$ values for each anti-N17 Adnectin™-HIV fusion peptide inhibitor Combinectin.

TABLE 4

Anti-N17 Adnectin TM - HIV Fusion Peptide Inhibitor Combinectin

| SEQ ID NO | Anti-viral $EC_{50}$ (nM) | Anti-N17 Adnectin ™ - HIV Fusion Peptide Inhibitor Protein Sequence |
|---|---|---|
| 410 | 2 | MGHHHHHHGGSVSDVPRDLEVVAATPTSLLISWEYKVNAYRYYRITYGETGGNSPVQEFTVPSVLSTATISGLKPGVDYTITVYAVTYGVDSDPISINYRTEIDGGGGSGGGGSGGGGSGGGGARIEEYAARIEALIRAAQEQQEKNEAALRELYKWAS |
| 411 | 4342 | MGHHHHHHGGSVSDVPRDLEVVAATPTSLLISWEYKVNAYRYYRITYGETGGNSPVQEFTVPSVLSTATISGLKPGVDYTITVYAVTYGVDSDPISINYRTEIDGGGGSGGGGSGGGGSGGGGTIAEYAARIEALIRAAQEQQEKNEAALRELYKWAS |
| 412 | 2980 | MGHHHHHHGGSVSDVPRDLEVVAATPTSLLISWEYKVNAYRYYRITYGETGGNSPVQEFTVPSVLSTATISGLKPGVDYTITVYAVTYGVDSDPISINYRTEIDGGGGSGGGGSGGGGSGGGGSEYEARIEALIRAAQEQQEKNEAALRELYKWAS |
| 413 | 6 | MGHHHHHHGVSDVPRDLEVVAATPTSLLISWKYKVHPYRYYRITYGETGGNSPVQEFTVPSVLSTATISGLKPGVDYTITVYAVTYGVNSLPISINYRTEIDGGGGSGGGGSGGGGSGGGGTEYEARIEALIRAAQEQQEKNEAALRELKEWASIWN |
| 414 | 4 | MGHHHHHHTSGVSDVPRDLEVVAATPTSLLISWDAPAVTVGWYHIGYNVEGEPASYQYFRVPGSKSTATISGLKPGVEYMIFVNAVTGSGAREEFSLPISINYRTEIDGGGGSGGGGSGGGGSGGGGSEYEARIEALIRAAQEQQEKNEAALRELDKWTGVWGNYEKV |
| 415 | >1,000 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELFKWAS |
| 416 | >1,000 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQQKNEAALRELDKWAS |
| 417 | 428 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWAS |
| 418 | 218 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELLKWAS |
| 419 | >1,000 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELQKWAS |
| 420 | 8 | MGHHHHHHGGSVSDVPRDLEVVAATPTSLLISWEYKVHPYRYYRITYGETGGNSPVQEFTVPSVLSTATISGLKPGVDYTITVYAVTYGDDSAPISINYRTEIDGGGGSGGGGSGGGGSGGGGSRIEALIRAAQEQQEKNEAALRELDKWAS |
| 421 | 50 | MGHHHHHHGVSDVPRDLEVVAATPTSLLISWVAGAEDYQYYRITYGETGGNSPVQEFTVPHDLVTATISGLKPGVDYTITVYAVTDMMHVEYTEHPISINYRTEIDGGGGSGGGGSGGGGSGGAIAEYAARIEALIRAAQEQQEKNEAALRELDKWAS |
| 422 | 3 | MGHHHHHHGVSDVPRDLEVVAATPTSLLISWKYKVHPYRYYRITYGETGGNSPVQEFTVPSVLSTATISGLKPGVDYTITVYAVTYGVNSLPISINYRTEIDGGGGSGGGGSGGGGSGGGGTEYEARIEALIRAAQEQQEKNEAALRELDK |
| 423 | 122 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWTS |
| 424 | 39 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWASLWI |
| 425 | 523 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWASRWN |
| 426 | 139 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWASSWN |
| 427 | 143 | MGHHHHHHGVSDVPRDLEVVAATPTSLLISWDAPAVTVRYYRITYGETGGNSPVQEFTVPGSKSTATISGLKPGVDYTITVYAVTGRGESPASSKPISINYRTEIDGGGGSGGGGSGGGGSGGGGSRIEALIRAAQEQQEKNEAALRELYKWGS |
| 428 | 50 | MGHHHHHHGVSDVPRDLEVVAATPTSLLISWEYKVNNYRYYRITYGETGGNSPVQEFTVPSVLSTATISGLKPGVDYTITVYAVTVGVHSSPISINYRTEIDGGGGSGGGGSGGGGSGGGGSRIEALIRAAQEQQEKNEAALRELDK |

In some embodiments, the anti-N17 Adnectin™-HIV fusion peptide inhibitor Combinectin or fusion proteins thereof comprise an amino acid sequence at least 70%, 75%, 80%, 85%, 90%, 95%, 98%, 99% or 100% identical to the non-linker regions of any one of SEQ ID NOs: 410-428.

In some embodiments, the anti-N17 Adnectin™-HIV fusion peptide inhibitor Combinectin or fusion proteins thereof comprise an amino acid sequence at least 70%, 75%, 80%, 85%, 90%, 95%, 98%, 99% or 100% identical to the non-linker regions of any one of SEQ ID NOs: 410-428, excluding any N-terminus extended region.

In other embodiments, anti-N17 Adnectin™-HIV fusion peptide inhibitor Combinectin comprises an anti-N17 Adnectin™ comprising an amino acid sequence at least 80%, 85%, 90%, 95%, 98%, 99% or 100% identical to the BC loop, DE loop and FG loop regions of SEQ ID NOs: 410-428.

In other embodiments, the anti-N17 Adnectin™-HIV fusion peptide inhibitor Combinectin comprises a HIV fusion peptide inhibitor comprising an amino acid sequence at least 80%, 85%, 90%, 95%, 98%, 99% or 100% identical to the HIV fusion peptide inhibitor of SEQ ID NOs: 410-428.

V. Anti-CD4 Adnectin™ Linked to an Anti-N17 Adnectin™ Linked to a HIV Fusion Peptide Inhibitor Combinectin The anti-CD4 Adnectin™ linked to an anti-N17 Adnectin™ linked to a HIV fusion peptide inhibitor Combinectin of the invention include but are not limited to the following sequences:

```
Combinectin 3137
                                       (SEQ ID NO: 3)
GVSDVPRDLEVVAATPTSLLISWDAPAVTVHSYHIQYWPLGSYQRYQ

VFSVPGSKSTATISGLKPGVEYQIRVYAETGRGESDQSLGWIQIGYR

TEESPEPETPEDEGVSDVPRDLEVVAATPTSLLISWQYKVHPYRYYR

ITYGETGGNSPVQEFTVPSVLSTAEISGLKPGVDYTITVYAVTRGVD

SAPISINYRTPGGGGSGGGGSGGGGSGGGGSEYEARIEALIRAAQEQ

QEKNEAALRELYKWAL

Combinectin 3151
                                       (SEQ ID NO: 5)
GVSDVPRDLEVVAATPTSLLISWDAPAVTVHSYHIQYWPLGSYQRYQ

VFSVPGSKSTATISGLKPGVEYQIRVYAETGRGESDQSLGWIQIGYR

TEESPEPETPEDEGVSDVPRDLEVVAATPTSLLISWEYNVNPYRYYR

ITYGETGGNSPVQEFTVPSVLSSAQISGLKPGVDYTITVYAVTRGVD

SAPISINYRTPGGGSGGGGSGGGGSGGGGSEYEARIEALIRAAQEQ

QEKNEAALRELWKWAS

Combinectin 3191
                                       (SEQ ID NO: 7)
GVSDVPRDLEVVAATPTSLLISWDAPAVTVHSYHIQYWPLGSYQRYQ

VFSVPGSKSTATISGLKPGVEYQIRVYAETGRGESDQSLGWIQIGYR

TPESPEPETPEDEGVSDVPRDLEVVAATPTSLLISWEYKVHPYRYYR

ITYGETEGGNSPVQEFTVPSVLSSAEISGLKPGVDYTITVYAVTYGI

DSPPISINYRTEGGGSGGGGSGGGGSGGGGSEYEARIEALIRAAQE

QQEKNEAALRELYKWAL

Combinectin 3202
                                       (SEQ ID NO: 9)
GVSDVPRDLEVVAATPTSLLISWDAPAVTVHSYHIQYWPLGSYQRYQ

VFSVPGSKSTATISGLKPGVEYQIRVYAETGGADSDQSFGWIQIGYR
```

```
-continued
TPESPEPETPEDEGVSDVPRDLEVVAATPTSLLISWEYKVHPYRYYR

ITYGETGGNSPVQEFTVPSVLSTAEISGLKPGVDYTITVYAVTRGVD

SAPISINYRTPGGGGSGGGGSGGGGSGGGGTIAEYAARIEALIRAAQ

EQQEKNEAALRELYKWAS
```

In the sequences above, the anti-CD4 Adnectin™ sequences are underlined. The anti-N17 Adnectin™ sequences are double underlined. The HIV fusion peptide inhibitor sequences are underlined in bold. The linker sequences are italicized.

In some embodiments, the Combinectin or fusion proteins thereof comprises an amino acid sequence at least 70%, 75%, 80%, 85%, 90%, 95%, 98%, 99% or 100% identical to any one of SEQ ID NOs: 3, 5, 7 and 9.

In some embodiments, the Combinectin or fusion proteins thereof comprises an amino acid sequence at least 70%, 75%, 80%, 85%, 90%, 95%, 98%, 99% or 100% identical to the non-linker regions of any one of SEQ ID NOs: 3, 5, 7 and 9.

In other embodiments, the Combinectin comprises an anti-CD4 Adnectin™ comprising an amino acid sequence at least 80%, 85%, 90%, 95%, 98%, 99% or 100% identical to the CD loop and FG loop regions of SEQ ID NOs: 3, 5, 7 and 9.

In other embodiments, the Combinectin comprises an anti-N17 Adnectin™ comprising an amino acid sequence at least 80%, 85%, 90%, 95%, 98%, 99% or 100% identical to the BC loop, DE loop and FG loop regions of SEQ ID NOs: 3, 5, 7 and 9.

In other embodiments, the Combinectin comprises a HIV fusion peptide inhibitor comprising an amino acid sequence at least 80%, 85%, 90%, 95%, 98%, 99% or 100% identical to the HIV fusion peptide inhibitor of SEQ ID NOs: 3, 5, 7 and 9.

VI. Pharmacokinetic Moieties

In one aspect, the application provides for an anti-CD4 moiety, an anti-gp41 moiety, a HIV fusion peptide inhibitor and combinations thereof further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The Combinectin of the invention may be attached to a moiety that reduces the clearance rate of the polypeptide in a mammal (e.g., mouse, rat, or human) by at least two-fold, at least 10-fold, at least 20-fold, at least 30-fold, at least 40-fold, at least 50-fold, at least 60-fold, at least 70-fold, at least 80-fold, at least 90-fold, at least 100-fold relative to the unmodified Combinectin. Other measures of improved pharmacokinetics may include serum half-life, which is often divided into an alpha phase and a beta phase. Either or both phases may be improved significantly by addition of an appropriate moiety. For example, the PK moiety may increase the serum half-life of the polypeptide by more than 5%, 10%, 20%, 30%, 40%, 50%, 60%, 70%, 80%, 90%, 100%, 120%, 150%, 200%, 400%, 600%, 800%, 1000% or more relative to the Combinectin alone.

Moieties that slow clearance of a protein from the blood, herein referred to as "PK moieties", include polyoxyalkylene moieties (e.g., polyethylene glycol), sugars (e.g., sialic acid), and well-tolerated protein moieties (e.g., Fc and fragments and variants thereof, transferrin, or serum albumin). The Combinectin of the invention may also be fused to albumin or a fragment (portion) or variant of albumin as described in U.S. Publication No. 2007/0048282, or may be fused to one or more Adnectins™ or other moieties that bind serum albumin, Fc, or transferrin.

Other PK moieties that can be used in the invention include those described in Kontermann et al., (*Current Opinion in Biotechnology*, 22:868-876 (2011)), herein incorporated by reference. Such PK moieties include, but are not limited to, human serum albumin fusions, human serum albumin conjugates, human serum albumin binders (e.g., Adnectin™ PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the invention provides a Combinectin fused to a PK moiety that is a polymeric sugar. In some embodiments, the PK moiety is a polyethylene glycol moiety or an Fc region. In some embodiments the PK moiety is a serum albumin binding protein such as those described in U.S. Publication Nos. 2007/0178082 and 2007/0269422. In some embodiments the PK moiety is human serum albumin. In some embodiments, the PK moiety is transferrin.

The Fc fusion-Combinectin of the invention include the sequences shown in 3137 (SEQ ID NO: 4) and 3151 (SEQ ID NO: 6) of FIG. 2.

In some embodiments, the Fc fusion-Combinectin or fusion proteins thereof comprises an amino acid sequence at least 70%, 75%, 80%, 85%, 90%, 95%, 98%, 99% or 100% identical to any one of SEQ ID NOs: 4 and 6.

In some embodiments, the Fc fusion-Combinectin or fusion proteins thereof comprises an amino acid sequence at least 70%, 75%, 80%, 85%, 90%, 95%, 98%, 99% or 100% identical to the non-linker regions of any one of SEQ ID NOs: 4 and 6.

In other embodiments, the Fc fusion-Combinectin comprises an anti-CD4 Adnectin™ comprising an amino acid sequence at least 80%, 85%, 90%, 95%, 98%, 99% or 100% identical to the CD loop and FG loop regions of SEQ ID NOs: 4 and 6.

In other embodiments, the Fc fusion-Combinectin comprises an anti-N17 Adnectin™ comprising an amino acid sequence at least 80%, 85%, 90%, 95%, 98%, 99% or 100% identical to the BC loop, DE loop and FG loop regions of SEQ ID NOs: 4 and 6.

In other embodiments, the Fc fusion-Combinectin comprises a fusion peptide inhibitor comprising an amino acid sequence at least 80%, 85%, 90%, 95%, 98%, 99% or 100% identical to the HIV fusion peptide inhibitor of SEQ ID NOs: 4 and 6.

The HSA fusion-Combinectin of the invention include the sequences shown in 3191 (SEQ ID NO: 8) and 3202 (SEQ ID NO: 10) of FIG. 2.

In some embodiments, the HSA fusion—Combinectin or fusion proteins thereof comprises an amino acid sequence at least 70%, 75%, 80%, 85%, 90%, 95%, 98%, 99% or 100% identical to any one of SEQ ID NOs: 8 and 10.

In some embodiments, the HSA fusion-Combinectin or fusion proteins thereof comprises an amino acid sequence at least 70%, 75%, 80%, 85%, 90%, 95%, 98%, 99% or 100% identical to the non-linker regions of any one of SEQ ID NOs: 8 and 10.

In other embodiments, the HSA fusion-Combinectin comprises an anti-CD4 Adnectin™ comprising an amino acid sequence at least 80%, 85%, 90%, 95%, 98%, 99% or 100% identical to the CD loop and FG loop regions of SEQ ID NOs: 8 and 10.

In other embodiments, the HSA fusion-Combinectin comprises an anti-N17 Adnectin™ comprising an amino acid sequence at least 80%, 85%, 90%, 95%, 98%, 99% or 100% identical to the BC loop, DE loop and FG loop regions of SEQ ID NOs: 8 and 10.

In other embodiments, the HSA fusion-Combinectin comprises a fusion peptide inhibitor comprising an amino acid sequence at least 80%, 85%, 90%, 95%, 98%, 99% or 100% identical to the HIV fusion peptide inhibitor of SEQ ID NOs: 8 and 10.

Polyethylene Glycol

In some embodiments, the anti-CD4 moiety, anti-gp41 moiety, HIV fusion peptide inhibitor and combinations thereof comprises polyethylene glycol (PEG). PEG is a well-known, water soluble polymer that is commercially available or can be prepared by ring-opening polymerization of ethylene glycol according to methods well known in the art (Sandler et al., Polymer Synthesis, Vol. 3, pp. 138-161, Academic Press, New York). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$, where n is 20 to 2300 and X is H or a terminal modification, e.g., a $C_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Published Application No. 473084A and U.S. Pat. No. 5,932,462.

One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop or strand residue positioned on a face of the polypeptide opposite the target-binding site; d) between the C-terminus and the most C-terminal beta strand or beta-like strand; e) within a linker sequence connecting two binding domains, and f) at the C-terminus.

PEGylation may be achieved by site-directed PEGylation, wherein a suitable reactive group is introduced into the protein to create a site where PEGylation preferentially occurs. In some embodiments, the protein is modified to introduce a cysteine residue at a desired position, permitting site-directed PEGylation on the cysteine. Mutations may be introduced into a protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework, based on which binding polypeptides are designed and evolved, has been solved (see Himanen et al., Nature, 414:933-938 (2001)) and thus the surface-exposed residues identified. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky, S. et al., "Use of Functionalized Poly(Ethylene Glycols) for Modification of Polypeptides" in Harris, J. M., *Polyethylene Glycol Chemistry: Biotechnical and Biomedical Applications*, Plenus Press, New York (1992), and in Zalipsky, *Advanced Drug Reviews*, 16:157-182 (1995).

PEG may vary widely in molecular weight and may be branched or linear. Typically, the weight-average molecular weight of PEG is from about 100 Daltons to about 150,000 Daltons. Exemplary weight-average molecular weights for PEG include about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In other embodiments, the PEG has four branches. In another embodiment, the PEG is a bis-PEG (NOF Corporation, DE-200MA), to which two Adnectins™ are conjugated.

Conventional separation and purification techniques known in the art can be used to purify PEGylated Adnectin™, such as size exclusion (e.g., gel filtration) and ion exchange chromatography. Products may also be separated using SDS-PAGE. Products that may be separated include mono-, di-, tri-, poly- and un-PEGylated Adnectins™, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated anti-CD4 moiety, anti-gp41 moiety, HIV fusion peptide inhibitor and combinations thereof will preferably retain at least about 25%, 50%, 60%, 70%, 80%, 85%, 90%, 95% or 100% of the biological activity associated with the unmodified anti-CD4 moiety, anti-gp41 moiety, Adnectin™ or Combinectin. In some embodiments, biological activity refers to its ability to bind to CD4 or gp41, as assessed by $K_d$, $k_{on}$, or $k_{off}$. In some embodiments, the PEGylated anti-CD4 moiety, anti-gp41 moiety, Adnectin™ or Combinectin thereof shows an increase in binding to CD4 or gp41 relative to unPEGylated anti-CD4 moiety, anti-gp41 moiety, Adnectin™ or Combinectin.

Immunoglobulin Fc Domain (and Fragments)

In some embodiments, the peptide of the invention is fused to an immunoglobulin Fc domain, or a fragment or variant thereof. As used herein, a "functional Fc region" is an Fc domain or fragment thereof which retains the ability to bind FcRn. In some embodiments, a functional Fc region binds to FcRn, but does not possess effector functions. The ability of the Fc region or fragment thereof to bind to FcRn can be determined by standard binding assays known in the art. In other embodiments, the Fc region or fragment thereof binds to FcRn and possesses at least one "effector function" of a native Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an anti-CD4 or ant-N-17 Adnectin™) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

In an exemplary embodiment, the Fc domain is derived from an IgG1 subclass, however, other subclasses (e.g., IgG2, IgG3, and IgG4) may also be used. Shown below is the sequence of a human IgG1 immunoglobulin Fc domain:

```
                                              (SEQ ID NO: 11)
DKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWL

NGKEYKCKVSNKALPAPIEKTISKAKGQPREPQVYTLPPSREEMTKN

QVSLTCLVKGFYPSDIAVEWESNGQPENNYKTTPPVLDSDGSFFLYS

KLTVDKSRWQQGNVFSCSVMHEALHNHYTQKSLSLSPGK
```

The core hinge sequence is underlined, and the CH2 and CH3 regions are in regular text. It should be understood that the C-terminal glycine and lysine are optional in the Combinectin of the invention.

The fusion may be formed by attaching an Adnectin™ of the invention to either end of the Fc molecule, i.e., Fc-Adnectin™ or Adnectin™-Fc arrangements. In certain embodiments, the Fc and Adnectin™ are fused via a linker.

In some embodiments, the Fc region used in the Adnectin™ fusion comprises the hinge region of an Fc molecule. As used herein, the "hinge" region comprises the core hinge residues spanning positions 1-16 of SEQ ID NO: 11 (DKTHTCPPCPAPELLG; SEQ ID NO: 12) of the IgG1 Fc region. In certain embodiments, the Adnectin™-Fc fusion adopts a multimeric structure (e.g., dimer) owing, in part, to the cysteine residues at positions 6 and 9 of SEQ ID NO: 11 within the hinge region.

In certain embodiments, an Adnectin-Fc fusion may have the following configurations: 1) Adnectin™-hinge-Fc or 2) hinge-Fc-Adnectin™. Therefore, any Adnectin™ of the present invention can be fused to an Fc region comprising a hinge sequence according to these configurations. In some embodiments, a linker may be used to join the Adnectin™ to the hinge-Fc moiety, for example, an exemplary fusion protein may have the configuration Adnectin™-linker-hinge-Fc or hinge-Fc-linker-Adnectin™ Additionally, depending on the system in which the fusion polypeptide is produced, a leader sequence may be placed at the N-terminus of the fusion polypeptide. For example, if the fusion is produced in a mammalian system, a leader sequence may be added to the N-terminus of the fusion molecule. If the fusion is produced in *E. coli*, the fusion sequence will be preceded by a methionine.

VII. Nucleic Acid-Protein Fusion Technology

In one aspect, the invention provides an Adnectin™ comprising fibronectin type III domains that binds CD4 or the n17 domain of gp41. One way to rapidly make and test Fn3 domains with specific binding properties is the nucleic acid-protein fusion technology. This disclosure utilizes the in vitro expression and tagging technology, termed 'PROfusion' which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018 and 6,818,418; Roberts et al., *Proc. Natl. Acad. Sci.*, 94:12297-12302 (1997); and Kurz et al., *Molecules*, 5:1259-1264 (2000), all of which are herein incorporated by reference.

VIII. Vectors and Polynucleotides

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See, for example, Mayfield et al., *Proc. Natl. Acad. Sci. USA*, 100(2):438-442 (Jan. 21, 2003); Sinclair et al., *Protein Expr. Purif.*, 26(I):96-105 (October 2002); Connell, N. D., *Curr. Opin. Biotechnol.*, 12(5):446-449 (October 2001); Makrides et al., *Microbiol. Rev.*, 60(3):512-538 (September 1996); and Sharp et al., *Yeast*, 7(7):657-678 (October 1991).

General techniques for nucleic acid manipulation are described in, for example, Sambrook et al., *Molecular Cloning: A Laboratory Manual, Second Edition*, Vols. 1-3, Cold Spring Harbor Laboratory Press (1989), or Ausubel, F. et al., *Current Protocols in Molecular Biology*, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding site, and sequences that control the termination of transcription and translation. The ability to replicate in a host, usually conferred by an origin of replication, and a selection gene to facilitate recognition of transformants is additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders.

For yeast secretion the native signal sequence may be substituted by, e.g., a yeast invertase leader, a factor leader (including *Saccharomyces* and *Kluyveromyces* alpha-factor leaders), or acid phosphatase leader, the *C. albicans* glucoamylase leader, or the signal sequence described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein of the invention. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding protein of the invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein of the invention. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include, but are not limited to, a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, Elsevier, New York (1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (*Bio/Technology*, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

IX. Protein Production

The present invention is also directed to cell lines that express a Combinectin or fusion protein thereof. Creation and isolation of cell lines producing a Combinectin can be accomplished using standard techniques known in the art, such as those described herein.

Host cells are transformed with the herein-described expression or cloning vectors for protein production and cultured in conventional nutrient media modified as appropriate for inducing promoters, selecting transformants, or amplifying the genes encoding the desired sequences. In the examples shown here, the host cells used for high-throughput protein production (HTPP) and mid-scale production were those from the HMS174-bacterial strain.

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma)) are suitable for culturing the host cells. In addition, many of the media described in Ham et al., *Meth. Enzymol.*, 58:44 (1979), Barites et al., *Anal. Biochem.*, 102:255 (1980), U.S. Pat. Nos. 4,767,704, 4,657,866, 4,927,762, 4,560,655, 5,122,469, 6,048,728, 5,672,502, or U.S. Patent No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-free translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Proteins of the invention can also be produced by chemical synthesis (e.g., by the methods described in *Solid Phase Peptide Synthesis*, Second Edition, The Pierce Chemical Co., Rockford, Ill. (1984)). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 98% pure. Regardless of the exact numerical value of the purity, the polypeptide is sufficiently pure for use as a pharmaceutical product.

X. Biophysical and Biochemical Characterization

Binding of the protein of the invention to a target molecule (e.g., CD4 or gp41) may be assessed in terms of equilibrium constants (e.g., dissociation, $K_d$) and in terms of kinetic constants (e.g., on-rate constant, $k_{on}$ and off-rate constant, $k_{off}$). The protein of the invention will generally bind to a target molecule with a $K_d$ of less than 500 nM, 100 nM, 10 nM, 1 nM, 500 pM, 200 pM, or 100 pM, although higher $K_d$ values may be tolerated where the $k_{off}$ is sufficiently low or the $k_{on}$ is sufficiently high.

In Vitro Assays for Binding Affinity

Proteins that bind CD4 or gp41 can be identified using various in vitro assays. Preferably, the assays are high-throughput assays that allow for screening multiple candidates simultaneously.

In some embodiments, biomolecular interactions can be monitored in real time with the BIACORE® system, which uses SPR to detect changes in the resonance angle of light at the surface of a thin gold film on a glass support due to changes in the refractive index of the surface up to 300 nm away. BIACORE® analysis generates association rate constants, dissociation rate constants, equilibrium dissociation constants, and affinity constants. Binding affinity is obtained by assessing the association and dissociation rate constants using a BIACORE® surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_d$'s are calculated from SPR measurements as $k_{off}/k_{on}$.

In some embodiments, the Combinectin of the invention exhibit a $K_d$ of 100 nM or less. Preferably, the $K_d$ is 10 nM or less. More preferably, the $K_d$ is 1 nM or less.

In some embodiments, the Combinectin of the invention exhibit an $IC_{50}$ of 5 nM or less, 4 nM or less, 3 nM or less, 2.5 nM or less, 2 nM or less, 1.5 nM or less, 1 nM or less, 0.5 nM or less, 0.2 nM or less, or 0.1 nM or less. Preferably, the $IC_{50}$ is 1.5 nM or less. More preferably, the $IC_{50}$ is 0.5 nM or less.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the Combinectin of the invention.

In the present invention, ELISA assays were utilized for identifying Adnectins™ that bind to CD4 or gp41, with affinities determined by BIACORE® SPR. FACS assays were also used to determine the $EC_{50}$ of binding of the CD4 Adnectin™ (alone and as part of the full Combinectin) to CD4 as presented naturally on T-cell surfaces. Peptide affinities were measured by BIACORE® SPR.

As described in Table 5 below, the range of binding affinities (by SPR) for CD4 Adnectins™ to CD4 was 0.3 nM to 140 nM; the range for N17 Adnectin™ binding to artificial gp41-based targets was 0.5 nM to 40 nM; the range for peptide binding was 0.2 nM to 70 nM. SPR-based affinities for the Combinectin of the invention and for the individual components thereof are shown in Table 5 below.

TABLE 5

Binding Affinities for Combinectin and Individual Components

| Protein | ID | Target | $K_{on}$ (1/Ms) | $K_{off}$ (1/s) | $K_d$ (nM) |
|---|---|---|---|---|---|
| CD4 Adnectin™ | ADX_6940_B01 | CD4 | 1.9E+05 | 7.6E−04 | 4 |
| N17 Adnectin™ | ADX_6200_A08 | gp41 (IZN24) | 7.0E+06 | 3.3E−03 | 0.5 |
| peptide | 203613-24 | gp41 (PRD-828) | 2.3E+06 | 2.5E−04 | 0.1 |
| HSA-Combinectin | BMT-180280 | CD4 | 7.6E+03 | 8.3E−04 | 109 |
| HSA-Combinectin | BMT-180280 | gp41 (IZN24) | 8.1E+05 | 1.7E−03 | 2 |
| HSA-Combinectin | BMT-180280 | gp41 (PRD-828) | 9.6E+05 | 1.8E−04 | 0.2 |

In Vitro Assays for Inhibition Activity

Various art-recognized in vitro systems exist that allow for examination of the potency of the Combinectin (or of individual inhibitors or combinations thereof) against HIV-1 infection. These include systems that allow for complete replication of laboratory-derived virus or clinical isolates of various strains in cultured cells or peripheral blood monocyte cultures. In addition, systems that recapitulate the early cell entry stages of infection, without using viable virus, could be used to analyze the effectiveness of the Combinectin, individual inhibitors or combinations thereof. These include, but are not limited to, "pseudotyped" viruses that contain deletions that make them unable to produce infectious virions or cells that express only the HIV gp160 gene that can be used to monitor the HIV-1specific fusion reaction to target cells.

In Vivo Models

One skilled in the art would know of various art-recognized animal models that allow for replication and in some cases recapitulate the symptoms of HIV infection. These models can be used to test the efficacy of the Combinectin, individual inhibitors or combinations thereof of the invention.

XI. Therapeutic Applications

In one aspect, the present invention provides Combinectins useful for the treatment of HIV. Accordingly, in certain embodiments the invention provides methods for attenuating or inhibiting HIV fusion in a subject comprising administering an effective amount of the Combinectin of the invention to a subject. In some embodiments, the subject is a human. In some embodiments, the Combinectin of the invention is pharmaceutically acceptable to a mammal, in particular a human. A "pharmaceutically acceptable" polypeptide refers to a polypeptide that is administered to an animal without significant adverse medical consequences.

In some embodiments, the Combinectin of the present invention will be administered to a subject in combination (concurrently or separately) with an agent known in the art to be useful for the particular disorder or disease being treated.

In some embodiments, the target patient population for Combinectin therapy is one that is not amenable to standard therapy for the disease being treated due to, e.g., age, pre-existing conditions, genetic makeup, and/or co-morbidities. The Combinectin of the invention can serve as an alternative to existing therapies that are associated with substantial side effects or safety concerns.

In some embodiments, the target patient population for Combinectin therapy is comprised of uninfected individuals at high risk of infection, due to lifestyle or other aggravating factors. The Combinectin is used to protect these individuals from getting infected by HIV (pre-exposure prophylaxis).

XII. Pharmaceutical Compositions

The present invention further provides pharmaceutical compositions comprising a Combinectin or fusion proteins thereof described herein, wherein the composition is essentially endotoxin free, or at least contain no more than acceptable levels of endotoxins as determined by the appropriate regulatory agency (e.g., FDA).

Compositions of the present invention can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration, or an atomizable suspension suitable for inhaled or intranasal administration.

Methods well known in the art for making compositions are found, for example, in Gennaro, A. R., ed., *Remington: The Science and Practice of Pharmacy,* 20th Edition, Lippincott Williams & Wilkins, Philadelphia, Pa. (2000). Compositions for parenteral administration may, for example, contain excipients, sterile water, saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Nanoparticulate compositions (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the composition varies depending upon a number of factors, including the dosage of the drug to be administered, and the route of administration.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Osol, A., ed., *Remington's Pharmaceutical Sciences,* 16th Edition (1980).

Sustained-release preparations may be prepared. Suitable examples of sustained-release preparations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins of the invention may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Compositions of the present invention for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Compositions for oral use may also be provided as chewable tablets, or as hard gelatin capsules wherein the active ingredient is mixed with an inert solid diluent, or as soft gelatin capsules wherein the active ingredient is mixed with water or an oil medium.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

The compositions herein may also contain more than one active compound as necessary for the particular indication being treated, preferably those with complementary activities that do not adversely affect each other. Such molecules are suitably present in combination in amounts that are effective for the purpose intended.

XIII. Administration

A pharmaceutical composition comprising a Combinectin or fusion protein thereof of the present invention can be administered to a subject with HIV using standard administration techniques including oral, parenteral, pulmonary, transdermal, intramuscular, intranasal, buccal, sublingual, or suppository administration. Preferably, administration of the Combinectins of the invention is parenteral. The term parenteral as used herein includes intravenous, intramuscular, subcutaneous, rectal, vaginal, or intraperitoneal administration. Peripheral systemic delivery by intravenous or intraperitoneal or subcutaneous injection is preferred.

A therapeutically effective dose refers to a dose that produces the therapeutic effects for which it is administered. An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient.

For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment, and may be ascertained using standard techniques. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. In general, the Combinectin of the present invention are administered at about 0.01 mg/kg to about 50 mg/kg per day, preferably about 0.01 mg/kg to about 30 mg/kg per day, most preferably about 0.01 mg/kg to about 20 mg/kg per day. In some embodiments, the Combinectin of the present invention are administered at weekly dosages of about 0.01 mg/kg to about 10 mg/kg, more preferably about 0.01 to about 5 mg/kg, most preferably about 0.01 to about 1 mg/kg. Alternatively, the Combinectin of the invention are administered at about 15 to about 100 mg/week, from about 20 to about 80 mg/week, from about 20 to about 60 mg/week, or about 20 to about 25 mg/week.

The frequency of dosing will depend upon the pharmacokinetic parameters of the binding agent molecule in the formulation used. Typically, a composition is administered until a dosage is reached that achieves the desired effect. The composition may therefore be administered as a single dose or as multiple doses (at the same or different concentrations/dosages) over time, or as a continuous infusion. Further refinement of the appropriate dosage is routinely made. Appropriate dosages may be ascertained through use of appropriate dose-response data. For example, the Combinectin may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art. The Combinectin is suitably administered to the patient at one time or over a series of treatments.

Administration of a Combinectin or a fusion thereof, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being administered.

XIV. Kits and Articles of Manufacture

The Combinectin of the invention can be provided in a kit, a packaged combination of reagents in predetermined amounts with instructions for use in the therapeutic or diagnostic methods of the invention.

For example, in one embodiment of the invention, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of the invention which is effective for treating HIV and may have a sterile access port (for example, the container may be an intravenous solution bag or a vial having a stopper pierceable by a hypodermic injection needle). The active agent in the composition is a Combinectin of the invention. The label on, or associated with, the container indicates that the composition is used for treating HIV. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

INCORPORATION BY REFERENCE

All documents and references, including patent documents and websites, described herein are individually incorporated by reference to into this document to the same extent as if there were written in this document in full or in part.

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

EXAMPLES

Example 1—Combinectin Production/Purification

HIV Combinectin Tandem—Bacterial

Transformed DNA into BL21(DE3) bacterial cells.

Cells grown up in bacterial culture at ~37° C. to a target $OD_{600}$

Culture temperature dropped to ~30° C., and culture is induced with IPTG and harvested after several hours.

Harvest is performed using a centrifuge.

Recovery of protein is performed using a chemical lysis and a MICROFLUIDIZER®, followed by clarification by centrifugation or tangential flow filtration. Lysate is processed immediately or frozen for later use.

Purification by Hydrophobic Interaction Chromatography followed by hydroxyapatite chromatography and/or ion exchange chromatography. Formulated and concentrated using tangential flow filtration.

HIV Combinectin-Fc Construct; Mammalian Cell Culture

DNA is transfected into appropriate mammalian cells.

Cells grown in cell culture.

Harvested by centrifugation and/or filtration.

Purification using affinity chromatography and ion exchange chromatography.

Formulated and concentrated using tangential flow filtration.

HIV Combinectin-HuSA construct; Mammalian Cell Culture

DNA is transfected into appropriate mammalian cells.

Cells grown in cell culture.

Harvested by centrifugation and/or filtration.

Purification by Hydrophobic Interaction Chromatography followed by hydroxyapatite chromatography and/or ion exchange chromatography.

Formulated and concentrated using tangential flow filtration.

Example 2—Combinectin Potency Assay

MT-2 cells, HEK 293T cells and the proviral DNA clone of NU-3 were obtained from the NIH AIDS Research and Reference Reagent Program. MT-2 cells were propagated in RPMI 1640 medium supplemented with 10% heat-inactivated fetal bovine serum (FBS), 10 mM HEPES buffer pH 7.55, and 2 mM L-glutamine. HEK 293T cells were propagated in DMEM media supplemented with 10% heat-inactivated FBS, 10 mM HEPES buffer pH 7.55 and 2 mM L-glutamine. Recombinant NL-Rluc virus, in which a section of the nef gene from the proviral clone of $NL_{4-3}$ was replaced with the *Renilla* luciferase gene, was constructed at Bristol-Myers Squibb. The replication-competent virus was harvested 3 days after transfection of HEK 293T cells with the modified pNL-Rluc proviral clone. Transfections were performed using Lipofectamine Plus (Invitrogen, Carlsbad, Calif.), according to manufacturer's instruction. Virus was titered in MT-2 cells using luciferase enzyme activity as a biomarker. The NL-Rluc virus used to infect MT-2 cells a multiplicity of 0.01 for 1 hour before adding to the peptides in 96-well plates. Peptides were serially diluted three-fold and 11 concentrations were plated in triplicate. After 4-5 days of incubation, cells were processed and quantitated for virus growth by the amount of expressed luciferase. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and then re-suspended in STOP & GLO® Substrate (2:1:1 ratio). A total of 50 pt of the mixture was added to each aspirated well on assay plates and luciferase activity was measured immediately on a Wallac TriLux (Perkin-Elmer, Waltham, Mass.). The 50% effective concentration ($EC_{50}$) was calculated by comparing the amount of luciferase produced in the presence of inhibitory peptide compared to wells where no peptide was added.

Example 3—Evaluation of Combinectin Pharmacokinetics

Human CD4 Transgenic Mouse Model

Male and female heterozygous human CD4 mice were obtained from Jackson Laboratories, Bar Harbor, Me.

WT Mouse PK Studies 8-21 day single IV bolus dose studies were run in female C57Bl/6 WT mice to assess the PK properties of the various Combinectins. Fc-Combinectin fusions were dosed at 10 mg/kg and HSA-Combinectin fusions were dosed at 8.8 mg/kg. Plasma samples were collected in CPD and stored at −80° C. until analysis.

hCD4 Mouse PK Studies 7-10 day single IV bolus dose studies were run in heterozygous hCD4 mice to assess the PK properties of various Combinectins in the presence of target. Combinectins doses and sample collection methods were the same as described above for the WT mice.

Cynomolgus Monkey Studies

A 1-week single dose study was conducted in female cynos to determine the PK of Combinectins. Following a 1 mg/kg dose, serum samples were collected at the indicated times, aliquoted and quick frozen for MSD or LC/MS analysis.

Pharmacokinetic Measurements

Drug levels were measured in mouse or cyno plasma using the Mesoscale technology platform or colorimetric ELISA formats. Fc-Combinectin fusions were captured via the protein PRD828 (BMS) that specifically binds the peptide component of Combinectins and detected using a Goat anti-Human IgG Fc-HRP conjugated pAb (Pierce #31413). HSA-Combinectin fusions were captured via PRD828 and detected using a goat pAb against HSA (Bethyl, TX #A80-229A) that was ruthenium labeled. Sample concentrations were calculated from a standard curve using a 5-parameter logarithmic fit. Non-compartmental analyses were performed using Phoenix WINNONLIN® 6.3 (Pharsight Corporation, Mountain View, Calif.) using a plasma model and linear up/log down calculation method.

We claim:

1. A polypeptide comprising two active domains, wherein one domain is a fibronectin-based scaffold domain protein that binds the N17 domain of glycoprotein 41 (gp41) and comprises the amino acid sequence that is at least 90% identical to the amino acid sequence of any one of SEQ ID NOs: 115-371; and the other domain is a cluster of differentiation 4 (CD4) binding moiety or a human immunodeficiency virus (HIV) fusion peptide inhibitor, wherein the CD4 binding moiety is selected from the group consisting of an anti-CD4 antibody or fragment thereof, and a fibronectin-based scaffold domain protein that binds CD4 and comprises the amino acid sequence that is at least 90% identical to the amino acid sequence of any one of SEQ ID NOs: 95-114.

2. The polypeptide of claim 1, wherein the two domains are connected to each other in any order by linkers.

3. The polypeptide of claim 1, further comprising one or more pharmacokinetic (PK) moieties selected from the group consisting of polyethylene glycol, sialic acid, Fc, Fc fragment, transferrin, serum albumin, a serum albumin binding protein, and a serum immunoglobulin binding protein.

4. The polypeptide of claim 3, wherein the PK moiety is Fc.

5. The polypeptide of claim 4, wherein the Fc is attached to the N-terminus of the polypeptide.

6. The polypeptide of claim 3, wherein the PK moiety is human serum albumin.

7. The polypeptide of claim 6, wherein the human serum albumin is attached to the N-terminus of the polypeptide.

* * * * *

UNITED STATES PATENT AND TRADEMARK OFFICE
CERTIFICATE OF CORRECTION

| | |
|---|---|
| PATENT NO. | : 11,155,602 B2 |
| APPLICATION NO. | : 16/533941 |
| DATED | : October 26, 2021 |
| INVENTOR(S) | : Krystal et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this
Seventh Day of February, 2023

Katherine Kelly Vidal
*Director of the United States Patent and Trademark Office*

SEQUENCE LISTING

<160> NUMBER OF SEQ ID NOS: 428

<210> SEQ ID NO 1
<211> LENGTH: 94
<212> TYPE: PRT
<213> ORGANISM: Artificial Sequence
<220> FEATURE:
<223> OTHER INFORMATION: Human fibronectin

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 172
<212> TYPE: PRT
<213> ORGANISM: Artificial Sequence
<220> FEATURE:
<223> OTHER INFORMATION: GP41 External domain

<400> SEQUENCE: 2

Ala Val Gly Ile Gly Ala Met Phe Leu Gly Phe Leu Gly Ala Ala Gly
1               5                   10                  15

Ser Thr Met Gly Ala Ala Ser Val Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Val Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Asp Glu Ile Trp
            100                 105                 110

Asn Asn Met Thr Trp Met Glu Trp Glu Arg Glu Ile Asp Asn Tyr Thr
        115                 120                 125

Gly Leu Ile Tyr Thr Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asp Ile Thr Asn Trp Leu Trp Tyr Ile Lys
                165                 170

<210> SEQ ID NO 3
<211> LENGTH: 251
<212> TYPE: PRT
<213> ORGANISM: Artificial Sequence
<220> FEATURE:

-continued

<223> OTHER INFORMATION: Combinectin

<400> SEQUENCE: 3

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val His Ser
            20                  25                  30

Tyr His Ile Gln Tyr Trp Pro Leu Gly Ser Tyr Gln Arg Tyr Gln Val
        35                  40                  45

Phe Ser Val Pro Gly Ser Lys Ser Thr Ala Thr Ile Ser Gly Leu Lys
    50                  55                  60

Pro Gly Val Glu Tyr Gln Ile Arg Val Tyr Ala Glu Thr Gly Arg Gly
65                  70                  75                  80

Glu Ser Asp Gln Ser Leu Gly Trp Ile Gln Ile Gly Tyr Arg Thr Glu
                85                  90                  95

Glu Ser Pro Glu Pro Glu Thr Pro Gly Asp Glu Gly Val Ser Asp Val
            100                 105                 110

Pro Arg Asp Leu Glu Val Val Ala Ala Thr Pro Thr Ser Leu Leu Ile
        115                 120                 125

Ser Trp Gln Tyr Lys Val His Pro Tyr Arg Tyr Arg Ile Thr Tyr
    130                 135                 140

Gly Glu Thr Gly Gly Asn Ser Pro Val Gln Glu Phe Thr Val Pro Ser
145                 150                 155                 160

Val Leu Ser Thr Ala Glu Ile Ser Gly Leu Lys Pro Gly Val Asp Tyr
                165                 170                 175

Thr Ile Thr Val Tyr Ala Val Thr Arg Gly Val Asp Ser Ala Pro Ile
            180                 185                 190

Ser Ile Asn Tyr Arg Thr Pro Gly Gly Gly Ser Gly Gly Gly Gly
        195                 200                 205

Ser Gly Gly Gly Gly Ser Gly Gly Gly Gly Ser Glu Tyr Glu Ala Arg
    210                 215                 220

Ile Glu Ala Leu Ile Arg Ala Ala Gln Glu Gln Gln Glu Lys Asn Glu
225                 230                 235                 240

Ala Ala Leu Arg Glu Leu Tyr Lys Trp Ala Leu
                245                 250

<210> SEQ ID NO 4
<211> LENGTH: 497
<212> TYPE: PRT
<213> ORGANISM: Artificial Sequence
<220> FEATURE:
<223> OTHER INFORMATION: Combinectin

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Ser Pro Glu Pro Glu Thr Pro Glu Asp Glu Ser Pro Glu Pro
225                 230                 235                 240

Glu Thr Pro Glu Asp Glu Gly Val Ser Asp Val Pro Arg Asp Leu Glu
                245                 250                 255

Val Val Ala Ala Thr Pro Thr Ser Leu Leu Ile Ser Trp Asp Ala Pro
            260                 265                 270

Ala Val Thr Val His Ser Tyr His Ile Gln Tyr Trp Pro Leu Gly Ser
        275                 280                 285

Tyr Gln Arg Tyr Gln Val Phe Ser Val Pro Gly Ser Lys Ser Thr Ala
    290                 295                 300

Thr Ile Ser Gly Leu Lys Pro Gly Val Glu Tyr Gln Ile Arg Val Tyr
305                 310                 315                 320

Ala Glu Thr Gly Arg Gly Glu Ser Asp Gln Ser Leu Gly Trp Ile Gln
                325                 330                 335

Ile Gly Tyr Arg Thr Glu Glu Ser Pro Glu Pro Glu Thr Pro Glu Asp
            340                 345                 350

Glu Gly Val Ser Asp Val Pro Arg Asp Leu Glu Val Val Ala Ala Thr
        355                 360                 365

Pro Thr Ser Leu Leu Ile Ser Trp Gln Tyr Lys Val His Pro Tyr Arg
370                 375                 380

Tyr Tyr Arg Ile Thr Tyr Gly Glu Thr Gly Gly Asn Ser Pro Val Gln
385                 390                 395                 400

Glu Phe Thr Val Pro Ser Val Leu Ser Thr Ala Glu Ile Ser Gly Leu
                405                 410                 415

Lys Pro Gly Val Asp Tyr Thr Ile Thr Val Tyr Ala Val Thr Arg Gly
            420                 425                 430

Val Asp Ser Ala Pro Ile Ser Ile Asn Tyr Arg Thr Pro Gly Gly Gly
        435                 440                 445

Gly Ser Gly Gly Gly Gly Ser Gly Gly Gly Gly Ser Gly Gly Gly Gly
    450                 455                 460

Ser Glu Tyr Glu Ala Arg Ile Glu Ala Leu Ile Arg Ala Ala Gln Glu
465                 470                 475                 480

Gln Gln Glu Lys Asn Glu Ala Ala Leu Arg Glu Leu Tyr Lys Trp Ala
                485                 490                 495

Leu
```

```
<210> SEQ ID NO 5
<211> LENGTH: 251
<212> TYPE: PRT
<213> ORGANISM: Artificial Sequence
<220> FEATURE:
<223> OTHER INFORMATION: Combinectin

<400> SEQUENCE: 5

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val His Ser
            20                  25                  30

Tyr His Ile Gln Tyr Trp Pro Leu Gly Ser Tyr Gln Arg Tyr Gln Val
        35                  40                  45

Phe Ser Val Pro Gly Ser Lys Ser Thr Ala Thr Ile Ser Gly Leu Lys
    50                  55                  60

Pro Gly Val Glu Tyr Gln Ile Arg Val Tyr Ala Glu Thr Gly Arg Gly
65                  70                  75                  80

Glu Ser Asp Gln Ser Leu Gly Trp Ile Gln Ile Gly Tyr Arg Thr Glu
                85                  90                  95

Glu Ser Pro Glu Pro Glu Thr Pro Glu Asp Glu Gly Val Ser Asp Val
            100                 105                 110

Pro Arg Asp Leu Glu Val Val Ala Ala Thr Pro Thr Ser Leu Leu Ile
        115                 120                 125

Ser Trp Glu Tyr Asn Val Asn Pro Tyr Arg Tyr Arg Ile Thr Tyr
    130                 135                 140

Gly Glu Thr Gly Gly Asn Ser Pro Val Gln Glu Phe Thr Val Pro Ser
145                 150                 155                 160

Val Leu Ser Ser Ala Gln Ile Ser Gly Leu Lys Pro Gly Val Asp Tyr
                165                 170                 175

Thr Ile Thr Val Tyr Ala Val Thr Arg Gly Val Asp Ser Ala Pro Ile
            180                 185                 190

Ser Ile Asn Tyr Arg Thr Pro Gly Gly Gly Ser Gly Gly Gly
        195                 200                 205

Ser Gly Gly Gly Gly Ser Gly Gly Gly Ser Glu Tyr Glu Ala Arg
    210                 215                 220

Ile Glu Ala Leu Ile Arg Ala Ala Gln Glu Gln Gln Glu Lys Asn Glu
225                 230                 235                 240

Ala Ala Leu Arg Glu Leu Trp Lys Trp Ala Ser
                245                 250

<210> SEQ ID NO 6
<211> LENGTH: 497
<212> TYPE: PRT
<213> ORGANISM: Artificial Sequence
<220> FEATURE:
<223> OTHER INFORMATION: Combinectin

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Glu Ser Pro Glu Pro Glu Thr Pro Glu Asp Glu Ser Pro Glu Pro
225                 230                 235                 240

Glu Thr Pro Glu Asp Glu Gly Val Ser Asp Val Pro Arg Asp Leu Glu
                245                 250                 255

Val Val Ala Ala Thr Pro Thr Ser Leu Leu Ile Ser Trp Asp Ala Pro
            260                 265                 270

Ala Val Thr Val His Ser Tyr His Ile Gln Tyr Trp Pro Leu Gly Ser
        275                 280                 285

Tyr Gln Arg Tyr Gln Val Phe Ser Val Pro Gly Ser Lys Ser Thr Ala
    290                 295                 300

Thr Ile Ser Gly Leu Lys Pro Gly Val Glu Tyr Gln Ile Arg Val Tyr
305                 310                 315                 320

Ala Glu Thr Gly Arg Gly Glu Ser Asp Gln Ser Leu Gly Trp Ile Gln
                325                 330                 335

Ile Gly Tyr Arg Thr Glu Glu Ser Pro Glu Pro Glu Thr Pro Glu Asp
            340                 345                 350

Glu Gly Val Ser Asp Val Pro Arg Asp Leu Glu Val Val Ala Ala Thr
        355                 360                 365

Pro Thr Ser Leu Leu Ile Ser Trp Glu Tyr Asn Val Asn Pro Tyr Arg
    370                 375                 380

Tyr Tyr Arg Ile Thr Tyr Gly Glu Thr Gly Gly Asn Ser Pro Val Gln
385                 390                 395                 400

Glu Phe Thr Val Pro Ser Val Leu Ser Ser Ala Gln Ile Ser Gly Leu
                405                 410                 415

Lys Pro Gly Val Asp Tyr Thr Ile Thr Val Tyr Ala Val Thr Arg Gly
            420                 425                 430

Val Asp Ser Ala Pro Ile Ser Ile Asn Tyr Arg Thr Pro Gly Gly Gly
        435                 440                 445

Gly Ser Gly Gly Gly Gly Ser Gly Gly Gly Gly Ser Gly Gly Gly Gly
    450                 455                 460

Ser Glu Tyr Glu Ala Arg Ile Glu Ala Leu Ile Arg Ala Ala Gln Glu
465                 470                 475                 480

Gln Gln Glu Lys Asn Glu Ala Ala Leu Arg Glu Leu Trp Lys Trp Ala
```

Ser

<210> SEQ ID NO 7
<211> LENGTH: 251
<212> TYPE: PRT
<213> ORGANISM: Artificial Sequence
<220> FEATURE:
<223> OTHER INFORMATION: Combinectin

<400> SEQUENCE: 7

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val His Ser
            20                  25                  30

Tyr His Ile Gln Tyr Trp Pro Leu Gly Ser Tyr Gln Arg Tyr Gln Val
        35                  40                  45

Phe Ser Val Pro Gly Ser Lys Ser Thr Ala Thr Ile Ser Gly Leu Lys
    50                  55                  60

Pro Gly Val Glu Tyr Gln Ile Arg Val Tyr Ala Glu Thr Gly Arg Gly
65                  70                  75                  80

Glu Ser Asp Gln Ser Leu Gly Trp Ile Gln Ile Gly Tyr Arg Thr Pro
                85                  90                  95

Glu Ser Pro Glu Pro Glu Thr Pro Glu Asp Glu Gly Val Ser Asp Val
            100                 105                 110

Pro Arg Asp Leu Glu Val Val Ala Ala Thr Pro Thr Ser Leu Leu Ile
        115                 120                 125

Ser Trp Glu Tyr Lys Val His Pro Tyr Arg Tyr Tyr Arg Ile Thr Tyr
    130                 135                 140

Gly Glu Thr Gly Gly Asn Ser Pro Val Gln Glu Phe Thr Val Pro Ser
145                 150                 155                 160

Val Leu Ser Ser Ala Glu Ile Ser Gly Leu Lys Pro Gly Val Asp Tyr
                165                 170                 175

Thr Ile Thr Val Tyr Ala Val Thr Tyr Gly Ile Asp Ser Pro Pro Ile
            180                 185                 190

Ser Ile Asn Tyr Arg Thr Glu Gly Gly Ser Gly Gly Gly
        195                 200                 205

Ser Gly Gly Gly Ser Gly Gly Gly Ser Glu Tyr Glu Ala Arg
    210                 215                 220

Ile Glu Ala Leu Ile Arg Ala Ala Gln Glu Gln Gln Glu Lys Asn Glu
225                 230                 235                 240

Ala Ala Leu Arg Glu Leu Tyr Lys Trp Ala Leu
                245                 250

<210> SEQ ID NO 8
<211> LENGTH: 857
<212> TYPE: PRT
<213> ORGANISM: Artificial Sequence
<220> FEATURE:
<223> OTHER INFORMATION: Combinectin

<400> SEQUENCE: 8

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu

```
            35                  40                  45
Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Glu Ser Pro Glu Pro Glu Thr
        580                 585                 590

Pro Glu Asp Glu Ser Pro Glu Pro Glu Thr Pro Glu Asp Glu Gly Val
            595                 600                 605

Ser Asp Val Pro Arg Asp Leu Glu Val Val Ala Ala Thr Pro Thr Ser
610                 615                 620

Leu Leu Ile Ser Trp Asp Ala Pro Ala Val Thr Val His Ser Tyr His
625                 630                 635                 640

Ile Gln Tyr Trp Pro Leu Gly Ser Tyr Gln Arg Tyr Gln Val Phe Ser
            645                 650                 655

Val Pro Gly Ser Lys Ser Thr Ala Thr Ile Ser Gly Leu Lys Pro Gly
        660                 665                 670

Val Glu Tyr Gln Ile Arg Val Tyr Ala Glu Thr Gly Arg Gly Glu Ser
            675                 680                 685

Asp Gln Ser Leu Gly Trp Ile Gln Ile Gly Tyr Arg Thr Pro Glu Ser
        690                 695                 700

Pro Glu Pro Glu Thr Pro Glu Asp Glu Gly Val Ser Asp Val Pro Arg
705                 710                 715                 720

Asp Leu Glu Val Val Ala Ala Thr Pro Thr Ser Leu Leu Ile Ser Trp
            725                 730                 735

Glu Tyr Lys Val His Pro Tyr Arg Tyr Tyr Arg Ile Thr Tyr Gly Glu
        740                 745                 750

Thr Gly Gly Asn Ser Pro Val Gln Glu Phe Thr Val Pro Ser Val Leu
        755                 760                 765

Ser Ser Ala Glu Ile Ser Gly Leu Lys Pro Gly Val Asp Tyr Thr Ile
        770                 775                 780

Thr Val Tyr Ala Val Thr Tyr Gly Ile Asp Ser Pro Pro Ile Ser Ile
785                 790                 795                 800

Asn Tyr Arg Thr Glu Gly Gly Gly Ser Gly Gly Gly Ser Gly
        805                 810                 815

Gly Gly Gly Ser Gly Gly Gly Ser Glu Tyr Glu Ala Arg Ile Glu
            820                 825                 830

Ala Leu Ile Arg Ala Ala Gln Glu Gln Gln Glu Lys Asn Glu Ala Ala
        835                 840                 845

Leu Arg Glu Leu Tyr Lys Trp Ala Leu
        850                 855
```

<210> SEQ ID NO 9
<211> LENGTH: 253

```
<212> TYPE: PRT
<213> ORGANISM: Artificial Sequence
<220> FEATURE:
<223> OTHER INFORMATION: Combinectin

<400> SEQUENCE: 9

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val His Ser
            20                  25                  30

Tyr His Ile Gln Tyr Trp Pro Leu Gly Ser Tyr Gln Arg Tyr Gln Val
        35                  40                  45

Phe Ser Val Pro Gly Ser Lys Ser Thr Ala Thr Ile Ser Gly Leu Lys
50                  55                  60

Pro Gly Val Glu Tyr Gln Ile Arg Val Tyr Ala Glu Thr Gly Gly Ala
65                  70                  75                  80

Asp Ser Asp Gln Ser Phe Gly Trp Ile Gln Ile Gly Tyr Arg Thr Pro
            85                  90                  95

Glu Ser Pro Glu Pro Glu Thr Pro Glu Asp Gly Val Ser Asp Val
        100                 105                 110

Pro Arg Asp Leu Glu Val Val Ala Ala Thr Pro Thr Ser Leu Leu Ile
        115                 120                 125

Ser Trp Glu Tyr Lys Val His Pro Tyr Arg Tyr Tyr Arg Ile Thr Tyr
    130                 135                 140

Gly Glu Thr Gly Gly Asn Ser Pro Val Gln Glu Phe Thr Val Pro Ser
145                 150                 155                 160

Val Leu Ser Thr Ala Glu Ile Ser Gly Leu Lys Pro Gly Val Asp Tyr
                165                 170                 175

Thr Ile Thr Val Tyr Ala Val Thr Arg Gly Val Asp Ser Ala Pro Ile
            180                 185                 190

Ser Ile Asn Tyr Arg Thr Pro Gly Gly Gly Ser Gly Gly Gly
        195                 200                 205

Ser Gly Gly Gly Ser Gly Gly Gly Thr Ile Ala Glu Tyr Ala
    210                 215                 220

Ala Arg Ile Glu Ala Leu Ile Arg Ala Ala Gln Glu Gln Gln Glu Lys
225                 230                 235                 240

Asn Glu Ala Ala Leu Arg Glu Leu Tyr Lys Trp Ala Ser
                245                 250

<210> SEQ ID NO 10
<211> LENGTH: 863
<212> TYPE: PRT
<213> ORGANISM: Artificial Sequence
<220> FEATURE:
<223> OTHER INFORMATION: Combinectin

<400> SEQUENCE: 10

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Gly Lys Lys Leu Val
                    565                 570                 575
Ala Ala Ser Gln Ala Ala Leu Gly Leu Gly Gly Gly Ser Gly Gly
                580                 585                 590
Gly Gly Ser Gly Gly Gly Gly Ser Gly Gly Gly Gly Ser Gly Gly Gly
            595                 600                 605
Gly Ser Gly Val Ser Asp Val Pro Arg Asp Leu Glu Val Val Ala Ala
            610                 615                 620
Thr Pro Thr Ser Leu Leu Ile Ser Trp Asp Ala Pro Ala Val Thr Val
625                 630                 635                 640
His Ser Tyr His Ile Gln Tyr Trp Pro Leu Gly Ser Tyr Gln Arg Tyr
                    645                 650                 655
Gln Val Phe Ser Val Pro Gly Ser Lys Ser Thr Ala Thr Ile Ser Gly
                660                 665                 670
Leu Lys Pro Gly Val Glu Tyr Gln Ile Arg Val Tyr Ala Glu Thr Gly
            675                 680                 685
Gly Ala Asp Ser Asp Gln Ser Phe Gly Trp Ile Gln Ile Gly Tyr Arg
            690                 695                 700
Thr Pro Glu Ser Pro Glu Pro Glu Thr Pro Glu Asp Glu Gly Val Ser
705                 710                 715                 720
Asp Val Pro Arg Asp Leu Glu Val Val Ala Ala Thr Pro Thr Ser Leu
                    725                 730                 735
Leu Ile Ser Trp Glu Tyr Lys Val His Pro Tyr Arg Tyr Tyr Arg Ile
                740                 745                 750
Thr Tyr Gly Glu Thr Gly Gly Asn Ser Pro Val Gln Glu Phe Thr Val
            755                 760                 765
Pro Ser Val Leu Ser Thr Ala Glu Ile Ser Gly Leu Lys Pro Gly Val
770                 775                 780
Asp Tyr Thr Ile Thr Val Tyr Ala Val Thr Arg Gly Val Asp Ser Ala
785                 790                 795                 800
Pro Ile Ser Ile Asn Tyr Arg Thr Pro Gly Gly Gly Ser Gly Gly
                    805                 810                 815
Gly Gly Ser Gly Gly Gly Gly Ser Gly Gly Gly Gly Thr Ile Ala Glu
            820                 825                 830
Tyr Ala Ala Arg Ile Glu Ala Leu Ile Arg Ala Ala Gln Glu Gln Gln
            835                 840                 845
Glu Lys Asn Glu Ala Ala Leu Arg Glu Leu Tyr Lys Trp Ala Ser
            850                 855                 860

<210> SEQ ID NO 11
<211> LENGTH: 227
<212> TYPE: PRT
<213> ORGANISM: Artificial Sequence
<220> FEATURE:
<223> OTHER INFORMATION: human IgG1 immunoglobulin Fc domain

<400> SEQUENCE: 11
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 12
<211> LENGTH: 16
<212> TYPE: PRT
<213> ORGANISM: Artificial Sequence
<220> FEATURE:
<223> OTHER INFORMATION: IgG1Fc hinge region

<400> SEQUENCE: 12

Asp Lys Thr His Thr Cys Pro Pro Cys Pro Ala Pro Glu Leu Leu Gly
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: Adnectin

<400> SEQUENCE: 13

His Ser Tyr His Ile Gln Tyr Trp Pro Leu Gly Ser Tyr Gln Arg Tyr
1               5                   10                  15

Gln Val Phe

<210> SEQ ID NO 14
<211> LENGTH: 25
<212> TYPE: PRT
<213> ORGANISM: Artificial Sequence
<220> FEATURE:

<223> OTHER INFORMATION: Adnectin

<400> SEQUENCE: 14

Glu Tyr Gln Ile Arg Val Tyr Ala Glu Thr Gly Gly Ala Asp Ser Asp
1               5                   10                  15

Gln Ser Met Gly Trp Ile Gln Ile Gly
            20                  25

<210> SEQ ID NO 15
<211> LENGTH: 19
<212> TYPE: PRT
<213> ORGANISM: Artificial Sequence
<220> FEATURE:
<223> OTHER INFORMATION: Adnectin

<400> SEQUENCE: 15

Leu Ser Tyr His Ile Gln Tyr Trp Pro Leu Gly Leu Tyr Gln Ala Tyr
1               5                   10                  15

Gln Val Phe

<210> SEQ ID NO 16
<211> LENGTH: 25
<212> TYPE: PRT
<213> ORGANISM: Artificial Sequence
<220> FEATURE:
<223> OTHER INFORMATION: Adnectin

<400> SEQUENCE: 16

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 17
<211> LENGTH: 19
<212> TYPE: PRT
<213> ORGANISM: Artificial Sequence
<220> FEATURE:
<223> OTHER INFORMATION: Adnectin

<400> SEQUENCE: 17

His Ala Tyr His Ile Gln Tyr Trp Pro Leu Gly Phe Tyr Gln Gly Tyr
1               5                   10                  15

Gln Val Phe

<210> SEQ ID NO 18
<211> LENGTH: 25
<212> TYPE: PRT
<213> ORGANISM: Artificial Sequence
<220> FEATURE:
<223> OTHER INFORMATION: Adnectin

<400> SEQUENCE: 18

Glu Tyr Gln Ile Arg Val Tyr Ala Glu Thr Gly Leu Gly Asp Ala His
1               5                   10                  15

Gln Ser Leu Gly Trp Ile Gln Ile Gly
            20                  25

<210> SEQ ID NO 19
<211> LENGTH: 19
<212> TYPE: PRT
<213> ORGANISM: Artificial Sequence
<220> FEATURE:
<223> OTHER INFORMATION: Adnectin

```
<400> SEQUENCE: 19

Leu Ala Tyr His Ile Gln Tyr Trp Pro Leu Gly Trp Tyr Gln Arg Tyr
1               5                   10                  15

Gln Ile Phe

<210> SEQ ID NO 20
<211> LENGTH: 25
<212> TYPE: PRT
<213> ORGANISM: Artificial Sequence
<220> FEATURE:
<223> OTHER INFORMATION: Adnectin

<400> SEQUENCE: 20

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 21
<211> LENGTH: 19
<212> TYPE: PRT
<213> ORGANISM: Artificial Sequence
<220> FEATURE:
<223> OTHER INFORMATION: Adnectin

<400> SEQUENCE: 21

Leu Ala Tyr His Ile Gln Tyr Trp Pro Leu Gly Trp Tyr Gln Arg Tyr
1               5                   10                  15

Gln Val Phe

<210> SEQ ID NO 22
<211> LENGTH: 25
<212> TYPE: PRT
<213> ORGANISM: Artificial Sequence
<220> FEATURE:
<223> OTHER INFORMATION: Adnectin

<400> SEQUENCE: 22

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 23
<211> LENGTH: 19
<212> TYPE: PRT
<213> ORGANISM: Artificial Sequence
<220> FEATURE:
<223> OTHER INFORMATION: Adnectin

<400> SEQUENCE: 23

His Phe Tyr His Ile Gln Tyr Trp Pro Leu Gly Leu Tyr His Leu Tyr
1               5                   10                  15

Gln Val Phe

<210> SEQ ID NO 24
<211> LENGTH: 25
<212> TYPE: PRT
<213> ORGANISM: Artificial Sequence
<220> FEATURE:
<223> OTHER INFORMATION: Adnectin

<400> SEQUENCE: 24
```

```
Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 25
<211> LENGTH: 19
<212> TYPE: PRT
<213> ORGANISM: Artificial Sequence
<220> FEATURE:
<223> OTHER INFORMATION: Adnectin

<400> SEQUENCE: 25

Tyr Ser Tyr His Ile Gln Tyr Trp Pro Leu Gly Trp Tyr His Arg Tyr
1               5                   10                  15

Gln Val Phe

<210> SEQ ID NO 26
<211> LENGTH: 25
<212> TYPE: PRT
<213> ORGANISM: Artificial Sequence
<220> FEATURE:
<223> OTHER INFORMATION: Adnectin

<400> SEQUENCE: 26

Glu Tyr Gln Ile Arg Val Tyr Ala Glu Thr Gly Ala Asp Asp Pro Val
1               5                   10                  15

Gln Ala Leu Gly Trp Ile Gln Ile Gly
            20                  25

<210> SEQ ID NO 27
<211> LENGTH: 19
<212> TYPE: PRT
<213> ORGANISM: Artificial Sequence
<220> FEATURE:
<223> OTHER INFORMATION: Adnectin

<400> SEQUENCE: 27

Arg Cys Tyr His Ile Gln Tyr Trp Pro Leu Gly Leu Tyr Pro Leu Tyr
1               5                   10                  15

Gln Val Phe

<210> SEQ ID NO 28
<211> LENGTH: 25
<212> TYPE: PRT
<213> ORGANISM: Artificial Sequence
<220> FEATURE:
<223> OTHER INFORMATION: Adnectin

<400> SEQUENCE: 28

Glu Tyr Gln Ile Arg Val Tyr Ala Glu Thr Gly Asp Glu Ser Ser Val
1               5                   10                  15

Gln Pro Phe Gly Trp Ile Gln Ile Gly
            20                  25

<210> SEQ ID NO 29
<211> LENGTH: 19
<212> TYPE: PRT
<213> ORGANISM: Artificial Sequence
<220> FEATURE:
<223> OTHER INFORMATION: Adnectin

<400> SEQUENCE: 29
```

```
Tyr Ser Tyr His Ile Gln Tyr Trp Pro Leu Gly Trp Tyr Gln Arg Tyr
1               5                   10                  15

Gln Val Phe

<210> SEQ ID NO 30
<211> LENGTH: 25
<212> TYPE: PRT
<213> ORGANISM: Artificial Sequence
<220> FEATURE:
<223> OTHER INFORMATION: Adnectin

<400> SEQUENCE: 30

Glu Tyr Gln Ile Arg Val Tyr Ala Glu Thr Asp Gly Gly Arg Ser Gln
1               5                   10                  15

Gln Ser Phe Gly Trp Ile Gln Ile Gly
            20                  25

<210> SEQ ID NO 31
<211> LENGTH: 19
<212> TYPE: PRT
<213> ORGANISM: Artificial Sequence
<220> FEATURE:
<223> OTHER INFORMATION: Adnectin

<400> SEQUENCE: 31

Ser Ser Tyr His Ile Gln Tyr Trp Pro Leu Gly Ala Tyr Gln Arg Tyr
1               5                   10                  15

Gln Val Phe

<210> SEQ ID NO 32
<211> LENGTH: 25
<212> TYPE: PRT
<213> ORGANISM: Artificial Sequence
<220> FEATURE:
<223> OTHER INFORMATION: Adnectin

<400> SEQUENCE: 32

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 33
<211> LENGTH: 19
<212> TYPE: PRT
<213> ORGANISM: Artificial Sequence
<220> FEATURE:
<223> OTHER INFORMATION: Adnectin

<400> SEQUENCE: 33

His Ala Tyr His Ile Gln Tyr Trp Pro Leu Gly Leu Tyr Gln Arg Tyr
1               5                   10                  15

Gln Val Phe

<210> SEQ ID NO 34
<211> LENGTH: 25
<212> TYPE: PRT
<213> ORGANISM: Artificial Sequence
<220> FEATURE:
<223> OTHER INFORMATION: Adnectin

<400> SEQUENCE: 34

Glu Tyr Gln Ile Arg Val Tyr Ala Glu Thr Gly Arg Gly Glu Ser Pro
1               5                   10                  15
```

```
Ala Ser Phe Gly Trp Ile Gln Ile Gly
            20                  25

<210> SEQ ID NO 35
<211> LENGTH: 19
<212> TYPE: PRT
<213> ORGANISM: Artificial Sequence
<220> FEATURE:
<223> OTHER INFORMATION: Adnectin

<400> SEQUENCE: 35

His Ala Tyr Tyr Ile Gln Tyr Trp Pro Leu Gly Ser Tyr Gln Phe Tyr
1               5                   10                  15

Gln Val Phe

<210> SEQ ID NO 36
<211> LENGTH: 25
<212> TYPE: PRT
<213> ORGANISM: Artificial Sequence
<220> FEATURE:
<223> OTHER INFORMATION: Adnectin

<400> SEQUENCE: 36

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 37
<211> LENGTH: 19
<212> TYPE: PRT
<213> ORGANISM: Artificial Sequence
<220> FEATURE:
<223> OTHER INFORMATION: Adnectin

<400> SEQUENCE: 37

His Ser Tyr His Ile Gln Tyr Trp Pro Leu Gly Ser Tyr Leu Arg Tyr
1               5                   10                  15

Gln Val Phe

<210> SEQ ID NO 38
<211> LENGTH: 25
<212> TYPE: PRT
<213> ORGANISM: Artificial Sequence
<220> FEATURE:
<223> OTHER INFORMATION: Adnectin

<400> SEQUENCE: 38

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 39
<211> LENGTH: 19
<212> TYPE: PRT
<213> ORGANISM: Artificial Sequence
<220> FEATURE:
<223> OTHER INFORMATION: Adnectin

<400> SEQUENCE: 39

Leu Ser Tyr His Ile Gln Tyr Trp Pro Leu Gly Phe Tyr Gln Arg Tyr
1               5                   10                  15
```

Gln Val Phe

<210> SEQ ID NO 40
<211> LENGTH: 25
<212> TYPE: PRT
<213> ORGANISM: Artificial Sequence
<220> FEATURE:
<223> OTHER INFORMATION: Adnectin

<400> SEQUENCE: 40

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 41
<211> LENGTH: 19
<212> TYPE: PRT
<213> ORGANISM: Artificial Sequence
<220> FEATURE:
<223> OTHER INFORMATION: Adnectin

<400> SEQUENCE: 41

Ser Ala Tyr His Ile Gln Tyr Trp Pro Leu Gly Trp Tyr His Arg Tyr
1               5                   10                  15

Gln Ile Phe

<210> SEQ ID NO 42
<211> LENGTH: 25
<212> TYPE: PRT
<213> ORGANISM: Artificial Sequence
<220> FEATURE:
<223> OTHER INFORMATION: Adnectin

<400> SEQUENCE: 42

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 43
<211> LENGTH: 19
<212> TYPE: PRT
<213> ORGANISM: Artificial Sequence
<220> FEATURE:
<223> OTHER INFORMATION: Adnectin

<400> SEQUENCE: 43

Tyr Ser Tyr His Ile Gln Tyr Trp Pro Leu Gly Ala Tyr Ser Arg His
1               5                   10                  15

Gln Leu Phe

<210> SEQ ID NO 44
<211> LENGTH: 25
<212> TYPE: PRT
<213> ORGANISM: Artificial Sequence
<220> FEATURE:
<223> OTHER INFORMATION: Adnectin

<400> SEQUENCE: 44

Glu Tyr Gln Ile Arg Val Tyr Ala Glu Thr Gly Gly Asp Gly Ser Glu
1               5                   10                  15

Met Tyr Phe Gly Trp Ile Gln Ile Gly
            20                  25

```
<210> SEQ ID NO 45
<211> LENGTH: 19
<212> TYPE: PRT
<213> ORGANISM: Artificial Sequence
<220> FEATURE:
<223> OTHER INFORMATION: Adnectin

<400> SEQUENCE: 45

Leu Ala Tyr His Ile Gln Tyr Trp Pro Leu Gly Trp Tyr His Leu Tyr
1               5                   10                  15

Gln Val Phe

<210> SEQ ID NO 46
<211> LENGTH: 25
<212> TYPE: PRT
<213> ORGANISM: Artificial Sequence
<220> FEATURE:
<223> OTHER INFORMATION: Adnectin

<400> SEQUENCE: 46

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 47
<211> LENGTH: 19
<212> TYPE: PRT
<213> ORGANISM: Artificial Sequence
<220> FEATURE:
<223> OTHER INFORMATION: Adnectin

<400> SEQUENCE: 47

Leu Ala Tyr His Ile Gln Tyr Trp Pro Leu Gly Trp Tyr Gln Leu Tyr
1               5                   10                  15

Lys Val Phe

<210> SEQ ID NO 48
<211> LENGTH: 25
<212> TYPE: PRT
<213> ORGANISM: Artificial Sequence
<220> FEATURE:
<223> OTHER INFORMATION: Adnectin

<400> SEQUENCE: 48

Asp Tyr Gln Ile Arg Val Tyr Ala Glu Thr Ser Gly Glu Ser Ser Glu
1               5                   10                  15

Gln Tyr Leu Gly Trp Ile Gln Ile Gly
            20                  25

<210> SEQ ID NO 49
<211> LENGTH: 19
<212> TYPE: PRT
<213> ORGANISM: Artificial Sequence
<220> FEATURE:
<223> OTHER INFORMATION: Adnectin

<400> SEQUENCE: 49

His Ser Tyr His Ile Gln Tyr Trp Pro Leu Gly Trp Tyr Gln Leu Tyr
1               5                   10                  15

Gln Val Phe
```

```
<210> SEQ ID NO 50
<211> LENGTH: 25
<212> TYPE: PRT
<213> ORGANISM: Artificial Sequence
<220> FEATURE:
<223> OTHER INFORMATION: Adnectin

<400> SEQUENCE: 50
```

Glu Tyr Gln Ile Arg Val Tyr Ala Glu Thr Glu Val Asp Ser Gly Gln
1               5                   10                  15

His Ser Phe Gly Trp Ile Gln Ile Gly
            20                  25

```
<210> SEQ ID NO 51
<211> LENGTH: 19
<212> TYPE: PRT
<213> ORGANISM: Artificial Sequence
<220> FEATURE:
<223> OTHER INFORMATION: Adnectin

<400> SEQUENCE: 51
```

Leu Ala Tyr His Ile Gln Tyr Trp Pro Leu Gly Trp Tyr Gln Arg Tyr
1               5                   10                  15

Gln Ile Phe

```
<210> SEQ ID NO 52
<211> LENGTH: 25
<212> TYPE: PRT
<213> ORGANISM: Artificial Sequence
<220> FEATURE:
<223> OTHER INFORMATION: Adnectin

<400> SEQUENCE: 52
```

Glu Tyr Gln Ile Arg Val Tyr Ala Glu Thr Gly Glu Ser Gly Ala Gln
1               5                   10                  15

Gln Ser Phe Gly Trp Ile Gln Ile Gly
            20                  25

```
<210> SEQ ID NO 53
<211> LENGTH: 19
<212> TYPE: PRT
<213> ORGANISM: Artificial Sequence
<220> FEATURE:
<223> OTHER INFORMATION: Adnectin

<400> SEQUENCE: 53
```

Gln Ser Tyr His Ile Gln Tyr Trp Pro Leu Gly Ala Tyr Gln Leu Tyr
1               5                   10                  15

Gln Leu Phe

```
<210> SEQ ID NO 54
<211> LENGTH: 25
<212> TYPE: PRT
<213> ORGANISM: Artificial Sequence
<220> FEATURE:
<223> OTHER INFORMATION: Adnectin

<400> SEQUENCE: 54
```

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

```
<210> SEQ ID NO 55
```

```
<211> LENGTH: 19
<212> TYPE: PRT
<213> ORGANISM: Artificial Sequence
<220> FEATURE:
<223> OTHER INFORMATION: Adnectin

<400> SEQUENCE: 55

His Ala Tyr His Ile Gln Tyr Trp Pro Leu Gly Phe Tyr Gln Gly Tyr
1               5                   10                  15

Gln Val Phe

<210> SEQ ID NO 56
<211> LENGTH: 25
<212> TYPE: PRT
<213> ORGANISM: Artificial Sequence
<220> FEATURE:
<223> OTHER INFORMATION: Adnectin

<400> SEQUENCE: 56

Glu Tyr Gln Ile Arg Val Tyr Ala Asp Thr Gly Arg Gly Tyr Gln Leu
1               5                   10                  15

Ser Tyr Ser Trp Ile Gln Ile Gly Tyr
            20                  25

<210> SEQ ID NO 57
<211> LENGTH: 19
<212> TYPE: PRT
<213> ORGANISM: Artificial Sequence
<220> FEATURE:
<223> OTHER INFORMATION: Adnectin

<400> SEQUENCE: 57

Phe Arg Tyr His Ile Gln Tyr Trp Pro Leu Gly Gly Tyr Glu Arg Tyr
1               5                   10                  15

Gln Val Phe

<210> SEQ ID NO 58
<211> LENGTH: 25
<212> TYPE: PRT
<213> ORGANISM: Artificial Sequence
<220> FEATURE:
<223> OTHER INFORMATION: Adnectin

<400> SEQUENCE: 58

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 59
<211> LENGTH: 19
<212> TYPE: PRT
<213> ORGANISM: Artificial Sequence
<220> FEATURE:
<223> OTHER INFORMATION: Adnectin

<400> SEQUENCE: 59

His Ser Tyr His Ile Gln Tyr Trp Pro Leu Gly Ser Tyr His Leu Tyr
1               5                   10                  15

Gln Leu Phe

<210> SEQ ID NO 60
<211> LENGTH: 25
<212> TYPE: PRT
```

```
<213> ORGANISM: Artificial Sequence
<220> FEATURE:
<223> OTHER INFORMATION: Adnectin

<400> SEQUENCE: 60

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 61
<211> LENGTH: 19
<212> TYPE: PRT
<213> ORGANISM: Artificial Sequence
<220> FEATURE:
<223> OTHER INFORMATION: Adnectin

<400> SEQUENCE: 61

His Ser Tyr His Ile Gln Tyr Trp Pro Leu Gly Trp Tyr Gln Leu Tyr
1               5                   10                  15

Gln Val Phe

<210> SEQ ID NO 62
<211> LENGTH: 25
<212> TYPE: PRT
<213> ORGANISM: Artificial Sequence
<220> FEATURE:
<223> OTHER INFORMATION: Adnectin

<400> SEQUENCE: 62

Glu Tyr Gln Ile Arg Val Tyr Ala Glu Thr Gly Gly Phe Gly Ser Pro
1               5                   10                  15

Pro Asn Phe Gly Trp Ile Gln Ile Gly
            20                  25

<210> SEQ ID NO 63
<211> LENGTH: 19
<212> TYPE: PRT
<213> ORGANISM: Artificial Sequence
<220> FEATURE:
<223> OTHER INFORMATION: Adnectin

<400> SEQUENCE: 63

Gln Phe Tyr His Ile Gln Tyr Trp Pro Leu Gly Ser Tyr Gln Arg Tyr
1               5                   10                  15

Gln Val Phe

<210> SEQ ID NO 64
<211> LENGTH: 25
<212> TYPE: PRT
<213> ORGANISM: Artificial Sequence
<220> FEATURE:
<223> OTHER INFORMATION: Adnectin

<400> SEQUENCE: 64

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 65
<211> LENGTH: 19
<212> TYPE: PRT
<213> ORGANISM: Artificial Sequence
```

<220> FEATURE:
<223> OTHER INFORMATION: Adnectin

<400> SEQUENCE: 65

Asn Ser Tyr His Ile Gln Tyr Trp Pro Leu Gly Trp Tyr His Arg Tyr
1               5                   10                  15

Gln Val Phe

<210> SEQ ID NO 66
<211> LENGTH: 25
<212> TYPE: PRT
<213> ORGANISM: Artificial Sequence
<220> FEATURE:
<223> OTHER INFORMATION: Adnectin

<400> SEQUENCE: 66

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 67
<211> LENGTH: 19
<212> TYPE: PRT
<213> ORGANISM: Artificial Sequence
<220> FEATURE:
<223> OTHER INFORMATION: Adnectin

<400> SEQUENCE: 67

His Ser Tyr His Ile Gln Tyr Trp Pro Leu Gly Arg Tyr Gln Leu Tyr
1               5                   10                  15

Gln Val Phe

<210> SEQ ID NO 68
<211> LENGTH: 25
<212> TYPE: PRT
<213> ORGANISM: Artificial Sequence
<220> FEATURE:
<223> OTHER INFORMATION: Adnectin

<400> SEQUENCE: 68

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 69
<211> LENGTH: 19
<212> TYPE: PRT
<213> ORGANISM: Artificial Sequence
<220> FEATURE:
<223> OTHER INFORMATION: Adnectin

<400> SEQUENCE: 69

Leu Ala Tyr His Ile Gln Tyr Trp Pro Leu Gly Trp Tyr His Leu Tyr
1               5                   10                  15

Gln Ile Phe

<210> SEQ ID NO 70
<211> LENGTH: 25
<212> TYPE: PRT
<213> ORGANISM: Artificial Sequence
<220> FEATURE:
<223> OTHER INFORMATION: Adnectin

```
<400> SEQUENCE: 70

Glu Tyr Gln Ile Arg Val Tyr Ala Glu Thr Gly Gly Val Gly Trp His
1               5                   10                  15

His Ser Phe Gly Trp Ile Gln Ile Gly
            20                  25

<210> SEQ ID NO 71
<211> LENGTH: 19
<212> TYPE: PRT
<213> ORGANISM: Artificial Sequence
<220> FEATURE:
<223> OTHER INFORMATION: Adnectin

<400> SEQUENCE: 71

His Val Tyr His Ile Gln Tyr Trp Pro Leu Gly Trp Tyr Pro Arg Tyr
1               5                   10                  15

Gln Val Phe

<210> SEQ ID NO 72
<211> LENGTH: 25
<212> TYPE: PRT
<213> ORGANISM: Artificial Sequence
<220> FEATURE:
<223> OTHER INFORMATION: Adnectin

<400> SEQUENCE: 72

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 73
<211> LENGTH: 19
<212> TYPE: PRT
<213> ORGANISM: Artificial Sequence
<220> FEATURE:
<223> OTHER INFORMATION: Adnectin

<400> SEQUENCE: 73

His Ser Tyr His Ile Pro Tyr Trp Glu Leu Ala Trp Tyr Gln Arg Tyr
1               5                   10                  15

Gln Val Phe

<210> SEQ ID NO 74
<211> LENGTH: 25
<212> TYPE: PRT
<213> ORGANISM: Artificial Sequence
<220> FEATURE:
<223> OTHER INFORMATION: Adnectin

<400> SEQUENCE: 74

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 75
<211> LENGTH: 19
<212> TYPE: PRT
<213> ORGANISM: Artificial Sequence
<220> FEATURE:
<223> OTHER INFORMATION: Adnectin
```

-continued

```
<400> SEQUENCE: 75

Glu Ser Tyr His Ile Gln Tyr Trp Pro Leu Gly Leu Tyr His Arg Tyr
1               5                   10                  15

Gln Val Phe

<210> SEQ ID NO 76
<211> LENGTH: 25
<212> TYPE: PRT
<213> ORGANISM: Artificial Sequence
<220> FEATURE:
<223> OTHER INFORMATION: Adnectin

<400> SEQUENCE: 76

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 77
<211> LENGTH: 19
<212> TYPE: PRT
<213> ORGANISM: Artificial Sequence
<220> FEATURE:
<223> OTHER INFORMATION: Adnectin

<400> SEQUENCE: 77

Leu Ala Tyr His Ile Gln Tyr Trp Pro Leu Gly Trp Tyr Gln Ala Tyr
1               5                   10                  15

Gln Val Phe

<210> SEQ ID NO 78
<211> LENGTH: 25
<212> TYPE: PRT
<213> ORGANISM: Artificial Sequence
<220> FEATURE:
<223> OTHER INFORMATION: Adnectin

<400> SEQUENCE: 78

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 79
<211> LENGTH: 19
<212> TYPE: PRT
<213> ORGANISM: Artificial Sequence
<220> FEATURE:
<223> OTHER INFORMATION: Adnectin

<400> SEQUENCE: 79

Tyr Leu Tyr His Ile Gln Tyr Trp Pro Leu Gly Trp Tyr His Arg Tyr
1               5                   10                  15

Gln Val Phe

<210> SEQ ID NO 80
<211> LENGTH: 25
<212> TYPE: PRT
<213> ORGANISM: Artificial Sequence
<220> FEATURE:
<223> OTHER INFORMATION: Adnectin

<400> SEQUENCE: 80
```

-continued

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 81
<211> LENGTH: 19
<212> TYPE: PRT
<213> ORGANISM: Artificial Sequence
<220> FEATURE:
<223> OTHER INFORMATION: Adnectin

<400> SEQUENCE: 81

Arg Phe Tyr His Ile Gln Tyr Trp Pro Leu Gly Trp Tyr His Cys Tyr
1               5                   10                  15

Gln Val Phe

<210> SEQ ID NO 82
<211> LENGTH: 25
<212> TYPE: PRT
<213> ORGANISM: Artificial Sequence
<220> FEATURE:
<223> OTHER INFORMATION: Adnectin

<400> SEQUENCE: 82

Glu Tyr Gln Ile Arg Val Tyr Ala Gln Thr Gly Asp Gly Ser Ser Gln
1               5                   10                  15

Glu Tyr Phe Gly Trp Ile Gln Ile Gly
            20                  25

<210> SEQ ID NO 83
<211> LENGTH: 19
<212> TYPE: PRT
<213> ORGANISM: Artificial Sequence
<220> FEATURE:
<223> OTHER INFORMATION: Adnectin

<400> SEQUENCE: 83

His Ser Tyr His Ile Gln Tyr Trp Pro Leu Gly Trp Tyr Tyr Arg Tyr
1               5                   10                  15

Gln Val Phe

<210> SEQ ID NO 84
<211> LENGTH: 25
<212> TYPE: PRT
<213> ORGANISM: Artificial Sequence
<220> FEATURE:
<223> OTHER INFORMATION: Adnectin

<400> SEQUENCE: 84

Glu Tyr Gln Ile Arg Val Tyr Ala Glu Thr Gly Gly Ser Gly Ser Gln
1               5                   10                  15

Gln Tyr Trp Gly Trp Ile Gln Ile Gly
            20                  25

<210> SEQ ID NO 85
<211> LENGTH: 19
<212> TYPE: PRT
<213> ORGANISM: Artificial Sequence
<220> FEATURE:
<223> OTHER INFORMATION: Adnectin

<400> SEQUENCE: 85

His Ala Tyr His Ile Gln Tyr Trp Pro Leu Gly Phe Tyr Gln Gly Tyr

<210> SEQ ID NO 86
<211> LENGTH: 25
<212> TYPE: PRT
<213> ORGANISM: Artificial Sequence
<220> FEATURE:
<223> OTHER INFORMATION: Adnectin

<400> SEQUENCE: 86

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 87
<211> LENGTH: 19
<212> TYPE: PRT
<213> ORGANISM: Artificial Sequence
<220> FEATURE:
<223> OTHER INFORMATION: Adnectin

<400> SEQUENCE: 87

His Ser Tyr His Ile Gln Tyr Trp Pro Leu Gly Leu Tyr Val Leu Tyr
1               5                   10                  15

Gln Val Phe

<210> SEQ ID NO 88
<211> LENGTH: 25
<212> TYPE: PRT
<213> ORGANISM: Artificial Sequence
<220> FEATURE:
<223> OTHER INFORMATION: Adnectin

<400> SEQUENCE: 88

Glu Tyr Gln Ile Arg Val Tyr Ala Glu Thr Gly Ala Gly Gly Ser Glu
1               5                   10                  15

His Ser Phe Gly Trp Ile Gln Ile Gly
            20                  25

<210> SEQ ID NO 89
<211> LENGTH: 19
<212> TYPE: PRT
<213> ORGANISM: Artificial Sequence
<220> FEATURE:
<223> OTHER INFORMATION: Adnectin

<400> SEQUENCE: 89

Leu Ser Tyr His Ile Gln Tyr Trp Pro Leu Gly Arg Tyr Glu Arg Tyr
1               5                   10                  15

Gln Val Phe

<210> SEQ ID NO 90
<211> LENGTH: 25
<212> TYPE: PRT
<213> ORGANISM: Artificial Sequence
<220> FEATURE:
<223> OTHER INFORMATION: Adnectin

<400> SEQUENCE: 90

Glu Tyr Gln Ile Arg Val Tyr Ala Glu Thr Val Gly Gly Glu Ser Leu
1               5                   10                  15

```
Asp Ser Phe Ser Trp Ile Gln Ile Gly
            20                  25

<210> SEQ ID NO 91
<211> LENGTH: 19
<212> TYPE: PRT
<213> ORGANISM: Artificial Sequence
<220> FEATURE:
<223> OTHER INFORMATION: Adnectin

<400> SEQUENCE: 91

Leu Ser Tyr His Ile Gln Tyr Trp Pro Leu Gly Trp Tyr Gln Leu Tyr
1               5                   10                  15

Gln Val Phe

<210> SEQ ID NO 92
<211> LENGTH: 25
<212> TYPE: PRT
<213> ORGANISM: Artificial Sequence
<220> FEATURE:
<223> OTHER INFORMATION: Adnectin

<400> SEQUENCE: 92

Glu Tyr Gln Ile Arg Val Tyr Ala Glu Thr Arg Val Gly Gly Ser Val
1               5                   10                  15

Ala Ser Phe Gly Trp Ile Gln Ile Gly
            20                  25

<210> SEQ ID NO 93
<211> LENGTH: 19
<212> TYPE: PRT
<213> ORGANISM: Artificial Sequence
<220> FEATURE:
<223> OTHER INFORMATION: Adnectin

<400> SEQUENCE: 93

Leu Ala Tyr His Ile Gln Tyr Trp Pro Leu Gly Arg Tyr Gln Leu Tyr
1               5                   10                  15

Gln Val Phe

<210> SEQ ID NO 94
<211> LENGTH: 25
<212> TYPE: PRT
<213> ORGANISM: Artificial Sequence
<220> FEATURE:
<223> OTHER INFORMATION: Adnectin

<400> SEQUENCE: 94

Glu Tyr Gln Ile Arg Val Tyr Ala Glu Thr Gly Arg Gly Glu Ser Pro
1               5                   10                  15

Ala Ser Phe Gly Trp Ile Gln Ile Gly
            20                  25

<210> SEQ ID NO 95
<211> LENGTH: 111
<212> TYPE: PRT
<213> ORGANISM: Artificial Sequence
<220> FEATURE:
<223> OTHER INFORMATION: Adnectin

<400> SEQUENCE: 95

Met Ala Ser Thr Ser Gly Val Ser Asp Val Pro Arg Asp Leu Glu Val
1               5                   10                  15

Val Ala Ala Thr Pro Thr Ser Leu Leu Ile Ser Trp Asp Ala Pro Ala
```

```
                    20                  25                  30
Val Thr Val His Ser Tyr His Ile Gln Tyr Trp Pro Leu Gly Trp Tyr
                35                  40                  45
Gln Arg Tyr Gln Val Phe Ser Val Pro Gly Ser Lys Ser Thr Ala Thr
         50                  55                  60
Ile Ser Gly Leu Lys Pro Glu Val Glu Tyr Gln Ile Arg Val Tyr Ala
 65                  70                  75                  80
Glu Thr Gly Gly Gly Ser Gln Gln Ser Phe Gly Trp Ile Gln Ile
                85                  90                  95
Gly Tyr Arg Thr Glu Gly Ser Gly Ser His His His His His His
                100                 105                 110
```

<210> SEQ ID NO 96
<211> LENGTH: 109
<212> TYPE: PRT
<213> ORGANISM: Artificial Sequence
<220> FEATURE:
<223> OTHER INFORMATION: Adnectin

<400> SEQUENCE: 96

```
Met Gly Val Ser Asp Val Pro Arg Asp Leu Glu Val Val Ala Ala Thr
 1               5                  10                  15
Pro Thr Ser Leu Leu Ile Ser Trp Asp Ala Pro Ala Val Thr Val Gln
                20                  25                  30
Ser Tyr His Ile Gln Tyr Trp Pro Leu Gly Ser Tyr Gln Arg Tyr Gln
                35                  40                  45
Val Phe Ser Val Pro Gly Ser Lys Ser Thr Ala Thr Ile Ser Gly Leu
         50                  55                  60
Lys Pro Gly Val Glu Tyr Gln Ile Arg Val Tyr Ala Glu Thr Gly Gly
 65                  70                  75                  80
Ala Asp Ser Asp Gln Ser Met Gly Trp Ile Gln Ile Gly Tyr Arg Thr
                85                  90                  95
Glu Gly Asp Lys Pro Ser Gln His His His His His
                100                 105
```

<210> SEQ ID NO 97
<211> LENGTH: 109
<212> TYPE: PRT
<213> ORGANISM: Artificial Sequence
<220> FEATURE:
<223> OTHER INFORMATION: Adnectin

<400> SEQUENCE: 97

```
Met Gly Val Ser Asp Val Pro Arg Asp Leu Glu Val Val Ala Ala Thr
 1               5                  10                  15
Pro Thr Ser Leu Leu Ile Ser Trp Asp Ala Pro Ala Val Thr Val His
                20                  25                  30
Ser Tyr His Ile Gln Tyr Trp Pro Leu Gly Trp Tyr Gln Arg Tyr Gln
                35                  40                  45
Val Phe Ser Val Pro Gly Ser Lys Ser Thr Ala Thr Ile Ser Gly Leu
         50                  55                  60
Lys Pro Gly Val Glu Tyr Gln Ile Arg Val Tyr Ala Glu Thr Arg Ser
 65                  70                  75                  80
Gly Leu Ala Asp Glu Ser Phe Gly Trp Ile Gln Ile Gly Tyr Arg Thr
                85                  90                  95
Glu Gly Asp Lys Pro Ser Gln His His His His His
                100                 105
```

```
<210> SEQ ID NO 98
<211> LENGTH: 109
<212> TYPE: PRT
<213> ORGANISM: Artificial Sequence
<220> FEATURE:
<223> OTHER INFORMATION: Adnectin

<400> SEQUENCE: 98

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val His
            20                  25                  30

Ser Tyr His Ile Gln Tyr Trp Pro Leu Gly Ser Tyr Gln Arg Tyr Gln
        35                  40                  45

Val Phe Ser Val Pro Gly Ser Lys Ser Thr Ala Thr Ile Ser Gly Leu
    50                  55                  60

Lys Pro Gly Val Glu Tyr Gln Ile Arg Val Tyr Ala Glu Thr Gly Gly
65                  70                  75                  80

Ala Asp Ser Asp Gln Ser Met Gly Trp Ile Gln Ile Gly Tyr Arg Thr
                85                  90                  95

Glu Gly Asp Lys Pro Ser Gln His His His His His
            100                 105

<210> SEQ ID NO 99
<211> LENGTH: 107
<212> TYPE: PRT
<213> ORGANISM: Artificial Sequence
<220> FEATURE:
<223> OTHER INFORMATION: Adnectin

<400> SEQUENCE: 99

Met Gly His His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Asp Ala Pro Ala Val Thr Val His Ser Tyr His Ile Gln Tyr Trp Pro
        35                  40                  45

Leu Gly Ser Tyr Gln Arg Tyr Gln Val Phe Ser Val Pro Gly Ser Lys
    50                  55                  60

Ser Thr Ala Thr Ile Ser Gly Leu Lys Pro Gly Val Glu Tyr Gln Ile
65                  70                  75                  80

Arg Val Tyr Ala Glu Thr Gly Gly Ala Asp Ser Asp Gln Ser Phe Gly
                85                  90                  95

Trp Ile Gln Ile Gly Tyr Arg Thr Pro Glu Ser
            100                 105

<210> SEQ ID NO 100
<211> LENGTH: 115
<212> TYPE: PRT
<213> ORGANISM: Artificial Sequence
<220> FEATURE:
<223> OTHER INFORMATION: Adnectin

<400> SEQUENCE: 100

Met Ala Ser Thr Ser Gly Ser Ser Ser Tyr Leu Met Pro Ser Asp Leu
1               5                   10                  15

Glu Val Val Ala Ala Thr Pro Thr Ser Leu Tyr Ile His Trp Tyr Pro
            20                  25                  30

Ile Ala Ser Thr Ile Ile Asn Phe Arg Ile Thr Tyr Gly Glu Thr Gly
```

```
                35                  40                  45
Gly Asn Ser Pro Val Gln Glu Phe Thr Val Pro Gly Ser Gln Val His
             50                  55                  60
Ala Thr Ile Ser Gly Leu Lys Pro Gly Val Asp Tyr Thr Ile Thr Val
 65                  70                  75                  80
Tyr Ala Val His Tyr Glu His Lys Tyr Ser Glu Leu Trp Met Gly His
                 85                  90                  95
Pro Ile Ser Ile Asn Tyr Arg Thr Glu Gly Ser Gly Ser His His His
                100                 105                 110
His His His
        115

<210> SEQ ID NO 101
<211> LENGTH: 115
<212> TYPE: PRT
<213> ORGANISM: Artificial Sequence
<220> FEATURE:
<223> OTHER INFORMATION: Adnectin

<400> SEQUENCE: 101

Met Ala Ser Thr Ser Gly Ser Ala Ser Tyr Leu Ile Pro Ser Asp Leu
 1               5                  10                  15
Glu Val Val Ala Ala Thr Pro Thr Ser Leu Ser Ile Tyr Trp Tyr Pro
                 20                  25                  30
Val Ala Ser Thr Ile Ile Asn Phe Arg Ile Thr Tyr Val Glu Thr Gly
                 35                  40                  45
Gly Asn Ser Pro Val Gln Glu Phe Thr Val Pro Gly Ser Lys Ser Thr
             50                  55                  60
Ala Thr Ile Ser Gly Leu Lys Pro Gly Val Asp Tyr Thr Ile Thr Val
 65                  70                  75                  80
Tyr Ala Val His Tyr Glu Gln Lys Tyr Ser Glu Tyr Trp Ile Gly His
                 85                  90                  95
Pro Ile Ser Ile Asn Tyr Arg Thr Glu Gly Ser Gly Ser His His His
                100                 105                 110
His His His
        115

<210> SEQ ID NO 102
<211> LENGTH: 115
<212> TYPE: PRT
<213> ORGANISM: Artificial Sequence
<220> FEATURE:
<223> OTHER INFORMATION: Adnectin

<400> SEQUENCE: 102

Met Ala Ser Thr Ser Gly Ser Ser Pro Tyr Leu Met Pro Tyr Asp Leu
 1               5                  10                  15
Glu Val Val Ala Ala Thr Pro Thr Ser Leu Phe Ile Arg Trp Tyr Gly
                 20                  25                  30
Ser Ala Ser Ser Ile Val Lys Phe Arg Ile Thr Tyr Gly Glu Thr Gly
                 35                  40                  45
Gly Asn Ser Pro Val Gln Glu Phe Thr Val Gly Gly Thr Gln Leu His
             50                  55                  60
Ala Thr Ile Ser Gly Leu Lys Pro Gly Val Asp Tyr Thr Ile Thr Val
 65                  70                  75                  80
Tyr Ala Val His Phe Glu His Lys Tyr Ser Glu Leu Trp Ile Gly His
                 85                  90                  95
```

Pro Ile Ser Ile Asn Tyr Arg Thr Glu Gly Ser Gly Ser His His His
                100                 105                 110

His His His
        115

<210> SEQ ID NO 103
<211> LENGTH: 115
<212> TYPE: PRT
<213> ORGANISM: Artificial Sequence
<220> FEATURE:
<223> OTHER INFORMATION: Adnectin

<400> SEQUENCE: 103

Met Ala Ser Thr Ser Gly Tyr Thr Ser Tyr Pro Ile Pro Tyr Asp Leu
1               5                   10                  15

Glu Val Val Ala Ala Thr Pro Thr Ser Leu Tyr Ile His Trp Tyr Trp
                20                  25                  30

Ile Ala Ala Thr Ile Ile Ser Phe Arg Ile Thr Tyr Gly Glu Thr Gly
            35                  40                  45

Gly Asn Ser Pro Val Gln Glu Phe Thr Val Pro Ala Gly Gln Asp His
        50                  55                  60

Ala Thr Ile Ser Gly Leu Lys Pro Gly Val Asp Tyr Thr Ile Thr Val
65                  70                  75                  80

Tyr Ala Val His Tyr Glu Glu Glu Tyr Ser Glu Phe Trp Thr Gly His
                85                  90                  95

Pro Ile Ser Ile Asn Tyr Arg Thr Glu Gly Ser Gly Ser His His His
                100                 105                 110

His His His
        115

<210> SEQ ID NO 104
<211> LENGTH: 116
<212> TYPE: PRT
<213> ORGANISM: Artificial Sequence
<220> FEATURE:
<223> OTHER INFORMATION: Adnectin

<400> SEQUENCE: 104

Met Ala Ser Thr Ser Gly Thr His Trp Phe Tyr Ser Ile Pro His Asp
1               5                   10                  15

Leu Glu Val Val Ala Ala Thr Pro Thr Ser Leu Thr Ile Ala Trp Glu
                20                  25                  30

Pro Pro His His Thr Ala Met Gly Tyr Arg Ile Thr Tyr Gly Glu Thr
            35                  40                  45

Gly Gly Asn Ser Pro Val Gln Glu Phe Thr Val Pro Gly Gly Tyr Thr
        50                  55                  60

Thr Ala Tyr Ile Ser Gly Leu Lys Pro Gly Val Asp Tyr Thr Ile Thr
65                  70                  75                  80

Val Tyr Ala Ala Tyr Tyr Glu Arg Glu Tyr Ser Glu His Trp Ile Ser
                85                  90                  95

His Pro Ile Ser Ile Asn Tyr Arg Thr Glu Gly Ser Gly Ser His His
                100                 105                 110

His His His His
        115

<210> SEQ ID NO 105
<211> LENGTH: 118
<212> TYPE: PRT
<213> ORGANISM: Artificial Sequence
<220> FEATURE:
<223> OTHER INFORMATION: Adnectin

<400> SEQUENCE: 105

Met Ala Ser Thr Ser Gly Glu Phe Tyr His Thr Lys Tyr Pro Tyr Asp
1               5                   10                  15

Leu Glu Val Val Ala Ala Thr Pro Thr Ser Leu Glu Ile Ser Trp Arg
                20                  25                  30

Ser Pro Thr Arg Asp Trp Gln Trp Phe Arg Ile Thr Tyr Gly Glu Thr
            35                  40                  45

Gly Gly Asn Ser Pro Val Gln Glu Phe Thr Val Ala Gly Pro Tyr Arg
        50                  55                  60

Asn Ala Ile Ile Ser Gly Leu Lys Pro Gly Val Asp Tyr Thr Ile Thr
65                  70                  75                  80

Val Tyr Ala Asp Val Tyr Met Pro Ser Glu Gly Gly Leu Val Val Asp
                85                  90                  95

Thr Tyr His Pro Ile Ser Ile Asn Tyr Arg Thr Glu Gly Ser Gly Ser
            100                 105                 110

His His His His His His
        115

<210> SEQ ID NO 106
<211> LENGTH: 116
<212> TYPE: PRT
<213> ORGANISM: Artificial Sequence
<220> FEATURE:
<223> OTHER INFORMATION: Adnectin

<400> SEQUENCE: 106

Met Ala Ser Thr Ser Gly Gln Ala Tyr Pro Glu Tyr Tyr Phe Val Asp
1               5                   10                  15

Leu Glu Val Val Ala Ala Thr Pro Thr Ser Leu Leu Ile Ser Trp Ser
                20                  25                  30

Lys Pro Tyr Tyr Asn Ala Tyr Ser Tyr Arg Ile Thr Tyr Gly Glu Thr
            35                  40                  45

Gly Gly Asn Ser Pro Val Gln Glu Phe Thr Val Leu Gly His Asp Thr
        50                  55                  60

Arg Ala Val Ile Ser Gly Leu Lys Pro Gly Val Asp Tyr Thr Ile Thr
65                  70                  75                  80

Val Tyr Ala Met Phe Ile Glu Tyr Ile Asp Gln Glu Ile Trp His Ala
                85                  90                  95

His Pro Ile Ser Ile Asn Tyr Arg Thr Glu Gly Ser Gly Ser His His
            100                 105                 110

His His His His
        115

<210> SEQ ID NO 107
<211> LENGTH: 109
<212> TYPE: PRT
<213> ORGANISM: Artificial Sequence
<220> FEATURE:
<223> OTHER INFORMATION: Adnectin

<400> SEQUENCE: 107

Met Gly Val Ser Asp Val Pro Arg Asp Leu Glu Val Val Ala Ala Thr
1               5                   10                  15

Pro Thr Ser Leu Leu Ile Ser Trp Asp Glu His Thr Asp Ile Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ala Met Glu His Thr Ala Thr Ile Ser Gly Leu
 50                  55                  60

Lys Pro Gly Val Asp Tyr Thr Ile Thr Val Tyr Ala Val Thr His Val
65                  70                  75                  80

Tyr Pro Ile Met Ile His Gln Tyr Pro Ile Ser Ile Asn Tyr Arg Thr
                85                  90                  95

Glu Ile Asp Lys Pro Ser Gln His His His His His
            100                 105

<210> SEQ ID NO 108
<211> LENGTH: 111
<212> TYPE: PRT
<213> ORGANISM: Artificial Sequence
<220> FEATURE:
<223> OTHER INFORMATION: Adnectin

<400> SEQUENCE: 108

Met Ala Ser Thr Ser Gly Val Ser Asp Val Pro Arg Asp Leu Glu Val
 1               5                  10                  15

Val Ala Ala Thr Pro Thr Ser Leu Leu Ile Ser Trp Asp Ala Pro Ala
             20                  25                  30

Val Thr Val Leu Glu Tyr Gln Ile Asp Tyr His Pro Ala Ala Val Trp
         35                  40                  45

His Ala Leu Gln Arg Phe Thr Val Pro Gly Ser Lys Ser Thr Ala Thr
 50                  55                  60

Ile Ser Gly Leu Lys Pro Gly Val His Tyr Lys Ile Ser Val Thr Ala
65                  70                  75                  80

Thr Thr His Ala Asp Asn Glu Ser Ile Met Trp His Pro Ile Ser Ile
                85                  90                  95

Tyr Tyr Arg Thr Glu Gly Ser Gly Ser His His His His His His
            100                 105                 110

<210> SEQ ID NO 109
<211> LENGTH: 109
<212> TYPE: PRT
<213> ORGANISM: Artificial Sequence
<220> FEATURE:
<223> OTHER INFORMATION: Adnectin

<400> SEQUENCE: 109

Met Gly Val Ser Asp Val Pro Arg Asp Leu Glu Val Val Ala Ala Thr
 1               5                  10                  15

Pro Thr Ser Leu Leu Ile Ser Trp Asp Tyr Pro Thr Val Thr Pro Arg
             20                  25                  30

Tyr Tyr Arg Ile Thr Tyr Gly Glu Thr Gly Gly Asn Ser Pro Val Gln
            35                  40                  45

Glu Phe Thr Val Pro Glu Tyr Ile Gly Thr Ala Thr Ile Ser Gly Leu
 50                  55                  60

Lys Pro Gly Val Asp Tyr Thr Ile Thr Val Tyr Ala Val Thr Asn Asp
65                  70                  75                  80

Thr Thr Ile Tyr Ser Ile Ser Arg Pro Ile Ser Ile Asn Tyr Arg Thr
                85                  90                  95

Glu Ile Asp Lys Pro Ser Gln His His His His His
            100                 105

<210> SEQ ID NO 110

```
<211> LENGTH: 107
<212> TYPE: PRT
<213> ORGANISM: Artificial Sequence
<220> FEATURE:
<223> OTHER INFORMATION: Adnectin

<400> SEQUENCE: 110

Met Gly His His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Asp Ala Pro Ala Val Thr Val His Ser Tyr His Ile Gln Tyr Trp Pro
        35                  40                  45

Leu Gly Ser Tyr Gln Arg Tyr Gln Val Phe Ser Val Pro Gly Ser Lys
    50                  55                  60

Ser Thr Ala Thr Ile Ser Gly Leu Lys Pro Gly Val Glu Tyr Gln Ile
65                  70                  75                  80

Arg Val Tyr Ala Glu Thr Gly Arg Gly Glu Ser Asp Gln Ser Leu Gly
                85                  90                  95

Trp Ile Gln Ile Gly Tyr Arg Thr Glu Glu Ser
            100                 105

<210> SEQ ID NO 111
<211> LENGTH: 107
<212> TYPE: PRT
<213> ORGANISM: Artificial Sequence
<220> FEATURE:
<223> OTHER INFORMATION: Adnectin

<400> SEQUENCE: 111

Met Gly His His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Asp Ala Pro Ala Val Thr Val His Ser Tyr His Ile Gln Tyr Trp Pro
        35                  40                  45

Leu Gly Ser Tyr Gln Arg Tyr Gln Val Phe Ser Val Pro Gly Ser Lys
    50                  55                  60

Ser Thr Ala Thr Ile Ser Gly Leu Lys Pro Gly Val Glu Tyr Gln Ile
65                  70                  75                  80

Arg Val Tyr Ala Glu Thr Gly Arg Gly Glu Ser Asp Gln Ser Phe Gly
                85                  90                  95

Trp Ile Gln Ile Gly Tyr Arg Thr Glu Glu Ser
            100                 105

<210> SEQ ID NO 112
<211> LENGTH: 107
<212> TYPE: PRT
<213> ORGANISM: Artificial Sequence
<220> FEATURE:
<223> OTHER INFORMATION: Adnectin

<400> SEQUENCE: 112

Met Gly His His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Asp Ala Pro Ala Val Thr Val His Ser Tyr His Ile Gln Tyr Trp Pro
        35                  40                  45
```

Leu Gly Ser Tyr Gln Arg Tyr Gln Val Phe Ser Val Pro Gly Ser Lys
        50                  55                  60

Ser Thr Ala Thr Ile Ser Gly Leu Lys Pro Gly Val Glu Tyr Gln Ile
 65                  70                  75                  80

Arg Val Tyr Ala Glu Thr Gly Arg Gly Glu Ser Asp Gln Ser Leu Gly
                 85                  90                  95

Trp Ile Gln Ile Gly Tyr Arg Thr Pro Glu Ser
                100                 105

<210> SEQ ID NO 113
<211> LENGTH: 107
<212> TYPE: PRT
<213> ORGANISM: Artificial Sequence
<220> FEATURE:
<223> OTHER INFORMATION: Adnectin

<400> SEQUENCE: 113

Met Gly His His His His His Gly Gly Val Ser Asp Val Pro Arg
 1               5                  10                  15

Asp Leu Glu Val Val Ala Ala Thr Pro Thr Ser Leu Leu Ile Ser Trp
                 20                  25                  30

Asp Ala Pro Ala Val Thr Val His Ser Tyr His Ile Gln Tyr Trp Pro
             35                  40                  45

Leu Gly Ser Tyr Gln Arg Tyr Gln Val Phe Ser Val Pro Gly Ser Lys
        50                  55                  60

Ser Thr Ala Thr Ile Ser Gly Leu Lys Pro Gly Val Glu Tyr Gln Ile
 65                  70                  75                  80

Arg Val Tyr Ala Glu Thr Gly Arg Gly Glu Ser Asp Gln Ser Phe Gly
                 85                  90                  95

Trp Ile Gln Ile Gly Tyr Arg Thr Pro Glu Ser
                100                 105

<210> SEQ ID NO 114
<211> LENGTH: 107
<212> TYPE: PRT
<213> ORGANISM: Artificial Sequence
<220> FEATURE:
<223> OTHER INFORMATION: Adnectin

<400> SEQUENCE: 114

Met Gly His His His His His Gly Gly Val Ser Asp Val Pro Arg
 1               5                  10                  15

Asp Leu Glu Val Val Ala Ala Thr Pro Thr Ser Leu Leu Ile Ser Trp
                 20                  25                  30

Asp Ala Pro Ala Val Thr Val His Ala Tyr His Ile Gln Tyr Trp Pro
             35                  40                  45

Leu Gly Phe Tyr Gln Gly Tyr Gln Val Phe Ser Val Pro Gly Ser Lys
        50                  55                  60

Ser Thr Ala Thr Ile Ser Gly Leu Lys Pro Gly Val Glu Tyr Gln Ile
 65                  70                  75                  80

Arg Val Tyr Ala Glu Thr Gly Leu Gly Asp Ala His Gln Ser Leu Gly
                 85                  90                  95

Trp Ile Gln Ile Gly Tyr Arg Thr Pro Glu Ser
                100                 105

<210> SEQ ID NO 115
<211> LENGTH: 105
<212> TYPE: PRT
<213> ORGANISM: Artificial Sequence

```
<220> FEATURE:
<223> OTHER INFORMATION: Adnectin

<400> SEQUENCE: 115

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Asn Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val His Ser Ser Pro Ile Ser Ile Asn Tyr Arg Thr Glu Ile Asp Lys
                85                  90                  95

Pro Ser Gln His His His His His His
            100                 105

<210> SEQ ID NO 116
<211> LENGTH: 111
<212> TYPE: PRT
<213> ORGANISM: Artificial Sequence
<220> FEATURE:
<223> OTHER INFORMATION: Adnectin

<400> SEQUENCE: 116

Met Ala Ser Thr Ser Gly Val Ser Asp Val Pro Arg Asp Leu Glu Val
1               5                   10                  15

Val Ala Ala Thr Pro Thr Ser Leu Leu Ile Ser Trp Asp Ala Pro Ala
            20                  25                  30

Val Thr Val Glu Gln Tyr Tyr Ile Ala Tyr Val Glu Gly Glu Pro
        35                  40                  45

Ser Ser Tyr Gln Tyr Phe Arg Val Pro Gly Ser Lys Ser Thr Ala Thr
    50                  55                  60

Ile Ser Gly Leu Lys Pro Gly Val Leu Tyr His Ile Tyr Val Asn Ala
65                  70                  75                  80

Val Thr Gly Ser Gly Leu Arg Pro Glu Phe Ser Leu Pro Ile Arg Ile
                85                  90                  95

Lys Tyr Arg Thr Glu Gly Ser Gly Ser His His His His His His
            100                 105                 110

<210> SEQ ID NO 117
<211> LENGTH: 104
<212> TYPE: PRT
<213> ORGANISM: Artificial Sequence
<220> FEATURE:
<223> OTHER INFORMATION: Adnectin

<400> SEQUENCE: 117

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Arg Ile Thr Tyr Gly
        35                  40                  45

Glu Thr Gly Gly Asn Ser Pro Val Gln Glu Phe Thr Val Pro Ser Val
    50                  55                  60
```

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 118
<211> LENGTH: 105
<212> TYPE: PRT
<213> ORGANISM: Artificial Sequence
<220> FEATURE:
<223> OTHER INFORMATION: Adnectin

<400> SEQUENCE: 118

Met Gly Val Ser Asp Val Pro Arg Asp Leu Glu Val Val Ala Ala Thr
1               5                   10                  15

Pro Thr Ser Leu Leu Ile Ser Trp Lys Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asn Ser Leu Pro Ile Ser Ile Asn Tyr Arg Thr Glu Ile Asp Lys
                85                  90                  95

Pro Ser Gln His His His His His
            100                 105

<210> SEQ ID NO 119
<211> LENGTH: 107
<212> TYPE: PRT
<213> ORGANISM: Artificial Sequence
<220> FEATURE:
<223> OTHER INFORMATION: Adnectin

<400> SEQUENCE: 119

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Gly
            20                  25                  30

Trp Tyr His Ile Gly Tyr Asn Val Glu Gly Glu Pro Ala Ser Tyr Gln
        35                  40                  45

Tyr Phe Arg Val Pro Gly Ser Lys Ser Thr Ala Thr Ile Ser Gly Leu
    50                  55                  60

Lys Pro Gly Val Glu Tyr Met Ile Phe Val Asn Ala Val Thr Gly Ser
65                  70                  75                  80

Gly Ala Arg Glu Glu Phe Ser Leu Pro Ile Ser Ile Asn Tyr Arg Thr
                85                  90                  95

Glu Gly Ser Gly Ser His His His His His
            100                 105

<210> SEQ ID NO 120
<211> LENGTH: 103
<212> TYPE: PRT
<213> ORGANISM: Artificial Sequence
<220> FEATURE:
<223> OTHER INFORMATION: Adnectin

<400> SEQUENCE: 120

Met Gly His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Glu Tyr Asn Val Asn Pro Tyr Arg Tyr Tyr Arg Ile Thr Tyr Gly Glu
        35                  40                  45

Thr Gly Gly Asn Ser Pro Val Gln Glu Phe Thr Val Pro Ser Val Leu
    50                  55                  60

Ser Ser Ala Gln Ile Ser Gly Leu Lys Pro Gly Val Asp Tyr Thr Ile
65                  70                  75                  80

Thr Val Tyr Ala Val Thr Arg Gly Val Asp Ser Ala Pro Ile Ser Ile
                85                  90                  95

Asn Tyr Arg Thr Pro Gly Gly
            100

<210> SEQ ID NO 121
<211> LENGTH: 103
<212> TYPE: PRT
<213> ORGANISM: Artificial Sequence
<220> FEATURE:
<223> OTHER INFORMATION: Adnectin

<400> SEQUENCE: 121

Met Gly His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Glu Tyr Asn Val Asn Pro Tyr Arg Tyr Tyr Arg Ile Thr Tyr Gly Glu
        35                  40                  45

Thr Gly Gly Asn Ser Pro Val Gln Glu Phe Thr Val Pro Ser Val Leu
    50                  55                  60

Ser Thr Ala Glu Ile Ser Gly Leu Lys Pro Gly Val Asp Tyr Thr Ile
65                  70                  75                  80

Thr Val Tyr Ala Val Thr Tyr Gly Val Asp Ser Asp Pro Ile Ser Ile
                85                  90                  95

Asn Tyr Arg Thr Pro Gly Gly
            100

<210> SEQ ID NO 122
<211> LENGTH: 103
<212> TYPE: PRT
<213> ORGANISM: Artificial Sequence
<220> FEATURE:
<223> OTHER INFORMATION: Adnectin

<400> SEQUENCE: 122

Met Gly His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Gln Tyr Lys Val His Pro Tyr Arg Tyr Tyr Arg Ile Thr Tyr Gly Glu
        35                  40                  45

Thr Gly Gly Asn Ser Pro Val Gln Glu Phe Thr Val Pro Ser Val Leu
    50                  55                  60

Ser Thr Ala Glu Ile Ser Gly Leu Lys Pro Gly Val Asp Tyr Thr Ile
65                  70                  75                  80

Thr Val Tyr Ala Val Thr Arg Gly Val Asp Ser Ala Pro Ile Ser Ile
                85                  90                  95

Asn Tyr Arg Thr Pro Gly Gly
            100

<210> SEQ ID NO 123
<211> LENGTH: 105
<212> TYPE: PRT
<213> ORGANISM: Artificial Sequence
<220> FEATURE:
<223> OTHER INFORMATION: Adnectin

<400> SEQUENCE: 123

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Arg Gly
65                  70                  75                  80

Val Asp Ser Ala Pro Ile Ser Ile Asn Tyr Arg Thr Glu Ile Asp Lys
                85                  90                  95

Pro Ser Gln His His His His His His
            100                 105

<210> SEQ ID NO 124
<211> LENGTH: 105
<212> TYPE: PRT
<213> ORGANISM: Artificial Sequence
<220> FEATURE:
<223> OTHER INFORMATION: Adnectin

<400> SEQUENCE: 124

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Glu Ile Ser Gly Leu
    50                  55                  60

Lys Pro Gly Val Asp Tyr Thr Ile Thr Val Tyr Ala Val Thr Arg Gly
65                  70                  75                  80

Val Asp Ser Ala Pro Ile Ser Ile Asn Tyr Arg Thr Pro Ile Asp Lys
                85                  90                  95

Pro Ser Gln His His His His His His
            100                 105

<210> SEQ ID NO 125
<211> LENGTH: 103
<212> TYPE: PRT
<213> ORGANISM: Artificial Sequence
<220> FEATURE:
<223> OTHER INFORMATION: Adnectin

<400> SEQUENCE: 125

Met Gly His His His His His His Gly Gly Val Ser Asp Val Pro Arg

```
                1               5                  10                 15
Asp Leu Glu Val Val Ala Ala Thr Pro Thr Ser Leu Leu Ile Ser Trp
                20                 25                 30

Glu Tyr Lys Val His Pro Tyr Arg Tyr Arg Ile Thr Tyr Gly Glu
            35                 40                 45

Thr Gly Gly Asn Ser Pro Val Gln Glu Phe Thr Val Pro Ser Val Leu
        50                 55                 60

Ser Thr Ala Thr Ile Ser Gly Leu Lys Pro Gly Val Asp Tyr Thr Ile
65                  70                 75                  80

Thr Val Tyr Ala Val Thr Tyr Gly Val Gln Ser Asp Pro Ile Ser Ile
                85                 90                 95

Asn Tyr Arg Thr Pro Gly Gly
            100

<210> SEQ ID NO 126
<211> LENGTH: 105
<212> TYPE: PRT
<213> ORGANISM: Artificial Sequence
<220> FEATURE:
<223> OTHER INFORMATION: Adnectin

<400> SEQUENCE: 126

Met Gly Val Ser Asp Val Pro Arg Asp Leu Glu Val Val Ala Ala Thr
1               5                  10                 15

Pro Thr Ser Leu Leu Ile Ser Trp Glu Tyr Lys Val His Pro Tyr Arg
                20                 25                 30

Tyr Tyr Arg Ile Thr Tyr Gly Glu Thr Gly Gly Asn Ser Pro Val Gln
            35                 40                 45

Glu Phe Thr Val Pro Ser Val Leu Ser Thr Ala Thr Ile Ser Gly Leu
        50                 55                 60

Lys Pro Gly Val Asp Tyr Thr Ile Thr Val Tyr Ala Val Thr Tyr Gly
65                  70                 75                  80

Ile Gln Ser Pro Pro Ile Ser Ile Asn Tyr Arg Thr Glu Ile Asp Lys
                85                 90                 95

Pro Ser Gln His His His His His His
            100                105

<210> SEQ ID NO 127
<211> LENGTH: 103
<212> TYPE: PRT
<213> ORGANISM: Artificial Sequence
<220> FEATURE:
<223> OTHER INFORMATION: Adnectin

<400> SEQUENCE: 127

Met Gly His His His His His His Gly Gly Val Ser Asp Val Pro Arg
1               5                  10                 15

Asp Leu Glu Val Val Ala Ala Thr Pro Thr Ser Leu Leu Ile Ser Trp
                20                 25                 30

Gln Tyr Lys Val His Pro Tyr Arg Tyr Tyr Arg Ile Thr Tyr Gly Glu
            35                 40                 45

Thr Gly Gly Asn Ser Pro Val Gln Glu Phe Thr Val Pro Ser Val Leu
        50                 55                 60

Ser Ser Ala Gln Ile Ser Gly Leu Lys Pro Gly Val Asp Tyr Thr Ile
65                  70                 75                  80

Thr Val Tyr Ala Val Thr Tyr Gly Ile Glu Ser Ser Pro Ile Ser Ile
                85                 90                 95
```

```
Asn Tyr Arg Thr Pro Gly Gly
            100
```

<210> SEQ ID NO 128
<211> LENGTH: 103
<212> TYPE: PRT
<213> ORGANISM: Artificial Sequence
<220> FEATURE:
<223> OTHER INFORMATION: Adnectin

<400> SEQUENCE: 128

```
Met Gly His His His His His Gly Gly Val Ser Asp Val Pro Arg
1               5                   10                  15

Asp Leu Glu Val Val Ala Ala Thr Pro Thr Ser Leu Leu Ile Ser Trp
            20                  25                  30

Glu Tyr Lys Val His Pro Tyr Arg Tyr Tyr Arg Ile Thr Tyr Gly Glu
        35                  40                  45

Thr Gly Gly Asn Ser Pro Val Gln Glu Phe Thr Val Pro Ser Val Leu
    50                  55                  60

Ser Ser Ala Glu Ile Ser Gly Leu Lys Pro Gly Val Asp Tyr Thr Ile
65                  70                  75                  80

Thr Val Tyr Ala Val Thr Tyr Gly Ile Asp Ser Ser Pro Ile Ser Ile
                85                  90                  95

Asn Tyr Arg Thr Pro Gly Gly
            100
```

<210> SEQ ID NO 129
<211> LENGTH: 105
<212> TYPE: PRT
<213> ORGANISM: Artificial Sequence
<220> FEATURE:
<223> OTHER INFORMATION: Adnectin

<400> SEQUENCE: 129

```
Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Ser Ala Glu Ile Ser Gly Leu
    50                  55                  60

Lys Pro Gly Val Asp Tyr Thr Ile Thr Val Tyr Ala Val Thr Tyr Gly
65                  70                  75                  80

Ile Asp Ser Pro Pro Ile Ser Ile Asn Tyr Arg Thr Glu Ile Asp Lys
                85                  90                  95

Pro Ser Gln His His His His His
            100                 105
```

<210> SEQ ID NO 130
<211> LENGTH: 104
<212> TYPE: PRT
<213> ORGANISM: Artificial Sequence
<220> FEATURE:
<223> OTHER INFORMATION: Adnectin

<400> SEQUENCE: 130

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
```

```
                    20                  25                  30

Trp Glu Tyr Asn Val His Tyr Asp Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Asp Gly Val His Ser Ser Pro Ile Ser
                85                  90                  95

Ile Asn Tyr Arg Thr Glu Ile Asp
                100

<210> SEQ ID NO 131
<211> LENGTH: 104
<212> TYPE: PRT
<213> ORGANISM: Artificial Sequence
<220> FEATURE:
<223> OTHER INFORMATION: Adnectin

<400> SEQUENCE: 131

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Leu Ser Ala Pro Ile Ser
                85                  90                  95

Ile Asn Tyr Arg Thr Glu Ile Asp
                100

<210> SEQ ID NO 132
<211> LENGTH: 108
<212> TYPE: PRT
<213> ORGANISM: Artificial Sequence
<220> FEATURE:
<223> OTHER INFORMATION: Adnectin

<400> SEQUENCE: 132

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Asp Ala Pro Ala Val Thr Val Glu Glu Tyr Tyr Ile Gly Tyr Tyr
            35                  40                  45

Val Glu Phe Glu Pro Ser Ser Tyr Gln Trp Phe Thr Val Pro Gly Ser
    50                  55                  60

Lys Ser Thr Ala Thr Ile Ser Gly Leu Lys Pro Gly Val Glu Tyr Ser
65                  70                  75                  80

Ile Tyr Val Asn Ala Val Thr Gly Met Gly Met Gln Pro Glu Met Ser
                85                  90                  95

Leu Pro Ile Ser Ile Asn Tyr Arg Thr Glu Gly Ser
                100                 105
```

<210> SEQ ID NO 133
<211> LENGTH: 104
<212> TYPE: PRT
<213> ORGANISM: Artificial Sequence
<220> FEATURE:
<223> OTHER INFORMATION: Adnectin

<400> SEQUENCE: 133

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Tyr Asp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Asp Ser Asp Pro Ile Ser
                85                  90                  95

Ile Asn Tyr Arg Thr Glu Ile Asp
            100

<210> SEQ ID NO 134
<211> LENGTH: 108
<212> TYPE: PRT
<213> ORGANISM: Artificial Sequence
<220> FEATURE:
<223> OTHER INFORMATION: Adnectin

<400> SEQUENCE: 134

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Asp Ala Pro Ala Val Thr Val Glu Gln Tyr Tyr Ile Ala Tyr Tyr
        35                  40                  45

Asp Glu Lys Glu Pro Ser Ser Tyr Gln Tyr Phe Arg Val Pro Gly Ser
    50                  55                  60

Lys Ser Thr Ala Thr Ile Ser Gly Leu Lys Pro Gly Val Glu Tyr Ala
65                  70                  75                  80

Ile Phe Val Asn Ala Val Thr Arg Ser Gly Val Leu Pro Glu Phe Ser
                85                  90                  95

Leu Pro Ile Ser Ile Asn Tyr Arg Thr Glu Gly Ser
            100                 105

<210> SEQ ID NO 135
<211> LENGTH: 104
<212> TYPE: PRT
<213> ORGANISM: Artificial Sequence
<220> FEATURE:
<223> OTHER INFORMATION: Adnectin

<400> SEQUENCE: 135

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Lys Tyr Asn Val Asn Ala Tyr Arg Tyr Tyr Arg Ile Thr Tyr Gly

```
                35                  40                  45
Glu Thr Gly Gly Asn Ser Pro Val Gln Glu Phe Thr Val Pro Ser Val
        50                  55                  60
Leu Ser Thr Ala Thr Ile Ser Gly Leu Lys Pro Gly Val Asp Tyr Thr
65                  70                  75                  80
Ile Thr Val Tyr Ala Val Thr Tyr Gly Val His Ser Ser Pro Ile Ser
                85                  90                  95
Ile Asn Tyr Arg Thr Glu Ile Asp
                100

<210> SEQ ID NO 136
<211> LENGTH: 108
<212> TYPE: PRT
<213> ORGANISM: Artificial Sequence
<220> FEATURE:
<223> OTHER INFORMATION: Adnectin

<400> SEQUENCE: 136

Met Gly His His His His His His Gly Gly Ser Val Ser Asp Val Pro
1               5                   10                  15
Arg Asp Leu Glu Val Val Ala Ala Thr Pro Thr Ser Leu Leu Ile Ser
                20                  25                  30
Trp Asp Ala Pro Ala Val Thr Val Glu Gln Tyr Tyr Ile Gly Tyr Tyr
            35                  40                  45
Val Glu Ala Glu Pro Ser Ser Tyr Gln Tyr Phe Phe Val Pro Gly Ser
        50                  55                  60
Lys Ser Thr Ala Thr Ile Ser Gly Leu Lys Pro Gly Val Asp Tyr Ala
65                  70                  75                  80
Ile Phe Val Asn Ala Val Thr Ala Ser Gly Arg Gly Pro Glu Tyr Ser
                85                  90                  95
Leu Pro Ile Ser Ile Asn Tyr Arg Thr Glu Gly Ser
                100                 105

<210> SEQ ID NO 137
<211> LENGTH: 109
<212> TYPE: PRT
<213> ORGANISM: Artificial Sequence
<220> FEATURE:
<223> OTHER INFORMATION: Adnectin

<400> SEQUENCE: 137

Met Gly Val Ser Asp Val Pro Arg Asp Leu Glu Val Val Ala Ala Thr
1               5                   10                  15
Pro Thr Ser Leu Leu Ile Ser Trp His Asp Gly Ile Gly Glu Glu Arg
                20                  25                  30
Tyr Tyr Arg Ile Thr Tyr Gly Glu Thr Gly Gly Asn Ser Pro Val Gln
            35                  40                  45
Glu Phe Thr Val Pro Met Asp Asp Ile Thr Ala Thr Ile Ser Gly Leu
        50                  55                  60
Lys Pro Gly Val Asp Tyr Thr Ile Thr Val Tyr Ala Val Thr Val Gly
65                  70                  75                  80
Asp Val Ile Ser Val Leu His Glu Pro Ile Ser Ile Asn Tyr Arg Thr
                85                  90                  95
Glu Ile Asp Lys Pro Ser Gln His His His His His
                100                 105

<210> SEQ ID NO 138
<211> LENGTH: 108
```

```
<212> TYPE: PRT
<213> ORGANISM: Artificial Sequence
<220> FEATURE:
<223> OTHER INFORMATION: Adnectin

<400> SEQUENCE: 138

Met Gly Val Ser Asp Val Pro Arg Asp Leu Glu Val Val Ala Ala Thr
1               5                   10                  15

Pro Thr Ser Leu Leu Ile Ser Trp His Tyr Pro Phe Glu Gly Tyr Val
            20                  25                  30

Thr Tyr Tyr Arg Ile Thr Tyr Gly Glu Thr Gly Gly Asn Ser His Val
        35                  40                  45

Gln Glu Phe Thr Val Pro Val Gly Tyr Thr Thr Ala Thr Ile Ser Gly
    50                  55                  60

Leu Lys Pro Gly Val Asp Tyr Thr Ile Thr Val Tyr Ala Val Thr Ser
65                  70                  75                  80

Ser Lys Gly Tyr Val Tyr Phe Pro Ile Ser Ile Asn Tyr Arg Thr Glu
                85                  90                  95

Ile Asp Lys Pro Ser Gln His His His His His
            100                 105

<210> SEQ ID NO 139
<211> LENGTH: 109
<212> TYPE: PRT
<213> ORGANISM: Artificial Sequence
<220> FEATURE:
<223> OTHER INFORMATION: Adnectin

<400> SEQUENCE: 139

Met Gly Val Ser Asp Val Pro Arg Asp Leu Glu Val Val Ala Ala Thr
1               5                   10                  15

Pro Thr Ser Leu Leu Ile Ser Trp Glu Asp Pro Glu Ala Ala Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Ile Asn Asp Leu His Ser Tyr Leu Ser Gly Leu
    50                  55                  60

Lys Pro Gly Val Asp Tyr Thr Ile Thr Val Tyr Ala Val Thr Glu Ala
65                  70                  75                  80

Thr Val Met Tyr Val Leu Asp Glu Pro Ile Ser Ile Asn Tyr Arg Thr
                85                  90                  95

Glu Ile Asp Lys Pro Ser Gln His His His His His
            100                 105

<210> SEQ ID NO 140
<211> LENGTH: 109
<212> TYPE: PRT
<213> ORGANISM: Artificial Sequence
<220> FEATURE:
<223> OTHER INFORMATION: Adnectin

<400> SEQUENCE: 140

Met Gly Val Ser Asp Val Pro Arg Asp Leu Glu Val Val Ala Ala Thr
1               5                   10                  15

Pro Thr Ser Leu Leu Ile Ser Trp Asp Leu Leu Glu Asp Met Ser Arg
            20                  25                  30

Tyr Tyr Arg Ile Thr Tyr Gly Glu Thr Gly Gly Asn Ser Pro Val Gln
        35                  40                  45

Glu Phe Thr Val Pro Thr Asp Ala Tyr Thr Ala Thr Ile Ser Gly Leu
```

```
                50                  55                  60
Lys Pro Gly Val Asp Tyr Thr Ile Thr Val Tyr Ala Val Thr Gln Asp
 65                  70                  75                  80

Ser His Val Ile Glu Leu Ser Tyr Pro Ile Ser Ile Asn Tyr Arg Thr
                 85                  90                  95

Glu Ile Asp Lys Pro Ser Gln His His His His His His
            100                 105
```

<210> SEQ ID NO 141
<211> LENGTH: 105
<212> TYPE: PRT
<213> ORGANISM: Artificial Sequence
<220> FEATURE:
<223> OTHER INFORMATION: Adnectin

<400> SEQUENCE: 141

```
Met Gly Val Ser Asp Val Pro Arg Asp Leu Glu Val Val Ala Ala Thr
 1               5                  10                  15

Pro Thr Ser Leu Leu Ile Ser Trp Gln Tyr Lys Val His Pro Tyr Arg
                20                  25                  30

Tyr Tyr Arg Ile Thr Tyr Gly Glu Thr Gly Gly Asn Ser Pro Val Gln
                35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Tyr Gly
 65                  70                  75                  80

Ile Gln Ser Pro Pro Ile Ser Ile Asn Tyr Arg Thr Glu Ile Asp Lys
                 85                  90                  95

Pro Ser Gln His His His His His His
            100                 105
```

<210> SEQ ID NO 142
<211> LENGTH: 105
<212> TYPE: PRT
<213> ORGANISM: Artificial Sequence
<220> FEATURE:
<223> OTHER INFORMATION: Adnectin

<400> SEQUENCE: 142

```
Met Gly Val Ser Asp Val Pro Arg Asp Leu Glu Val Val Ala Ala Thr
 1               5                  10                  15

Pro Thr Ser Leu Leu Ile Ser Trp Arg Tyr Arg Val His Pro Tyr Arg
                20                  25                  30

Tyr Tyr Arg Ile Thr Tyr Gly Glu Thr Gly Gly Asn Ser Pro Val Gln
                35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Asp Gly
 65                  70                  75                  80

Val Gln Ser Ser Pro Ile Ser Ile Asn Tyr Arg Thr Glu Ile Asp Lys
                 85                  90                  95

Pro Ser Gln His His His His His His
            100                 105
```

<210> SEQ ID NO 143
<211> LENGTH: 105
<212> TYPE: PRT
<213> ORGANISM: Artificial Sequence
<220> FEATURE:

<223> OTHER INFORMATION: Adnectin

<400> SEQUENCE: 143

Met Gly Val Ser Asp Val Pro Arg Asp Leu Glu Val Val Ala Ala Thr
1               5                   10                  15

Pro Thr Ser Leu Leu Ile Ser Trp Glu Tyr Asn Val Asn Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Ile Glu Ser Ser Pro Ile Ser Ile Asn Tyr Arg Thr Glu Ile Asp Lys
                85                  90                  95

Pro Ser Gln His His His His His His
            100                 105

<210> SEQ ID NO 144
<211> LENGTH: 105
<212> TYPE: PRT
<213> ORGANISM: Artificial Sequence
<220> FEATURE:
<223> OTHER INFORMATION: Adnectin

<400> SEQUENCE: 144

Met Gly Val Ser Asp Val Pro Arg Asp Leu Glu Val Val Ala Ala Thr
1               5                   10                  15

Pro Thr Ser Leu Leu Ile Ser Trp Gln Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Glu Ser Ser Pro Ile Ser Ile Asn Tyr Arg Thr Glu Ile Asp Lys
                85                  90                  95

Pro Ser Gln His His His His His His
            100                 105

<210> SEQ ID NO 145
<211> LENGTH: 105
<212> TYPE: PRT
<213> ORGANISM: Artificial Sequence
<220> FEATURE:
<223> OTHER INFORMATION: Adnectin

<400> SEQUENCE: 145

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly

```
                 65                  70                  75                  80

Val Asn Ser Leu Pro Ile Ser Ile Asn Tyr Arg Thr Glu Ile Asp Lys
                 85                  90                  95

Pro Ser Gln His His His His His His
            100                 105

<210> SEQ ID NO 146
<211> LENGTH: 105
<212> TYPE: PRT
<213> ORGANISM: Artificial Sequence
<220> FEATURE:
<223> OTHER INFORMATION: Adnectin

<400> SEQUENCE: 146

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Ile Asp Ser Pro Pro Ile Ser Ile Asn Tyr Arg Thr Glu Ile Asp Lys
                85                  90                  95

Pro Ser Gln His His His His His His
            100                 105

<210> SEQ ID NO 147
<211> LENGTH: 105
<212> TYPE: PRT
<213> ORGANISM: Artificial Sequence
<220> FEATURE:
<223> OTHER INFORMATION: Adnectin

<400> SEQUENCE: 147

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Val Asp Ser Asp Pro Ile Ser Ile Asn Tyr Arg Thr Glu Ile Asp Lys
                85                  90                  95

Pro Ser Gln His His His His His His
            100                 105

<210> SEQ ID NO 148
<211> LENGTH: 105
<212> TYPE: PRT
<213> ORGANISM: Artificial Sequence
<220> FEATURE:
<223> OTHER INFORMATION: Adnectin

<400> SEQUENCE: 148
```

Met Gly Val Ser Asp Val Pro Arg Asp Leu Glu Val Val Ala Ala Thr
1               5                   10                  15

Pro Thr Ser Leu Leu Ile Ser Trp Glu Tyr Asn Val Asn Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Ile Asp Ser Pro Pro Ile Ser Ile Asn Tyr Arg Thr Glu Ile Asp Lys
                85                  90                  95

Pro Ser Gln His His His His His His
            100                 105

<210> SEQ ID NO 149
<211> LENGTH: 104
<212> TYPE: PRT
<213> ORGANISM: Artificial Sequence
<220> FEATURE:
<223> OTHER INFORMATION: Adnectin

<400> SEQUENCE: 149

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Lys Asp Ser Ala Pro Ile Ser
                85                  90                  95

Ile Asn Tyr Arg Thr Glu Ile Asp
            100

<210> SEQ ID NO 150
<211> LENGTH: 105
<212> TYPE: PRT
<213> ORGANISM: Artificial Sequence
<220> FEATURE:
<223> OTHER INFORMATION: Adnectin

<400> SEQUENCE: 150

Met Gly Val Ser Asp Val Pro Arg Asp Leu Glu Val Val Ala Ala Thr
1               5                   10                  15

Pro Thr Ser Leu Leu Ile Ser Trp Glu Tyr Asn Val Asn Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Glu Ser Ser Pro Ile Ser Ile Asn Tyr Arg Thr Glu Ile Asp Lys

-continued

```
                    85                  90                  95

Pro Ser Gln His His His His His
                100                 105

<210> SEQ ID NO 151
<211> LENGTH: 105
<212> TYPE: PRT
<213> ORGANISM: Artificial Sequence
<220> FEATURE:
<223> OTHER INFORMATION: Adnectin

<400> SEQUENCE: 151

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Ile Asp Ser Ser Pro Ile Ser Ile Asn Tyr Arg Thr Glu Ile Asp Lys
                85                  90                  95

Pro Ser Gln His His His His His
                100                 105

<210> SEQ ID NO 152
<211> LENGTH: 105
<212> TYPE: PRT
<213> ORGANISM: Artificial Sequence
<220> FEATURE:
<223> OTHER INFORMATION: Adnectin

<400> SEQUENCE: 152

Met Gly Val Ser Asp Val Pro Arg Asp Leu Glu Val Val Ala Ala Thr
1               5                   10                  15

Pro Thr Ser Leu Leu Ile Ser Trp Glu Tyr Asn Val Asn Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Val Gln Ser Asp Pro Ile Ser Ile Asn Tyr Arg Thr Glu Ile Asp Lys
                85                  90                  95

Pro Ser Gln His His His His His
                100                 105

<210> SEQ ID NO 153
<211> LENGTH: 104
<212> TYPE: PRT
<213> ORGANISM: Artificial Sequence
<220> FEATURE:
<223> OTHER INFORMATION: Adnectin

<400> SEQUENCE: 153

Met Gly His His His His His Gly Gly Ser Val Ser Asp Val Pro
1               5                   10                  15
```

-continued

Arg Asp Leu Glu Val Ala Ala Thr Pro Thr Ser Leu Leu Ile Ser
            20                  25                  30

Trp Glu Tyr Lys Val His Pro Tyr Arg Tyr Arg Ile Thr Tyr Gly
            35                  40                  45

Glu Thr Gly Gly Asn Ser Pro Val Gln Glu Phe Thr Val Pro Ser Val
 50                      55                  60

Leu Ser Thr Ala Gln Ile Ser Gly Leu Lys Pro Gly Val Asp Tyr Thr
65                   70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 154
<211> LENGTH: 105
<212> TYPE: PRT
<213> ORGANISM: Artificial Sequence
<220> FEATURE:
<223> OTHER INFORMATION: Adnectin

<400> SEQUENCE: 154

Met Gly Val Ser Asp Val Pro Arg Asp Leu Glu Val Val Ala Ala Thr
 1               5                  10                  15

Pro Thr Ser Leu Leu Ile Ser Trp Glu Tyr Asn Val Asn Pro Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
 50                      55                  60

Lys Pro Gly Val Asp Tyr Thr Ile Thr Val Tyr Ala Val Thr Tyr Gly
65                   70                  75                  80

Val Asn Ser Leu Pro Ile Ser Ile Asn Tyr Arg Thr Glu Ile Asp Lys
                85                  90                  95

Pro Ser Gln His His His His His His
            100                 105

<210> SEQ ID NO 155
<211> LENGTH: 105
<212> TYPE: PRT
<213> ORGANISM: Artificial Sequence
<220> FEATURE:
<223> OTHER INFORMATION: Adnectin

<400> SEQUENCE: 155

Met Gly Val Ser Asp Val Pro Arg Asp Leu Glu Val Val Ala Ala Thr
 1               5                  10                  15

Pro Thr Ser Leu Leu Ile Ser Trp Gln Tyr Lys Val His Pro Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
 50                      55                  60

Lys Pro Gly Val Asp Tyr Thr Ile Thr Val Tyr Ala Val Thr His Gly
65                   70                  75                  80

Val His Ser Ala Pro Ile Ser Ile Asn Tyr Arg Thr Glu Ile Asp Lys
                85                  90                  95

Pro Ser Gln His His His His His His

<210> SEQ ID NO 156
<211> LENGTH: 105
<212> TYPE: PRT
<213> ORGANISM: Artificial Sequence
<220> FEATURE:
<223> OTHER INFORMATION: Adnectin

<400> SEQUENCE: 156

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Pro Trp Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Ile Glu Ser Ser Pro Ile Ser Ile Asn Tyr Arg Thr Glu Ile Asp Lys
                85                  90                  95

Pro Ser Gln His His His His His His
            100                 105

<210> SEQ ID NO 157
<211> LENGTH: 105
<212> TYPE: PRT
<213> ORGANISM: Artificial Sequence
<220> FEATURE:
<223> OTHER INFORMATION: Adnectin

<400> SEQUENCE: 157

Met Gly Val Ser Asp Val Pro Arg Asp Leu Glu Val Val Ala Ala Thr
1               5                   10                  15

Pro Thr Ser Leu Leu Ile Ser Trp Gln Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asn Ser Ile Pro Ile Ser Ile Asn Tyr Arg Thr Glu Ile Asp Lys
                85                  90                  95

Pro Ser Gln His His His His His His
            100                 105

<210> SEQ ID NO 158
<211> LENGTH: 105
<212> TYPE: PRT
<213> ORGANISM: Artificial Sequence
<220> FEATURE:
<223> OTHER INFORMATION: Adnectin

<400> SEQUENCE: 158

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Tyr Asp Arg
            20                  25                  30

```
Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
         50                  55                  60

Lys Pro Gly Val Asp Tyr Thr Ile Thr Val Tyr Ala Val Thr Tyr Gly
 65                  70                  75                  80

Ile Gln Ser Pro Pro Ile Ser Ile Asn Tyr Arg Thr Glu Ile Asp Lys
                 85                  90                  95

Pro Ser Gln His His His His His His
            100                 105

<210> SEQ ID NO 159
<211> LENGTH: 104
<212> TYPE: PRT
<213> ORGANISM: Artificial Sequence
<220> FEATURE:
<223> OTHER INFORMATION: Adnectin

<400> SEQUENCE: 159

Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
         35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Pro Tyr Arg Thr Pro Gly Gly
            100

<210> SEQ ID NO 160
<211> LENGTH: 105
<212> TYPE: PRT
<213> ORGANISM: Artificial Sequence
<220> FEATURE:
<223> OTHER INFORMATION: Adnectin

<400> SEQUENCE: 160

Met Gly Val Ser Asp Val Pro Arg Asp Leu Glu Val Val Ala Ala Thr
 1               5                  10                  15

Pro Thr Ser Leu Leu Ile Ser Trp Glu Tyr Lys Val Asp Pro Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
         50                  55                  60

Lys Pro Gly Val Asp Tyr Thr Ile Thr Val Tyr Ala Val Thr Tyr Gly
 65                  70                  75                  80

Val Glu Ser Ser Pro Ile Ser Ile Asn Tyr Arg Thr Glu Ile Asp Lys
                 85                  90                  95

Pro Ser Gln His His His His His His
            100                 105
```

```
<210> SEQ ID NO 161
<211> LENGTH: 104
<212> TYPE: PRT
<213> ORGANISM: Artificial Sequence
<220> FEATURE:
<223> OTHER INFORMATION: Adnectin

<400> SEQUENCE: 161

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Glu Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 162
<211> LENGTH: 104
<212> TYPE: PRT
<213> ORGANISM: Artificial Sequence
<220> FEATURE:
<223> OTHER INFORMATION: Adnectin

<400> SEQUENCE: 162

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Gln Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 163
<211> LENGTH: 104
<212> TYPE: PRT
<213> ORGANISM: Artificial Sequence
<220> FEATURE:
<223> OTHER INFORMATION: Adnectin

<400> SEQUENCE: 163

Met Gly His His His His His His Gly Gly Ser Val Ser Asp Val Pro
1               5                   10                  15

Arg Tyr Leu Glu Val Val Ala Ala Thr Pro Thr Ser Leu Leu Ile Ser
            20                  25                  30

Trp Gln Tyr Lys Val His Pro Tyr Arg Trp Tyr Arg Ile Thr Tyr Gly
        35                  40                  45
```

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Val Asn Ser Ile Pro Ile Ser
                 85                  90                  95

Ile Asn Tyr Arg Thr Glu Ile Asp
            100

<210> SEQ ID NO 164
<211> LENGTH: 104
<212> TYPE: PRT
<213> ORGANISM: Artificial Sequence
<220> FEATURE:
<223> OTHER INFORMATION: Adnectin

<400> SEQUENCE: 164

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Lys Tyr Gln Val His Ala Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Val Tyr Ser Ala Pro Ile Ser
                 85                  90                  95

Ile Asn Tyr Arg Thr Glu Ile Asp
            100

<210> SEQ ID NO 165
<211> LENGTH: 104
<212> TYPE: PRT
<213> ORGANISM: Artificial Sequence
<220> FEATURE:
<223> OTHER INFORMATION: Adnectin

<400> SEQUENCE: 165

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val Asn Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Val His Ser Ser Pro Ile Ser
                 85                  90                  95

Ile Asn Tyr Arg Thr Glu Ile Asp
            100

<210> SEQ ID NO 166
<211> LENGTH: 104
<212> TYPE: PRT

<213> ORGANISM: Artificial Sequence
<220> FEATURE:
<223> OTHER INFORMATION: Adnectin

<400> SEQUENCE: 166

```
Met Gly His His His His His Gly Gly Ser Val Ser Asp Val Pro
1               5                   10                  15
Arg Asp Leu Glu Val Val Ala Ala Thr Pro Thr Ser Leu Leu Ile Ser
            20                  25                  30
Trp Lys Tyr Asn Leu His Pro Tyr Arg Tyr Tyr Arg Ile Thr Tyr Gly
        35                  40                  45
Glu Thr Gly Gly Asn Ser Pro Val Gln Glu Phe Thr Val Pro Ser Val
    50                  55                  60
Leu Ser Thr Ala Thr Ile Ser Gly Leu Lys Pro Gly Val Asp Tyr Thr
65                  70                  75                  80
Ile Thr Val Tyr Ala Val Thr Tyr Gly Ile Ile Ser Glu Pro Ile Ser
                85                  90                  95
Ile Asn Tyr Arg Thr Glu Ile Asp
            100
```

<210> SEQ ID NO 167
<211> LENGTH: 104
<212> TYPE: PRT
<213> ORGANISM: Artificial Sequence
<220> FEATURE:
<223> OTHER INFORMATION: Adnectin

<400> SEQUENCE: 167

```
Met Gly His His His His His Gly Gly Ser Val Ser Asp Val Pro
1               5                   10                  15
Arg Asp Leu Glu Val Val Ala Ala Thr Pro Thr Ser Leu Leu Ile Ser
            20                  25                  30
Trp Glu Tyr Arg Val Asn Pro Tyr Arg Tyr Tyr Arg Ile Thr Tyr Gly
        35                  40                  45
Glu Thr Gly Gly Asn Ser Pro Val Gln Glu Phe Thr Val Pro Ser Val
    50                  55                  60
Leu Ser Thr Ala Thr Ile Ser Gly Leu Lys Pro Gly Val Asp Tyr Thr
65                  70                  75                  80
Ile Thr Val Tyr Ala Val Thr Tyr Gly Val Gln Ser Pro Pro Ile Ser
                85                  90                  95
Ile Asn Tyr Arg Thr Glu Ile Asp
            100
```

<210> SEQ ID NO 168
<211> LENGTH: 104
<212> TYPE: PRT
<213> ORGANISM: Artificial Sequence
<220> FEATURE:
<223> OTHER INFORMATION: Adnectin

<400> SEQUENCE: 168

```
Met Gly His His His His His Gly Gly Ser Val Ser Asp Val Pro
1               5                   10                  15
Arg Asp Leu Glu Val Val Ala Ala Thr Pro Thr Ser Leu Leu Ile Ser
            20                  25                  30
Trp Glu Tyr Lys Val Asn Ala Tyr Arg Tyr Tyr Arg Ile Thr Tyr Gly
        35                  40                  45
Glu Thr Gly Gly Asn Ser Pro Val Gln Glu Phe Thr Val Pro Ser Val
    50                  55                  60
```

```
Leu Ser Thr Ala Thr Ile Ser Gly Leu Lys Pro Gly Val Asp Tyr Thr
 65                  70                  75                  80

Ile Thr Val Tyr Ala Val Thr Tyr Gly Val Leu Ser Pro Pro Ile Ser
                 85                  90                  95

Ile Asn Tyr Arg Thr Glu Ile Asp
            100

<210> SEQ ID NO 169
<211> LENGTH: 104
<212> TYPE: PRT
<213> ORGANISM: Artificial Sequence
<220> FEATURE:
<223> OTHER INFORMATION: Adnectin

<400> SEQUENCE: 169

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Asn Val Asn Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Arg Gly Val Asp Ser Ala Pro Ile Ser
                 85                  90                  95

Ile Asn Tyr Arg Thr Glu Ile Asp
            100

<210> SEQ ID NO 170
<211> LENGTH: 104
<212> TYPE: PRT
<213> ORGANISM: Artificial Sequence
<220> FEATURE:
<223> OTHER INFORMATION: Adnectin

<400> SEQUENCE: 170

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val Ser Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Phe Gly Ile Arg Ser Ser Pro Ile Ser
                 85                  90                  95

Ile Asn Tyr Arg Thr Glu Ile Asp
            100

<210> SEQ ID NO 171
<211> LENGTH: 104
<212> TYPE: PRT
<213> ORGANISM: Artificial Sequence
<220> FEATURE:
<223> OTHER INFORMATION: Adnectin
```

<400> SEQUENCE: 171

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Lys Tyr Gln Val His Ala Tyr Arg Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ile Ile Ser Glu Pro Ile Ser
                85                  90                  95

Ile Asn Tyr Arg Thr Glu Ile Asp
            100

<210> SEQ ID NO 172
<211> LENGTH: 104
<212> TYPE: PRT
<213> ORGANISM: Artificial Sequence
<220> FEATURE:
<223> OTHER INFORMATION: Adnectin

<400> SEQUENCE: 172

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ile Asp Ser Ser Pro Ile Ser
                85                  90                  95

Ile Asn Tyr Arg Thr Glu Ile Asp
            100

<210> SEQ ID NO 173
<211> LENGTH: 104
<212> TYPE: PRT
<213> ORGANISM: Artificial Sequence
<220> FEATURE:
<223> OTHER INFORMATION: Adnectin

<400> SEQUENCE: 173

Met Gly His His His His His Gly Gly Ala Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Pro Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

```
Ile Thr Val Tyr Ala Val Thr Tyr Gly Val His Ser Ser Pro Ile Ser
                85                  90                  95

Ile Asn Tyr Arg Thr Glu Ile Asp
            100
```

<210> SEQ ID NO 174
<211> LENGTH: 104
<212> TYPE: PRT
<213> ORGANISM: Artificial Sequence
<220> FEATURE:
<223> OTHER INFORMATION: Adnectin

<400> SEQUENCE: 174

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Asn Val Asn Ala Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ile Ile Ser Glu Pro Ile Ser
                85                  90                  95

Ile Asn Tyr Arg Thr Glu Ile Asp
            100
```

<210> SEQ ID NO 175
<211> LENGTH: 104
<212> TYPE: PRT
<213> ORGANISM: Artificial Sequence
<220> FEATURE:
<223> OTHER INFORMATION: Adnectin

<400> SEQUENCE: 175

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Tyr Asp Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Gln Ser Thr Pro Ile Ser
                85                  90                  95

Ile Asn Tyr Arg Thr Glu Ile Asp
            100
```

<210> SEQ ID NO 176
<211> LENGTH: 104
<212> TYPE: PRT
<213> ORGANISM: Artificial Sequence
<220> FEATURE:
<223> OTHER INFORMATION: Adnectin

<400> SEQUENCE: 176

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His His Asp Arg Tyr Tyr Arg Ile Thr Tyr Gly
                35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ile Glu Ser Ser Pro Ile Ser
                85                  90                  95

Ile Asn Tyr Arg Thr Glu Ile Asp
            100
```

<210> SEQ ID NO 177
<211> LENGTH: 104
<212> TYPE: PRT
<213> ORGANISM: Artificial Sequence
<220> FEATURE:
<223> OTHER INFORMATION: Adnectin

<400> SEQUENCE: 177

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Pro Tyr Arg Thr Pro Gly Gly
            100
```

<210> SEQ ID NO 178
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 178

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
                35                  40                  45
```

```
Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Xaa Asp Ser Xaa Pro Ile Ser
                 85                  90                  95

Ile Asn Tyr Arg Thr Glu Ile Asp
                100
```

```
<210> SEQ ID NO 179
<211> LENGTH: 104
<212> TYPE: PRT
<213> ORGANISM: Artificial Sequence
<220> FEATURE:
<223> OTHER INFORMATION: Adnectin

<400> SEQUENCE: 179
```

```
Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Arg Pro Ile Ser
                 85                  90                  95

Ile Asn Tyr Arg Thr Glu Ile Asp
                100
```

```
<210> SEQ ID NO 180
<211> LENGTH: 104
<212> TYPE: PRT
<213> ORGANISM: Artificial Sequence
<220> FEATURE:
<223> OTHER INFORMATION: Adnectin

<400> SEQUENCE: 180
```

```
Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Lys Asp Ser Ala Pro Ile Ser
                 85                  90                  95

Ile Asn Tyr Arg Thr Glu Ile Asp
                100
```

```
<210> SEQ ID NO 181
<211> LENGTH: 104
<212> TYPE: PRT
<213> ORGANISM: Artificial Sequence
```

```
<220> FEATURE:
<223> OTHER INFORMATION: Adnectin

<400> SEQUENCE: 181

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp His Ser Ala Pro Ile Ser
                85                  90                  95

Ile Asn Tyr Arg Thr Glu Ile Asp
            100

<210> SEQ ID NO 182
<211> LENGTH: 104
<212> TYPE: PRT
<213> ORGANISM: Artificial Sequence
<220> FEATURE:
<223> OTHER INFORMATION: Adnectin

<400> SEQUENCE: 182

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Gln Ser Ala Pro Ile Ser
                85                  90                  95

Ile Asn Tyr Arg Thr Glu Ile Asp
            100

<210> SEQ ID NO 183
<211> LENGTH: 104
<212> TYPE: PRT
<213> ORGANISM: Artificial Sequence
<220> FEATURE:
<223> OTHER INFORMATION: Adnectin

<400> SEQUENCE: 183

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
        50                  55                  60
```

```
Leu Ser Thr Ala Thr Ile Ser Gly Leu Lys Pro Gly Val Asp Tyr Thr
 65                  70                  75                  80

Ile Thr Val Tyr Ala Val Thr Tyr Gly Ile Asp Ser Ala Pro Ile Ser
                 85                  90                  95

Ile Asn Tyr Arg Thr Glu Ile Asp
            100

<210> SEQ ID NO 184
<211> LENGTH: 104
<212> TYPE: PRT
<213> ORGANISM: Artificial Sequence
<220> FEATURE:
<223> OTHER INFORMATION: Adnectin

<400> SEQUENCE: 184

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Val Ser Ala Pro Ile Ser
                 85                  90                  95

Ile Asn Tyr Arg Thr Glu Ile Asp
            100

<210> SEQ ID NO 185
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (90)..(90)
<223> OTHER INFORMATION: Xaa can be any naturally occurring amino acid

<400> SEQUENCE: 185

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Xaa Asp Ser Ala Pro Ile Ser
                 85                  90                  95

Ile Asn Tyr Arg Thr Glu Ile Asp
            100

<210> SEQ ID NO 186
<211> LENGTH: 104
<212> TYPE: PRT
```

```
<213> ORGANISM: Artificial Sequence
<220> FEATURE:
<223> OTHER INFORMATION: Adnectin

<400> SEQUENCE: 186

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Glu Asp Ser Ala Pro Ile Ser
                85                  90                  95

Ile Asn Tyr Arg Thr Glu Ile Asp
            100

<210> SEQ ID NO 187
<211> LENGTH: 104
<212> TYPE: PRT
<213> ORGANISM: Artificial Sequence
<220> FEATURE:
<223> OTHER INFORMATION: Adnectin

<400> SEQUENCE: 187

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Lys Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 188
<211> LENGTH: 104
<212> TYPE: PRT
<213> ORGANISM: Artificial Sequence
<220> FEATURE:
<223> OTHER INFORMATION: Adnectin

<400> SEQUENCE: 188

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60
```

-continued

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Leu Ser Ala Pro Ile Ser
                 85                  90                  95

Ile Asn Tyr Arg Thr Glu Ile Asp
            100

<210> SEQ ID NO 189
<211> LENGTH: 104
<212> TYPE: PRT
<213> ORGANISM: Artificial Sequence
<220> FEATURE:
<223> OTHER INFORMATION: Adnectin

<400> SEQUENCE: 189

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Lys Asp Ser Ala Pro Ile Ser
                 85                  90                  95

Ile Asn Tyr Arg Thr Glu Ile Asp
            100

<210> SEQ ID NO 190
<211> LENGTH: 104
<212> TYPE: PRT
<213> ORGANISM: Artificial Sequence
<220> FEATURE:
<223> OTHER INFORMATION: Adnectin

<400> SEQUENCE: 190

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
         50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Ala Asp Ser Ala Pro Ile Ser
                 85                  90                  95

Ile Asn Tyr Arg Thr Glu Ile Asp
            100

<210> SEQ ID NO 191
<211> LENGTH: 104
<212> TYPE: PRT
<213> ORGANISM: Artificial Sequence
<220> FEATURE:
<223> OTHER INFORMATION: Adnectin

<400> SEQUENCE: 191

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Thr Asp Ser Ala Pro Ile Ser
                85                  90                  95

Ile Asn Tyr Arg Thr Glu Ile Asp
            100

<210> SEQ ID NO 192
<211> LENGTH: 104
<212> TYPE: PRT
<213> ORGANISM: Artificial Sequence
<220> FEATURE:
<223> OTHER INFORMATION: Adnectin

<400> SEQUENCE: 192

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Thr Asp Ser Ala Pro Ile Ser
                85                  90                  95

Ile Asn Tyr Arg Thr Glu Ile Asp
            100

<210> SEQ ID NO 193
<211> LENGTH: 104
<212> TYPE: PRT
<213> ORGANISM: Artificial Sequence
<220> FEATURE:
<223> OTHER INFORMATION: Adnectin

<400> SEQUENCE: 193

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Lys Asp Ser Ala Pro Ile Ser
            85                  90                  95

Ile Asn Tyr Arg Thr Glu Ile Asp
            100

<210> SEQ ID NO 194
<211> LENGTH: 104
<212> TYPE: PRT
<213> ORGANISM: Artificial Sequence
<220> FEATURE:
<223> OTHER INFORMATION: Adnectin

<400> SEQUENCE: 194

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Pro Ser Ala Pro Ile Ser
            85                  90                  95

Ile Asn Tyr Arg Thr Glu Ile Asp
            100

<210> SEQ ID NO 195
<211> LENGTH: 104
<212> TYPE: PRT
<213> ORGANISM: Artificial Sequence
<220> FEATURE:
<223> OTHER INFORMATION: Adnectin

<400> SEQUENCE: 195

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Ser Gln Pro Ile Ser
            85                  90                  95

Ile Asn Tyr Arg Thr Glu Ile Asp
            100

<210> SEQ ID NO 196
<211> LENGTH: 104
<212> TYPE: PRT
<213> ORGANISM: Artificial Sequence
<220> FEATURE:
<223> OTHER INFORMATION: Adnectin

<400> SEQUENCE: 196

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Val Ser Ala Pro Ile Ser
                85                  90                  95

Ile Asn Tyr Arg Thr Glu Ile Asp
                100

<210> SEQ ID NO 197
<211> LENGTH: 104
<212> TYPE: PRT
<213> ORGANISM: Artificial Sequence
<220> FEATURE:
<223> OTHER INFORMATION: Adnectin

<400> SEQUENCE: 197

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Gly Pro Ile Ser
                85                  90                  95

Ile Asn Tyr Arg Thr Glu Ile Asp
                100

<210> SEQ ID NO 198
<211> LENGTH: 104
<212> TYPE: PRT
<213> ORGANISM: Artificial Sequence
<220> FEATURE:
<223> OTHER INFORMATION: Adnectin

<400> SEQUENCE: 198

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

```
Ile Gln Tyr Arg Thr Glu Ile Asp
            100

<210> SEQ ID NO 199
<211> LENGTH: 104
<212> TYPE: PRT
<213> ORGANISM: Artificial Sequence
<220> FEATURE:
<223> OTHER INFORMATION: Adnectin

<400> SEQUENCE: 199

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Ser Gln Pro Ile Ser
                85                  90                  95

Ile Asn Tyr Arg Thr Glu Ile Asp
            100

<210> SEQ ID NO 200
<211> LENGTH: 104
<212> TYPE: PRT
<213> ORGANISM: Artificial Sequence
<220> FEATURE:
<223> OTHER INFORMATION: Adnectin

<400> SEQUENCE: 200

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Thr
            35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 201
<211> LENGTH: 104
<212> TYPE: PRT
<213> ORGANISM: Artificial Sequence
<220> FEATURE:
<223> OTHER INFORMATION: Adnectin

<400> SEQUENCE: 201

Met Gly His His His His His Gly Gly Ser Val Ser Asp Val Pro
1               5                   10                  15
```

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Gln Ser Ala Pro Ile Ser
                85                  90                  95

Ile Asn Tyr Arg Thr Glu Ile Asp
            100

<210> SEQ ID NO 202
<211> LENGTH: 104
<212> TYPE: PRT
<213> ORGANISM: Artificial Sequence
<220> FEATURE:
<223> OTHER INFORMATION: Adnectin

<400> SEQUENCE: 202

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Lys Pro Ile Ser
                85                  90                  95

Ile Asn Tyr Arg Thr Glu Ile Asp
            100

<210> SEQ ID NO 203
<211> LENGTH: 104
<212> TYPE: PRT
<213> ORGANISM: Artificial Sequence
<220> FEATURE:
<223> OTHER INFORMATION: Adnectin

<400> SEQUENCE: 203

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Gly Pro Ile Ser
                85                  90                  95

Ile Asn Tyr Arg Thr Glu Ile Asp
            100

<210> SEQ ID NO 204
<211> LENGTH: 104
<212> TYPE: PRT
<213> ORGANISM: Artificial Sequence
<220> FEATURE:
<223> OTHER INFORMATION: Adnectin

<400> SEQUENCE: 204

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Arg
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 205
<211> LENGTH: 104
<212> TYPE: PRT
<213> ORGANISM: Artificial Sequence
<220> FEATURE:
<223> OTHER INFORMATION: Adnectin

<400> SEQUENCE: 205

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Asp Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 206
<211> LENGTH: 104
<212> TYPE: PRT
<213> ORGANISM: Artificial Sequence
<220> FEATURE:
<223> OTHER INFORMATION: Adnectin

<400> SEQUENCE: 206

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

```
Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Lys Pro Ile Ser
                85                  90                  95

Ile Asn Tyr Arg Thr Glu Ile Asp
            100
```

```
<210> SEQ ID NO 207
<211> LENGTH: 104
<212> TYPE: PRT
<213> ORGANISM: Artificial Sequence
<220> FEATURE:
<223> OTHER INFORMATION: Adnectin

<400> SEQUENCE: 207

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Trp
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

```
<210> SEQ ID NO 208
<211> LENGTH: 104
<212> TYPE: PRT
<213> ORGANISM: Artificial Sequence
<220> FEATURE:
<223> OTHER INFORMATION: Adnectin

<400> SEQUENCE: 208

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Thr Pro Ile Ser
                85                  90                  95

Ile Asn Tyr Arg Thr Glu Ile Asp
            100
```

```
<210> SEQ ID NO 209
```

```
<211> LENGTH: 104
<212> TYPE: PRT
<213> ORGANISM: Artificial Sequence
<220> FEATURE:
<223> OTHER INFORMATION: Adnectin

<400> SEQUENCE: 209

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Thr Pro Ile Ser
                85                  90                  95

Ile Asn Tyr Arg Thr Glu Ile Asp
            100

<210> SEQ ID NO 210
<211> LENGTH: 104
<212> TYPE: PRT
<213> ORGANISM: Artificial Sequence
<220> FEATURE:
<223> OTHER INFORMATION: Adnectin

<400> SEQUENCE: 210

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ser Pro Ile Ser
                85                  90                  95

Ile Asn Tyr Arg Thr Glu Ile Asp
            100

<210> SEQ ID NO 211
<211> LENGTH: 104
<212> TYPE: PRT
<213> ORGANISM: Artificial Sequence
<220> FEATURE:
<223> OTHER INFORMATION: Adnectin

<400> SEQUENCE: 211

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45
```

```
Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Arg Gly Asp Asp Ser Ala Pro Ile Ser
                 85                  90                  95

Ile Asn Tyr Arg Thr Glu Ile Asp
            100
```

<210> SEQ ID NO 212
<211> LENGTH: 104
<212> TYPE: PRT
<213> ORGANISM: Artificial Sequence
<220> FEATURE:
<223> OTHER INFORMATION: Adnectin

<400> SEQUENCE: 212

```
Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr His Gly Asp Asp Ser Ala Pro Ile Ser
                 85                  90                  95

Ile Asn Tyr Arg Thr Glu Ile Asp
            100
```

<210> SEQ ID NO 213
<211> LENGTH: 104
<212> TYPE: PRT
<213> ORGANISM: Artificial Sequence
<220> FEATURE:
<223> OTHER INFORMATION: Adnectin

<400> SEQUENCE: 213

```
Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Trp Pro Ile Ser
                 85                  90                  95

Ile Asn Tyr Arg Thr Glu Ile Asp
            100
```

<210> SEQ ID NO 214
<211> LENGTH: 104
<212> TYPE: PRT
<213> ORGANISM: Artificial Sequence
<220> FEATURE:
<223> OTHER INFORMATION: Adnectin

<400> SEQUENCE: 214

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
                50                  55                  60

Leu Ser Thr Ala Thr Ile Ser Gly Leu Lys Pro Gly Val Asp Tyr Thr
65                  70                  75                  80

Ile Thr Val Tyr Ala Val Thr His Gly Asp Asp Ser Ala Pro Ile Ser
                85                  90                  95

Ile Asn Tyr Arg Thr Glu Ile Asp
                100

<210> SEQ ID NO 215
<211> LENGTH: 104
<212> TYPE: PRT
<213> ORGANISM: Artificial Sequence
<220> FEATURE:
<223> OTHER INFORMATION: Adnectin

<400> SEQUENCE: 215

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Lys Tyr Asp Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
                50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100

<210> SEQ ID NO 216
<211> LENGTH: 104
<212> TYPE: PRT
<213> ORGANISM: Artificial Sequence
<220> FEATURE:
<223> OTHER INFORMATION: Adnectin

<400> SEQUENCE: 216

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
                35                  40                  45

Glu Thr Gly Gly Asn Ser Pro Val Gln Glu Phe Thr Val Pro Ser Val
                50                  55                  60

-continued

Leu Ser Thr Ala Thr Ile Ser Asp Leu Lys Pro Gly Val Asp Tyr Thr
 65                 70                  75                  80

Ile Thr Val Tyr Ala Val Thr Tyr Gly Asp Asp Ser His Pro Ile Ser
                 85                  90                  95

Ile Asn Tyr Arg Thr Glu Ile Asp
            100

<210> SEQ ID NO 217
<211> LENGTH: 104
<212> TYPE: PRT
<213> ORGANISM: Artificial Sequence
<220> FEATURE:
<223> OTHER INFORMATION: Adnectin

<400> SEQUENCE: 217

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Arg Gly Asp Asp Ser Ala Pro Ile Ser
                 85                  90                  95

Ile Asn Tyr Arg Thr Glu Ile Asp
            100

<210> SEQ ID NO 218
<211> LENGTH: 104
<212> TYPE: PRT
<213> ORGANISM: Artificial Sequence
<220> FEATURE:
<223> OTHER INFORMATION: Adnectin

<400> SEQUENCE: 218

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Arg Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 219
<211> LENGTH: 104
<212> TYPE: PRT
<213> ORGANISM: Artificial Sequence
<220> FEATURE:
<223> OTHER INFORMATION: Adnectin

```
<400> SEQUENCE: 219

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Lys Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 220
<211> LENGTH: 104
<212> TYPE: PRT
<213> ORGANISM: Artificial Sequence
<220> FEATURE:
<223> OTHER INFORMATION: Adnectin

<400> SEQUENCE: 220

Met Gly His His His His His Cys Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala His Asn Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 221
<211> LENGTH: 104
<212> TYPE: PRT
<213> ORGANISM: Artificial Sequence
<220> FEATURE:
<223> OTHER INFORMATION: Adnectin

<400> SEQUENCE: 221

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Tyr Gly Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80
```

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 222
<211> LENGTH: 104
<212> TYPE: PRT
<213> ORGANISM: Artificial Sequence
<220> FEATURE:
<223> OTHER INFORMATION: Adnectin

<400> SEQUENCE: 222

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp His Gln Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 223
<211> LENGTH: 104
<212> TYPE: PRT
<213> ORGANISM: Artificial Sequence
<220> FEATURE:
<223> OTHER INFORMATION: Adnectin

<400> SEQUENCE: 223

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Tyr Arg Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 224
<211> LENGTH: 104
<212> TYPE: PRT
<213> ORGANISM: Artificial Sequence
<220> FEATURE:
<223> OTHER INFORMATION: Adnectin

<400> SEQUENCE: 224

Met Gly His His His His His His Gly Gly Ser Val Ser Asp Val Pro

```
                1               5                    10                   15
            Arg Asp Leu Glu Val Val Ala Ala Thr Pro Thr Ser Leu Leu Ile Ser
                            20                   25                   30

Trp Glu Tyr Lys Val Ala Tyr Asp Arg Tyr Tyr Arg Ile Thr Tyr Gly
                            35                   40                   45

Glu Thr Gly Gly Asn Ser Pro Val Gln Glu Phe Thr Val Pro Ser Val
                            50                   55                   60

Leu Ser Thr Ala Thr Ile Ser Gly Leu Lys Pro Gly Val Asp Tyr Thr
             65                   70                   75                   80

Ile Thr Val Tyr Ala Val Thr Tyr Gly Asp Asp Ser Ala Pro Ile Ser
                            85                   90                   95

Ile Asn Tyr Arg Thr Glu Ile Asp
                           100

<210> SEQ ID NO 225
<211> LENGTH: 104
<212> TYPE: PRT
<213> ORGANISM: Artificial Sequence
<220> FEATURE:
<223> OTHER INFORMATION: Adnectin

<400> SEQUENCE: 225

Met Gly His His His His His Gly Gly Ser Val Ser Asp Val Pro
             1               5                    10                   15

Arg Asp Leu Glu Val Val Ala Ala Thr Pro Thr Ser Leu Leu Ile Ser
                            20                   25                   30

Trp Glu Tyr Lys Val Thr Ser Tyr Arg Tyr Tyr Arg Ile Thr Tyr Gly
                            35                   40                   45

Glu Thr Gly Gly Asn Ser Pro Val Gln Glu Phe Thr Val Pro Ser Val
                            50                   55                   60

Leu Ser Thr Ala Thr Ile Ser Gly Leu Lys Pro Gly Val Asp Tyr Thr
             65                   70                   75                   80

Ile Thr Val Tyr Ala Val Thr Tyr Gly Asp Asp Ser Ala Pro Ile Ser
                            85                   90                   95

Ile Asn Tyr Arg Thr Glu Ile Asp
                           100

<210> SEQ ID NO 226
<211> LENGTH: 103
<212> TYPE: PRT
<213> ORGANISM: Artificial Sequence
<220> FEATURE:
<223> OTHER INFORMATION: Adnectin

<400> SEQUENCE: 226

Met Gly His His His His His Gly Gly Ser Val Ser Asp Val Pro
             1               5                    10                   15

Arg Asp Leu Glu Val Val Ala Ala Thr Pro Thr Ser Leu Leu Ile Ser
                            20                   25                   30

Trp Glu Tyr Lys Val His Pro Tyr Arg Tyr Tyr Arg Ile Ile His Glu
                            35                   40                   45

Thr Gly Gly Asn Ser Pro Val Gln Glu Phe Thr Val Pro Ser Val Leu
                            50                   55                   60

Ser Thr Ala Thr Ile Ser Gly Leu Lys Pro Gly Val Asp Tyr Thr Ile
             65                   70                   75                   80

Thr Val Tyr Ala Val Thr Tyr Gly Asp Asp Ser Ala Pro Ile Ser Ile
                            85                   90                   95
```

```
Asn Tyr Arg Thr Glu Ile Asp
            100
```

<210> SEQ ID NO 227
<211> LENGTH: 105
<212> TYPE: PRT
<213> ORGANISM: Artificial Sequence
<220> FEATURE:
<223> OTHER INFORMATION: Adnectin

<400> SEQUENCE: 227

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Lys Glu Ala Glu Leu
            100                 105
```

<210> SEQ ID NO 228
<211> LENGTH: 104
<212> TYPE: PRT
<213> ORGANISM: Artificial Sequence
<220> FEATURE:
<223> OTHER INFORMATION: Adnectin

<400> SEQUENCE: 228

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn His Gln Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 229
<211> LENGTH: 104
<212> TYPE: PRT
<213> ORGANISM: Artificial Sequence
<220> FEATURE:
<223> OTHER INFORMATION: Adnectin

<400> SEQUENCE: 229

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
```

```
                    20                  25                  30

Trp Glu Tyr Lys Val Asp His Arg Arg Tyr Tyr Arg Ile Thr Tyr Gly
                35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100

<210> SEQ ID NO 230
<211> LENGTH: 104
<212> TYPE: PRT
<213> ORGANISM: Artificial Sequence
<220> FEATURE:
<223> OTHER INFORMATION: Adnectin

<400> SEQUENCE: 230

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Val Asp Ser Asp Pro Ile Ser Ile Asn Tyr Arg Thr Asp Asp Lys Pro
                85                  90                  95

Ser Gln His His His His His His
            100

<210> SEQ ID NO 231
<211> LENGTH: 105
<212> TYPE: PRT
<213> ORGANISM: Artificial Sequence
<220> FEATURE:
<223> OTHER INFORMATION: Adnectin

<400> SEQUENCE: 231

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
                20                  25                  30

Tyr Tyr Arg Ile Thr Tyr Gly Glu Thr Gly Gly Asn Ser Pro Val Gln
            35                  40                  45

Glu Phe Thr Val Pro Ser Val Leu Ser Thr Ala Thr Ile Ser Gly Leu
        50                  55                  60

Lys Pro Gly Val Asp Tyr Thr Ile Thr Val Tyr Ala Val Thr Tyr Gly
65                  70                  75                  80

Val Asn Ser Ile Pro Ile Ser Ile Asn Tyr Arg Thr Glu Ile Asp Lys
                85                  90                  95

Pro Ser Gln His His His His His
            100                 105
```

-continued

<210> SEQ ID NO 232
<211> LENGTH: 105
<212> TYPE: PRT
<213> ORGANISM: Artificial Sequence
<220> FEATURE:
<223> OTHER INFORMATION: Adnectin

<400> SEQUENCE: 232

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Ala Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Ile Glu Ser Ser Pro Ile Ser Ile Asn Tyr Arg Thr Glu Ile Asp Lys
                85                  90                  95

Pro Ser Gln His His His His His His
            100                 105

<210> SEQ ID NO 233
<211> LENGTH: 105
<212> TYPE: PRT
<213> ORGANISM: Artificial Sequence
<220> FEATURE:
<223> OTHER INFORMATION: Adnectin

<400> SEQUENCE: 233

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Asp Gly
65                  70                  75                  80

Val Gln Ser Ser Pro Ile Ser Ile Asn Tyr Arg Thr Glu Ile Asp Lys
                85                  90                  95

Pro Ser Gln His His His His His His
            100                 105

<210> SEQ ID NO 234
<211> LENGTH: 105
<212> TYPE: PRT
<213> ORGANISM: Artificial Sequence
<220> FEATURE:
<223> OTHER INFORMATION: Adnectin

<400> SEQUENCE: 234

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Ala Tyr Arg
            20                  25                  30

Tyr Tyr Arg Ile Thr Tyr Gly Glu Thr Gly Gly Asn Ser Pro Val Gln

```
              35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Tyr Gly
 65                  70                  75                  80

Ile Asp Ser Ser Pro Ile Ser Ile Asn Tyr Arg Thr Glu Ile Asp Lys
                 85                  90                  95

Pro Ser Gln His His His His His His
            100                 105

<210> SEQ ID NO 235
<211> LENGTH: 105
<212> TYPE: PRT
<213> ORGANISM: Artificial Sequence
<220> FEATURE:
<223> OTHER INFORMATION: Adnectin

<400> SEQUENCE: 235

Met Gly Val Ser Asp Val Pro Arg Asp Leu Glu Val Val Ala Ala Thr
 1                   5                  10                  15

Pro Thr Ser Leu Leu Ile Ser Trp Glu Tyr Lys Val His Tyr Asp Arg
                 20                  25                  30

Tyr Tyr Arg Ile Thr Tyr Gly Glu Thr Gly Gly Asn Ser Pro Val Gln
             35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Asn Gly
 65                  70                  75                  80

Val Leu Ser Ser Pro Ile Ser Ile Asn Tyr Arg Thr Glu Ile Asp Lys
                 85                  90                  95

Pro Ser Gln His His His His His His
            100                 105

<210> SEQ ID NO 236
<211> LENGTH: 105
<212> TYPE: PRT
<213> ORGANISM: Artificial Sequence
<220> FEATURE:
<223> OTHER INFORMATION: Adnectin

<400> SEQUENCE: 236

Met Gly Val Ser Asp Val Pro Arg Asp Leu Glu Val Val Ala Ala Thr
 1                   5                  10                  15

Pro Thr Ser Leu Leu Ile Ser Trp Glu Tyr Lys Val Asn Pro Trp Arg
                 20                  25                  30

Tyr Tyr Arg Ile Thr Tyr Gly Glu Thr Gly Gly Asn Ser Pro Val Gln
             35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Arg Gly
 65                  70                  75                  80

Val Asp Ser Ala Pro Ile Ser Ile Asn Tyr Arg Thr Glu Ile Asp Lys
                 85                  90                  95

Pro Ser Gln His His His His His His
            100                 105

<210> SEQ ID NO 237
<211> LENGTH: 105
```

<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid

<400> SEQUENCE: 237

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val His Pro Xaa Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asx Ser Xaa Pro Ile Ser Ile Asn Tyr Arg Thr Glu Ile Asp Lys
                85                  90                  95

Pro Ser Gln His His His His His His
            100                 105

<210> SEQ ID NO 238
<211> LENGTH: 105
<212> TYPE: PRT
<213> ORGANISM: Artificial Sequence
<220> FEATURE:
<223> OTHER INFORMATION: Adnectin

<400> SEQUENCE: 238

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Pro Trp Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Ile Gln Ser Pro Pro Ile Ser Ile Asn Tyr Arg Thr Glu Ile Asp Lys
                85                  90                  95

Pro Ser Gln His His His His His His
            100                 105

<210> SEQ ID NO 239
<211> LENGTH: 105
<212> TYPE: PRT
<213> ORGANISM: Artificial Sequence
<220> FEATURE:
<223> OTHER INFORMATION: Adnectin

<400> SEQUENCE: 239

Met Gly Val Ser Asp Val Pro Arg Asp Leu Glu Val Val Ala Ala Thr
1               5                   10                  15

Pro Thr Ser Leu Leu Ile Ser Trp Gln Tyr Lys Val His Pro Tyr Arg
            20                  25                  30

Trp Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asn Ser Ile Pro Ile Ser Ile Asn Tyr Arg Thr Glu Ile Asp Lys
                85                  90                  95

Pro Ser Gln His His His His His His
            100                 105

<210> SEQ ID NO 240
<211> LENGTH: 105
<212> TYPE: PRT
<213> ORGANISM: Artificial Sequence
<220> FEATURE:
<223> OTHER INFORMATION: Adnectin

<400> SEQUENCE: 240

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Ser Pro Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asn Ser Ile Pro Ile Ser Ile Asn Tyr Arg Thr Glu Ile Asp Lys
                85                  90                  95

Pro Ser Gln His His His His His His
            100                 105

<210> SEQ ID NO 241
<211> LENGTH: 105
<212> TYPE: PRT
<213> ORGANISM: Artificial Sequence
<220> FEATURE:
<223> OTHER INFORMATION: Adnectin

<400> SEQUENCE: 241

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Pro Trp Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asn Ser Leu Pro Ile Ser Ile Asn Tyr Arg Thr Glu Ile Asp Lys
                85                  90                  95

Pro Ser Gln His His His His His His

<210> SEQ ID NO 242
<211> LENGTH: 105
<212> TYPE: PRT
<213> ORGANISM: Artificial Sequence
<220> FEATURE:
<223> OTHER INFORMATION: Adnectin

<400> SEQUENCE: 242

Met Gly Val Ser Asp Val Pro Arg Asp Leu Glu Val Val Ala Ala Thr
1               5                   10                  15

Pro Thr Ser Leu Leu Ile Ser Trp Glu Tyr Asn Val His Tyr Asp Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asp Ser Asp Pro Ile Ser Ile Asn Tyr Arg Thr Glu Ile Asp Lys
                85                  90                  95

Pro Ser Gln His His His His His His
            100                 105

<210> SEQ ID NO 243
<211> LENGTH: 105
<212> TYPE: PRT
<213> ORGANISM: Artificial Sequence
<220> FEATURE:
<223> OTHER INFORMATION: Adnectin

<400> SEQUENCE: 243

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asn Pro Trp Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Val Leu Ser Thr Ala Thr Ile Ser Gly Leu
    50                  55                  60

Lys Pro Gly Val Asp Tyr Thr Ile Thr Val Tyr Ala Val Thr Tyr Gly
65                  70                  75                  80

Val Asp Ser Asp Pro Ile Ser Ile Asn Tyr Arg Thr Glu Ile Asp Lys
                85                  90                  95

Pro Ser Gln His His His His His His
            100                 105

<210> SEQ ID NO 244
<211> LENGTH: 105
<212> TYPE: PRT
<213> ORGANISM: Artificial Sequence
<220> FEATURE:
<223> OTHER INFORMATION: Adnectin

<400> SEQUENCE: 244

Met Gly Val Ser Asp Val Pro Arg Asp Leu Glu Val Val Ala Ala Thr
1               5                   10                  15

Pro Thr Ser Leu Leu Ile Ser Trp Glu Tyr Lys Val Asp Pro Tyr Arg
            20                  25                  30

-continued

Tyr Tyr Arg Ile Thr Tyr Gly Glu Thr Gly Gly Asn Ser Pro Val Gln
         35                  40                  45

Glu Phe Thr Val Pro Ser Val Leu Ser Thr Ala Thr Ile Ser Gly Leu
 50                  55                  60

Lys Pro Gly Val Asp Tyr Thr Ile Thr Val Tyr Ala Val Thr Tyr Gly
 65                  70                  75                  80

Val Asp Ser Asp Pro Ile Ser Ile Asn Tyr Arg Thr Glu Ile Asp Lys
                 85                  90                  95

Pro Ser Gln His His His His His His
         100                 105

<210> SEQ ID NO 245
<211> LENGTH: 104
<212> TYPE: PRT
<213> ORGANISM: Artificial Sequence
<220> FEATURE:
<223> OTHER INFORMATION: Adnectin

<400> SEQUENCE: 245

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Lys Tyr Gln Val His Ala Tyr Arg Tyr Tyr Arg Ile Thr Tyr Gly
         35                  40                  45

Glu Thr Gly Gly Asn Ser Pro Val Gln Glu Phe Thr Val Pro Ser Val
 50                  55                  60

Leu Ser Thr Ala Thr Ile Asn Gly Leu Lys Pro Gly Val Asp Tyr Thr
 65                  70                  75                  80

Ile Thr Val Tyr Ala Val Thr Tyr Gly Ile Ile Ser Glu Pro Ile Ser
                 85                  90                  95

Ile Asn Tyr Arg Thr Glu Ile Asp
         100

<210> SEQ ID NO 246
<211> LENGTH: 104
<212> TYPE: PRT
<213> ORGANISM: Artificial Sequence
<220> FEATURE:
<223> OTHER INFORMATION: Adnectin

<400> SEQUENCE: 246

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val Asn Tyr Asn Arg Tyr Tyr Arg Ile Thr Tyr Gly
         35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Glu Gly Val Gln Ser Ala Pro Ile Ser
                 85                  90                  95

Ile Asn Tyr Arg Thr Glu Ile Asp
         100

```
<210> SEQ ID NO 247
<211> LENGTH: 104
<212> TYPE: PRT
<213> ORGANISM: Artificial Sequence
<220> FEATURE:
<223> OTHER INFORMATION: Adnectin

<400> SEQUENCE: 247

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Pro Gly Gly
            100

<210> SEQ ID NO 248
<211> LENGTH: 104
<212> TYPE: PRT
<213> ORGANISM: Artificial Sequence
<220> FEATURE:
<223> OTHER INFORMATION: Adnectin

<400> SEQUENCE: 248

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Thr Pro Val Gln Glu Phe Arg Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Ala Asp Ala Ser Ala Pro Ile Ser
                85                  90                  95

Ile Asn Tyr Arg Thr Glu Ile Asp
            100

<210> SEQ ID NO 249
<211> LENGTH: 104
<212> TYPE: PRT
<213> ORGANISM: Artificial Sequence
<220> FEATURE:
<223> OTHER INFORMATION: Adnectin

<400> SEQUENCE: 249

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45
```

Glu Thr Gly Gly Asn Ser Pro Val Gln Glu Phe Thr Val Pro Ser Val
          50                  55                  60

Leu Ser Ser Ala Thr Leu Asn Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 250
<211> LENGTH: 104
<212> TYPE: PRT
<213> ORGANISM: Artificial Sequence
<220> FEATURE:
<223> OTHER INFORMATION: Adnectin

<400> SEQUENCE: 250

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Lys Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 251
<211> LENGTH: 104
<212> TYPE: PRT
<213> ORGANISM: Artificial Sequence
<220> FEATURE:
<223> OTHER INFORMATION: Adnectin

<400> SEQUENCE: 251

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Asn Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 252
<211> LENGTH: 104
<212> TYPE: PRT

```
<213> ORGANISM: Artificial Sequence
<220> FEATURE:
<223> OTHER INFORMATION: Adnectin

<400> SEQUENCE: 252

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala His Arg Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 253
<211> LENGTH: 104
<212> TYPE: PRT
<213> ORGANISM: Artificial Sequence
<220> FEATURE:
<223> OTHER INFORMATION: Adnectin

<400> SEQUENCE: 253

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Ala Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 254
<211> LENGTH: 104
<212> TYPE: PRT
<213> ORGANISM: Artificial Sequence
<220> FEATURE:
<223> OTHER INFORMATION: Adnectin

<400> SEQUENCE: 254

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Ser Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60
```

```
Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100
```

<210> SEQ ID NO 255
<211> LENGTH: 104
<212> TYPE: PRT
<213> ORGANISM: Artificial Sequence
<220> FEATURE:
<223> OTHER INFORMATION: Adnectin

<400> SEQUENCE: 255

```
Met Gly His His His His His Gly Gly Ser Val Ser Asp Val Pro
  1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100
```

<210> SEQ ID NO 256
<211> LENGTH: 104
<212> TYPE: PRT
<213> ORGANISM: Artificial Sequence
<220> FEATURE:
<223> OTHER INFORMATION: Adnectin

<400> SEQUENCE: 256

```
Met Gly His His His His His Gly Gly Ser Val Ser Asp Val Pro
  1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Ala Ser Ala Pro Ile Ser
                 85                  90                  95

Ile Asn Tyr Arg Thr Glu Ile Asp
            100
```

<210> SEQ ID NO 257
<211> LENGTH: 104
<212> TYPE: PRT
<213> ORGANISM: Artificial Sequence
<220> FEATURE:
<223> OTHER INFORMATION: Adnectin -continued

<400> SEQUENCE: 257

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Asn Gly Asp Asp Ser Ala Pro Ile Ser
                85                  90                  95

Ile Asn Tyr Arg Thr Glu Ile Asp
            100

<210> SEQ ID NO 258
<211> LENGTH: 104
<212> TYPE: PRT
<213> ORGANISM: Artificial Sequence
<220> FEATURE:
<223> OTHER INFORMATION: Adnectin

<400> SEQUENCE: 258

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Thr Ile Arg Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 259
<211> LENGTH: 104
<212> TYPE: PRT
<213> ORGANISM: Artificial Sequence
<220> FEATURE:
<223> OTHER INFORMATION: Adnectin

<400> SEQUENCE: 259

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Lys Ile Ser Gly Leu Lys Pro Gly Val Asp Tyr Thr
65                  70                  75                  80

```
Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 260
<211> LENGTH: 104
<212> TYPE: PRT
<213> ORGANISM: Artificial Sequence
<220> FEATURE:
<223> OTHER INFORMATION: Adnectin

<400> SEQUENCE: 260

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Arg Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 261
<211> LENGTH: 104
<212> TYPE: PRT
<213> ORGANISM: Artificial Sequence
<220> FEATURE:
<223> OTHER INFORMATION: Adnectin

<400> SEQUENCE: 261

```
Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Pro Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 262
<211> LENGTH: 104
<212> TYPE: PRT
<213> ORGANISM: Artificial Sequence
<220> FEATURE:
<223> OTHER INFORMATION: Adnectin

<400> SEQUENCE: 262

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asp Gly Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100

<210> SEQ ID NO 263
<211> LENGTH: 104
<212> TYPE: PRT
<213> ORGANISM: Artificial Sequence
<220> FEATURE:
<223> OTHER INFORMATION: Adnectin

<400> SEQUENCE: 263

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asp Thr Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100

<210> SEQ ID NO 264
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (28)..(28)
<223> OTHER INFORMATION: Xaa can be any naturally occurring amino acid

<400> SEQUENCE: 264

Met Gly His His His His His Gly Gly Ser Val Ser Asp Val Pro
1               5                   10                  15

Arg Asp Leu Glu Val Val Ala Ala Thr Pro Thr Xaa Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr

```
                65                  70                  75                  80
Ile Thr Val Tyr Ala Val Thr Tyr Gly Asp Asp Ser Ala Pro Ile Ser
                    85                  90                  95
Ile Asn Tyr Arg Thr Glu Ile Asp
                100

<210> SEQ ID NO 265
<211> LENGTH: 104
<212> TYPE: PRT
<213> ORGANISM: Artificial Sequence
<220> FEATURE:
<223> OTHER INFORMATION: Adnectin

<400> SEQUENCE: 265

Met Gly His His His His His Gly Gly Ser Val Ser Asp Val Pro
1               5                   10                  15
Arg Asp Leu Glu Val Val Ala Ala Thr Pro Thr Ser Leu Leu Ile Ser
                20                  25                  30
Trp Glu Tyr Lys Val His Pro Tyr Arg Tyr Tyr Arg Ile Thr Tyr Gly
                    35                  40                  45
Glu Thr Gly Gly Asn Ser Pro Val Gln Glu Phe Thr Val Pro Ser Val
        50                  55                  60
Leu Ser Thr Ala Thr Ile Ser Gly Leu Lys Pro Gly Val Asp Tyr Thr
65              70                  75                  80
Ile Thr Val Tyr Ala Val Thr Tyr Gly Ala Asp Ser Ala Pro Ile Ser
                    85                  90                  95
Ile Asn Tyr Arg Thr Glu Ile Asp
                100

<210> SEQ ID NO 266
<211> LENGTH: 104
<212> TYPE: PRT
<213> ORGANISM: Artificial Sequence
<220> FEATURE:
<223> OTHER INFORMATION: Adnectin

<400> SEQUENCE: 266

Met Gly His His His His His Gly Gly Ser Val Ser Asp Val Pro
1               5                   10                  15
Arg Asp Leu Glu Val Val Ala Ala Thr Pro Thr Ser Leu Leu Ile Ser
                20                  25                  30
Trp Glu Tyr Lys Val His Pro Tyr Arg Tyr Tyr Arg Ile Thr Tyr Gly
                    35                  40                  45
Glu Thr Gly Gly Asn Ser Pro Val Gln Glu Phe Thr Val Pro Ser Val
        50                  55                  60
Leu Ser Thr Ala Thr Ile Ser Gly Leu Lys Pro Gly Val Asp Tyr Thr
65              70                  75                  80
Ile Thr Val Tyr Ala Val Thr Arg Gly Asp Asp Ser Ala Pro Ile Ser
                    85                  90                  95
Ile Asn Tyr Arg Thr Glu Ile Asp
                100

<210> SEQ ID NO 267
<211> LENGTH: 104
<212> TYPE: PRT
<213> ORGANISM: Artificial Sequence
<220> FEATURE:
<223> OTHER INFORMATION: Adnectin

<400> SEQUENCE: 267
```

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Asp Phe Thr Val Pro Ser Val
        50                  55                  60

Leu Ser Thr Ala Thr Ile Arg Gly Leu Lys Pro Gly Val Asp Tyr Thr
65                  70                  75                  80

Ile Thr Val Tyr Ala Val Thr Tyr Gly Asp Ser Ala Pro Ile Ser
                85                  90                  95

Ile Asn Tyr Arg Thr Glu Ile Asp
            100

<210> SEQ ID NO 268
<211> LENGTH: 104
<212> TYPE: PRT
<213> ORGANISM: Artificial Sequence
<220> FEATURE:
<223> OTHER INFORMATION: Adnectin

<400> SEQUENCE: 268

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Asn Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 269
<211> LENGTH: 104
<212> TYPE: PRT
<213> ORGANISM: Artificial Sequence
<220> FEATURE:
<223> OTHER INFORMATION: Adnectin

<400> SEQUENCE: 269

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Ala Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser

-continued

```
                    85                  90                  95

Ile Asn Tyr Arg Thr Glu Ile Asp
            100

<210> SEQ ID NO 270
<211> LENGTH: 104
<212> TYPE: PRT
<213> ORGANISM: Artificial Sequence
<220> FEATURE:
<223> OTHER INFORMATION: Adnectin

<400> SEQUENCE: 270

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 271
<211> LENGTH: 104
<212> TYPE: PRT
<213> ORGANISM: Artificial Sequence
<220> FEATURE:
<223> OTHER INFORMATION: Adnectin

<400> SEQUENCE: 271

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Gly Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 272
<211> LENGTH: 104
<212> TYPE: PRT
<213> ORGANISM: Artificial Sequence
<220> FEATURE:
<223> OTHER INFORMATION: Adnectin

<400> SEQUENCE: 272

Met Gly His His His His His Gly Gly Ser Val Ser Asp Val Pro
1               5                   10                  15
```

Arg Asp Leu Glu Val Val Ala Ala Thr Pro Thr Ser Leu Leu Ile Ser
            20                  25                  30

Trp Glu Tyr Lys Val Asp Thr Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 273
<211> LENGTH: 104
<212> TYPE: PRT
<213> ORGANISM: Artificial Sequence
<220> FEATURE:
<223> OTHER INFORMATION: Adnectin

<400> SEQUENCE: 273

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Glu Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 274
<211> LENGTH: 104
<212> TYPE: PRT
<213> ORGANISM: Artificial Sequence
<220> FEATURE:
<223> OTHER INFORMATION: Adnectin

<400> SEQUENCE: 274

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Arg Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp

<210> SEQ ID NO 275
<211> LENGTH: 104
<212> TYPE: PRT
<213> ORGANISM: Artificial Sequence
<220> FEATURE:
<223> OTHER INFORMATION: Adnectin

<400> SEQUENCE: 275

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Ser Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ala Asp Ser Ala Pro Ile Ser
                85                  90                  95

Ile Asn Tyr Arg Thr Glu Ile Asp
            100

<210> SEQ ID NO 276
<211> LENGTH: 104
<212> TYPE: PRT
<213> ORGANISM: Artificial Sequence
<220> FEATURE:
<223> OTHER INFORMATION: Adnectin

<400> SEQUENCE: 276

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Arg Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 277
<211> LENGTH: 104
<212> TYPE: PRT
<213> ORGANISM: Artificial Sequence
<220> FEATURE:
<223> OTHER INFORMATION: Adnectin

<400> SEQUENCE: 277

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

```
Trp Glu Tyr Lys Val His Pro Tyr Arg Tyr Arg Ile Thr Tyr Gly
        35                  40                  45

Glu Thr Gly Gly Asn Ser Pro Val Gln Asp Phe Thr Val Pro Ser Val
    50                  55                  60

Leu Ser Thr Ala Thr Ile Ser Gly Leu Lys Pro Gly Val Asp Tyr Thr
65              70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100
```

<210> SEQ ID NO 278
<211> LENGTH: 104
<212> TYPE: PRT
<213> ORGANISM: Artificial Sequence
<220> FEATURE:
<223> OTHER INFORMATION: Adnectin

<400> SEQUENCE: 278

```
Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Ala Arg Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65              70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100
```

<210> SEQ ID NO 279
<211> LENGTH: 104
<212> TYPE: PRT
<213> ORGANISM: Artificial Sequence
<220> FEATURE:
<223> OTHER INFORMATION: Adnectin

<400> SEQUENCE: 279

```
Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asp His Gln Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65              70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
                100
```

-continued

```
<210> SEQ ID NO 280
<211> LENGTH: 104
<212> TYPE: PRT
<213> ORGANISM: Artificial Sequence
<220> FEATURE:
<223> OTHER INFORMATION: Adnectin

<400> SEQUENCE: 280

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Tyr Gly Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 281
<211> LENGTH: 104
<212> TYPE: PRT
<213> ORGANISM: Artificial Sequence
<220> FEATURE:
<223> OTHER INFORMATION: Adnectin

<400> SEQUENCE: 281

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Lys Tyr Gly Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 282
<211> LENGTH: 104
<212> TYPE: PRT
<213> ORGANISM: Artificial Sequence
<220> FEATURE:
<223> OTHER INFORMATION: Adnectin

<400> SEQUENCE: 282

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Ser Val His Pro Tyr Arg Tyr Tyr Arg Ile Thr Tyr Gly
        35                  40                  45
```

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 283
<211> LENGTH: 104
<212> TYPE: PRT
<213> ORGANISM: Artificial Sequence
<220> FEATURE:
<223> OTHER INFORMATION: Adnectin

<400> SEQUENCE: 283

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Asp Gly Asp Asp Ser Ala Pro Ile Ser
                85                  90                  95

Ile Asn Tyr Arg Thr Glu Ile Asp
            100

<210> SEQ ID NO 284
<211> LENGTH: 104
<212> TYPE: PRT
<213> ORGANISM: Artificial Sequence
<220> FEATURE:
<223> OTHER INFORMATION: Adnectin

<400> SEQUENCE: 284

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Ser Gly Asp Asp Ser Ala Pro Ile Ser
                85                  90                  95

Ile Asn Tyr Arg Thr Glu Ile Asp
            100

<210> SEQ ID NO 285
<211> LENGTH: 104
<212> TYPE: PRT

-continued

<213> ORGANISM: Artificial Sequence
<220> FEATURE:
<223> OTHER INFORMATION: Adnectin

<400> SEQUENCE: 285

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Thr Leu Arg Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 286
<211> LENGTH: 104
<212> TYPE: PRT
<213> ORGANISM: Artificial Sequence
<220> FEATURE:
<223> OTHER INFORMATION: Adnectin

<400> SEQUENCE: 286

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Ala Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 287
<211> LENGTH: 104
<212> TYPE: PRT
<213> ORGANISM: Artificial Sequence
<220> FEATURE:
<223> OTHER INFORMATION: Adnectin

<400> SEQUENCE: 287

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Thr Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

```
Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 288
<211> LENGTH: 104
<212> TYPE: PRT
<213> ORGANISM: Artificial Sequence
<220> FEATURE:
<223> OTHER INFORMATION: Adnectin

<400> SEQUENCE: 288

Met Gly His His His His His Gly Gly Ser Val Ser Asp Val Pro
  1               5                  10                  15

Arg Asp Leu Glu Val Val Ala Ala Thr Thr Thr Ser Leu Leu Ile Ser
                 20                  25                  30

Trp Glu Tyr Lys Val Asp Tyr His Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 289
<211> LENGTH: 104
<212> TYPE: PRT
<213> ORGANISM: Artificial Sequence
<220> FEATURE:
<223> OTHER INFORMATION: Adnectin

<400> SEQUENCE: 289

Met Gly His His His His His Gly Gly Ser Val Ser Asp Val Pro
  1               5                  10                  15

Arg Asp Leu Glu Val Val Ala Ala Thr Pro Thr Ser Leu Leu Ile Ser
                 20                  25                  30

Trp Glu Tyr Gly Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 290
<211> LENGTH: 104
<212> TYPE: PRT
<213> ORGANISM: Artificial Sequence
<220> FEATURE:
<223> OTHER INFORMATION: Adnectin
```

```
<220> FEATURE:
<221> NAME/KEY: misc_feature
<222> LOCATION: (36)..(36)
<223> OTHER INFORMATION: Xaa can be any naturally occurring amino acid

<400> SEQUENCE: 290
```

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Lys Tyr Xaa Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

```
<210> SEQ ID NO 291
<211> LENGTH: 104
<212> TYPE: PRT
<213> ORGANISM: Artificial Sequence
<220> FEATURE:
<223> OTHER INFORMATION: Adnectin

<400> SEQUENCE: 291
```

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Gly Gly Asp Asp Ser Ala Pro Ile Ser
                85                  90                  95

Ile Asn Tyr Arg Thr Glu Ile Asp
            100

```
<210> SEQ ID NO 292
<211> LENGTH: 104
<212> TYPE: PRT
<213> ORGANISM: Artificial Sequence
<220> FEATURE:
<223> OTHER INFORMATION: Adnectin

<400> SEQUENCE: 292
```

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val 50                  55                  60
Leu Ser Thr Ala Thr Ile His Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 293
<211> LENGTH: 104
<212> TYPE: PRT
<213> ORGANISM: Artificial Sequence
<220> FEATURE:
<223> OTHER INFORMATION: Adnectin

<400> SEQUENCE: 293

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Leu Arg Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 294
<211> LENGTH: 104
<212> TYPE: PRT
<213> ORGANISM: Artificial Sequence
<220> FEATURE:
<223> OTHER INFORMATION: Adnectin

<400> SEQUENCE: 294

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Ser Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 295
<211> LENGTH: 104
<212> TYPE: PRT
<213> ORGANISM: Artificial Sequence
<220> FEATURE:

<223> OTHER INFORMATION: Adnectin

<400> SEQUENCE: 295

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Ala Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 296
<211> LENGTH: 104
<212> TYPE: PRT
<213> ORGANISM: Artificial Sequence
<220> FEATURE:
<223> OTHER INFORMATION: Adnectin

<400> SEQUENCE: 296

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Thr Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 297
<211> LENGTH: 104
<212> TYPE: PRT
<213> ORGANISM: Artificial Sequence
<220> FEATURE:
<223> OTHER INFORMATION: Adnectin

<400> SEQUENCE: 297

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Pro Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr 65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 298
<211> LENGTH: 104
<212> TYPE: PRT
<213> ORGANISM: Artificial Sequence
<220> FEATURE:
<223> OTHER INFORMATION: Adnectin

<400> SEQUENCE: 298

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asp Tyr Gln Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 299
<211> LENGTH: 104
<212> TYPE: PRT
<213> ORGANISM: Artificial Sequence
<220> FEATURE:
<223> OTHER INFORMATION: Adnectin

<400> SEQUENCE: 299

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Lys Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 300
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (36)..(36)
<223> OTHER INFORMATION: Xaa can be any naturally occurring amino acid

<400> SEQUENCE: 300

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Xaa Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Ser Ala Pro Ile Ser
                85                  90                  95

Ile Asn Tyr Arg Thr Glu Ile Asp
            100

<210> SEQ ID NO 301
<211> LENGTH: 105
<212> TYPE: PRT
<213> ORGANISM: Artificial Sequence
<220> FEATURE:
<223> OTHER INFORMATION: Adnectin

<400> SEQUENCE: 301

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr His Gly Asp Asp Phe Ala Pro Ile Ser
                85                  90                  95

Ile Asn Tyr Arg Thr Glu Met Leu Ile
            100                 105

<210> SEQ ID NO 302
<211> LENGTH: 104
<212> TYPE: PRT
<213> ORGANISM: Artificial Sequence
<220> FEATURE:
<223> OTHER INFORMATION: Adnectin

<400> SEQUENCE: 302

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Ser Ala Thr Ile Asn Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 303
<211> LENGTH: 104
<212> TYPE: PRT
<213> ORGANISM: Artificial Sequence
<220> FEATURE:
<223> OTHER INFORMATION: Adnectin

<400> SEQUENCE: 303

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Arg Ile Thr Tyr Gly
        35                  40                  45

Glu Thr Gly Gly Asn Ser Pro Val Gln Glu Phe Lys Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 304
<211> LENGTH: 104
<212> TYPE: PRT
<213> ORGANISM: Artificial Sequence
<220> FEATURE:
<223> OTHER INFORMATION: Adnectin

<400> SEQUENCE: 304

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala His Asp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 305
<211> LENGTH: 104
<212> TYPE: PRT
<213> ORGANISM: Artificial Sequence
<220> FEATURE:
<223> OTHER INFORMATION: Adnectin

<400> SEQUENCE: 305

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 306
<211> LENGTH: 104
<212> TYPE: PRT
<213> ORGANISM: Artificial Sequence
<220> FEATURE:
<223> OTHER INFORMATION: Adnectin

<400> SEQUENCE: 306

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asp Tyr Arg Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 307
<211> LENGTH: 104
<212> TYPE: PRT
<213> ORGANISM: Artificial Sequence
<220> FEATURE:
<223> OTHER INFORMATION: Adnectin

<400> SEQUENCE: 307

Met Gly His His His His His Gly Gly Ser Val Ser Asp Val Pro
1               5                   10                  15

Arg Asp Leu Glu Val Val Ala Ala Thr Pro Thr Gly Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 308
<211> LENGTH: 104
<212> TYPE: PRT
<213> ORGANISM: Artificial Sequence
<220> FEATURE:
<223> OTHER INFORMATION: Adnectin

<400> SEQUENCE: 308

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asn Ala Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 309
<211> LENGTH: 104
<212> TYPE: PRT
<213> ORGANISM: Artificial Sequence
<220> FEATURE:
<223> OTHER INFORMATION: Adnectin

<400> SEQUENCE: 309

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr His Gly Asp Asp Ser Ala Pro Ile Ser
                85                  90                  95

Ile Asn Tyr Arg Thr Glu Ile Asp
            100

<210> SEQ ID NO 310
<211> LENGTH: 104
<212> TYPE: PRT
<213> ORGANISM: Artificial Sequence
<220> FEATURE:
<223> OTHER INFORMATION: Adnectin

<400> SEQUENCE: 310

Met Gly His His His His His Gly Gly Ser Val Ser Asp Val Pro

```
1               5                   10                  15
Arg Asp Leu Glu Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Asn Gly Leu Lys Pro Gly Val Asp Tyr Thr
65                  70                  75                  80

Ile Thr Val Tyr Ala Val Thr Tyr Gly Asp Asp Ser Ala Pro Ile Ser
                    85                  90                  95

Ile Asn Tyr Arg Thr Glu Ile Asp
            100

<210> SEQ ID NO 311
<211> LENGTH: 104
<212> TYPE: PRT
<213> ORGANISM: Artificial Sequence
<220> FEATURE:
<223> OTHER INFORMATION: Adnectin

<400> SEQUENCE: 311

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Glu Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                    85                  90                  95

Ile Asn Tyr Arg Thr Glu Ile Asp
            100

<210> SEQ ID NO 312
<211> LENGTH: 104
<212> TYPE: PRT
<213> ORGANISM: Artificial Sequence
<220> FEATURE:
<223> OTHER INFORMATION: Adnectin

<400> SEQUENCE: 312

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Leu Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                    85                  90                  95
```

```
Ile Asn Tyr Arg Thr Glu Ile Asp
            100
```

<210> SEQ ID NO 313
<211> LENGTH: 104
<212> TYPE: PRT
<213> ORGANISM: Artificial Sequence
<220> FEATURE:
<223> OTHER INFORMATION: Adnectin

<400> SEQUENCE: 313

```
Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala His Gly Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 314
<211> LENGTH: 104
<212> TYPE: PRT
<213> ORGANISM: Artificial Sequence
<220> FEATURE:
<223> OTHER INFORMATION: Adnectin

<400> SEQUENCE: 314

```
Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ala Tyr Lys Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 315
<211> LENGTH: 104
<212> TYPE: PRT
<213> ORGANISM: Artificial Sequence
<220> FEATURE:
<223> OTHER INFORMATION: Adnectin

<400> SEQUENCE: 315

```
Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
```

```
                    20                  25                  30

Trp Glu Tyr Lys Val Asp Arg Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 316
<211> LENGTH: 104
<212> TYPE: PRT
<213> ORGANISM: Artificial Sequence
<220> FEATURE:
<223> OTHER INFORMATION: Adnectin

<400> SEQUENCE: 316

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Ala Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 317
<211> LENGTH: 104
<212> TYPE: PRT
<213> ORGANISM: Artificial Sequence
<220> FEATURE:
<223> OTHER INFORMATION: Adnectin

<400> SEQUENCE: 317

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Ala Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100
```

<210> SEQ ID NO 318
<211> LENGTH: 104
<212> TYPE: PRT
<213> ORGANISM: Artificial Sequence
<220> FEATURE:
<223> OTHER INFORMATION: Adnectin

<400> SEQUENCE: 318

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Gly Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 319
<211> LENGTH: 104
<212> TYPE: PRT
<213> ORGANISM: Artificial Sequence
<220> FEATURE:
<223> OTHER INFORMATION: Adnectin

<400> SEQUENCE: 319

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ser His Gly Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 320
<211> LENGTH: 104
<212> TYPE: PRT
<213> ORGANISM: Artificial Sequence
<220> FEATURE:
<223> OTHER INFORMATION: Adnectin

<400> SEQUENCE: 320

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Thr Thr Trp Arg Tyr Tyr Arg Ile Thr Tyr Gly

```
                35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 321
<211> LENGTH: 104
<212> TYPE: PRT
<213> ORGANISM: Artificial Sequence
<220> FEATURE:
<223> OTHER INFORMATION: Adnectin

<400> SEQUENCE: 321

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Ser Ala Glx Leu Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 322
<211> LENGTH: 104
<212> TYPE: PRT
<213> ORGANISM: Artificial Sequence
<220> FEATURE:
<223> OTHER INFORMATION: Adnectin

<400> SEQUENCE: 322

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Thr Asp Ser Ala Pro Ile Ser
                 85                  90                  95

Ile Asn Tyr Arg Thr Glu Ile Asp
            100

<210> SEQ ID NO 323
<211> LENGTH: 104
```

```
<212> TYPE: PRT
<213> ORGANISM: Artificial Sequence
<220> FEATURE:
<223> OTHER INFORMATION: Adnectin

<400> SEQUENCE: 323

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Gln Ser Ala Pro Ile Ser
                85                  90                  95

Ile Asn Tyr Arg Thr Glu Ile Asp
            100

<210> SEQ ID NO 324
<211> LENGTH: 104
<212> TYPE: PRT
<213> ORGANISM: Artificial Sequence
<220> FEATURE:
<223> OTHER INFORMATION: Adnectin

<400> SEQUENCE: 324

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Asn Pro Ile Ser
                85                  90                  95

Ile Asn Tyr Arg Thr Glu Ile Asp
            100

<210> SEQ ID NO 325
<211> LENGTH: 104
<212> TYPE: PRT
<213> ORGANISM: Artificial Sequence
<220> FEATURE:
<223> OTHER INFORMATION: Adnectin

<400> SEQUENCE: 325

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn His Asp Arg Tyr Tyr Arg Ile Thr Tyr Gly
            35                  40                  45

Glu Thr Gly Gly Asn Ser Pro Val Gln Glu Phe Thr Val Pro Ser Val
```

```
            50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 326
<211> LENGTH: 104
<212> TYPE: PRT
<213> ORGANISM: Artificial Sequence
<220> FEATURE:
<223> OTHER INFORMATION: Adnectin

<400> SEQUENCE: 326

Met Gly His His His His His Gly Gly Ser Val Ser Asp Val Pro
  1               5                  10                  15

Arg Asp Leu Glu Val Val Ala Ala Thr Pro Thr Ser Leu Leu Ile Ser
                 20                  25                  30

Trp Glu Tyr Lys Val Ser His Arg Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 327
<211> LENGTH: 104
<212> TYPE: PRT
<213> ORGANISM: Artificial Sequence
<220> FEATURE:
<223> OTHER INFORMATION: Adnectin

<400> SEQUENCE: 327

Met Gly His His His His His Gly Gly Ser Val Ser Asp Val Pro
  1               5                  10                  15

Arg Asp Leu Glu Val Val Ala Ala Thr Pro Thr Ser Leu Leu Ile Ser
                 20                  25                  30

Trp Glu Tyr Lys Val Thr Tyr Glu Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 328
<211> LENGTH: 104
<212> TYPE: PRT
<213> ORGANISM: Artificial Sequence
<220> FEATURE:
```

<223> OTHER INFORMATION: Adnectin
<220> FEATURE:
<221> NAME/KEY: misc_feature
<222> LOCATION: (70)..(71)
<223> OTHER INFORMATION: Xaa can be any naturally occurring amino acid

<400> SEQUENCE: 328

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
50                      55                  60

Leu Ser Ser Ala Thr Xaa Xaa Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 329
<211> LENGTH: 104
<212> TYPE: PRT
<213> ORGANISM: Artificial Sequence
<220> FEATURE:
<223> OTHER INFORMATION: Adnectin

<400> SEQUENCE: 329

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
50                      55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Val Ser Ala Pro Ile Ser
                85                  90                  95

Ile Asn Tyr Arg Thr Glu Ile Asp
            100

<210> SEQ ID NO 330
<211> LENGTH: 104
<212> TYPE: PRT
<213> ORGANISM: Artificial Sequence
<220> FEATURE:
<223> OTHER INFORMATION: Adnectin

<400> SEQUENCE: 330

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

```
Glu Thr Gly Gly Asn Ser Pro Val Gln Glu Phe Thr Val Pro Ser Val
 50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Asp Asp Ser Pro Pro Ile Ser
                 85                  90                  95
Ile Asn Tyr Arg Thr Glu Ile Asp
                100
```

<210> SEQ ID NO 331
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (93)..(93)
<223> OTHER INFORMATION: Xaa can be any naturally occurring amino acid

<400> SEQUENCE: 331

```
Met Gly His His His His His Gly Gly Ser Val Ser Asp Val Pro
 1               5                  10                  15
Arg Asp Leu Glu Val Val Ala Ala Thr Pro Thr Ser Leu Leu Ile Ser
                 20                  25                  30
Trp Glu Tyr Lys Val His Pro Tyr Arg Tyr Tyr Arg Ile Thr Tyr Gly
             35                  40                  45
Glu Thr Gly Gly Asn Ser Pro Val Gln Glu Phe Thr Val Pro Ser Val
 50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Asp Asp Ser Xaa Pro Ile Ser
                 85                  90                  95
Ile Asn Tyr Arg Thr Glu Ile Asp
                100
```

<210> SEQ ID NO 332
<211> LENGTH: 104
<212> TYPE: PRT
<213> ORGANISM: Artificial Sequence
<220> FEATURE:
<223> OTHER INFORMATION: Adnectin

<400> SEQUENCE: 332

```
Met Gly His His His His His Gly Gly Ser Val Ser Asp Val Pro
 1               5                  10                  15
Arg Asp Leu Glu Val Val Ala Ala Thr Pro Thr Ser Leu Leu Ile Ser
                 20                  25                  30
Trp Glu Tyr Lys Val Asn Arg Trp Arg Tyr Tyr Arg Ile Thr Tyr Gly
             35                  40                  45
Glu Thr Gly Gly Asn Ser Pro Val Gln Glu Phe Thr Val Pro Ser Val
 50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Asp Asp Ser Ala Pro Ile Ser
                 85                  90                  95
Ile Asn Tyr Arg Thr Glu Ile Asp
                100
```

```
<210> SEQ ID NO 333
<211> LENGTH: 104
<212> TYPE: PRT
<213> ORGANISM: Artificial Sequence
<220> FEATURE:
<223> OTHER INFORMATION: Adnectin

<400> SEQUENCE: 333
```

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Ser Pro Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

```
<210> SEQ ID NO 334
<211> LENGTH: 104
<212> TYPE: PRT
<213> ORGANISM: Artificial Sequence
<220> FEATURE:
<223> OTHER INFORMATION: Adnectin

<400> SEQUENCE: 334
```

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Thr Tyr Arg Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

```
<210> SEQ ID NO 335
<211> LENGTH: 104
<212> TYPE: PRT
<213> ORGANISM: Artificial Sequence
<220> FEATURE:
<223> OTHER INFORMATION: Adnectin

<400> SEQUENCE: 335
```

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

```
Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Glu Ser Ala Pro Ile Ser
                 85                  90                  95

Ile Asn Tyr Arg Thr Glu Ile Asp
            100
```

<210> SEQ ID NO 336
<211> LENGTH: 104
<212> TYPE: PRT
<213> ORGANISM: Artificial Sequence
<220> FEATURE:
<223> OTHER INFORMATION: Adnectin

<400> SEQUENCE: 336

```
Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Asp Pro Ile Ser
                 85                  90                  95

Ile Asn Tyr Arg Thr Glu Ile Asp
            100
```

<210> SEQ ID NO 337
<211> LENGTH: 104
<212> TYPE: PRT
<213> ORGANISM: Artificial Sequence
<220> FEATURE:
<223> OTHER INFORMATION: Adnectin

<400> SEQUENCE: 337

```
Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Tyr Pro Ile Ser
                 85                  90                  95

Ile Asn Tyr Arg Thr Glu Ile Asp
            100
```

<210> SEQ ID NO 338
<211> LENGTH: 104
<212> TYPE: PRT

-continued

<213> ORGANISM: Artificial Sequence
<220> FEATURE:
<223> OTHER INFORMATION: Adnectin

<400> SEQUENCE: 338

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Arg Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 339
<211> LENGTH: 104
<212> TYPE: PRT
<213> ORGANISM: Artificial Sequence
<220> FEATURE:
<223> OTHER INFORMATION: Adnectin

<400> SEQUENCE: 339

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ser Arg Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 340
<211> LENGTH: 104
<212> TYPE: PRT
<213> ORGANISM: Artificial Sequence
<220> FEATURE:
<223> OTHER INFORMATION: Adnectin
<220> FEATURE:
<221> NAME/KEY: misc_feature
<222> LOCATION: (38)..(39)
<223> OTHER INFORMATION: Xaa can be any naturally occurring amino acid

<400> SEQUENCE: 340

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Xaa Xaa Tyr Arg Tyr Tyr Arg Ile Thr Tyr Gly 35                  40                  45
Glu Thr Gly Gly Asn Ser Pro Val Gln Glu Phe Thr Val Pro Ser Val
         50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Asp Asp Ser Ala Pro Ile Ser
                 85                  90                  95
Ile Asn Tyr Arg Thr Glu Ile Asp
                100

<210> SEQ ID NO 341
<211> LENGTH: 104
<212> TYPE: PRT
<213> ORGANISM: Artificial Sequence
<220> FEATURE:
<223> OTHER INFORMATION: Adnectin

<400> SEQUENCE: 341

Met Gly His His His His His Gly Gly Ser Val Ser Asp Val Pro
 1               5                  10                  15
Arg Asp Leu Glu Val Val Ala Ala Thr Pro Thr Ser Leu Leu Ile Ser
                 20                  25                  30
Trp Glu Tyr Lys Val His Pro Tyr Arg Tyr Tyr Arg Ile Thr Tyr Gly
             35                  40                  45
Glu Thr Gly Gly Asn Ser Pro Val Gln Ser Phe Thr Val Pro Ser Val
         50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Asp Asp Ser Ala Pro Ile Ser
                 85                  90                  95
Ile Asn Tyr Arg Thr Glu Ile Asp
                100

<210> SEQ ID NO 342
<211> LENGTH: 104
<212> TYPE: PRT
<213> ORGANISM: Artificial Sequence
<220> FEATURE:
<223> OTHER INFORMATION: Adnectin

<400> SEQUENCE: 342

Met Gly His His His His His Gly Gly Ser Val Ser Asp Val Pro
 1               5                  10                  15
Arg Asp Leu Glu Val Val Ala Ala Thr Pro Thr Ser Leu Leu Ile Ser
                 20                  25                  30
Trp Glu Tyr Lys Val His Pro Tyr Arg Tyr Tyr Arg Ile Thr Tyr Gly
             35                  40                  45
Glu Thr Gly Gly Asn Ser Pro Val Gln Glu Phe Thr Val Pro Ser Val
         50                  55                  60
Leu Ser Thr Ala Thr Ile Ser Gly Leu Lys Pro Gly Val Asp Tyr Thr
 65                  70                  75                  80
Ile Thr Val Tyr Ala Val Thr Tyr Gly Ile Asp Ser Ala Pro Ile Ser
                 85                  90                  95
Ile Asn Tyr Arg Thr Glu Ile Asp
                100

<210> SEQ ID NO 343
<211> LENGTH: 104

```
<212> TYPE: PRT
<213> ORGANISM: Artificial Sequence
<220> FEATURE:
<223> OTHER INFORMATION: Adnectin

<400> SEQUENCE: 343

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp His Ser Ala Pro Ile Ser
                85                  90                  95

Ile Asn Tyr Arg Thr Glu Ile Asp
            100

<210> SEQ ID NO 344
<211> LENGTH: 104
<212> TYPE: PRT
<213> ORGANISM: Artificial Sequence
<220> FEATURE:
<223> OTHER INFORMATION: Adnectin

<400> SEQUENCE: 344

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Glu Pro Ile Ser
                85                  90                  95

Ile Asn Tyr Arg Thr Glu Ile Asp
            100

<210> SEQ ID NO 345
<211> LENGTH: 104
<212> TYPE: PRT
<213> ORGANISM: Artificial Sequence
<220> FEATURE:
<223> OTHER INFORMATION: Adnectin

<400> SEQUENCE: 345

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
```

```
                50                  55                  60
Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Arg Pro Ile Ser
                 85                  90                  95

Ile Asn Tyr Arg Thr Glu Ile Asp
            100

<210> SEQ ID NO 346
<211> LENGTH: 104
<212> TYPE: PRT
<213> ORGANISM: Artificial Sequence
<220> FEATURE:
<223> OTHER INFORMATION: Adnectin

<400> SEQUENCE: 346

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val His Pro Tyr Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Gln Tyr Arg Thr Glu Ile Asp
            100

<210> SEQ ID NO 347
<211> LENGTH: 104
<212> TYPE: PRT
<213> ORGANISM: Artificial Sequence
<220> FEATURE:
<223> OTHER INFORMATION: Adnectin

<400> SEQUENCE: 347

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
                 20                  25                  30

Trp Glu Tyr Lys Val Asn Tyr Arg Arg Tyr Tyr Arg Ile Thr Tyr Gly
             35                  40                  45

Glu Thr Gly Gly Asn Ser Pro Val Gln Glu Phe Thr Val Pro Ser Val
 50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                 85                  90                  95

Ile Asn Tyr Arg Thr Glu Ile Asp
            100

<210> SEQ ID NO 348
<211> LENGTH: 104
<212> TYPE: PRT
<213> ORGANISM: Artificial Sequence
<220> FEATURE:
```

<223> OTHER INFORMATION: Adnectin

<400> SEQUENCE: 348

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ser Thr Trp Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 349
<211> LENGTH: 104
<212> TYPE: PRT
<213> ORGANISM: Artificial Sequence
<220> FEATURE:
<223> OTHER INFORMATION: Adnectin

<400> SEQUENCE: 349

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Tyr Ala Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 350
<211> LENGTH: 104
<212> TYPE: PRT
<213> ORGANISM: Artificial Sequence
<220> FEATURE:
<223> OTHER INFORMATION: Adnectin

<400> SEQUENCE: 350

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Thr Phe Thr Val Pro Ser Val
    50                  55                  60

Leu Ser Thr Ala Thr Ile Ser Gly Leu Lys Pro Gly Val Asp Tyr Thr

-continued

```
                65                  70                  75                  80
Ile Thr Val Tyr Ala Val Thr Tyr Gly Asp Asp Ser Ala Pro Ile Ser
                    85                  90                  95

Ile Asn Tyr Arg Thr Glu Ile Asp
            100

<210> SEQ ID NO 351
<211> LENGTH: 104
<212> TYPE: PRT
<213> ORGANISM: Artificial Sequence
<220> FEATURE:
<223> OTHER INFORMATION: Adnectin

<400> SEQUENCE: 351

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Ala Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Lys Asp Ser Ala Pro Ile Ser
                    85                  90                  95

Ile Asn Tyr Arg Thr Glu Ile Asp
            100

<210> SEQ ID NO 352
<211> LENGTH: 104
<212> TYPE: PRT
<213> ORGANISM: Artificial Sequence
<220> FEATURE:
<223> OTHER INFORMATION: Adnectin

<400> SEQUENCE: 352

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Leu Ser Ala Pro Ile Ser
                    85                  90                  95

Ile Asn Tyr Arg Thr Glu Ile Asp
            100

<210> SEQ ID NO 353
<211> LENGTH: 104
<212> TYPE: PRT
<213> ORGANISM: Artificial Sequence
<220> FEATURE:
<223> OTHER INFORMATION: Adnectin

<400> SEQUENCE: 353
```

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Gly Pro Ile Ser
                85                  90                  95

Ile Asn Tyr Arg Thr Glu Ile Asp
            100

<210> SEQ ID NO 354
<211> LENGTH: 104
<212> TYPE: PRT
<213> ORGANISM: Artificial Sequence
<220> FEATURE:
<223> OTHER INFORMATION: Adnectin

<400> SEQUENCE: 354

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Ser Ala Trp Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 355
<211> LENGTH: 104
<212> TYPE: PRT
<213> ORGANISM: Artificial Sequence
<220> FEATURE:
<223> OTHER INFORMATION: Adnectin

<400> SEQUENCE: 355

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Ser Thr Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser

Ile Asn Tyr Arg Thr Glu Ile Asp
            100

<210> SEQ ID NO 356
<211> LENGTH: 104
<212> TYPE: PRT
<213> ORGANISM: Artificial Sequence
<220> FEATURE:
<223> OTHER INFORMATION: Adnectin

<400> SEQUENCE: 356

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Glu Leu Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 357
<211> LENGTH: 104
<212> TYPE: PRT
<213> ORGANISM: Artificial Sequence
<220> FEATURE:
<223> OTHER INFORMATION: Adnectin

<400> SEQUENCE: 357

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Leu Ser Ala Pro Ile Ser
                85                  90                  95

Ile Asn Tyr Arg Thr Glu Ile Asp
            100

<210> SEQ ID NO 358
<211> LENGTH: 104
<212> TYPE: PRT
<213> ORGANISM: Artificial Sequence
<220> FEATURE:
<223> OTHER INFORMATION: Adnectin

<400> SEQUENCE: 358

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Thr Pro Ile Ser
                85                  90                  95

Ile Asn Tyr Arg Thr Glu Ile Asp
            100

<210> SEQ ID NO 359
<211> LENGTH: 104
<212> TYPE: PRT
<213> ORGANISM: Artificial Sequence
<220> FEATURE:
<223> OTHER INFORMATION: Adnectin

<400> SEQUENCE: 359

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Ser Ala Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 360
<211> LENGTH: 104
<212> TYPE: PRT
<213> ORGANISM: Artificial Sequence
<220> FEATURE:
<223> OTHER INFORMATION: Adnectin

<400> SEQUENCE: 360

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Thr Gly Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp

-continued

```
                100

<210> SEQ ID NO 361
<211> LENGTH: 104
<212> TYPE: PRT
<213> ORGANISM: Artificial Sequence
<220> FEATURE:
<223> OTHER INFORMATION: Adnectin

<400> SEQUENCE: 361

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Tyr His Gly Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 362
<211> LENGTH: 104
<212> TYPE: PRT
<213> ORGANISM: Artificial Sequence
<220> FEATURE:
<223> OTHER INFORMATION: Adnectin

<400> SEQUENCE: 362

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Lys Leu Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 363
<211> LENGTH: 104
<212> TYPE: PRT
<213> ORGANISM: Artificial Sequence
<220> FEATURE:
<223> OTHER INFORMATION: Adnectin

<400> SEQUENCE: 363

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30
```

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asn Asp Ser Ala Pro Ile Ser
                85                  90                  95

Ile Asn Tyr Arg Thr Glu Ile Asp
            100

<210> SEQ ID NO 364
<211> LENGTH: 104
<212> TYPE: PRT
<213> ORGANISM: Artificial Sequence
<220> FEATURE:
<223> OTHER INFORMATION: Adnectin

<400> SEQUENCE: 364

Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Pro Ser Ala Pro Ile Ser
                85                  90                  95

Ile Asn Tyr Arg Thr Glu Ile Asp
            100

<210> SEQ ID NO 365
<211> LENGTH: 104
<212> TYPE: PRT
<213> ORGANISM: Artificial Sequence
<220> FEATURE:
<223> OTHER INFORMATION: Adnectin

<400> SEQUENCE: 365

Met Gly His His His His His His Gly Gly Ser Val Ser Asp Val Pro
 1               5                  10                  15

Arg Asp Leu Glu Val Val Ala Ala Thr Pro Thr Ser Leu Leu Ile Ser
            20                  25                  30

Trp Glu Tyr Lys Val Ser Gly Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

-continued

```
<210> SEQ ID NO 366
<211> LENGTH: 104
<212> TYPE: PRT
<213> ORGANISM: Artificial Sequence
<220> FEATURE:
<223> OTHER INFORMATION: Adnectin

<400> SEQUENCE: 366

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Tyr His Asn Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 367
<211> LENGTH: 104
<212> TYPE: PRT
<213> ORGANISM: Artificial Sequence
<220> FEATURE:
<223> OTHER INFORMATION: Adnectin

<400> SEQUENCE: 367

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Ser Ala Gln Leu Ser Gly Leu Lys Pro Gly Val Asp Tyr Thr
65                  70                  75                  80

Ile Thr Val Tyr Ala Val Thr Tyr Gly Asp Asp Ser Ala Pro Ile Ser
                85                  90                  95

Ile Asn Tyr Arg Thr Glu Ile Asp
            100

<210> SEQ ID NO 368
<211> LENGTH: 104
<212> TYPE: PRT
<213> ORGANISM: Artificial Sequence
<220> FEATURE:
<223> OTHER INFORMATION: Adnectin

<400> SEQUENCE: 368

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45
```

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Thr Asp Ser Ala Pro Ile Ser
                 85                  90                  95

Ile Asn Tyr Arg Thr Glu Ile Asp
            100

<210> SEQ ID NO 369
<211> LENGTH: 104
<212> TYPE: PRT
<213> ORGANISM: Artificial Sequence
<220> FEATURE:
<223> OTHER INFORMATION: Adnectin

<400> SEQUENCE: 369

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Pro Ser Ala Pro Ile Ser
                 85                  90                  95

Ile Asn Tyr Arg Thr Glu Ile Asp
            100

<210> SEQ ID NO 370
<211> LENGTH: 104
<212> TYPE: PRT
<213> ORGANISM: Artificial Sequence
<220> FEATURE:
<223> OTHER INFORMATION: Adnectin

<400> SEQUENCE: 370

Met Gly His His His His His Gly Gly Ser Val Ser Asp Val Pro
 1               5                  10                  15

Arg Asp Leu Glu Val Val Ala Ala Thr Pro Thr Ser Leu Leu Ile Ser
            20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
 65                  70                  75                  80

Ile Thr Val Tyr Ala Val Thr Tyr Gly Asp Asp Ser Lys Pro Ile Ser
                 85                  90                  95

Ile Asn Tyr Arg Thr Glu Ile Asp
            100

<210> SEQ ID NO 371
<211> LENGTH: 104
<212> TYPE: PRT

```
<213> ORGANISM: Artificial Sequence
<220> FEATURE:
<223> OTHER INFORMATION: Adnectin

<400> SEQUENCE: 371

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val His Pro Tyr Arg Tyr Tyr Arg Ile Thr Tyr Gly
            35                  40                  45

Glu Thr Gly Gly Asn Ser Pro Val Gln Glu Phe Thr Val Pro Ser Val
        50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Ile Asp Ser Thr Pro Ile Ser
                85                  90                  95

Ile Asn Tyr Arg Thr Glu Ile Asp
            100

<210> SEQ ID NO 372
<211> LENGTH: 33
<212> TYPE: PRT
<213> ORGANISM: Artificial Sequence
<220> FEATURE:
<223> OTHER INFORMATION: HIV fusion peptide inhibitor

<400> SEQUENCE: 372

Ser Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Tyr Lys Trp Ala
                20                  25                  30

Leu

<210> SEQ ID NO 373
<211> LENGTH: 33
<212> TYPE: PRT
<213> ORGANISM: Artificial Sequence
<220> FEATURE:
<223> OTHER INFORMATION: HIV fusion peptide inhibitor

<400> SEQUENCE: 373

Ser Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Trp Lys Trp Ala
                20                  25                  30

Ser

<210> SEQ ID NO 374
<211> LENGTH: 35
<212> TYPE: PRT
<213> ORGANISM: Artificial Sequence
<220> FEATURE:
<223> OTHER INFORMATION: HIV fusion peptide inhibitor

<400> SEQUENCE: 374

Thr Ile Ala Glu Tyr Ala Ala Arg Ile Glu Ala Leu Ile Arg Ala Ala
1               5                   10                  15

Gln Glu Gln Gln Glu Lys Asn Glu Ala Ala Leu Arg Glu Leu Tyr Lys
                20                  25                  30
```

Trp Ala Ser
        35

<210> SEQ ID NO 375
<211> LENGTH: 36
<212> TYPE: PRT
<213> ORGANISM: Artificial Sequence
<220> FEATURE:
<223> OTHER INFORMATION: HIV fusion peptide inhibitor

<400> SEQUENCE: 375

Ala Arg Ile Glu Glu Tyr Ala Ala Arg Ile Glu Ala Leu Ile Arg Ala
1               5                   10                  15

Ala Gln Glu Gln Gln Glu Lys Asn Glu Ala Ala Leu Arg Glu Leu Tyr
            20                  25                  30

Lys Trp Ala Ser
        35

<210> SEQ ID NO 376
<211> LENGTH: 33
<212> TYPE: PRT
<213> ORGANISM: Artificial Sequence
<220> FEATURE:
<223> OTHER INFORMATION: HIV fusion peptide inhibitor

<400> SEQUENCE: 376

Ser Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Tyr Lys Trp Ala
            20                  25                  30

Ser

<210> SEQ ID NO 377
<211> LENGTH: 36
<212> TYPE: PRT
<213> ORGANISM: Artificial Sequence
<220> FEATURE:
<223> OTHER INFORMATION: HIV fusion peptide inhibitor

<400> SEQUENCE: 377

Thr Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Lys Glu Trp Ala
            20                  25                  30

Ser Ile Trp Asn
        35

<210> SEQ ID NO 378
<211> LENGTH: 41
<212> TYPE: PRT
<213> ORGANISM: Artificial Sequence
<220> FEATURE:
<223> OTHER INFORMATION: HIV fusion peptide inhibitor

<400> SEQUENCE: 378

Ser Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Asp Lys Trp Thr
            20                  25                  30

Gly Val Trp Gly Asn Tyr Glu Lys Val
        35                  40

```
<210> SEQ ID NO 379
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 379

Ser Arg Ile Glu Ala Leu Ile Arg Ala Ala Gln Glu Gln Gln Glu Lys
1               5                   10                  15

Asn Glu Ala Ala Leu Arg Glu Leu Phe Lys Trp Ala Ser
            20                  25

<210> SEQ ID NO 380
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 380

Ser Arg Ile Glu Ala Leu Ile Arg Ala Ala Gln Glu Gln Gln Glu Lys
1               5                   10                  15

Asn Glu Ala Ala Leu Arg Glu Leu Asp Lys Trp Ala Ser
            20                  25

<210> SEQ ID NO 381
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 381

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Ala Ser
            20                  25

<210> SEQ ID NO 382
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 382

Ser Arg Ile Glu Ala Leu Ile Arg Ala Ala Gln Glu Gln Gln Glu Lys
1               5                   10                  15

Asn Glu Ala Ala Leu Arg Glu Leu Leu Lys Trp Ala Ser
            20                  25

<210> SEQ ID NO 383
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 383

Ser Arg Ile Glu Ala Leu Ile Arg Ala Ala Gln Glu Gln Gln Glu Lys
1               5                   10                  15

Asn Glu Ala Ala Leu Arg Glu Leu Gln Lys Trp Ala Ser
            20                  25
```

<210> SEQ ID NO 384
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 384

Ser Arg Ile Glu Ala Leu Ile Arg Ala Ala Gln Glu Gln Gln Glu Lys
1               5                   10                  15

Asn Glu Ala Ala Leu Arg Glu Leu Asp Lys Trp Ala Ser
            20                  25

<210> SEQ ID NO 385
<211> LENGTH: 35
<212> TYPE: PRT
<213> ORGANISM: Artificial Sequence
<220> FEATURE:
<223> OTHER INFORMATION: HIV fusion peptide inhibitor

<400> SEQUENCE: 385

Ala Ile Ala Glu Tyr Ala Ala Arg Ile Glu Ala Leu Ile Arg Ala Ala
1               5                   10                  15

Gln Glu Gln Gln Glu Lys Asn Glu Ala Ala Leu Arg Glu Leu Asp Lys
            20                  25                  30

Trp Ala Ser
        35

<210> SEQ ID NO 386
<211> LENGTH: 30
<212> TYPE: PRT
<213> ORGANISM: Artificial Sequence
<220> FEATURE:
<223> OTHER INFORMATION: HIV fusion peptide inhibitor

<400> SEQUENCE: 386

Thr Glu Tyr Glu Ala Arg Ile Glu Ala Leu Ile Arg Ala Ala Gln Glu
1               5                   10                  15

Gln Gln Glu Lys Asn Glu Ala Ala Leu Arg Glu Leu Asp Lys
            20                  25                  30

<210> SEQ ID NO 387
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 387

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Thr Ser
            20                  25

<210> SEQ ID NO 388
<211> LENGTH: 32
<212> TYPE: PRT
<213> ORGANISM: Artificial Sequence
<220> FEATURE:
<223> OTHER INFORMATION: HIV fusion peptide inhibitor

<400> SEQUENCE: 388

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Ala Ser Leu Trp Ile
            20                  25                  30

<210> SEQ ID NO 389
<211> LENGTH: 32
<212> TYPE: PRT
<213> ORGANISM: Artificial Sequence
<220> FEATURE:
<223> OTHER INFORMATION: HIV fusion peptide inhibitor

<400> SEQUENCE: 389

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Ala Ser Arg Trp Asn
            20                  25                  30

<210> SEQ ID NO 390
<211> LENGTH: 32
<212> TYPE: PRT
<213> ORGANISM: Artificial Sequence
<220> FEATURE:
<223> OTHER INFORMATION: HIV fusion peptide inhibitor

<400> SEQUENCE: 390

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Ala Ser Ser Trp Asn
            20                  25                  30

<210> SEQ ID NO 391
<211> LENGTH: 29
<212> TYPE: PRT
<213> ORGANISM: Artificial Sequence
<220> FEATURE:
<223> OTHER INFORMATION: HIV fusion peptide inhibitor

<400> SEQUENCE: 391

Ser Arg Ile Glu Ala Leu Ile Arg Ala Ala Gln Glu Gln Gln Glu Lys
1               5                   10                  15

Asn Glu Ala Ala Leu Arg Glu Leu Tyr Lys Trp Gly Ser
            20                  25

<210> SEQ ID NO 392
<211> LENGTH: 26
<212> TYPE: PRT
<213> ORGANISM: Artificial Sequence
<220> FEATURE:
<223> OTHER INFORMATION: HIV fusion peptide inhibitor

<400> SEQUENCE: 392

Ser Arg Ile Glu Ala Leu Ile Arg Ala Ala Gln Glu Gln Gln Glu Lys
1               5                   10                  15

Asn Glu Ala Ala Leu Arg Glu Leu Asp Lys
            20                  25

<210> SEQ ID NO 393
<211> LENGTH: 14
<212> TYPE: PRT
<213> ORGANISM: Artificial Sequence
<220> FEATURE:
<223> OTHER INFORMATION: Linker (GS)7

<400> SEQUENCE: 393

Gly Ser Gly Ser Gly Ser Gly Ser Gly Ser Gly Ser Gly Ser

```
1               5               10
```

<210> SEQ ID NO 394
<211> LENGTH: 13
<212> TYPE: PRT
<213> ORGANISM: Artificial Sequence
<220> FEATURE:
<223> OTHER INFORMATION: Linker G(GS)6

<400> SEQUENCE: 394

```
Gly Gly Ser Gly Ser Gly Ser Gly Ser Gly Ser Gly Ser
1               5                   10
```

<210> SEQ ID NO 395
<211> LENGTH: 16
<212> TYPE: PRT
<213> ORGANISM: Artificial Sequence
<220> FEATURE:
<223> OTHER INFORMATION: Linker G(GS)7G

<400> SEQUENCE: 395

```
Gly Gly Ser Gly Ser Gly Ser Gly Ser Gly Ser Gly Ser Gly Ser Gly
1               5                   10                  15
```

<210> SEQ ID NO 396
<211> LENGTH: 15
<212> TYPE: PRT
<213> ORGANISM: Artificial Sequence
<220> FEATURE:
<223> OTHER INFORMATION: Linker (GSE)5

<400> SEQUENCE: 396

```
Gly Ser Glu Gly Ser Glu Gly Ser Glu Gly Ser Glu Gly Ser Glu
1               5                   10                  15
```

<210> SEQ ID NO 397
<211> LENGTH: 8
<212> TYPE: PRT
<213> ORGANISM: Artificial Sequence
<220> FEATURE:
<223> OTHER INFORMATION: Linker GGSEGGSE

<400> SEQUENCE: 397

```
Gly Gly Ser Glu Gly Gly Ser Glu
1               5
```

<210> SEQ ID NO 398
<211> LENGTH: 8
<212> TYPE: PRT
<213> ORGANISM: Artificial Sequence
<220> FEATURE:
<223> OTHER INFORMATION: Linker (GS)4

<400> SEQUENCE: 398

```
Gly Ser Gly Ser Gly Ser Gly Ser
1               5
```

<210> SEQ ID NO 399
<211> LENGTH: 35
<212> TYPE: PRT
<213> ORGANISM: Artificial Sequence
<220> FEATURE:
<223> OTHER INFORMATION: Linker (GGGGS)7

<400> SEQUENCE: 399

```
Gly Gly Gly Gly Ser Gly Gly Gly Gly Ser Gly Gly Gly Gly Ser Gly
1               5                   10                  15
```

```
Gly Gly Gly Ser Gly Gly Gly Ser Gly Gly Gly Ser Gly Gly
            20                  25                  30
Gly Gly Ser
        35

<210> SEQ ID NO 400
<211> LENGTH: 25
<212> TYPE: PRT
<213> ORGANISM: Artificial Sequence
<220> FEATURE:
<223> OTHER INFORMATION: Linker (GGGGS)5

<400> SEQUENCE: 400

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 401
<211> LENGTH: 20
<212> TYPE: PRT
<213> ORGANISM: Artificial Sequence
<220> FEATURE:
<223> OTHER INFORMATION: Linker (GGGGS)4

<400> SEQUENCE: 401

Gly Gly Gly Gly Ser Gly Gly Gly Gly Ser Gly Gly Gly Gly Ser Gly
1               5                   10                  15

Gly Gly Gly Ser
            20

<210> SEQ ID NO 402
<211> LENGTH: 16
<212> TYPE: PRT
<213> ORGANISM: Artificial Sequence
<220> FEATURE:
<223> OTHER INFORMATION: Linker (GGGGS)3G

<400> SEQUENCE: 402

Gly Gly Gly Gly Ser Gly Gly Gly Gly Ser Gly Gly Gly Gly Ser Gly
1               5                   10                  15

<210> SEQ ID NO 403
<211> LENGTH: 7
<212> TYPE: PRT
<213> ORGANISM: Artificial Sequence
<220> FEATURE:
<223> OTHER INFORMATION: Linker (GP)3G

<400> SEQUENCE: 403

Gly Pro Gly Pro Gly Pro Gly
1               5

<210> SEQ ID NO 404
<211> LENGTH: 11
<212> TYPE: PRT
<213> ORGANISM: Artificial Sequence
<220> FEATURE:
<223> OTHER INFORMATION: Linker (GP)5G

<400> SEQUENCE: 404

Gly Pro Gly Pro Gly Pro Gly Pro Gly Pro Gly
1               5                   10
```

<210> SEQ ID NO 405
<211> LENGTH: 6
<212> TYPE: PRT
<213> ORGANISM: Artificial Sequence
<220> FEATURE:
<223> OTHER INFORMATION: Linker (PA)3

<400> SEQUENCE: 405

Pro Ala Pro Ala Pro Ala
1               5

<210> SEQ ID NO 406
<211> LENGTH: 12
<212> TYPE: PRT
<213> ORGANISM: Artificial Sequence
<220> FEATURE:
<223> OTHER INFORMATION: Linker (PA)6

<400> SEQUENCE: 406

Pro Ala Pro Ala Pro Ala Pro Ala Pro Ala Pro Ala
1               5                   10

<210> SEQ ID NO 407
<211> LENGTH: 18
<212> TYPE: PRT
<213> ORGANISM: Artificial Sequence
<220> FEATURE:
<223> OTHER INFORMATION: Linker (PA)9

<400> SEQUENCE: 407

Pro Ala Pro Ala Pro Ala Pro Ala Pro Ala Pro Ala Pro Ala Pro Ala
1               5                   10                  15

Pro Ala

<210> SEQ ID NO 408
<211> LENGTH: 11
<212> TYPE: PRT
<213> ORGANISM: Artificial Sequence
<220> FEATURE:
<223> OTHER INFORMATION: Linker ESPEPETPEDE

<400> SEQUENCE: 408

Glu Ser Pro Glu Pro Glu Thr Pro Glu Asp Glu
1               5                   10

<210> SEQ ID NO 409
<211> LENGTH: 21
<212> TYPE: PRT
<213> ORGANISM: Artificial Sequence
<220> FEATURE:
<223> OTHER INFORMATION: Linker (ESPEPETPED)2E

<400> SEQUENCE: 409

Glu Ser Pro Glu Pro Glu Thr Pro Glu Asp Glu Ser Pro Glu Pro Glu
1               5                   10                  15

Thr Pro Glu Asp Glu
            20

<210> SEQ ID NO 410
<211> LENGTH: 159
<212> TYPE: PRT
<213> ORGANISM: Artificial Sequence
<220> FEATURE:
<223> OTHER INFORMATION: Anti-N17 Adnectin - HIV fusion peptide Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asn Ala Tyr Arg Tyr Tyr Arg Ile Thr Tyr Gly
                35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Asp Ser Asp Pro Ile Ser
                85                  90                  95

Ile Asn Tyr Arg Thr Glu Ile Asp Gly Gly Gly Ser Gly Gly Gly
                100                 105                 110

Gly Ser Gly Gly Gly Ser Gly Gly Gly Ala Arg Ile Glu Glu
            115                 120                 125

Tyr Ala Ala Arg Ile Glu Ala Leu Ile Arg Ala Ala Gln Glu Gln Gln
            130                 135                 140

Glu Lys Asn Glu Ala Ala Leu Arg Glu Leu Tyr Lys Trp Ala Ser
145                 150                 155

<210> SEQ ID NO 411
<211> LENGTH: 158
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 411

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
                20                  25                  30

Trp Glu Tyr Lys Val Asn Ala Tyr Arg Tyr Tyr Arg Ile Thr Tyr Gly
                35                  40                  45

Glu Thr Gly Gly Asn Ser Pro Val Gln Glu Phe Thr Val Pro Ser Val
            50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Asp Ser Asp Pro Ile Ser
                85                  90                  95

Ile Asn Tyr Arg Thr Glu Ile Asp Gly Gly Gly Ser Gly Gly Gly
                100                 105                 110

Gly Ser Gly Gly Gly Ser Gly Gly Gly Thr Ile Ala Glu Tyr
            115                 120                 125

Ala Ala Arg Ile Glu Ala Leu Ile Arg Ala Ala Gln Glu Gln Gln Glu
            130                 135                 140

Lys Asn Glu Ala Ala Leu Arg Glu Leu Tyr Lys Trp Ala inhibitor Combinectin

<400> SEQUENCE: 412

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Ala Tyr Arg Tyr Tyr Arg Ile Thr Tyr Gly
        35                  40                  45

Glu Thr Gly Gly Asn Ser Pro Val Gln Glu Phe Thr Val Pro Ser Val
    50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Asp Ser Asp Pro Ile Ser
                85                  90                  95

Ile Asn Tyr Arg Thr Glu Ile Asp Gly Gly Gly Ser Gly Gly Gly
            100                 105                 110

Gly Ser Gly Gly Gly Ser Gly Gly Gly Ser Glu Tyr Glu Ala
        115                 120                 125

Arg Ile Glu Ala Leu Ile Arg Ala Ala Gln Glu Gln Gln Glu Lys Asn
    130                 135                 140

Glu Ala Ala Leu Arg Glu Leu Tyr Lys Trp Ala Ser
145                 150                 155

<210> SEQ ID NO 413
<211> LENGTH: 157
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 413

Met Gly His His His His His Gly Val Ser Asp Val Pro Arg Asp
1               5                   10                  15

Leu Glu Val Val Ala Ala Thr Pro Thr Ser Leu Leu Ile Ser Trp Lys
            20                  25                  30

Tyr Lys Val His Pro Tyr Arg Tyr Tyr Arg Ile Thr Tyr Gly Glu Thr
        35                  40                  45

Gly Gly Asn Ser Pro Val Gln Glu Phe Thr Val Pro Ser Val Leu Ser
    50                  55                  60

Thr Ala Thr Ile Ser Gly Leu Lys Pro Gly Val Asp Tyr Thr Ile Thr
65                  70                  75                  80

Val Tyr Ala Val Thr Tyr Gly Val Asn Ser Leu Pro Ile Ser Ile Asn
                85                  90                  95

Tyr Arg Thr Glu Ile Asp Gly Gly Gly Ser Gly Gly Gly Ser
            100                 105                 110

Gly Gly Gly Gly Ser Gly Gly Gly Thr Glu Tyr Glu Ala Arg Ile
        115                 120                 125

Glu Ala Leu Ile Arg Ala Ala Gln Glu Gln Gln Glu Lys Asn Glu Ala
    130                 135                 140

Ala Leu Arg Glu Leu Lys Glu Trp Ala Ser Ile Trp Asn
145                 150                 155

<210> SEQ ID NO 414
<211> LENGTH: 168
<212> TYPE: PRT

```
<213> ORGANISM: Artificial Sequence
<220> FEATURE:
<223> OTHER INFORMATION: Anti-N17 Adnectin - HIV fusion pe 145                  150

```
<210> SEQ ID NO 416
<211> LENGTH: 154
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 416
```

Met Gly His His His His His Gly Val Ser Asp Val Pro Arg Asp
1                5                    10               15

Leu Glu Val Val Ala Ala Thr Pro Thr Ser Leu Leu Ile Ser Trp Asp
            20                   25                 30

Ala Pro Ala Val Thr Val Arg Tyr Tyr Arg Ile Thr Tyr Gly Glu Thr
            35                   40               45

Gly Gly Asn Ser Pro Val Gln Glu Phe Thr Val Pro Gly Ser Lys Ser
    50                 55                 60

Thr Ala Thr Ile Ser Gly Leu Lys Pro Gly Val Asp Tyr Thr Ile Thr
65                70                  75             80

Val Tyr Ala Val Thr Gly Arg Gly Glu Ser Pro Ala Ser Ser Lys Pro
            85                   90               95

Ile Ser Ile Asn Tyr Arg Thr Glu Ile Asp Gly Gly Gly Ser Gly
            100               105              110

Gly Gly Gly Ser Gly Gly Gly Gly Ser Gly Gly Gly Ser Arg Ile
        115               120              125

Glu Ala Leu Ile Arg Ala Ala Gln Glu Gln Gln Gln Lys Asn Glu Ala
    130                135                140

Ala Leu Arg Glu Leu Asp Lys Trp Ala Ser
145                150

```
<210> SEQ ID NO 417
<211> LENGTH: 154
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 417
```

Met Gly His His His His His Gly Val Ser Asp Val Pro Arg Asp
1                5                    10               15

Leu Glu Val Val Ala Ala Thr Pro Thr Ser Leu Leu Ile Ser Trp Asp
            20                   25                 30

Ala Pro Ala Val Thr Val Arg Tyr Tyr Arg Ile Thr Tyr Gly Glu Thr
            35                   40               45

Gly Gly Asn Ser Pro Val Gln Glu Phe Thr Val Pro Gly Ser Lys Ser
    50                 55                 60

Thr Ala Thr Ile Ser Gly Leu Lys Pro Gly Val Asp Tyr Thr Ile Thr
65                70                  75             80

Val Tyr Ala Val Thr Gly Arg Gly Glu Ser Pro Ala Ser Ser Lys Pro
            85                   90               95

Ile Ser Ile Asn Tyr Arg Thr Glu Ile Asp Gly Gly Gly Ser Gly
            100               105              110

Gly Gly Gly Ser Gly Gly Gly Gly Ser Gly Gly Gly Ser Arg Ile
        115               120              125

Glu Ala Leu Ile Arg Ala Ala Gln Glu Gln Gln Glu Lys Asn Glu Ala

Ala Leu Arg Glu Leu Tyr Lys Trp Ala Ser
145                 150

<210> SEQ ID NO 418
<211> LENGTH: 154
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 418

Met Gly His His His His His Gly Val Ser Asp Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
        35                  40                  45

Gly Gly Asn Ser Pro Val Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Arg Gly Glu Ser Pro Ala Ser Ser Lys Pro
                85                  90                  95

Ile Ser Ile Asn Tyr Arg Thr Glu Ile Asp Gly Gly Gly Gly Ser Gly
            100                 105                 110

Gly Gly Gly Ser Gly Gly Gly Ser Gly Gly Gly Gly Ser Arg Ile
        115                 120                 125

Glu Ala Leu Ile Arg Ala Ala Gln Glu Gln Gln Glu Lys Asn Glu Ala
    130                 135                 140

Ala Leu Arg Glu Leu Leu Lys Trp Ala Ser
145                 150

<210> SEQ ID NO 419
<211> LENGTH: 154
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 419

Met Gly His His His His His Gly Val Ser Asp Val Pro Arg Asp
1               5                   10                  15

Leu Glu Val Val Ala Ala Thr Pro Thr Ser Leu Leu Ile Ser Trp Asp
            20                  25                  30

Ala Pro Ala Val Thr Val Arg Tyr Tyr Arg Ile Thr Tyr Gly Glu Thr
        35                  40                  45

Gly Gly Asn Ser Pro Val Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Arg Gly Glu Ser Pro Ala Ser Ser Lys Pro
                85                  90                  95

Ile Ser Ile Asn Tyr Arg Thr Glu Ile Asp Gly Gly Gly Ser Gly
            100                 105                 110

Gly Gly Gly Ser Gly Gly Gly Ser Gly Gly Gly Gly Ser Arg Ile

```
            115                 120                 125
Glu Ala Leu Ile Arg Ala Ala Gln Glu Gln Gln Glu Lys Asn Glu Ala
            130                 135                 140

Ala Leu Arg Glu Leu Gln Lys Trp Ala Ser
145                 150

<210> SEQ ID NO 420
<211> LENGTH: 152
<212> TYPE: PRT
<213> ORGANISM: Artificial Sequence
<220> FEATURE:
<223> OTHER INFORMATION: Anti-N17 Adnectin - HIV fusion peptide

```
                    100                 105                 110
Gly Gly Gly Ser Gly Gly Gly Ser Gly Gly Ala Ile Ala Glu Tyr
            115                 120                 125
Ala Ala Arg Ile Glu Ala Leu Ile Arg Ala Ala Gln Glu Gln Gln Glu
            130                 135                 140
Lys Asn Glu Ala Ala Leu Arg Glu Leu Asp Lys Trp Ala Ser
145                 150                 155
```

<210> SEQ ID NO 422
<211> LENGTH: 151
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 422

```
Met Gly His His His His His Gly Val Ser Asp Val Pro Arg Asp
1               5                   10                  15
Leu Glu Val Val Ala Ala Thr Pro Thr Ser Leu Leu Ile Ser Trp Lys
            20                  25                  30
Tyr Lys Val His Pro Tyr Arg Tyr Arg Ile Thr Tyr Gly Glu Thr
            35                  40                  45
Gly Gly Asn Ser Pro Val Gln Glu Phe Thr Val Pro Ser Val Leu Ser
        50                  55                  60
Thr Ala Thr Ile Ser Gly Leu Lys Pro Gly Val Asp Tyr Thr Ile Thr
65                  70                  75                  80
Val Tyr Ala Val Thr Tyr Gly Val Asn Ser Leu Pro Ile Ser Ile Asn
                85                  90                  95
Tyr Arg Thr Glu Ile Asp Gly Gly Gly Ser Gly Gly Gly Gly Ser
            100                 105                 110
Gly Gly Gly Gly Ser Gly Gly Gly Gly Thr Glu Tyr Glu Ala Arg Ile
            115                 120                 125
Glu Ala Leu Ile Arg Ala Ala Gln Glu Gln Gln Glu Lys Asn Glu Ala
            130                 135                 140
Ala Leu Arg Glu Leu Asp Lys
145                 150
```

<210> SEQ ID NO 423
<211> LENGTH: 154
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 423

```
Met Gly His His His His His Gly Val Ser Asp Val Pro Arg Asp
1               5                   10                  15
Leu Glu Val Val Ala Ala Thr Pro Thr Ser Leu Leu Ile Ser Trp Asp
            20                  25                  30
Ala Pro Ala Val Thr Val Arg Tyr Tyr Arg Ile Thr Tyr Gly Glu Thr
            35                  40                  45
Gly Gly Asn Ser Pro Val Gln Glu Phe Thr Val Pro Gly Ser Lys Ser
        50                  55                  60
Thr Ala Thr Ile Ser Gly Leu Lys Pro Gly Val Asp Tyr Thr Ile Thr
65                  70                  75                  80
Val Tyr Ala Val Thr Gly Arg Gly Glu Ser Pro Ala Ser Ser Lys Pro
```

85                  90                  95

Ile Ser Ile Asn Tyr Arg Thr Glu Ile Asp Gly Gly Gly Ser Gly
            100                 105                 110

Gly Gly Gly Ser Gly Gly Gly Ser Gly Gly Gly Ser Arg Ile
        115                 120                 125

Glu Ala Leu Ile Arg Ala Ala Gln Glu Gln Gln Glu Lys Asn Glu Ala
    130                 135                 140

Ala Leu Arg Glu Leu Tyr Lys Trp Thr Ser
145                 150

<210> SEQ ID NO 424
<211> LENGTH: 159
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 424

Met Gly His His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Ala Tyr Arg Tyr Tyr Ar

```
                65                   70                  75                  80
Ile Thr Val Tyr Ala Val Thr Tyr Gly Val Asp Ser Asp Pro Ile Ser
                    85                  90                  95

Ile Asn Tyr Arg Thr Glu Ile Asp Gly Gly Gly Ser Gly Gly Gly
            100                 105                 110

Gly Ser Gly Gly Gly Ser Gly Gly Gly Thr Ile Ala Glu Tyr
        115                 120                 125

Ala Ala Arg Ile Glu Ala Leu Ile Arg Ala Ala Gln Glu Gln Gln Glu
130                 135                 140

Lys Asn Glu Ala Ala Leu Arg Glu Leu Tyr Lys Trp Ala Ser
145                 150                 155

<210> SEQ ID NO 426
<211> LENGTH: 156
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 426

Met Gly His His His His His Gly Gly Ser Val Ser Asp Val Pro
1               5                   10                  15

Arg Asp Leu Glu Val Val Ala Ala Thr Pro Thr Ser Leu Leu Ile Ser
            20                  25                  30

Trp Glu Tyr Lys Val Asn Ala Tyr Arg Tyr Tyr Arg Ile Thr Tyr Gly
        35                  40                  45

Glu Thr Gly Gly Asn Ser Pro Val Gln Glu Phe Thr Val Pro Ser Val
50                  55                  60

Leu Ser Thr Ala Thr Ile Ser Gly Leu Lys Pro Gly Val Asp Tyr Thr
65                  70                  75                  80

Ile Thr Val Tyr Ala Val Thr Tyr Gly Val Asp Ser Asp Pro Ile Ser
                85                  90                  95

Ile Asn Tyr Arg Thr Glu Ile Asp Gly Gly Gly Ser Gly Gly Gly
            100                 105                 110

Gly Ser Gly Gly Gly Ser Gly Gly Gly Ser Glu Tyr Glu Ala
        115                 120                 125

Arg Ile Glu Ala Leu Ile Arg Ala Ala Gln Glu Gln Gln Glu Lys Asn
    130                 135                 140

Glu Ala Ala Leu Arg Glu Leu Tyr Lys Trp Ala Ser
145                 150                 155

<210> SEQ ID NO 427
<211> LENGTH: 157
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 427

Met Gly His His His His His Gly Val Ser Asp Val Pro Arg Asp
1               5                   10                  15

Leu Glu Val Val Ala Ala Thr Pro Thr Ser Leu Leu Ile Ser Trp Lys
            20                  25                  30

Tyr Lys Val His Pro Tyr Arg Tyr Tyr Arg Ile Thr Tyr Gly Glu Thr
        35                  40                  45

Gly Gly Asn Ser Pro Val Gln Glu Phe Thr Val Pro Ser Val Leu Ser
```

```
                50                  55                  60
Thr Ala Thr Ile Ser Gly Leu Lys Pro Gly Val Asp Tyr Thr Ile Thr
 65                  70                  75                  80

Val Tyr Ala Val Thr Tyr Gly Val Asn Ser Leu Pro Ile Ser Ile Asn
                 85                  90                  95

Tyr Arg Thr Glu Ile Asp Gly Gly Gly Ser Gly Gly Gly Gly Gly Ser
                100                 105                 110

Gly Gly Gly Gly Ser Gly Gly Gly Thr Glu Tyr Glu Ala Arg Ile
            115                 120                 125

Glu Ala Leu Ile Arg Ala Ala Gln Gly Gln Gln Glu Lys Asn Glu Ala
            130                 135                 140

Ala Leu Arg Glu Leu Lys Glu Trp Ala Ser Ile Trp Asn
145                 150                 155

<210> SEQ ID NO 428
<211> LENGTH: 168
<212> TYPE: PRT
<213> ORGANISM: Artificial Sequence
<220> FEATURE:
<223> OTHER INFORMATION: Anti-N17 Adnectin - HIV fusion peptide
      inhibitor Combinectin

<400> SEQUENCE: 428

Met Gly His His His His His His Thr Ser Gly Val Ser Val Pro
 1               5                  10                  15

Arg Asp Leu Glu Val Val Ala Ala Thr Pro Thr Ser Leu Leu Ile Ser
                 20                  25                  30

Trp Asp Ala Pro Ala Val Thr Val Gly Trp Tyr His Ile Gly Tyr Asn
             35                  40                  45

Val Glu Gly Glu Pro Ala Ser Tyr Gln Tyr Phe Arg Val Pro Gly Ser
         50                  55                  60

Lys Ser Thr Ala Thr Ile Ser Gly Leu Lys Pro Gly Val Glu Tyr Met
 65                  70                  75                  80

Ile Phe Val Asn Ala Val Thr Gly Ser Gly Ala Arg Glu Glu Phe Ser
                 85                  90                  95

Leu Pro Ile Ser Ile Asn Tyr Arg Thr Glu Ile Asp Gly Gly Gly Gly
                100                 105                 110

Ser Gly Gly Gly Gly Ser Gly Gly Gly Gly Ser Gly Gly Gly Gly Ser
            115                 120                 125

Glu Tyr Glu Ala Arg Ile Glu Ala Leu Ile Arg Ala Ala Gln Glu Gln
            130                 135                 140

Gln Glu Lys Asn Glu Ala Ala Leu Arg Glu Leu Asp Lys Trp Thr Gly
145                 150                 155                 160

Val Trp Gly Asn Tyr Glu Lys Val
                165
```